US007262005B1

(12) United States Patent
Stack et al.

(10) Patent No.: US 7,262,005 B1
(45) Date of Patent: Aug. 28, 2007

(54) METHODS OF PROTEIN DESTABILIZATION AND USES THEREOF

(75) Inventors: Jeffrey Stack, San Diego, CA (US); Michael Whitney, San Diego, CA (US); Andrew B. Cubitt, San Diego, CA (US); Brian Pollok, San Diego, CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/498,098

(22) Filed: Feb. 4, 2000

(51) Int. Cl.
*C12Q 1/68* (2006.01)

(52) U.S. Cl. .......................... 435/6; 435/325; 536/23.4

(58) Field of Classification Search ............... 435/69.7, 435/69.1, 91.1, 6, 325; 514/2, 44; 800/3, 800/8; 536/23.4
See application file for complete search history.

(56) References Cited

U.S. PATENT DOCUMENTS

| | | | | |
|---|---|---|---|---|
| 5,093,242 | A | | 3/1992 | Bachmair et al. |
| 5,122,463 | A | | 6/1992 | Varshavsky et al. |
| 5,132,213 | A | * | 7/1992 | Bachmair et al. ............. 435/69 |
| 5,196,321 | A | | 3/1993 | Bachmair et al. |
| 5,358,857 | A | | 10/1994 | Stengelin et al. |
| 5,366,871 | A | | 11/1994 | Rechsteiner et al. |
| 5,459,051 | A | | 10/1995 | Mascarenhas |
| 5,496,721 | A | | 3/1996 | Bachmair et al. |
| 5,503,977 | A | | 4/1996 | Johnsson et al. |
| 5,532,142 | A | | 7/1996 | Johnston et al. |
| 5,563,046 | A | | 10/1996 | Mascarenhas et al. |
| 5,563,123 | A | | 10/1996 | Innis et al. |
| 5,585,245 | A | | 12/1996 | Johnsson et al. |
| 5,589,359 | A | | 12/1996 | Innis et al. |
| 5,625,048 | A | | 4/1997 | Tsien et al. |
| 5,646,017 | A | | 7/1997 | Bachmair et al. |
| 5,721,133 | A | | 2/1998 | Dasmahapatra |
| 5,741,657 | A | | 4/1998 | Tsien et al. |
| 5,763,212 | A | | 6/1998 | Varshavsky et al. |
| 5,763,225 | A | | 6/1998 | Rechsteiner et al. |
| 5,777,079 | A | | 7/1998 | Tsien et al. |
| 5,817,494 | A | | 10/1998 | Bandman et al. |
| 5,847,097 | A | | 12/1998 | Bachmair et al. |
| 5,955,604 | A | | 9/1999 | Tsien et al. |
| 5,981,200 | A | | 11/1999 | Tsien et al. |

FOREIGN PATENT DOCUMENTS

| | | | |
|---|---|---|---|
| EP | 479912 | | 6/1990 |
| WO | WO88/02406 | | 4/1988 |
| WO | WO97/01627 | | 1/1997 |
| WO | 99/47640 | * | 9/1999 |
| WO | WO9947640 | | 9/1999 |
| WO | WO99/54348 | | 10/1999 |

OTHER PUBLICATIONS

Corish et al., Attenuation of green fluorescent protein half-life in mammalian cells, 1999, Protein Engineering, vol. 12, No. 2 pp. 1035-1040.*

Pinket, Transgenic Animal Technology, 1994, Academic Press, pp. 96-98.*

Wall, Transgenic Livestock: Progress and Prospects for the Future, 1996, Theriogenology, vol. 45, pp. 57-68.*

Mullins et al., Fulminant hypertension in transgenic rats harbouring the mouse REN-2 gene, Apr. 5, 1990, Nature, vol. 344, pp. 541-544.*

Mullins et al., Expression of the DBA/2J Ren-2 gene in the adrenal gland of transgenic mice, 1989, The EMBO Journal, vol. 8, No. 13, pp. 4065-4072.*

Hammer et al., Spontaneous Inflammatory Disease in Transgenic Rats Expressing HLA-B27 and Human B2m: An Animal Model of HLA-B27-Associated Human Disorders, Nov. 30, 1990, Cell, vol. 63, pp. 1099-1112.*

Taurog et al., Cell Surface Expression and Recognition as an Alloantigen in the Absence of Human B2-Microglobulin, Dec. 1, 1988, The Journal of Immunology, vol. 141, pp. 4020-4023.*

Johnson et al., Ubiquitin as a degradation signal, 1992, The EMBO Journal, vol. 11, No. 2, pp. 497-505.*

Hochstrasser, Ubiquitin-Dependent Protein Degradation, 1996, Annu. Rev. Genet., vol. 30, pp. 405-439.*

Johnson et al., A Proteolytic Pathway That Recognize Ubiquitin as a Degradation Signal, 1995, Biological Chemistry, vol. 270, No. 29, p. 17442-17456.*

Anderson (Nature 1998; 392(suppl):25-30).*

(Continued)

*Primary Examiner*—Jon E. Angell
(74) *Attorney, Agent, or Firm*—DLA Piper US LLP

(57) ABSTRACT

This invention is directed towards methods of destabilizing proteins in living cells, and their use for the development of novel assays. In one embodiment, the invention comprises the use of non-cleavable multimerized ubiquitin fusion proteins to destabilize a target protein, such as a reporter moiety. In one aspect of this method the constructs also comprises a linker that operatively couples the reporter moiety to the multimerized ubiquitin fusion protein. In this embodiment, enzymatic modification of the linker results in a modulation of the coupling of the reporter protein to the multimerized ubiquitin domains resulting in a change in the stability of the reporter moiety. The level of the reporter moiety in the cell can then be used as a measure of the enzymatic activity in the cell. In another embodiment the invention provides for a generalized way of coordinately regulating the cellular concentration of a plurality of target proteins. In one aspect of this method, the target proteins are operatively coupled to a ubiquitin fusion protein via a linker containing a protease cleavage site. Cleavage of the linker by a protease results in uncoupling of the target protein from the multimerized ubiquitin construct, and results in an increase in the stability and concentration of the target protein.

31 Claims, 11 Drawing Sheets

OTHER PUBLICATIONS

Dang et al. (Clinical Cancer Research 1999; 5:471-474).*

Levine et al. (Molecular Medicine Today 1999; 5:165-171).*

Dantuma, Nico P., "Short-Lived Green Fluorescent Proteins For Quantifying Ubiquitin/Proteasome-Dependent Proteolysis In Living Cells," *Nature Biotechnology,* vol. 18, May 2000, pp. 538-543.

Deichsel, Heike et al., "Green Fluorescent Proteins With Short Half-Lives As Reporters In *Dictyostelium discoidium," Dev. Genes Evol.*, vol. 209, 1999, pp. 63-68.

Stack, Jeffrey H. et al., "A Ubiquitin-Based Tagging System for Controlled Modulation of Protein Stability," *Nature Biotechnology*, vol. 18, Dec. 2000, pp. 1298-1302.

Bachmair, Andreas et al., "Use of a reporter transgene to generate *Arabidopis* mutants in ubiquitin-dependent protein degradation," *Proc. Natl. Acad. Sci.,* vol. 90, pp. 418-421. Jan. 1993.

Couture, Clement, et al., "Regulation of the Lck SH2 Domain by Tyrosine Phosphorylation", *J. Biol. Chem,* vol. 271, pp. 24880-24884, 1996.

Hondred, David, et al., "Use of Ubiquitin Fusions to Augment Protein Expression in Transgenic Plants", *Plant Physiology,* vol. 119, pp. 713-723, 1999.

Shih, Susan C., et al, "Monoubiquitin carries a novel internalization signal that is appended to activated receptors", *European Molecular Biology Organization,* vol. 19, No. 2, pp. 187-198, 2000.

Tsirigotis, M., et al., "Analysis of Ubiquitination In Vivo Using a Transgenic Mouse Model", *Biotechniques,* vol. 31, pp. 120-130, 2001.

Gu, Jijie et al. "Identification of a Sequence Element from p53 That Signals for Mdm2-Targeted Degradation," *Molecular and Cellular Biology,* vol. 20, No. 4, pp. 1243-1253; Feb. 2000.

Bachmair et al., In Vivo half-life of a Protein is a Function of Its Amino-Terminal Residue, *Science* 234, pp. 179-186, (1986).

Bachmair et al., The Degradation Signal in a short-lived Protein, *Cell* 56, pp. 1019-1032, (1989).

Butt et al., Ubiquitin-Metallothionein Fusion Protein Expression in Yeast, *The Journal of Biological Chemistry* 263, pp. 16364-16371, (1988).

Ciechanover et al., The Ubiquitin-Mediated Proteolytic Pathway and the Mechanism of Energy-Dependent Intracellular Protein Degradation, *Journal of Cellular Biochemistry* 24, pp. 27-53 (1984).

Ciechanover, The ubiquitin-proteasome pathway: on protein death and cell life, *The EMBO Journal* 17, pp. 7151-7160, (1998).

Fiering et al., Improved FAC-Gal: Flow Cytometric Analysis and Sorting of Viable Eukaryotic Cells Expressing Reporter Gene Constructs, *Cytometry* 12, pp. 291-301, (1991).

Finley et al., The Ubiquitin System: functions and mechanisms, *TIBS,* pp. 343-347, (1985).

Gonda et al., Universality and Structure of the N-end Rule, *The Journal of Biological Chemistry* 264, pp. 16700-16712, (1989).

Hershko et al., The Ubiquitin System, *Annual Review of Biochemistry* 67, pp. 425-479, (1998).

Hochstrasser, Ubiquitin-Dependent Protein Degradation, *Annual Review of Genetics* 30, pp. 405-439, (1996).

Johnson et al., Proteolytic Pathway that Recognizes Ubiquitin as a Degradation Signal, *The Journal of Biological Chemistry* 270, pp. 17442-17456, 91995).

Johnson et al., Ubiquitin as a Degradation Signal, *The EMBO Journal* 11, pp. 497-505, (1992).

Jonnalagadda et al., Multiple Protein Endoproteases in Cells, *The Journal of Biological Chemisty*, 264, pp. 10637-10642, (1989).

Koepp et al., How the Cyclin Became a Cyclin: Regulated Proteolysis in the Cell Cycle, *Cell* 97, pp. 431-434, (1999).

Laney et al., Substrate Targeting in the Ubiquitin System, *Cell* 97, pp. 427-430, (1999).

Lawler, et al., Viral Protease Assay Based on GAL4 Inactivation Is Applicable to High-Throughput Screening in Mammalian Cells, *Analytical Biochemistry* 269, pp. 133-138, (1999).

Lee et al., Proteasome inhibitors: valuable new tools for cell biologists, *Cell Biology 8*, pp. 397-403, (1998).

Li et al., Generation of Destabilized Green Fluorescent Protein as a Transcription Reporter, *The Journal of Biological Chemistry* 272, pp. 34970-34975, (1998).

Marcotte et al., Detecting Protein Function and Protein—Protein Interactions from Genome Sequences, *Science* 285, pp. 751-753 (1999).

Ozkaynak et al., The yeast ubiquitin gene: head-to-tail repeats encoding a polyubiquitin precursor protein, *Nature* 312, pp. 663-666, (1984).

Thompson et al., Modulation of Firefly Luciferase Stability and Impact on Studies of Gene Regulation, *Gene* 103, pp. 171-177, (1991).

Thrower et al., Recognition of the Polyubiquitin Proteolytic Signal, *The EMBO Journal* 19, pp. 94-102, (2000).

Varshavsky, The N-end Rule, *Cell* 69, pp. 725-735, (1992).

Varshavsky, The N-End: Functions, Mysteries, Uses, *Proc. Natl. Acad. Sci. USA* 93, pp. 12142-1214, (1996).

Varshavsky, The Ubiquitin System, *TIBS* 22, pp. 383-387, (1997).

Worley et al., Engineering in vivo instability of firefly luciferase and *Escherichia coli* Beta-glucuronidase in higher plants using recognition elements from the ubiquitin pathway, *Plant Molecular Biology* 37, pp. 337-347, (1998).

* cited by examiner

SEQUENCE LISTING

```
<160> NUMBER OF SEQ ID NOS: 74

<210> SEQ ID NO 1
<211> LENGTH: 6
<212> TYPE: PRT
<213> ORGANISM: Eukaryote
<220> FEATURE:
<221> NAME/KEY: VARIANT
<222> LOCATION: 2, 6
<223> OTHER INFORMATION: Phosphoserine

<400> SEQUENCE: 1

Asp Ser Gly Leu Asp Ser
 1               5
```

-continued

<210> SEQ ID NO 2
<211> LENGTH: 228
<212> TYPE: DNA
<213> ORGANISM: Eukaryote

<400> SEQUENCE: 2

```
atggagatct tcgtgaagac tctgactggt aagaccatca ccctcgaagt ggagccgagt     60

gacaccattg agaatgtcaa ggcaaagatc caagacaagg aaggcatccc tcctgaccag    120

cagaggttga tctttgctgg gaaacagctg gaagatggac gcaccctgtc tgactacaac    180

atccagaaag agtccaccct gcacctggta ctccgtctca gaggtggg                 228
```

<210> SEQ ID NO 3
<211> LENGTH: 795
<212> TYPE: DNA
<213> ORGANISM: Artificial Sequence
<220> FEATURE:
<221> NAME/KEY: CDS
<222> LOCATION: (1)...(795)
<223> OTHER INFORMATION: cloning vector

<400> SEQUENCE: 3

```
atg agt cac cca gaa acg ctg gtg aaa gta aaa gat gct gaa gat cag       48
Met Ser His Pro Glu Thr Leu Val Lys Val Lys Asp Ala Glu Asp Gln
 1               5                  10                  15

ttg ggt gca cga gtg ggt tac atc gaa ctg gat ctc aac agc ggt aag       96
Leu Gly Ala Arg Val Gly Tyr Ile Glu Leu Asp Leu Asn Ser Gly Lys
            20                  25                  30

atc ctt gag agt ttt cgc ccc gaa gaa cgt ttt cca atg atg agc act      144
Ile Leu Glu Ser Phe Arg Pro Glu Glu Arg Phe Pro Met Met Ser Thr
        35                  40                  45

ttt aaa gtt ctg cta tgt ggc gcg gta tta tcc cgt gtt gac gcc ggg      192
Phe Lys Val Leu Leu Cys Gly Ala Val Leu Ser Arg Val Asp Ala Gly
    50                  55                  60

caa gag caa ctc ggt cgc cgc ata cac tat tct cag aat gac ttg gtt      240
Gln Glu Gln Leu Gly Arg Arg Ile His Tyr Ser Gln Asn Asp Leu Val
 65                  70                  75                  80

gag tac tca cca gtc aca gaa aag cat ctt acg gat ggc atg aca gta      288
Glu Tyr Ser Pro Val Thr Glu Lys His Leu Thr Asp Gly Met Thr Val
                85                  90                  95

aga gaa tta tgc agt gct gcc ata acc atg agt gat aac act gcg gcc      336
Arg Glu Leu Cys Ser Ala Ala Ile Thr Met Ser Asp Asn Thr Ala Ala
            100                 105                 110

aac tta ctt ctg aca acg atc gga gga ccg aag gag cta acc gct ttt      384
Asn Leu Leu Leu Thr Thr Ile Gly Gly Pro Lys Glu Leu Thr Ala Phe
        115                 120                 125

ttg cac aac atg ggg gat cat gta act cgc ctt gat cgt tgg gaa ccg      432
Leu His Asn Met Gly Asp His Val Thr Arg Leu Asp Arg Trp Glu Pro
    130                 135                 140

gag ctg aat gaa gcc ata cca aac gac gag cgt gac acc acg atg cct      480
Glu Leu Asn Glu Ala Ile Pro Asn Asp Glu Arg Asp Thr Thr Met Pro
145                 150                 155                 160

gca gca atg gca aca acg ttg cgc aaa cta tta act ggc gaa cta ctt      528
Ala Ala Met Ala Thr Thr Leu Arg Lys Leu Leu Thr Gly Glu Leu Leu
                165                 170                 175

act cta gct tcc cgg caa caa tta ata gac tgg atg gag gcg gat aaa      576
Thr Leu Ala Ser Arg Gln Gln Leu Ile Asp Trp Met Glu Ala Asp Lys
            180                 185                 190

gtt gca gga cca ctt ctg cgc tcg gcc ctt ccg gct ggc tgg ttt att      624
Val Ala Gly Pro Leu Leu Arg Ser Ala Leu Pro Ala Gly Trp Phe Ile
```

-continued

```
        195                 200                 205

gct gat aaa tct gga gcc ggt gag cgt ggg tct cgc ggt atc att gca       672
Ala Asp Lys Ser Gly Ala Gly Glu Arg Gly Ser Arg Gly Ile Ile Ala
    210                 215                 220

gca ctg ggg cca gat ggt aag ccc tcc cgt atc gta gtt atc tac acg       720
Ala Leu Gly Pro Asp Gly Lys Pro Ser Arg Ile Val Val Ile Tyr Thr
225                 230                 235                 240

acg ggg agt cag gca act atg gat gaa cga aat aga cag atc gct gag       768
Thr Gly Ser Gln Ala Thr Met Asp Glu Arg Asn Arg Gln Ile Ala Glu
                245                 250                 255

ata ggt gcc tca ctg att aag cat tgg                                   795
Ile Gly Ala Ser Leu Ile Lys His Trp
            260                 265


<210> SEQ ID NO 4
<211> LENGTH: 858
<212> TYPE: DNA
<213> ORGANISM: Artificial Sequence
<220> FEATURE:
<221> NAME/KEY: CDS
<222> LOCATION: (1)...(858)
<223> OTHER INFORMATION: cloning vector

<400> SEQUENCE: 4

atg aga att caa cat ttc cgt gtc gcc ctt att ccc ttt ttt gcg gca        48
Met Arg Ile Gln His Phe Arg Val Ala Leu Ile Pro Phe Phe Ala Ala
 1               5                  10                  15

ttt tgc ctt cct gtt ttt ggt cac cca gaa acg ctg gtg aaa gta aaa        96
Phe Cys Leu Pro Val Phe Gly His Pro Glu Thr Leu Val Lys Val Lys
            20                  25                  30

gat gct gaa gat cag ttg ggt gca cga gtg ggt tac atc gaa ctg gat       144
Asp Ala Glu Asp Gln Leu Gly Ala Arg Val Gly Tyr Ile Glu Leu Asp
        35                  40                  45

ctc aac agc ggt aag atc ctt gag agt ttt cgc ccc gaa gaa cgt ttt       192
Leu Asn Ser Gly Lys Ile Leu Glu Ser Phe Arg Pro Glu Glu Arg Phe
    50                  55                  60

cca atg atg agc act ttt aaa gtt ctg cta tgt ggc gcg gta tta tcc       240
Pro Met Met Ser Thr Phe Lys Val Leu Leu Cys Gly Ala Val Leu Ser
 65                 70                  75                  80

cgt gtt gac gcc ggg caa gag caa ctc ggt cgc cgc ata cac tat tct       288
Arg Val Asp Ala Gly Gln Glu Gln Leu Gly Arg Arg Ile His Tyr Ser
                85                  90                  95

cag aat gac ttg gtt gag tac tca cca gtc aca gaa aag cat ctt acg       336
Gln Asn Asp Leu Val Glu Tyr Ser Pro Val Thr Glu Lys His Leu Thr
            100                 105                 110

gat ggc atg aca gta aga gaa tta tgc agt gct gcc ata acc atg agt       384
Asp Gly Met Thr Val Arg Glu Leu Cys Ser Ala Ala Ile Thr Met Ser
        115                 120                 125

gat aac act gcg gcc aac tta ctt ctg aca acg atc gga gga ccg aag       432
Asp Asn Thr Ala Ala Asn Leu Leu Leu Thr Thr Ile Gly Gly Pro Lys
    130                 135                 140

gag cta acc gct ttt ttg cac aac atg ggg gat cat gta act cgc ctt       480
Glu Leu Thr Ala Phe Leu His Asn Met Gly Asp His Val Thr Arg Leu
145                 150                 155                 160

gat cgt tgg gaa ccg gag ctg aat gaa gcc ata cca aac gac gag cgt       528
Asp Arg Trp Glu Pro Glu Leu Asn Glu Ala Ile Pro Asn Asp Glu Arg
                165                 170                 175

gac acc acg atg cct gca gca atg gca aca acg ttg cgc aaa cta tta       576
Asp Thr Thr Met Pro Ala Ala Met Ala Thr Thr Leu Arg Lys Leu Leu
            180                 185                 190

act ggc gaa cta ctt act cta gct tcc cgg caa caa tta ata gac tgg       624
```

-continued

```
Thr Gly Glu Leu Leu Thr Leu Ala Ser Arg Gln Gln Leu Ile Asp Trp
        195                 200                 205

atg gag gcg gat aaa gtt gca gga cca ctt ctg cgc tcg gcc ctt ccg      672
Met Glu Ala Asp Lys Val Ala Gly Pro Leu Leu Arg Ser Ala Leu Pro
    210                 215                 220

gct ggc tgg ttt att gct gat aaa tct gga gcc ggt gag cgt ggg tct      720
Ala Gly Trp Phe Ile Ala Asp Lys Ser Gly Ala Gly Glu Arg Gly Ser
225                 230                 235                 240

cgc ggt atc att gca gca ctg ggg cca gat ggt aag ccc tcc cgt atc      768
Arg Gly Ile Ile Ala Ala Leu Gly Pro Asp Gly Lys Pro Ser Arg Ile
                245                 250                 255

gta gtt atc tac acg acg ggg agt cag gca act atg gat gaa cga aat      816
Val Val Ile Tyr Thr Thr Gly Ser Gln Ala Thr Met Asp Glu Arg Asn
            260                 265                 270

aga cag atc gct gag ata ggt gcc tca ctg att aag cat tgg              858
Arg Gln Ile Ala Glu Ile Gly Ala Ser Leu Ile Lys His Trp
        275                 280                 285


<210> SEQ ID NO 5
<211> LENGTH: 795
<212> TYPE: DNA
<213> ORGANISM: Artificial Sequence
<220> FEATURE:
<221> NAME/KEY: CDS
<222> LOCATION: (1)...(795)
<223> OTHER INFORMATION: cloning vector

<400> SEQUENCE: 5

atg ggg cac cca gaa acg ctg gtg aaa gta aaa gat gct gaa gat cag       48
Met Gly His Pro Glu Thr Leu Val Lys Val Lys Asp Ala Glu Asp Gln
 1               5                  10                  15

ttg ggt gca cga gtg ggt tac atc gaa ctg gat ctc aac agc ggt aag       96
Leu Gly Ala Arg Val Gly Tyr Ile Glu Leu Asp Leu Asn Ser Gly Lys
            20                  25                  30

atc ctt gag agt ttt cgc ccc gaa gaa cgt ttt cca atg atg agc act      144
Ile Leu Glu Ser Phe Arg Pro Glu Glu Arg Phe Pro Met Met Ser Thr
        35                  40                  45

ttt aaa gtt ctg cta tgt ggc gcg gta tta tcc cgt gat gac gcc ggg      192
Phe Lys Val Leu Leu Cys Gly Ala Val Leu Ser Arg Asp Asp Ala Gly
    50                  55                  60

caa gag caa ctc ggt cgc cgc ata cac tat tct cag aat gac ttg gtt      240
Gln Glu Gln Leu Gly Arg Arg Ile His Tyr Ser Gln Asn Asp Leu Val
 65                  70                  75                  80

gag tac tca cca gtc aca gaa aag cat ctt acg gat ggc atg aca gta      288
Glu Tyr Ser Pro Val Thr Glu Lys His Leu Thr Asp Gly Met Thr Val
                85                  90                  95

aga gaa tta tgc agt gct gcc ata acc atg agt gat aac act gcg gcc      336
Arg Glu Leu Cys Ser Ala Ala Ile Thr Met Ser Asp Asn Thr Ala Ala
            100                 105                 110

aac tta ctt ctg aca acg atc gga gga ccg aag gag cta acc gct ttt      384
Asn Leu Leu Leu Thr Thr Ile Gly Gly Pro Lys Glu Leu Thr Ala Phe
        115                 120                 125

ttg cac aac atg ggg gat cat gta act cgc ctt gat cat tgg gaa ccg      432
Leu His Asn Met Gly Asp His Val Thr Arg Leu Asp His Trp Glu Pro
    130                 135                 140

gag ctg aat gaa gcc ata cca aac gac gag cgt gac acc acg atg cct      480
Glu Leu Asn Glu Ala Ile Pro Asn Asp Glu Arg Asp Thr Thr Met Pro
145                 150                 155                 160

gta gca atg gca aca acg ttg cgc aaa cta tta act ggc gaa cta ctt      528
Val Ala Met Ala Thr Thr Leu Arg Lys Leu Leu Thr Gly Glu Leu Leu
                165                 170                 175
```

-continued

```
act cta gct tcc cgg caa caa tta ata gac tgg atg gag gcg gat aaa      576
Thr Leu Ala Ser Arg Gln Gln Leu Ile Asp Trp Met Glu Ala Asp Lys
            180                 185                 190

gtt gca gga cca ctt ctg cgc tcg gcc ctt ccg gct ggc tgg ttt att      624
Val Ala Gly Pro Leu Leu Arg Ser Ala Leu Pro Ala Gly Trp Phe Ile
        195                 200                 205

gct gat aaa tct gga gcc ggt gag cgt ggg tct cgc ggt atc att gca      672
Ala Asp Lys Ser Gly Ala Gly Glu Arg Gly Ser Arg Gly Ile Ile Ala
    210                 215                 220

gca ctg ggg cca gat ggt aag ccc tcc cgt atc gta gtt atc tac acg      720
Ala Leu Gly Pro Asp Gly Lys Pro Ser Arg Ile Val Val Ile Tyr Thr
225                 230                 235                 240

acg ggg agt cag gca act atg gat gaa cga aat aga cag atc gct gag      768
Thr Gly Ser Gln Ala Thr Met Asp Glu Arg Asn Arg Gln Ile Ala Glu
                245                 250                 255

ata ggt gcc tca ctg att aag cat tgg                                  795
Ile Gly Ala Ser Leu Ile Lys His Trp
            260                 265
```

<210> SEQ ID NO 6
<211> LENGTH: 792
<212> TYPE: DNA
<213> ORGANISM: Artificial Sequence
<220> FEATURE:
<221> NAME/KEY: CDS
<222> LOCATION: (1)...(792)
<223> OTHER INFORMATION: cloning vector

<400> SEQUENCE: 6

```
atg gac cca gaa acg ctg gtg aaa gta aaa gat gct gaa gat cag ttg       48
Met Asp Pro Glu Thr Leu Val Lys Val Lys Asp Ala Glu Asp Gln Leu
 1               5                  10                  15

ggt gca cga gtg ggt tac atc gaa ctg gat ctc aac agc ggt aag atc       96
Gly Ala Arg Val Gly Tyr Ile Glu Leu Asp Leu Asn Ser Gly Lys Ile
            20                  25                  30

ctt gag agt ttt cgc ccc gaa gaa cgt ttt cca atg atg agc act ttt      144
Leu Glu Ser Phe Arg Pro Glu Glu Arg Phe Pro Met Met Ser Thr Phe
        35                  40                  45

aaa gtt ctg cta tgt ggc gcg gta tta tcc cgt att gac gcc ggg caa      192
Lys Val Leu Leu Cys Gly Ala Val Leu Ser Arg Ile Asp Ala Gly Gln
    50                  55                  60

gag caa ctc ggt cgc cgc ata cac tat tct cag aat gac ttg gtt gag      240
Glu Gln Leu Gly Arg Arg Ile His Tyr Ser Gln Asn Asp Leu Val Glu
 65                  70                  75                  80

tac tca cca gtc aca gaa aag cat ctt acg gat ggc atg aca gta aga      288
Tyr Ser Pro Val Thr Glu Lys His Leu Thr Asp Gly Met Thr Val Arg
                85                  90                  95

gaa tta tgc agt gct gcc ata acc atg agt gat aac act gcg gcc aac      336
Glu Leu Cys Ser Ala Ala Ile Thr Met Ser Asp Asn Thr Ala Ala Asn
            100                 105                 110

tta ctt ctg aca acg atc gga gga ccg aag gag cta acc gct ttt ttg      384
Leu Leu Leu Thr Thr Ile Gly Gly Pro Lys Glu Leu Thr Ala Phe Leu
        115                 120                 125

cac aac atg ggg gat cat gta act cgc ctt gat cat tgg gaa ccg gag      432
His Asn Met Gly Asp His Val Thr Arg Leu Asp His Trp Glu Pro Glu
    130                 135                 140

ctg aat gaa gcc ata cca aac gac gag cgt gac acc acg atg cct gta      480
Leu Asn Glu Ala Ile Pro Asn Asp Glu Arg Asp Thr Thr Met Pro Val
145                 150                 155                 160

gca atg gca aca acg ttg cgc aaa cta tta act ggc gaa cta ctt act      528
Ala Met Ala Thr Thr Leu Arg Lys Leu Leu Thr Gly Glu Leu Leu Thr
                165                 170                 175
```

-continued

```
cta gct tcc cgg caa caa tta ata gac tgg atg gag gcg gat aaa gtt      576
Leu Ala Ser Arg Gln Gln Leu Ile Asp Trp Met Glu Ala Asp Lys Val
            180                 185                 190

gca gga cca ctt ctg cgc tcg gcc ctt ccg gct ggc tgg ttt att gct      624
Ala Gly Pro Leu Leu Arg Ser Ala Leu Pro Ala Gly Trp Phe Ile Ala
        195                 200                 205

gat aaa tct gga gcc ggt gag cgt ggg tct cgc ggt atc att gca gca      672
Asp Lys Ser Gly Ala Gly Glu Arg Gly Ser Arg Gly Ile Ile Ala Ala
    210                 215                 220

ctg ggg cca gat ggt aag ccc tcc cgt atc gta gtt atc tac acg acg      720
Leu Gly Pro Asp Gly Lys Pro Ser Arg Ile Val Val Ile Tyr Thr Thr
225                 230                 235                 240

ggg agt cag gca act atg gat gaa cga aat aga cag atc gct gag ata      768
Gly Ser Gln Ala Thr Met Asp Glu Arg Asn Arg Gln Ile Ala Glu Ile
                245                 250                 255

ggt gcc tca ctg att aag cat tgg                                      792
Gly Ala Ser Leu Ile Lys His Trp
            260


<210> SEQ ID NO 7
<211> LENGTH: 786
<212> TYPE: DNA
<213> ORGANISM: Artificial Sequence
<220> FEATURE:
<221> NAME/KEY: CDS
<222> LOCATION: (1)...(786)
<223> OTHER INFORMATION: cloning vector

<400> SEQUENCE: 7

atg aaa gat gat ttt gca aaa ctt gag gaa caa ttt gat gca aaa ctc       48
Met Lys Asp Asp Phe Ala Lys Leu Glu Glu Gln Phe Asp Ala Lys Leu
 1               5                  10                  15

ggg atc ttt gca ttg gat aca ggt aca aac cgg acg gta gcg tat cgg       96
Gly Ile Phe Ala Leu Asp Thr Gly Thr Asn Arg Thr Val Ala Tyr Arg
            20                  25                  30

ccg gat gag cgt ttt gct ttt gct tcg acg att aag gct tta act gta      144
Pro Asp Glu Arg Phe Ala Phe Ala Ser Thr Ile Lys Ala Leu Thr Val
        35                  40                  45

ggc gtg ctt ttg caa cag aaa tca ata gaa gat ctg aac cag aga ata      192
Gly Val Leu Leu Gln Gln Lys Ser Ile Glu Asp Leu Asn Gln Arg Ile
    50                  55                  60

aca tat aca cgt gat gat ctt gta aac tac aac ccg att acg gaa aag      240
Thr Tyr Thr Arg Asp Asp Leu Val Asn Tyr Asn Pro Ile Thr Glu Lys
 65                  70                  75                  80

cac gtt gat acg gga atg acg ctc aaa gag ctt gcg gat gct tcg ctt      288
His Val Asp Thr Gly Met Thr Leu Lys Glu Leu Ala Asp Ala Ser Leu
                85                  90                  95

cga tat agt gac aat gcg gca cag aat ctc att ctt aaa caa att ggc      336
Arg Tyr Ser Asp Asn Ala Ala Gln Asn Leu Ile Leu Lys Gln Ile Gly
            100                 105                 110

gga cct gaa agt ttg aaa aag gaa ctg agg aag att ggt gat gag gtt      384
Gly Pro Glu Ser Leu Lys Lys Glu Leu Arg Lys Ile Gly Asp Glu Val
        115                 120                 125

aca aat ccc gaa cga ttc gaa cca gag tta aat gaa gtg aat ccg ggt      432
Thr Asn Pro Glu Arg Phe Glu Pro Glu Leu Asn Glu Val Asn Pro Gly
    130                 135                 140

gaa act cag gat acc agt aca gca aga gca ctt gtc aca agc ctt cga      480
Glu Thr Gln Asp Thr Ser Thr Ala Arg Ala Leu Val Thr Ser Leu Arg
145                 150                 155                 160

gcc ttt gct ctt gaa gat aaa ctt cca agt gaa aaa cgc gag ctt tta      528
Ala Phe Ala Leu Glu Asp Lys Leu Pro Ser Glu Lys Arg Glu Leu Leu
```

-continued

```
                165                 170                 175

atc gat tgg atg aaa cga aat acc act gga gac gcc tta atc cgt gcc      576
Ile Asp Trp Met Lys Arg Asn Thr Thr Gly Asp Ala Leu Ile Arg Ala
            180                 185                 190

gga gcg gca tca tat gga acc cgg aat gac att gcc atc att tgg ccg      624
Gly Ala Ala Ser Tyr Gly Thr Arg Asn Asp Ile Ala Ile Ile Trp Pro
        195                 200                 205

cca aaa gga gat cct gtc ggt gtg ccg gac ggt tgg gaa gtg gct gat      672
Pro Lys Gly Asp Pro Val Gly Val Pro Asp Gly Trp Glu Val Ala Asp
    210                 215                 220

aaa act gtt ctt gca gta tta tcc agc agg gat aaa aag gac gcc aag      720
Lys Thr Val Leu Ala Val Leu Ser Ser Arg Asp Lys Lys Asp Ala Lys
225                 230                 235                 240

tat gat gat aaa ctt att gca gag gca aca aag gtg gta atg aaa gcc      768
Tyr Asp Asp Lys Leu Ile Ala Glu Ala Thr Lys Val Val Met Lys Ala
                245                 250                 255

tta aac atg aac ggc aaa                                              786
Leu Asn Met Asn Gly Lys
            260
```

```
<210> SEQ ID NO 8
<211> LENGTH: 720
<212> TYPE: DNA
<213> ORGANISM: Aequorea victoria

<400> SEQUENCE: 8

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccttctccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aacctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720

<210> SEQ ID NO 9
<211> LENGTH: 690
<212> TYPE: DNA
<213> ORGANISM: Anemonia majano

<400> SEQUENCE: 9

atggctcttt caaacaagtt tatcggagat gacatgaaaa tgacctacca tatggatggc     60

tgtgtcaatg ggcattactt taccgtcaaa ggtgaaggca acgggaagcc atacgaaggg    120

acgcagactt cgacttttaa agtcaccatg gccaacggtg ggccccttgc attctccttt    180

gacatactat ctacagtgtt caaatatgga aatcgatgct ttactgcgta tcctaccagt    240

atgcccgact atttcaaaca agcatttcct gacggaatgt catatgaaag gacttttacc    300

tatgaagatg gaggagttgc tacagccagt tgggaaataa gccttaaagg caactgcttt    360

gagcacaaat ccacgtttca tggagtgaac tttcctgctg atggacctgt gatggcgaag    420
```

-continued aagacaactg gttgggaccc atcttttgag aaaatgactg tctgcgatgg aatattgaag 480
ggtgatgtca ccgcgttcct catgctgcaa ggaggtggca attacagatg ccaattccac 540
acttcttaca agacaaaaaa accggtgacg atgccaccaa accatgtggt ggaacatcgc 600
attgcgagga ccgaccttga caaaggtggc aacagtgttc agctgacgga gcacgctgtt 660
gcacatataa cctctgttgt ccctttctga 690

<210> SEQ ID NO 10
<211> LENGTH: 696
<212> TYPE: DNA
<213> ORGANISM: Zoanthus sp.

<400> SEQUENCE: 10
atggctcagt caaagcacgg tctaacaaaa gaaatgacaa tgaaataccg tatggaaggg 60
tgcgtcgatg gacataaatt tgtgatcacg ggagagggca ttggatatcc gttcaaaggg 120
aaacaggcta ttaatctgtg tgtggtcgaa ggtggaccat tgccatttgc cgaagacata 180
ttgtcagctg cctttaacta cggaaacagg gttttcactg aatatcctca agacatagtt 240
gactatttca agaactcgtg tcctgctgga tatacatggg acaggtcttt tctctttgag 300
gatggagcag tttgcatatg taatgcagat ataacagtga gtgttgaaga aaactgcatg 360
tatcatgagt ccaaatttta tggagtgaat tttcctgctg atggacctgt gatgaaaaag 420
atgacagata actgggagcc atcctgcgag aagatcatac cagtacctaa gcaggggata 480
ttgaaagggg atgtctccat gtacctcctt ctgaaggatg gtgggcgttt acggtgccaa 540
ttcgacacag tttacaaagc aaagtctgtg ccaagaaaga tgccggactg gcacttcatc 600
cagcataagc tcacccgtga agaccgcagc gatgctaaga atcagaaatg gcatctgaca 660
gaacatgcta ttgcatccgg atctgcattg ccctga 696

<210> SEQ ID NO 11
<211> LENGTH: 696
<212> TYPE: DNA
<213> ORGANISM: Zoanthus sp.

<400> SEQUENCE: 11
atggctcatt caaagcacgg tctaaaagaa gaaatgacaa tgaaatacca catggaaggg 60
tgcgtcaacg gacataaatt tgtgatcacg ggcgaaggca ttggatatcc gttcaaaggg 120
aaacagacta ttaatctgtg tgtgatcgaa gggggaccat tgccattttc cgaagacata 180
ttgtcagctg gctttaagta cggagacagg attttcactg aatatcctca agacatagta 240
gactatttca agaactcgtg tcctgctgga tatacatggg gcaggtcttt tctctttgag 300
gatggagcag tctgcatatg caatgtagat ataacagtga gtgtcaaaga aaactgcatt 360
tatcataaga gcatatttaa tggaatgaat tttcctgctg atggacctgt gatgaaaaag 420
atgacaacta actgggaagc atcctgcgag aagatcatgc cagtacctaa gcaggggata 480
ctgaaagggg atgtctccat gtacctcctt ctgaaggatg gtgggcgtta ccggtgccag 540
ttcgacacag tttacaaagc aaagtctgtg ccaagtaaga tgccggagtg gcacttcatc 600
cagcataagc tcctccgtga agaccgcagc gatgctaaga atcagaagtg gcagctgaca 660
gagcatgcta ttgcattccc ttctgccttg gcctga 696

<210> SEQ ID NO 12
<211> LENGTH: 699
<212> TYPE: DNA

-continued

<213> ORGANISM: Discosoma striata

<400> SEQUENCE: 12
atgagttgtt ccaagagtgt gatcaaggaa gaaatgttga tcgatcttca tctggaagga 60
acgttcaatg ggcactactt tgaaataaaa ggcaaaggaa aaggacagcc taatgaaggc 120
accaataccg tcacgctcga ggttaccaag ggtggacctc tgccatttgg ttggcatatt 180
ttgtgcccac aatttcagta tggaaacaag gcatttgtcc accaccctga caacatacat 240
gattatctaa agctgtcatt tccggaggga tatacatggg aacggtccat gcactttgaa 300
gacggtggct tgtgttgtat caccaatgat atcagtttga caggcaactg tttctactac 360
gacatcaagt tcactggctt gaactttcct ccaaatggac ccgttgtgca gaagaagaca 420
actggctggg aaccgagcac tgagcgtttg tatcctcgtg atggtgtgtt gataggagac 480
atccatcatg ctctgacagt tgaaggaggt ggtcattacg catgtgacat taaaactgtt 540
tacagggcca agaaggccgc cttgaagatg ccagggtatc actatgttga caccaaactg 600
gttatatgga acaacgacaa agaattcatg aaagttgagg agcatgaaat cgccgttgca 660
cgccaccatc cgttctatga gccaaagaag gataagtaa 699

<210> SEQ ID NO 13
<211> LENGTH: 678
<212> TYPE: DNA
<213> ORGANISM: Discosoma sp.

<400> SEQUENCE: 13
atgaggtctt ccaagaatgt tatcaaggag ttcatgaggt ttaaggttcg catggaagga 60
acggtcaatg ggcacgagtt tgaaatagaa ggcgaaggag aggggaggcc atacgaaggc 120
cacaataccg taaagcttaa ggtaaccaag gggggacctt tgccatttgc ttgggatatt 180
ttgtcaccac aatttcagta tggaagcaag gtatatgtca agcaccctgc cgacatacca 240
gactataaaa agctgtcatt tcctgaagga tttaaatggg aaagggtcat gaactttgaa 300
gacggtggcg tcgttactgt aacccaggat tccagtttgc aggatggctg tttcatctac 360
aaggtcaagt tcattggcgt gaactttcct tccgatggac ctgttatgca aaagaagaca 420
atgggctggg aagccagcac tgagcgtttg tatcctcgtg atggcgtgtt gaaaggagag 480
attcataagg ctctgaagct gaaagacggt ggtcattacc tagttgaatt caaaagtatt 540
tacatggcaa agaagcctgt gcagctacca gggtactact atgttgactc caaactggat 600
ataacaagcc acaacgaaga ctatacaatc gttgagcagt atgaaagaac cgagggacgc 660
caccatctgt tcctttaa 678

<210> SEQ ID NO 14
<211> LENGTH: 801
<212> TYPE: DNA
<213> ORGANISM: Clavularia sp.

<400> SEQUENCE: 14
atgaagtgta aatttgtgtt ctgcctgtcc ttcttggtcc tcgccatcac aaacgcgaac 60 attttttga gaaacgaggc tgacttagaa gagaagacat tgagaatacc aaaagctcta 120
accaccatgg gtgtgattaa accagacatg aagattaagc tgaagatgga aggaaatgta 180
aacgggcatg cttttgtgat cgaaggagaa ggagaaggaa agccttacga tgggacacac 240
actttaaacc tggaagtgaa ggaaggtgcg cctctgcctt tttcttacga tatcttgtca 300
aacgcgttcc agtacggaaa cagagcattg acaaaatacc cagacgatat agcagactat 360

-continued

```
ttcaagcagt cgtttcccga gggatattcc tgggaaagaa ccatgacttt tgaagacaaa    420

ggcattgtca aagtgaaaag tgacataagc atggaggaag actcctttat ctatgaaatt    480

cgttttgatg ggatgaactt tcctcccaat ggtccggtta tgcagaaaaa aactttgaag    540

tgggaaccat ccactgagat tatgtacgtg cgtgatggag tgctggtcgg agatattagc    600

cattctctgt tgctggaggg aggtggccat taccgatgtg acttcaaaag tatttacaaa    660

gcaaaaaaag ttgtcaaatt gccagactat cactttgtgg accatcgcat tgagatcttg    720

aaccatgaca aggattacaa caaagtaacg ctgtatgaga atgcagttgc tcgctattct    780

ttgctgccaa gtcaggccta g                                              801


<210> SEQ ID NO 15
<211> LENGTH: 37
<212> TYPE: DNA
<213> ORGANISM: Artificial Sequence
<220> FEATURE:
<223> OTHER INFORMATION: primer for PCR

<400> SEQUENCE: 15

gatcggtacc accatggaga tcttcgtgaa gactctg                              37


<210> SEQ ID NO 16
<211> LENGTH: 40
<212> TYPE: DNA
<213> ORGANISM: Artificial Sequence
<220> FEATURE:
<223> OTHER INFORMATION: primer for PCR

<400> SEQUENCE: 16

tgcaggatcc gtgcatccca cctctgagac ggagtaccag                           40


<210> SEQ ID NO 17
<211> LENGTH: 228
<212> TYPE: DNA
<213> ORGANISM: Artificial Sequence
<220> FEATURE:
<223> OTHER INFORMATION: UbquitinG76V mutant

<400> SEQUENCE: 17

atggagatct tcgtgaagac tctgactggt aagaccatca ccctcgaagt ggagccgagt     60

gacaccattg agaatgtcaa ggcaaagatc caagacaagg aaggcatccc tcctgaccag    120

cagaggttga tctttgctgg gaaacagctg gaagatggac gcaccctgtc tgactacaac    180

atccagaaag agtccaccct gcacctggta ctccgtctca gaggtgtg                 228


<210> SEQ ID NO 18
<211> LENGTH: 32
<212> TYPE: DNA
<213> ORGANISM: Artificial Sequence
<220> FEATURE:
<223> OTHER INFORMATION: primer for PCR

<400> SEQUENCE: 18

cgagatctac catggaaatc ttcgtgaaga ct                                   32


<210> SEQ ID NO 19
<211> LENGTH: 22
<212> TYPE: DNA
<213> ORGANISM: Artificial Sequence
<220> FEATURE:
<223> OTHER INFORMATION: primer for PCR
```

-continued

<400> SEQUENCE: 19
ggatccgtgg tgcacacctc tg 22

<210> SEQ ID NO 20
<211> LENGTH: 49
<212> TYPE: DNA
<213> ORGANISM: Artificial Sequence
<220> FEATURE:
<223> OTHER INFORMATION: primer for PCR

<400> SEQUENCE: 20
gataggatcc ggggcgtggc tgcacccaga aacgctggtg aaagtaaaa 49

<210> SEQ ID NO 21
<211> LENGTH: 28
<212> TYPE: DNA
<213> ORGANISM: Artificial Sequence
<220> FEATURE:
<223> OTHER INFORMATION: primer for PCR

<400> SEQUENCE: 21
gaactctaga ttaccaatgc ttaatcag 28

<210> SEQ ID NO 22
<211> LENGTH: 6180
<212> TYPE: DNA
<213> ORGANISM: Artificial Sequence
<220> FEATURE:
<223> OTHER INFORMATION: pcDNA3-Bla construct

<400> SEQUENCE: 22
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
gagctcggat ccggggcgtg gctgcaccca gaaacgctgg tgaaagtaaa agatgctgaa 960
gatcagttgg gtgcacgagt gggttacatc gaactggatc tcaacagcgg taagatcctt 1020
gagagttttc gccccgaaga acgttttcca atgatgagca cttttaaagt tctgctatgt 1080
ggcgcggtat tatcccgtat tgacgccggg caagagcaac tcggtcgccg catacactat 1140
tctcagaatg acttggttga gtactcacca gtcacagaaa agcatcttac ggatggcatg 1200
acagtaagag aattatgcag tgctgccata accatgagtg ataacactgc ggccaactta 1260

-continued

```
cttctgacaa cgatcggagg accgaaggag ctaaccgctt ttttgcacaa catgggggat   1320
catgtaactc gccttgatcg ttgggaaccg gagctgaatg aagccatacc aaacgacgag   1380
cgtgacacca cgatgcctgt agcaatggca acaacgttgc gcaaactatt aactggcgaa   1440
ctacttactc tagcttcccg gcaacaatta atagactgga tggaggcgga taaagttgca   1500
ggaccacttc tgcgctcggc ccttccggct ggctggttta ttgctgataa atctggagcc   1560
ggtgagcgtg ggtctcgcgg tatcattgca gcactggggc cagatggtaa gccctcccgt   1620
atcgtagtta tctacacgac ggggagtcag gcaactatgg atgaacgaaa tagacagatc   1680
gctgagatag gtgcctcact gattaagcat tggtaatcta gagggcccta ttctatagtg   1740
tcacctaaat gctagagctc gctgatcagc ctcgactgtg ccttctagtt gccagccatc   1800
tgttgtttgc ccctcccccg tgccttcctt gaccctggaa ggtgccactc ccactgtcct   1860
ttcctaataa aatgaggaaa ttgcatcgca ttgtctgagt aggtgtcatt ctattctggg   1920
gggtggggtg gggcaggaca gcaaggggga ggattgggaa gacaatagca ggcatgctgg   1980
ggatgcggtg ggctctatgg cttctgaggc ggaaagaacc agctggggct ctagggggta   2040
tccccacgcg ccctgtagcg gcgcattaag cgcggcgggt gtggtggtta cgcgcagcgt   2100
gaccgctaca cttgccagcg ccctagcgcc cgctcctttc gctttcttcc cttcctttct   2160
cgccacgttc gccggctttc cccgtcaagc tctaaatcgg ggcatccctt tagggttccg   2220
atttagtgct ttacggcacc tcgaccccaa aaaacttgat tagggtgatg gttcacgtag   2280
tgggccatcg ccctgataga cggtttttcg ccctttgacg ttggagtcca cgttctttaa   2340
tagtggactc ttgttccaaa ctggaacaac actcaaccct atctcggtct attcttttga   2400
tttataaggg attttgggga tttcggccta ttggttaaaa aatgagctga tttaacaaaa   2460
atttaacgcg aattaattct gtggaatgtg tgtcagttag ggtgtggaaa gtccccaggc   2520
tccccaggca ggcagaagta tgcaaagcat gcatctcaat tagtcagcaa ccaggtgtgg   2580
aaagtcccca ggctccccag caggcagaag tatgcaaagc atgcatctca attagtcagc   2640
aaccatagtc ccgcccctaa ctccgcccat cccgccccta actccgccca gttccgccca   2700
ttctccgccc catggctgac taattttttt tatttatgca gaggccgagg ccgcctctgc   2760
ctctgagcta ttccagaagt agtgaggagg cttttttgga ggcctaggct tttgcaaaaa   2820
gctcccggga gcttgtatat ccattttcgg atctgatcaa gagacaggat gaggatcgtt   2880
tcgcatgatt gaacaagatg gattgcacgc aggttctccg gccgcttggg tggagaggct   2940
attcggctat gactgggcac aacagacaat cggctgctct gatgccgccg tgttccggct   3000
gtcagcgcag gggcgcccgg ttctttttgt caagaccgac ctgtccggtg ccctgaatga   3060
actgcaggac gaggcagcgc ggctatcgtg gctggccacg acgggcgttc cttgcgcagc   3120
tgtgctcgac gttgtcactg aagcgggaag ggactggctg ctattgggcg aagtgccggg   3180
gcaggatctc ctgtcatctc accttgctcc tgccgagaaa gtatccatca tggctgatgc   3240
aatgcggcgg ctgcatacgc ttgatccggc tacctgccca ttcgaccacc aagcgaaaca   3300
tcgcatcgag cgagcacgta ctcggatgga agccggtctt gtcgatcagg atgatctgga   3360
cgaagagcat caggggctcg cgccagccga actgttcgcc aggctcaagg cgcgcatgcc   3420
cgacggcgag gatctcgtcg tgacccatgg cgatgcctgc ttgccgaata tcatggtgga   3480
aaatggccgc ttttctggat tcatcgactg tggccggctg ggtgtggcgg accgctatca   3540
ggacatagcg ttggctaccc gtgatattgc tgaagagctt ggcggcgaat gggctgaccg   3600
```

-continued

```
cttcctcgtg ctttacggta tcgccgctcc cgattcgcag cgcatcgcct tctatcgcct   3660
tcttgacgag ttcttctgag cgggactctg gggttcgaaa tgaccgacca agcgacgccc   3720
aacctgccat cacgagattt cgattccacc gccgccttct atgaaaggtt gggcttcgga   3780
atcgttttcc gggacgccgg ctggatgatc ctccagcgcg gggatctcat gctggagttc   3840
ttcgcccacc ccaacttgtt tattgcagct tataatggtt acaaataaag caatagcatc   3900
acaaatttca caaataaagc atttttttca ctgcattcta gttgtggttt gtccaaactc   3960
atcaatgtat cttatcatgt ctgtataccg tcgacctcta gctagagctt ggcgtaatca   4020
tggtcatagc tgtttcctgt gtgaaattgt tatccgctca caattccaca caacatacga   4080
gccggaagca taaagtgtaa agcctggggt gcctaatgag tgagctaact cacattaatt   4140
gcgttgcgct cactgcccgc tttccagtcg ggaaacctgt cgtgccagct gcattaatga   4200
atcggccaac gcgcggggag aggcggtttg cgtattgggc gctcttccgc ttcctcgctc   4260
actgactcgc tgcgctcggt cgttcggctg cggcgagcgg tatcagctca ctcaaaggcg   4320
gtaatacggt tatccacaga atcaggggat aacgcaggaa agaacatgtg agcaaaaggc   4380
cagcaaaagg ccaggaaccg taaaaaggcc gcgttgctgg cgtttttcca taggctccgc   4440
ccccctgacg agcatcacaa aaatcgacgc tcaagtcaga ggtggcgaaa cccgacagga   4500
ctataaagat accaggcgtt tccccctgga agctccctcg tgcgctctcc tgttccgacc   4560
ctgccgctta ccggatacct gtccgccttt ctcccttcgg gaagcgtggc gctttctcaa   4620
tgctcacgct gtaggtatct cagttcggtg taggtcgttc gctccaagct gggctgtgtg   4680
cacgaacccc ccgttcagcc cgaccgctgc gccttatccg gtaactatcg tcttgagtcc   4740
aacccggtaa gacacgactt atcgccactg gcagcagcca ctggtaacag gattagcaga   4800
gcgaggtatg taggcggtgc tacagagttc ttgaagtggt ggcctaacta cggctacact   4860
agaaggacag tatttggtat ctgcgctctg ctgaagccag ttaccttcgg aaaaagagtt   4920
ggtagctctt gatccggcaa acaaaccacc gctggtagcg gtggtttttt tgtttgcaag   4980
cagcagatta cgcgcagaaa aaaaggatct caagaagatc ctttgatctt ttctacgggg   5040
tctgacgctc agtggaacga aaactcacgt taagggattt tggtcatgag attatcaaaa   5100
aggatcttca cctagatcct tttaaattaa aaatgaagtt ttaaatcaat ctaaagtata   5160
tatgagtaaa cttggtctga cagttaccaa tgcttaatca gtgaggcacc tatctcagcg   5220
atctgtctat ttcgttcatc catagttgcc tgactccccg tcgtgtagat aactacgata   5280
cgggagggct taccatctgg ccccagtgct gcaatgatac cgcgagaccc acgctcaccg   5340
gctccagatt tatcagcaat aaaccagcca gccggaaggg ccgagcgcag aagtggtcct   5400
gcaactttat ccgcctccat ccagtctatt aattgttgcc gggaagctag agtaagtagt   5460
tcgccagtta atagtttgcg caacgttgtt gccattgcta caggcatcgt ggtgtcacgc   5520
tcgtcgtttg gtatggcttc attcagctcc ggttcccaac gatcaaggcg agttacatga   5580
tcccccatgt tgtgcaaaaa agcggttagc tccttcggtc ctccgatcgt tgtcagaagt   5640
aagttggccg cagtgttatc actcatggtt atggcagcac tgcataattc tcttactgtc   5700
atgccatccg taagatgctt ttctgtgact ggtgagtact caaccaagtc attctgagaa   5760
tagtgtatgc ggcgaccgag ttgctcttgc ccggcgtcaa tacgggataa taccgcgcca   5820
catagcagaa ctttaaaagt gctcatcatt ggaaaacgtt cttcggggcg aaaactctca   5880
aggatcttac cgctgttgag atccagttcg atgtaaccca ctcgtgcacc caactgatct   5940
tcagcatctt ttactttcac cagcgtttct gggtgagcaa aaacaggaag gcaaaatgcc   6000
```

-continued gcaaaaaagg gaataagggc gacacggaaa tgttgaatac tcatactctt cctttttcaa 6060
tattattgaa gcatttatca gggttattgt ctcatgagcg gatacatatt tgaatgtatt 6120
tagaaaaata aacaaatagg ggttccgcgc acatttcccc gaaaagtgcc acctgacgtc 6180

<210> SEQ ID NO 23
<211> LENGTH: 6411
<212> TYPE: DNA
<213> ORGANISM: Artificial Sequence
<220> FEATURE:
<223> OTHER INFORMATION: pcDNA3-1XUb-Bla construct

<400> SEQUENCE: 23
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
accatggaga tcttcgtgaa gactctgact ggtaagacca tcactctcga agtggagccg 960
agtgacacca ttgagaatgt caaggcaaag atccaagaca aggaaggcat ccctcctgac 1020
cagcagaggt tgatctttgc tgggaaacag ctggaagatg gacgcaccct gtctgactac 1080
aacatccaga aagagtccac cctgcacctg gtactccgtc tcagaggtgt gcaccacgga 1140
tccggggcgt ggctgcaccc agaaacgctg gtgaaagtaa aagatgctga agatcagttg 1200
ggtgcacgag tgggttacat cgaactggat ctcaacagcg gtaagatcct tgagagtttt 1260
cgccccgaag aacgttttcc aatgatgagc acttttaaag ttctgctatg tggcgcggta 1320
ttatcccgta ttgacgccgg gcaagagcaa ctcggtcgcc gcatacacta ttctcagaat 1380
gacttggttg agtactcacc agtcacagaa aagcatctta cggatggcat gacagtaaga 1440
gaattatgca gtgctgccat aaccatgagt gataacactg cggccaactt acttctgaca 1500
acgatcggag gaccgaagga gctaaccgct tttttgcaca acatggggga tcatgtaact 1560
cgccttgatc gttgggaacc ggagctgaat gaagccatac caaacgacga gcgtgacacc 1620
acgatgcctg tagcaatggc aacaacgttg cgcaaactat taactggcga actacttact 1680
ctagcttccc ggcaacaatt aatagactgg atggaggcgg ataaagttgc aggaccactt 1740
ctgcgctcgg cccttccggc tggctggttt attgctgata aatctggagc cggtgagcgt 1800
gggtctcgcg gtatcattgc agcactgggg ccagatggta agccctcccg tatcgtagtt 1860

-continued

```
atctacacga cggggagtca ggcaactatg gatgaacgaa atagacagat cgctgagata   1920
ggtgcctcac tgattaagca ttggtaatct agagggccct attctatagt gtcacctaaa   1980
tgctagagct cgctgatcag cctcgactgt gccttctagt tgccagccat ctgttgtttg   2040
cccctccccc gtgccttcct tgaccctgga aggtgccact cccactgtcc tttcctaata   2100
aaatgaggaa attgcatcgc attgtctgag taggtgtcat tctattctgg ggggtggggt   2160
ggggcaggac agcaaggggg aggattggga agacaatagc aggcatgctg gggatgcggt   2220
gggctctatg gcttctgagg cggaaagaac cagctggggc tctagggggt atccccacgc   2280
gccctgtagc ggcgcattaa gcgcggcggg tgtggtggtt acgcgcagcg tgaccgctac   2340
acttgccagc gccctagcgc ccgctccttt cgctttcttc ccttcctttc tcgccacgtt   2400
cgccggcttt ccccgtcaag ctctaaatcg ggcatccct ttagggttcc gatttagtgc   2460
tttacggcac ctcgacccca aaaaacttga ttagggtgat ggttcacgta gtgggccatc   2520
gccctgatag acggtttttc gccctttgac gttggagtcc acgttcttta atagtggact   2580
cttgttccaa actggaacaa cactcaaccc tatctcggtc tattcttttg atttataagg   2640
gattttgggg atttcggcct attggttaaa aaatgagctg atttaacaaa aatttaacgc   2700
gaattaattc tgtggaatgt gtgtcagtta gggtgtggaa agtccccagg ctccccaggc   2760
aggcagaagt atgcaaagca tgcatctcaa ttagtcagca accaggtgtg gaaagtcccc   2820
aggctcccca gcaggcagaa gtatgcaaag catgcatctc aattagtcag caaccatagt   2880
cccgccccta actccgccca tcccgcccct aactccgccc agttccgccc attctccgcc   2940
ccatggctga ctaatttttt ttatttatgc agaggccgag gccgcctctg cctctgagct   3000
attccagaag tagtgaggag gcttttttgg aggcctaggc ttttgcaaaa agctcccggg   3060
agcttgtata tccattttcg gatctgatca agagacagga tgaggatcgt ttcgcatgat   3120
tgaacaagat ggattgcacg caggttctcc ggccgcttgg gtggagaggc tattcggcta   3180
tgactgggca caacagacaa tcggctgctc tgatgccgcc gtgttccggc tgtcagcgca   3240
ggggcgcccg gttctttttg tcaagaccga cctgtccggt gccctgaatg aactgcagga   3300
cgaggcagcg cggctatcgt ggctggccac gacgggcgtt ccttgcgcag ctgtgctcga   3360
cgttgtcact gaagcgggaa gggactggct gctattgggc gaagtgccgg ggcaggatct   3420
cctgtcatct caccttgctc ctgccgagaa agtatccatc atggctgatg caatgcggcg   3480
gctgcatacg cttgatccgg ctacctgccc attcgaccac caagcgaaac atcgcatcga   3540
gcgagcacgt actcggatgg aagccggtct tgtcgatcag gatgatctgg acgaagagca   3600
tcaggggctc gcgccagccg aactgttcgc caggctcaag gcgcgcatgc ccgacggcga   3660
ggatctcgtc gtgacccatg gcgatgcctg cttgccgaat atcatggtgg aaaatggccg   3720
cttttctgga ttcatcgact gtggccggct gggtgtggcg gaccgctatc aggacatagc   3780
gttggctacc cgtgatattg ctgaagagct tggcggcgaa tgggctgacc gcttcctcgt   3840
gctttacggt atcgccgctc ccgattcgca gcgcatcgcc ttctatcgcc ttcttgacga   3900
gttcttctga gcgggactct ggggttcgaa atgaccgacc aagcgacgcc caacctgcca   3960
tcacgagatt tcgattccac cgccgccttc tatgaaaggt tgggcttcgg aatcgttttc   4020
cgggacgccg gctggatgat cctccagcgc ggggatctca tgctggagtt cttcgcccac   4080
cccaacttgt ttattgcagc ttataatggt tacaaataaa gcaatagcat cacaaatttc   4140
acaaataaag catttttttc actgcattct agttgtggtt tgtccaaact catcaatgta   4200
tcttatcatg tctgtatacc gtcgacctct agctagagct tggcgtaatc atggtcatag   4260
```

-continued ctgtttcctg tgtgaaattg ttatccgctc acaattccac acaacatacg agccggaagc 4320
ataaagtgta aagcctgggg tgcctaatga gtgagctaac tcacattaat tgcgttgcgc 4380
tcactgcccg ctttccagtc gggaaacctg tcgtgccagc tgcattaatg aatcggccaa 4440
cgcgcgggga gaggcggttt gcgtattggg cgctcttccg cttcctcgct cactgactcg 4500
ctgcgctcgg tcgttcggct gcggcgagcg gtatcagctc actcaaaggc ggtaatacgg 4560
ttatccacag aatcagggga taacgcagga aagaacatgt gagcaaaagg ccagcaaaag 4620
gccaggaacc gtaaaaaggc cgcgttgctg gcgtttttcc ataggctccg cccccctgac 4680
gagcatcaca aaaatcgacg ctcaagtcag aggtggcgaa acccgacagg actataaaga 4740
taccaggcgt ttccccctgg aagctccctc gtgcgctctc ctgttccgac cctgccgctt 4800
accggatacc tgtccgcctt tctcccttcg ggaagcgtgg cgctttctca atgctcacgc 4860
tgtaggtatc tcagttcggt gtaggtcgtt cgctccaagc tgggctgtgt gcacgaaccc 4920
cccgttcagc ccgaccgctg cgccttatcc ggtaactatc gtcttgagtc caacccggta 4980
agacacgact tatcgccact ggcagcagcc actggtaaca ggattagcag agcgaggtat 5040
gtaggcggtg ctacagagtt cttgaagtgg tggcctaact acggctacac tagaaggaca 5100
gtatttggta tctgcgctct gctgaagcca gttaccttcg gaaaaagagt tggtagctct 5160
tgatccggca aacaaaccac cgctggtagc ggtggttttt ttgtttgcaa gcagcagatt 5220
acgcgcagaa aaaaaggatc tcaagaagat cctttgatct tttctacggg gtctgacgct 5280
cagtggaacg aaaactcacg ttaagggatt ttggtcatga gattatcaaa aaggatcttc 5340
acctagatcc ttttaaatta aaaatgaagt tttaaatcaa tctaaagtat atatgagtaa 5400
acttggtctg acagttacca atgcttaatc agtgaggcac ctatctcagc gatctgtcta 5460
tttcgttcat ccatagttgc ctgactcccc gtcgtgtaga taactacgat acgggagggc 5520
ttaccatctg gccccagtgc tgcaatgata ccgcgagacc cacgctcacc ggctccagat 5580
ttatcagcaa taaaccagcc agccggaagg gccgagcgca gaagtggtcc tgcaacttta 5640
tccgcctcca tccagtctat taattgttgc cgggaagcta gagtaagtag ttcgccagtt 5700
aatagtttgc gcaacgttgt tgccattgct acaggcatcg tggtgtcacg ctcgtcgttt 5760
ggtatggctt cattcagctc cggttcccaa cgatcaaggc gagttacatg atcccccatg 5820
ttgtgcaaaa aagcggttag ctccttcggt cctccgatcg ttgtcagaag taagttggcc 5880
gcagtgttat cactcatggt tatggcagca ctgcataatt ctcttactgt catgccatcc 5940
gtaagatgct tttctgtgac tggtgagtac tcaaccaagt cattctgaga atagtgtatg 6000
cggcgaccga gttgctcttg cccggcgtca atacgggata ataccgcgcc acatagcaga 6060
actttaaaag tgctcatcat tggaaaacgt tcttcggggc gaaaactctc aaggatctta 6120
ccgctgttga gatccagttc gatgtaaccc actcgtgcac ccaactgatc ttcagcatct 6180
tttactttca ccagcgtttc tgggtgagca aaaacaggaa ggcaaaatgc cgcaaaaaag 6240
ggaataaggg cgacacggaa atgttgaata ctcatactct tcctttttca atattattga 6300
agcatttatc agggttattg tctcatgagc ggatacatat ttgaatgtat ttagaaaaat 6360
aaacaaatag gggttccgcg cacatttccc cgaaaagtgc cacctgacgt c 6411

<210> SEQ ID NO 24
<211> LENGTH: 6678
<212> TYPE: DNA
<213> ORGANISM: Artificial Sequence
<220> FEATURE:

-continued

<223> OTHER INFORMATION: pcDNA3-2XUb-Bla construct

<400> SEQUENCE: 24

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatcc ggggcgtggc tgcacccaga aacgctggtg   1440
aaagtaaaag atgctgaaga tcagttgggt gcacgagtgg gttacatcga actggatctc   1500
aacagcggta agatccttga gagttttcgc cccgaagaac gttttccaat gatgagcact   1560
tttaaagttc tgctatgtgg cgcggtatta tcccgtattg acgccgggca agagcaactc   1620
ggtcgccgca tacactattc tcagaatgac ttggttgagt actcaccagt cacagaaaag   1680
catcttacgg atggcatgac agtaagagaa ttatgcagtg ctgccataac catgagtgat   1740
aacactgcgg ccaacttact tctgacaacg atcggaggac cgaaggagct aaccgctttt   1800
ttgcacaaca tgggggatca tgtaactcgc cttgatcgtt gggaaccgga gctgaatgaa   1860
gccataccaa acgacgagcg tgacaccacg atgcctgtag caatggcaac aacgttgcgc   1920
aaactattaa ctggcgaact acttactcta gcttcccggc aacaattaat agactggatg   1980
gaggcggata aagttgcagg accacttctg cgctcggccc ttccggctgg ctggtttatt   2040
gctgataaat ctggagccgg tgagcgtggg tctcgcggta tcattgcagc actggggcca   2100
gatggtaagc cctcccgtat cgtagttatc tacacgacgg ggagtcaggc aactatggat   2160
gaacgaaata gacagatcgc tgagataggt gcctcactga ttaagcattg gtaatctaga   2220
gggccctatt ctatagtgtc acctaaatgc tagagctcgc tgatcagcct cgactgtgcc   2280
```

-continued

```
ttctagttgc cagccatctg ttgtttgccc ctcccccgtg ccttccttga ccctggaagg   2340
tgccactccc actgtccttt cctaataaaa tgaggaaatt gcatcgcatt gtctgagtag   2400
gtgtcattct attctggggg gtggggtggg gcaggacagc aagggggagg attgggaaga   2460
caatagcagg catgctgggg atgcggtggg ctctatggct tctgaggcgg aaagaaccag   2520
ctggggctct agggggtatc cccacgcgcc ctgtagcggc gcattaagcg cggcgggtgt   2580
ggtggttacg cgcagcgtga ccgctacact tgccagcgcc ctagcgcccg ctcctttcgc   2640
tttcttccct tcctttctcg ccacgttcgc cggctttccc cgtcaagctc taaatcgggg   2700
catcccttta gggttccgat ttagtgcttt acggcacctc gaccccaaaa aacttgatta   2760
gggtgatggt tcacgtagtg ggccatcgcc ctgatagacg gtttttcgcc ctttgacgtt   2820
ggagtccacg ttctttaata gtggactctt gttccaaact ggaacaacac tcaaccctat   2880
ctcggtctat tcttttgatt tataagggat tttggggatt tcggcctatt ggttaaaaaa   2940
tgagctgatt taacaaaaat ttaacgcgaa ttaattctgt ggaatgtgtg tcagttaggg   3000
tgtggaaagt ccccaggctc cccaggcagg cagaagtatg caaagcatgc atctcaatta   3060
gtcagcaacc aggtgtggaa agtccccagg ctccccagca ggcagaagta tgcaaagcat   3120
gcatctcaat tagtcagcaa ccatagtccc gcccctaact ccgcccatcc cgcccctaac   3180
tccgcccagt tccgcccatt ctccgcccca tggctgacta attttttta tttatgcaga   3240
ggccgaggcc gcctctgcct ctgagctatt ccagaagtag tgaggaggct tttttggagg   3300
cctaggcttt tgcaaaaagc tcccgggagc ttgtatatcc attttcggat ctgatcaaga   3360
gacaggatga ggatcgtttc gcatgattga acaagatgga ttgcacgcag gttctccggc   3420
cgcttgggtg gagaggctat tcggctatga ctgggcacaa cagacaatcg gctgctctga   3480
tgccgccgtg ttccggctgt cagcgcaggg gcgcccggtt ctttttgtca agaccgacct   3540
gtccggtgcc ctgaatgaac tgcaggacga ggcagcgcgg ctatcgtggc tggccacgac   3600
gggcgttcct tgcgcagctg tgctcgacgt tgtcactgaa gcgggaaggg actggctgct   3660
attgggcgaa gtgccggggc aggatctcct gtcatctcac cttgctcctg ccgagaaagt   3720
atccatcatg gctgatgcaa tgcggcggct gcatacgctt gatccggcta cctgcccatt   3780
cgaccaccaa gcgaaacatc gcatcgagcg agcacgtact cggatggaag ccggtcttgt   3840
cgatcaggat gatctggacg aagagcatca ggggctcgcg ccagccgaac tgttcgccag   3900
gctcaaggcg cgcatgcccg acggcgagga tctcgtcgtg acccatggcg atgcctgctt   3960
gccgaatatc atggtggaaa atggccgctt ttctggattc atcgactgtg gccggctggg   4020
tgtggcggac cgctatcagg acatagcgtt ggctacccgt gatattgctg aagagcttgg   4080
cggcgaatgg gctgaccgct tcctcgtgct ttacggtatc gccgctcccg attcgcagcg   4140
catcgccttc tatcgccttc ttgacgagtt cttctgagcg ggactctggg gttcgaaatg   4200
accgaccaag cgacgcccaa cctgccatca cgagatttcg attccaccgc cgccttctat   4260
gaaaggttgg gcttcggaat cgttttccgg gacgccggct ggatgatcct ccagcgcggg   4320
gatctcatgc tggagttctt cgcccacccc aacttgttta ttgcagctta taatggttac   4380
aaataaagca atagcatcac aaatttcaca aataaagcat ttttttcact gcattctagt   4440
tgtggtttgt ccaaactcat caatgtatct tatcatgtct gtataccgtc gacctctagc   4500
tagagcttgg cgtaatcatg gtcatagctg tttcctgtgt gaaattgtta tccgctcaca   4560
attccacaca acatacgagc cggaagcata aagtgtaaag cctggggtgc ctaatgagtg   4620
```

-continued

```
agctaactca cattaattgc gttgcgctca ctgcccgctt tccagtcggg aaacctgtcg   4680
tgccagctgc attaatgaat cggccaacgc gcggggagag gcggtttgcg tattgggcgc   4740
tcttccgctt cctcgctcac tgactcgctg cgctcggtcg ttcggctgcg gcgagcggta   4800
tcagctcact caaaggcggt aatacggtta tccacagaat caggggataa cgcaggaaag   4860
aacatgtgag caaaaggcca gcaaaaggcc aggaaccgta aaaaggccgc gttgctggcg   4920
tttttccata ggctccgccc ccctgacgag catcacaaaa atcgacgctc aagtcagagg   4980
tggcgaaacc cgacaggact ataaagatac caggcgtttc cccctggaag ctccctcgtg   5040
cgctctcctg ttccgaccct gccgcttacc ggatacctgt ccgcctttct cccttcggga   5100
agcgtggcgc tttctcaatg ctcacgctgt aggtatctca gttcggtgta ggtcgttcgc   5160
tccaagctgg gctgtgtgca cgaacccccc gttcagcccg accgctgcgc cttatccggt   5220
aactatcgtc ttgagtccaa cccggtaaga cacgacttat cgccactggc agcagccact   5280
ggtaacagga ttagcagagc gaggtatgta ggcggtgcta cagagttctt gaagtggtgg   5340
cctaactacg gctacactag aaggacagta tttggtatct gcgctctgct gaagccagtt   5400
accttcggaa aaagagttgg tagctcttga tccggcaaac aaaccaccgc tggtagcggt   5460
ggtttttttg tttgcaagca gcagattacg cgcagaaaaa aaggatctca agaagatcct   5520
ttgatctttt ctacggggtc tgacgctcag tggaacgaaa actcacgtta agggattttg   5580
gtcatgagat tatcaaaaag gatcttcacc tagatccttt taaattaaaa atgaagtttt   5640
aaatcaatct aaagtatata tgagtaaact tggtctgaca gttaccaatg cttaatcagt   5700
gaggcaccta tctcagcgat ctgtctattt cgttcatcca tagttgcctg actccccgtc   5760
gtgtagataa ctacgatacg ggagggctta ccatctggcc ccagtgctgc aatgataccg   5820
cgagacccac gctcaccggc tccagattta tcagcaataa accagccagc cggaagggcc   5880
gagcgcagaa gtggtcctgc aactttatcc gcctccatcc agtctattaa ttgttgccgg   5940
gaagctagag taagtagttc gccagttaat agtttgcgca acgttgttgc cattgctaca   6000
ggcatcgtgg tgtcacgctc gtcgtttggt atggcttcat tcagctccgg ttcccaacga   6060
tcaaggcgag ttacatgatc ccccatgttg tgcaaaaaag cggttagctc cttcggtcct   6120
ccgatcgttg tcagaagtaa gttggccgca gtgttatcac tcatggttat ggcagcactg   6180
cataattctc ttactgtcat gccatccgta agatgctttt ctgtgactgg tgagtactca   6240
accaagtcat tctgagaata gtgtatgcgg cgaccgagtt gctcttgccc ggcgtcaata   6300
cgggataata ccgcgccaca tagcagaact ttaaaagtgc tcatcattgg aaaacgttct   6360
tcggggcgaa aactctcaag gatcttaccg ctgttgagat ccagttcgat gtaacccact   6420
cgtgcaccca actgatcttc agcatctttt actttcacca gcgtttctgg gtgagcaaaa   6480
acaggaaggc aaaatgccgc aaaaaaggga ataagggcga cacggaaatg ttgaatactc   6540
atactcttcc tttttcaata ttattgaagc atttatcagg gttattgtct catgagcgga   6600
tacatatttg aatgtattta gaaaaataaa caaatagggg ttccgcgcac atttccccga   6660
aaagtgccac ctgacgtc                                                 6678
```

<210> SEQ ID NO 25
<211> LENGTH: 6921
<212> TYPE: DNA
<213> ORGANISM: Artificial Sequence
<220> FEATURE:
<223> OTHER INFORMATION: pcDNA3-3XUb-Bla construct

<400> SEQUENCE: 25

-continued

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccggggcgt ggctgcaccc agaaacgctg   1680
gtgaaagtaa aagatgctga agatcagttg ggtgcacgag tgggttacat cgaactggat   1740
ctcaacagcg gtaagatcct tgagagtttt cgccccgaag aacgttttcc aatgatgagc   1800
acttttaaag ttctgctatg tggcgcggta ttatcccgta ttgacgccgg gcaagagcaa   1860
ctcggtcgcc gcatacacta ttctcagaat gacttggttg agtactcacc agtcacagaa   1920
aagcatctta cggatggcat gacagtaaga gaattatgca gtgctgccat aaccatgagt   1980
gataacactg cggccaactt acttctgaca acgatcggag gaccgaagga gctaaccgct   2040
tttttgcaca acatggggga tcatgtaact cgccttgatc gttgggaacc ggagctgaat   2100
gaagccatac caaacgacga gcgtgacacc acgatgcctg tagcaatggc aacaacgttg   2160
cgcaaactat taactggcga actacttact ctagcttccc ggcaacaatt aatagactgg   2220
atggaggcgg ataaagttgc aggaccactt ctgcgctcgg cccttccggc tggctggttt   2280
attgctgata aatctggagc cggtgagcgt gggtctcgcg gtatcattgc agcactgggg   2340
```

-continued

```
ccagatggta agccctcccg tatcgtagtt atctacacga cggggagtca ggcaactatg   2400
gatgaacgaa atagacagat cgctgagata ggtgcctcac tgattaagca ttggtaatct   2460
agagggccct attctatagt gtcacctaaa tgctagagct cgctgatcag cctcgactgt   2520
gccttctagt tgccagccat ctgttgtttg cccctccccc gtgccttcct tgaccctgga   2580
aggtgccact cccactgtcc tttcctaata aaatgaggaa attgcatcgc attgtctgag   2640
taggtgtcat tctattctgg ggggtggggt ggggcaggac agcaaggggg aggattggga   2700
agacaatagc aggcatgctg gggatgcggt gggctctatg gcttctgagg cggaaagaac   2760
cagctggggc tctagggggt atccccacgc gccctgtagc ggcgcattaa gcgcggcggg   2820
tgtggtggtt acgcgcagcg tgaccgctac acttgccagc gccctagcgc ccgctccttt   2880
cgctttcttc ccttcctttc tcgccacgtt cgccggcttt ccccgtcaag ctctaaatcg   2940
gggcatccct ttagggttcc gatttagtgc tttacggcac ctcgacccca aaaaacttga   3000
ttagggtgat ggttcacgta gtgggccatc gccctgatag acggtttttc gccctttgac   3060
gttggagtcc acgttcttta atagtggact cttgttccaa actggaacaa cactcaaccc   3120
tatctcggtc tattcttttg atttataagg gattttgggg atttcggcct attggttaaa   3180
aaatgagctg atttaacaaa aatttaacgc gaattaattc tgtggaatgt gtgtcagtta   3240
gggtgtggaa agtccccagg ctccccaggc aggcagaagt atgcaaagca tgcatctcaa   3300
ttagtcagca accaggtgtg gaaagtcccc aggctcccca gcaggcagaa gtatgcaaag   3360
catgcatctc aattagtcag caaccatagt cccgccccta actccgccca tcccgcccct   3420
aactccgccc agttccgccc attctccgcc ccatggctga ctaatttttt ttatttatgc   3480
agaggccgag gccgcctctg cctctgagct attccagaag tagtgaggag gcttttttgg   3540
aggcctaggc ttttgcaaaa agctcccggg agcttgtata tccattttcg gatctgatca   3600
agagacagga tgaggatcgt ttcgcatgat tgaacaagat ggattgcacg caggttctcc   3660
ggccgcttgg gtggagaggc tattcggcta tgactgggca caacagacaa tcggctgctc   3720
tgatgccgcc gtgttccggc tgtcagcgca ggggcgcccg gttctttttg tcaagaccga   3780
cctgtccggt gccctgaatg aactgcagga cgaggcagcg cggctatcgt ggctggccac   3840
gacgggcgtt ccttgcgcag ctgtgctcga cgttgtcact gaagcgggaa gggactggct   3900
gctattgggc gaagtgccgg ggcaggatct cctgtcatct caccttgctc ctgccgagaa   3960
agtatccatc atggctgatg caatgcggcg gctgcatacg cttgatccgg ctacctgccc   4020
attcgaccac caagcgaaac atcgcatcga gcgagcacgt actcggatgg aagccggtct   4080
tgtcgatcag gatgatctgg acgaagagca tcaggggctc gcgccagccg aactgttcgc   4140
caggctcaag gcgcgcatgc ccgacggcga ggatctcgtc gtgacccatg gcgatgcctg   4200
cttgccgaat atcatggtgg aaaatggccg cttttctgga ttcatcgact gtggccggct   4260
gggtgtggcg gaccgctatc aggacatagc gttggctacc cgtgatattg ctgaagagct   4320
tggcggcgaa tgggctgacc gcttcctcgt gctttacggt atcgccgctc ccgattcgca   4380
gcgcatcgcc ttctatcgcc ttcttgacga gttcttctga gcgggactct ggggttcgaa   4440
atgaccgacc aagcgacgcc caacctgcca tcacgagatt tcgattccac cgccgccttc   4500
tatgaaaggt tgggcttcgg aatcgttttc cgggacgccg gctggatgat cctccagcgc   4560
ggggatctca tgctggagtt cttcgcccac cccaacttgt ttattgcagc ttataatggt   4620
tacaaataaa gcaatagcat cacaaatttc acaaataaag catttttttc actgcattct   4680
agttgtggtt tgtccaaact catcaatgta tcttatcatg tctgtatacc gtcgacctct   4740
```

-continued

```
agctagagct tggcgtaatc atggtcatag ctgtttcctg tgtgaaattg ttatccgctc   4800
acaattccac acaacatacg agccggaagc ataaagtgta aagcctgggg tgcctaatga   4860
gtgagctaac tcacattaat tgcgttgcgc tcactgcccg ctttccagtc gggaaacctg   4920
tcgtgccagc tgcattaatg aatcggccaa cgcgcgggga gaggcggttt gcgtattggg   4980
cgctcttccg cttcctcgct cactgactcg ctgcgctcgg tcgttcggct gcggcgagcg   5040
gtatcagctc actcaaaggc ggtaatacgg ttatccacag aatcagggga taacgcagga   5100
aagaacatgt gagcaaaagg ccagcaaaag gccaggaacc gtaaaaaggc cgcgttgctg   5160
gcgtttttcc ataggctccg cccccctgac gagcatcaca aaaatcgacg ctcaagtcag   5220
aggtggcgaa acccgacagg actataaaga taccaggcgt ttccccctgg aagctccctc   5280
gtgcgctctc ctgttccgac cctgccgctt accggatacc tgtccgcctt tctcccttcg   5340
ggaagcgtgg cgctttctca atgctcacgc tgtaggtatc tcagttcggt gtaggtcgtt   5400
cgctccaagc tgggctgtgt gcacgaaccc cccgttcagc ccgaccgctg cgccttatcc   5460
ggtaactatc gtcttgagtc caacccggta agacacgact tatcgccact ggcagcagcc   5520
actggtaaca ggattagcag agcgaggtat gtaggcggtg ctacagagtt cttgaagtgg   5580
tggcctaact acggctacac tagaaggaca gtatttggta tctgcgctct gctgaagcca   5640
gttaccttcg gaaaaagagt tggtagctct tgatccggca aacaaaccac cgctggtagc   5700
ggtggttttt ttgtttgcaa gcagcagatt acgcgcagaa aaaaaggatc tcaagaagat   5760
cctttgatct tttctacggg gtctgacgct cagtggaacg aaaactcacg ttaagggatt   5820
ttggtcatga gattatcaaa aaggatcttc acctagatcc ttttaaatta aaaatgaagt   5880
tttaaatcaa tctaaagtat atatgagtaa acttggtctg acagttacca atgcttaatc   5940
agtgaggcac ctatctcagc gatctgtcta tttcgttcat ccatagttgc ctgactcccc   6000
gtcgtgtaga taactacgat acgggagggc ttaccatctg gccccagtgc tgcaatgata   6060
ccgcgagacc cacgctcacc ggctccagat ttatcagcaa taaaccagcc agccggaagg   6120
gccgagcgca gaagtggtcc tgcaacttta tccgcctcca tccagtctat taattgttgc   6180
cgggaagcta gagtaagtag ttcgccagtt aatagtttgc gcaacgttgt tgccattgct   6240
acaggcatcg tggtgtcacg ctcgtcgttt ggtatggctt cattcagctc cggttcccaa   6300
cgatcaaggc gagttacatg atcccccatg ttgtgcaaaa aagcggttag ctccttcggt   6360
cctccgatcg ttgtcagaag taagttggcc gcagtgttat cactcatggt tatggcagca   6420
ctgcataatt ctcttactgt catgccatcc gtaagatgct tttctgtgac tggtgagtac   6480
tcaaccaagt cattctgaga atagtgtatg cggcgaccga gttgctcttg cccggcgtca   6540
atacgggata ataccgcgcc acatagcaga actttaaaag tgctcatcat tggaaaacgt   6600
tcttcggggc gaaaactctc aaggatctta ccgctgttga gatccagttc gatgtaaccc   6660
actcgtgcac ccaactgatc ttcagcatct tttactttca ccagcgtttc tgggtgagca   6720
aaaacaggaa ggcaaaatgc cgcaaaaaag ggaataaggg cgacacggaa atgttgaata   6780
ctcatactct tcctttttca atattattga agcatttatc agggttattg tctcatgagc   6840
ggatacatat ttgaatgtat ttagaaaaat aaacaaatag gggttccgcg cacatttccc   6900
cgaaaagtgc cacctgacgt c                                             6921
```

<210> SEQ ID NO 26
<211> LENGTH: 7164
<212> TYPE: DNA

-continued

<213> ORGANISM: Artificial Sequence
<220> FEATURE:
<223> OTHER INFORMATION: pcDNA3-4XUb-Bla construct

<400> SEQUENCE: 26
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgatatc 900
gaattcctgc agcccggggg atctaccatg gaaatcttcg tgaagactct gactggtaag 960
accatcactc tcgaagtgga gccgagtgac accattgaga atgtcaaggc aaagatccaa 1020
gacaaggaag gcatccctcc tgaccagcag aggttgatct ttgctgggaa acagctggaa 1080
gatggacgca ccctgtctga ctacaacatc cagaaagagt ccaccctgca cctggtactc 1140
cgtctcagag gtgtgcacca cggatctacc atggaaatct tcgtgaagac tctgactggt 1200
aagaccatca ctctcgaagt ggagccgagt gacaccattg agaatgtcaa ggcaaagatc 1260
caagacaagg aaggcatccc tcctgaccag cagaggttga tctttgctgg gaaacagctg 1320
gaagatggac gcaccctgtc tgactacaac atccagaaag agtccaccct gcacctggta 1380
ctccgtctca gaggtgtgca ccacggatct accatggaaa tcttcgtgaa gactctgact 1440
ggtaagacca tcactctcga agtggagccg agtgacacca ttgagaatgt caaggcaaag 1500
atccaagaca aggaaggcat ccctcctgac cagcagaggt tgatctttgc tgggaaacag 1560
ctggaagatg gacgcaccct gtctgactac aacatccaga aagagtccac cctgcacctg 1620
gtactccgtc tcagaggtgt gcaccacgga tctaccatgg aaatcttcgt gaagactctg 1680
actggtaaga ccatcactct cgaagtggag ccgagtgaca ccattgagaa tgtcaaggca 1740
aagatccaag acaaggaagg catccctcct gaccagcaga ggttgatctt tgctgggaaa 1800
cagctggaag atggacgcac cctgtctgac tacaacatcc agaaagagtc caccctgcac 1860
ctggtactcc gtctcagagg tgtgcaccac ggatccgggg cgtggctgca cccagaaacg 1920
ctggtgaaag taaaagatgc tgaagatcag ttgggtgcac gagtgggtta catcgaactg 1980
gatctcaaca gcggtaagat ccttgagagt tttcgccccg aagaacgttt tccaatgatg 2040
agcactttta aagttctgct atgtggcgcg gtattatccc gtattgacgc cgggcaagag 2100
caactcggtc gccgcataca ctattctcag aatgacttgg ttgagtactc accagtcaca 2160
gaaaagcatc ttacggatgg catgacagta agagaattat gcagtgctgc cataaccatg 2220

-continued

```
agtgataaca ctgcggccaa cttacttctg acaacgatcg gaggaccgaa ggagctaacc   2280
gctttttttgc acaacatggg ggatcatgta actcgccttg atcgttggga accggagctg   2340
aatgaagcca taccaaacga cgagcgtgac accacgatgc ctgtagcaat ggcaacaacg   2400
ttgcgcaaac tattaactgg cgaactactt actctagctt cccggcaaca attaatagac   2460
tggatggagg cggataaagt tgcaggacca cttctgcgct cggcccttcc ggctggctgg   2520
tttattgctg ataaatctgg agccggtgag cgtgggtctc gcggtatcat tgcagcactg   2580
gggccagatg gtaagccctc ccgtatcgta gttatctaca cgacggggag tcaggcaact   2640
atggatgaac gaaatagaca gatcgctgag ataggtgcct cactgattaa gcattggtaa   2700
tctagagggc cctattctat agtgtcacct aaatgctaga gctcgctgat cagcctcgac   2760
tgtgccttct agttgccagc catctgttgt ttgcccctcc cccgtgcctt ccttgaccct   2820
ggaaggtgcc actcccactg tcctttccta ataaaatgag gaaattgcat cgcattgtct   2880
gagtaggtgt cattctattc tggggggtgg ggtggggcag gacagcaagg gggaggattg   2940
ggaagacaat agcaggcatg ctggggatgc ggtgggctct atggcttctg aggcggaaag   3000
aaccagctgg ggctctaggg ggtatcccca cgcgccctgt agcggcgcat taagcgcggc   3060
gggtgtggtg gttacgcgca gcgtgaccgc tacacttgcc agcgccctag cgcccgctcc   3120
tttcgctttc ttcccttcct ttctcgccac gttcgccggc tttccccgtc aagctctaaa   3180
tcggggcatc cctttagggt tccgatttag tgctttacgg cacctcgacc ccaaaaaact   3240
tgattagggt gatggttcac gtagtgggcc atcgccctga tagacggttt ttcgcccttt   3300
gacgttggag tccacgttct ttaatagtgg actcttgttc caaactggaa caacactcaa   3360
ccctatctcg gtctattctt ttgatttata agggattttg gggatttcgg cctattggtt   3420
aaaaaatgag ctgatttaac aaaaatttaa cgcgaattaa ttctgtggaa tgtgtgtcag   3480
ttagggtgtg gaaagtcccc aggctcccca ggcaggcaga agtatgcaaa gcatgcatct   3540
caattagtca gcaaccaggt gtggaaagtc cccaggctcc ccagcaggca gaagtatgca   3600
aagcatgcat ctcaattagt cagcaaccat agtcccgccc ctaactccgc ccatcccgcc   3660
cctaactccg cccagttccg cccattctcc gccccatggc tgactaattt tttttattta   3720
tgcagaggcc gaggccgcct ctgcctctga gctattccag aagtagtgag gaggcttttt   3780
tggaggccta ggcttttgca aaaagctccc gggagcttgt atatccattt tcggatctga   3840
tcaagagaca ggatgaggat cgtttcgcat gattgaacaa gatggattgc acgcaggttc   3900
tccggccgct tgggtggaga ggctattcgg ctatgactgg gcacaacaga caatcggctg   3960
ctctgatgcc gccgtgttcc ggctgtcagc gcaggggcgc ccggttcttt ttgtcaagac   4020
cgacctgtcc ggtgccctga atgaactgca ggacgaggca gcgcggctat cgtggctggc   4080
cacgacgggc gttccttgcg cagctgtgct cgacgttgtc actgaagcgg gaagggactg   4140
gctgctattg ggcgaagtgc cggggcagga tctcctgtca tctcaccttg ctcctgccga   4200
gaaagtatcc atcatggctg atgcaatgcg gcggctgcat acgcttgatc cggctacctg   4260
cccattcgac caccaagcga aacatcgcat cgagcgagca cgtactcgga tggaagccgg   4320
tcttgtcgat caggatgatc tggacgaaga gcatcagggg ctcgcgccag ccgaactgtt   4380
cgccaggctc aaggcgcgca tgcccgacgg cgaggatctc gtcgtgaccc atggcgatgc   4440
ctgcttgccg aatatcatgg tggaaaatgg ccgcttttct ggattcatcg actgtggccg   4500
gctgggtgtg gcggaccgct atcaggacat agcgttggct acccgtgata ttgctgaaga   4560
```

-continued gcttggcggc gaatgggctg accgcttcct cgtgctttac ggtatcgccg ctcccgattc 4620
gcagcgcatc gccttctatc gccttcttga cgagttcttc tgagcgggac tctggggttc 4680
gaaatgaccg accaagcgac gcccaacctg ccatcacgag atttcgattc caccgccgcc 4740
ttctatgaaa ggttgggctt cggaatcgtt ttccgggacg ccggctggat gatcctccag 4800
cgcggggatc tcatgctgga gttcttcgcc caccccaact tgtttattgc agcttataat 4860
ggttacaaat aaagcaatag catcacaaat ttcacaaata aagcattttt ttcactgcat 4920
tctagttgtg gtttgtccaa actcatcaat gtatcttatc atgtctgtat accgtcgacc 4980
tctagctaga gcttggcgta atcatggtca tagctgtttc ctgtgtgaaa ttgttatccg 5040
ctcacaattc cacacaacat acgagccgga agcataaagt gtaaagcctg gggtgcctaa 5100
tgagtgagct aactcacatt aattgcgttg cgctcactgc ccgctttcca gtcgggaaac 5160
ctgtcgtgcc agctgcatta atgaatcggc caacgcgcgg ggagaggcgg tttgcgtatt 5220
gggcgctctt ccgcttcctc gctcactgac tcgctgcgct cggtcgttcg gctgcggcga 5280
gcggtatcag ctcactcaaa ggcggtaata cggttatcca cagaatcagg ggataacgca 5340
ggaaagaaca tgtgagcaaa aggccagcaa aaggccagga accgtaaaaa ggccgcgttg 5400
ctggcgtttt tccataggct ccgcccccct gacgagcatc acaaaaatcg acgctcaagt 5460
cagaggtggc gaaacccgac aggactataa agataccagg cgtttccccc tggaagctcc 5520
ctcgtgcgct ctcctgttcc gaccctgccg cttaccggat acctgtccgc ctttctccct 5580
tcgggaagcg tggcgctttc tcaatgctca cgctgtaggt atctcagttc ggtgtaggtc 5640
gttcgctcca agctgggctg tgtgcacgaa ccccccgttc agcccgaccg ctgcgcctta 5700
tccggtaact atcgtcttga gtccaacccg gtaagacacg acttatcgcc actggcagca 5760
gccactggta acaggattag cagagcgagg tatgtaggcg gtgctacaga gttcttgaag 5820
tggtggccta actacggcta cactagaagg acagtatttg gtatctgcgc tctgctgaag 5880
ccagttacct tcggaaaaag agttggtagc tcttgatccg gcaaacaaac caccgctggt 5940
agcggtggtt tttttgtttg caagcagcag attacgcgca gaaaaaaagg atctcaagaa 6000
gatcctttga tcttttctac ggggtctgac gctcagtgga acgaaaactc acgttaaggg 6060
attttggtca tgagattatc aaaaaggatc ttcacctaga tccttttaaa ttaaaaatga 6120
agttttaaat caatctaaag tatatatgag taaacttggt ctgacagtta ccaatgctta 6180
atcagtgagg cacctatctc agcgatctgt ctatttcgtt catccatagt tgcctgactc 6240
cccgtcgtgt agataactac gatacgggag ggcttaccat ctggccccag tgctgcaatg 6300
ataccgcgag acccacgctc accggctcca gatttatcag caataaacca gccagccgga 6360
agggccgagc gcagaagtgg tcctgcaact ttatccgcct ccatccagtc tattaattgt 6420
tgccgggaag ctagagtaag tagttcgcca gttaatagtt tgcgcaacgt tgttgccatt 6480
gctacaggca tcgtggtgtc acgctcgtcg tttggtatgg cttcattcag ctccggttcc 6540
caacgatcaa ggcgagttac atgatccccc atgttgtgca aaaaagcggt tagctccttc 6600
ggtcctccga tcgttgtcag aagtaagttg gccgcagtgt tatcactcat ggttatggca 6660
gcactgcata attctcttac tgtcatgcca tccgtaagat gcttttctgt gactggtgag 6720
tactcaacca agtcattctg agaatagtgt atgcggcgac cgagttgctc ttgcccggcg 6780
tcaatacggg ataataccgc gccacatagc agaactttaa aagtgctcat cattggaaaa 6840
cgttcttcgg ggcgaaaact ctcaaggatc ttaccgctgt tgagatccag ttcgatgtaa 6900
cccactcgtg cacccaactg atcttcagca tcttttactt tcaccagcgt ttctgggtga 6960

-continued gcaaaaacag gaaggcaaaa tgccgcaaaa aagggaataa gggcgacacg gaaatgttga 7020
atactcatac tcttcctttt tcaatattat tgaagcattt atcagggtta ttgtctcatg 7080
agcggataca tatttgaatg tatttagaaa aataaacaaa taggggttcc gcgcacattt 7140
ccccgaaaag tgccacctga cgtc 7164

<210> SEQ ID NO 27
<211> LENGTH: 6411
<212> TYPE: DNA
<213> ORGANISM: Artificial Sequence
<220> FEATURE:
<223> OTHER INFORMATION: pcDNA3-Ub-Met-Bla construct

<400> SEQUENCE: 27
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
accatggaga tcttcgtgaa gactctgact ggtaagacca tcactctcga agtggagccg 960
agtgacacca ttgagaatgt caaggcaaag atccaagaca aggaaggcat ccctcctgac 1020
cagcagaggt tgatctttgc tgggaaacag ctggaagatg gacgcaccct gtctgactac 1080
aacatccaga aagagtccac cctgcacctg gtactccgtc tcagaggtgg gatgcacgga 1140
tccggggcgt ggctgcaccc agaaacgctg gtgaaagtaa aagatgctga agatcagttg 1200
ggtgcacgag tgggttacat cgaactggat ctcaacagcg gtaagatcct tgagagtttt 1260
cgccccgaag aacgttttcc aatgatgagc acttttaaag ttctgctatg tggcgcggta 1320
ttatcccgta ttgacgccgg gcaagagcaa ctcggtcgcc gcatacacta ttctcagaat 1380
gacttggttg agtactcacc agtcacagaa aagcatctta cggatggcat gacagtaaga 1440
gaattatgca gtgctgccat aaccatgagt gataacactg cggccaactt acttctgaca 1500
acgatcggag gaccgaagga gctaaccgct tttttgcaca acatggggga tcatgtaact 1560
cgccttgatc gttgggaacc ggagctgaat gaagccatac caaacgacga gcgtgacacc 1620
acgatgcctg tagcaatggc aacaacgttg cgcaaactat taactggcga actacttact 1680
ctagcttccc ggcaacaatt aatagactgg atggaggcgg ataaagttgc aggaccactt 1740
ctgcgctcgg cccttccggc tggctggttt attgctgata aatctggagc cggtgagcgt 1800

-continued

```
gggtctcgcg gtatcattgc agcactgggg ccagatggta agccctcccg tatcgtagtt   1860
atctacacga cggggagtca ggcaactatg gatgaacgaa atagacagat cgctgagata   1920
ggtgcctcac tgattaagca ttggtaatct agagggccct attctatagt gtcacctaaa   1980
tgctagagct cgctgatcag cctcgactgt gccttctagt tgccagccat ctgttgtttg   2040
cccctccccc gtgccttcct tgaccctgga aggtgccact cccactgtcc tttcctaata   2100
aaatgaggaa attgcatcgc attgtctgag taggtgtcat tctattctgg ggggtggggt   2160
ggggcaggac agcaaggggg aggattggga agacaatagc aggcatgctg gggatgcggt   2220
gggctctatg gcttctgagg cggaaagaac cagctggggc tctagggggt atccccacgc   2280
gccctgtagc ggcgcattaa gcgcggcggg tgtggtggtt acgcgcagcg tgaccgctac   2340
acttgccagc gccctagcgc ccgctccttt cgctttcttc ccttcctttc tcgccacgtt   2400
cgccggcttt ccccgtcaag ctctaaatcg gggcatccct ttagggttcc gatttagtgc   2460
tttacggcac ctcgacccca aaaaacttga ttagggtgat ggttcacgta gtgggccatc   2520
gccctgatag acggtttttc gccctttgac gttggagtcc acgttcttta atagtggact   2580
cttgttccaa actggaacaa cactcaaccc tatctcggtc tattcttttg atttataagg   2640
gattttgggg atttcggcct attggttaaa aaatgagctg atttaacaaa aatttaacgc   2700
gaattaattc tgtggaatgt gtgtcagtta gggtgtggaa agtccccagg ctccccaggc   2760
aggcagaagt atgcaaagca tgcatctcaa ttagtcagca accaggtgtg gaaagtcccc   2820
aggctcccca gcaggcagaa gtatgcaaag catgcatctc aattagtcag caaccatagt   2880
cccgccccta actccgccca tcccgcccct aactccgccc agttccgccc attctccgcc   2940
ccatggctga ctaatttttt ttatttatgc agaggccgag gccgcctctg cctctgagct   3000
attccagaag tagtgaggag gcttttttgg aggcctaggc ttttgcaaaa agctcccggg   3060
agcttgtata tccattttcg gatctgatca agagacagga tgaggatcgt ttcgcatgat   3120
tgaacaagat ggattgcacg caggttctcc ggccgcttgg gtggagaggc tattcggcta   3180
tgactgggca caacagacaa tcggctgctc tgatgccgcc gtgttccggc tgtcagcgca   3240
ggggcgcccg gttctttttg tcaagaccga cctgtccggt gccctgaatg aactgcagga   3300
cgaggcagcg cggctatcgt ggctggccac gacgggcgtt ccttgcgcag ctgtgctcga   3360
cgttgtcact gaagcgggaa gggactggct gctattgggc gaagtgccgg ggcaggatct   3420
cctgtcatct caccttgctc ctgccgagaa agtatccatc atggctgatg caatgcggcg   3480
gctgcatacg cttgatccgg ctacctgccc attcgaccac caagcgaaac atcgcatcga   3540
gcgagcacgt actcggatgg aagccggtct tgtcgatcag gatgatctgg acgaagagca   3600
tcaggggctc gcgccagccg aactgttcgc caggctcaag gcgcgcatgc ccgacggcga   3660
ggatctcgtc gtgacccatg gcgatgcctg cttgccgaat atcatggtgg aaaatggccg   3720
cttttctgga ttcatcgact gtggccggct gggtgtggcg gaccgctatc aggacatagc   3780
gttggctacc cgtgatattg ctgaagagct tggcggcgaa tgggctgacc gcttcctcgt   3840
gctttacggt atcgccgctc ccgattcgca gcgcatcgcc ttctatcgcc ttcttgacga   3900
gttcttctga gcgggactct ggggttcgaa atgaccgacc aagcgacgcc caacctgcca   3960
tcacgagatt tcgattccac cgccgccttc tatgaaaggt tgggcttcgg aatcgttttc   4020
cgggacgccg gctggatgat cctccagcgc ggggatctca tgctggagtt cttcgcccac   4080
cccaacttgt ttattgcagc ttataatggt tacaaataaa gcaatagcat cacaaatttc   4140
acaaataaag cattttttttc actgcattct agttgtggtt tgtccaaact catcaatgta   4200
```

-continued

```
tcttatcatg tctgtatacc gtcgacctct agctagagct tggcgtaatc atggtcatag   4260
ctgtttcctg tgtgaaattg ttatccgctc acaattccac acaacatacg agccggaagc   4320
ataaagtgta aagcctgggg tgcctaatga gtgagctaac tcacattaat tgcgttgcgc   4380
tcactgcccg ctttccagtc gggaaacctg tcgtgccagc tgcattaatg aatcggccaa   4440
cgcgcgggga gaggcggttt gcgtattggg cgctcttccg cttcctcgct cactgactcg   4500
ctgcgctcgg tcgttcggct gcggcgagcg gtatcagctc actcaaaggc ggtaatacgg   4560
ttatccacag aatcagggga taacgcagga aagaacatgt gagcaaaagg ccagcaaaag   4620
gccaggaacc gtaaaaaggc cgcgttgctg gcgtttttcc ataggctccg cccccctgac   4680
gagcatcaca aaaatcgacg ctcaagtcag aggtggcgaa acccgacagg actataaaga   4740
taccaggcgt ttccccctgg aagctccctc gtgcgctctc ctgttccgac cctgccgctt   4800
accggatacc tgtccgcctt tctcccttcg ggaagcgtgg cgctttctca atgctcacgc   4860
tgtaggtatc tcagttcggt gtaggtcgtt cgctccaagc tgggctgtgt gcacgaaccc   4920
cccgttcagc ccgaccgctg cgccttatcc ggtaactatc gtcttgagtc caacccggta   4980
agacacgact tatcgccact ggcagcagcc actggtaaca ggattagcag agcgaggtat   5040
gtaggcggtg ctacagagtt cttgaagtgg tggcctaact acggctacac tagaaggaca   5100
gtatttggta tctgcgctct gctgaagcca gttaccttcg gaaaaagagt tggtagctct   5160
tgatccggca aacaaaccac cgctggtagc ggtggttttt ttgtttgcaa gcagcagatt   5220
acgcgcagaa aaaaaggatc tcaagaagat cctttgatct tttctacggg gtctgacgct   5280
cagtggaacg aaaactcacg ttaagggatt ttggtcatga gattatcaaa aaggatcttc   5340
acctagatcc ttttaaatta aaaatgaagt tttaaatcaa tctaaagtat atatgagtaa   5400
acttggtctg acagttacca atgcttaatc agtgaggcac ctatctcagc gatctgtcta   5460
tttcgttcat ccatagttgc ctgactcccc gtcgtgtaga taactacgat acgggagggc   5520
ttaccatctg gccccagtgc tgcaatgata ccgcgagacc cacgctcacc ggctccagat   5580
ttatcagcaa taaaccagcc agccggaagg gccgagcgca gaagtggtcc tgcaacttta   5640
tccgcctcca tccagtctat taattgttgc cgggaagcta gagtaagtag ttcgccagtt   5700
aatagtttgc gcaacgttgt tgccattgct acaggcatcg tggtgtcacg ctcgtcgttt   5760
ggtatggctt cattcagctc cggttcccaa cgatcaaggc gagttacatg atcccccatg   5820
ttgtgcaaaa aagcggttag ctccttcggt cctccgatcg ttgtcagaag taagttggcc   5880
gcagtgttat cactcatggt tatggcagca ctgcataatt ctcttactgt catgccatcc   5940
gtaagatgct tttctgtgac tggtgagtac tcaaccaagt cattctgaga atagtgtatg   6000
cggcgaccga gttgctcttg cccggcgtca atacgggata ataccgcgcc acatagcaga   6060
actttaaaag tgctcatcat tggaaaacgt tcttcggggc gaaaactctc aaggatctta   6120
ccgctgttga gatccagttc gatgtaaccc actcgtgcac ccaactgatc ttcagcatct   6180
tttactttca ccagcgtttc tgggtgagca aaaacaggaa ggcaaaatgc cgcaaaaaag   6240
ggaataaggg cgacacggaa atgttgaata ctcatactct tcctttttca atattattga   6300
agcatttatc agggttattg tctcatgagc ggatacatat ttgaatgtat ttagaaaaat   6360
aaacaaatag gggttccgcg cacatttccc cgaaaagtgc cacctgacgt c            6411
```

<210> SEQ ID NO 28
<211> LENGTH: 720
<212> TYPE: DNA

-continued

<213> ORGANISM: Artificial Sequence
<220> FEATURE:
<223> OTHER INFORMATION: green fluorescent protein mutant Emerald

<400> SEQUENCE: 28
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccttcaccta cggcgtgcag tgcttcgccc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaag gtctatatca ccgccgacaa gcagaagaac 480
ggcatcaagg tgaacttcaa gacccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 29
<211> LENGTH: 24
<212> TYPE: DNA
<213> ORGANISM: Artificial Sequence
<220> FEATURE:
<223> OTHER INFORMATION: oligonucleotide for PCR

<400> SEQUENCE: 29
ggatccgaat tcgccaccat ggtg 24

<210> SEQ ID NO 30
<211> LENGTH: 30
<212> TYPE: DNA
<213> ORGANISM: Artificial Sequence
<220> FEATURE:
<223> OTHER INFORMATION: oligonucleotide for PCR

<400> SEQUENCE: 30
ccggaatcaa agcgcttctc agacttactt 30

<210> SEQ ID NO 31
<211> LENGTH: 6340
<212> TYPE: DNA
<213> ORGANISM: Artificial Sequence
<220> FEATURE:
<223> OTHER INFORMATION: pcDNA3-1XUb-GFP construct

<400> SEQUENCE: 31
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480

-continued

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
accatggaga tcttcgtgaa gactctgact ggtaagacca tcactctcga agtggagccg    960
agtgacacca ttgagaatgt caaggcaaag atccaagaca aggaaggcat ccctcctgac   1020
cagcagaggt tgatctttgc tgggaaacag ctggaagatg gacgcaccct gtctgactac   1080
aacatccaga aagagtccac cctgcacctg gtactccgtc tcagaggtgt gcaccacgga   1140
tccgaattcg ccaccatggt gagcaagggc gaggagctgt tcaccggggt ggtgcccatc   1200
ctggtcgagc tggacggcga cgtaaacggc cacaagttca gcgtgtccgg cgagggcgag   1260
ggcgatgcca cctacggcaa gctgaccctg aagttcatct gcaccaccgg caagctgccc   1320
gtgccctggc ccaccctcgt gaccaccttc acctacggcg tgcagtgctt cgcccgctac   1380
cccgaccaca tgaagcagca cgacttcttc aagtccgcca tgcccgaagg ctacgtccag   1440
gagcgcacca tcttcttcaa ggacgacggc aactacaaga cccgcgccga ggtgaagttc   1500
gagggcgaca ccctggtgaa ccgcatcgag ctgaagggca tcgacttcaa ggaggacggc   1560
aacatcctgg ggcacaagct ggagtacaac tacaacagcc acaaggtcta tatcaccgcc   1620
gacaagcaga agaacggcat caaggtgaac ttcaagaccc gccacaacat cgaggacggc   1680
agcgtgcagc tcgccgacca ctaccagcag aacaccccca tcggcgacgg ccccgtgctg   1740
ctgcccgaca accactacct gagcacccag tccgccctga gcaaagaccc caacgagaag   1800
cgcgatcaca tggtcctgct ggagttcgtg accgccgccg ggatcactct cggcatggac   1860
gagctgtaca agtaagtcta gagggcccta ttctatagtg tcacctaaat gctagagctc   1920
gctgatcagc ctcgactgtg ccttctagtt gccagccatc tgttgtttgc ccctcccccg   1980
tgccttcctt gaccctggaa ggtgccactc ccactgtcct ttcctaataa aatgaggaaa   2040
ttgcatcgca ttgtctgagt aggtgtcatt ctattctggg gggtggggtg gggcaggaca   2100
gcaaggggga ggattgggaa gacaatagca ggcatgctgg ggatgcggtg ggctctatgg   2160
cttctgaggc ggaaagaacc agctggggct ctagggggta tccccacgcg ccctgtagcg   2220
gcgcattaag cgcggcgggt gtggtggtta cgcgcagcgt gaccgctaca cttgccagcg   2280
ccctagcgcc cgctcctttc gctttcttcc cttcctttct cgccacgttc gccggctttc   2340
cccgtcaagc tctaaatcgg ggcatccctt tagggttccg atttagtgct ttacggcacc   2400
tcgaccccaa aaaacttgat tagggtgatg gttcacgtag tgggccatcg ccctgataga   2460
cggtttttcg ccctttgacg ttggagtcca cgttctttaa tagtggactc ttgttccaaa   2520
ctggaacaac actcaaccct atctcggtct attcttttga tttataaggg attttgggga   2580
tttcggccta ttggttaaaa aatgagctga tttaacaaaa atttaacgcg aattaattct   2640
gtggaatgtg tgtcagttag ggtgtggaaa gtccccaggc tccccaggca ggcagaagta   2700
tgcaaagcat gcatctcaat tagtcagcaa ccaggtgtgg aaagtcccca ggctccccag   2760
caggcagaag tatgcaaagc atgcatctca attagtcagc aaccatagtc ccgcccctaa   2820
```

-continued

```
ctccgcccat cccgccccta actccgccca gttccgccca ttctccgccc catggctgac   2880
taattttttt tatttatgca gaggccgagg ccgcctctgc ctctgagcta ttccagaagt   2940
agtgaggagg cttttttgga ggcctaggct tttgcaaaaa gctcccggga gcttgtatat   3000
ccattttcgg atctgatcaa gagacaggat gaggatcgtt tcgcatgatt gaacaagatg   3060
gattgcacgc aggttctccg gccgcttggg tggagaggct attcggctat gactgggcac   3120
aacagacaat cggctgctct gatgccgccg tgttccggct gtcagcgcag gggcgcccgg   3180
ttctttttgt caagaccgac ctgtccggtg ccctgaatga actgcaggac gaggcagcgc   3240
ggctatcgtg gctggccacg acgggcgttc cttgcgcagc tgtgctcgac gttgtcactg   3300
aagcgggaag ggactggctg ctattgggcg aagtgccggg gcaggatctc ctgtcatctc   3360
accttgctcc tgccgagaaa gtatccatca tggctgatgc aatgcggcgg ctgcatacgc   3420
ttgatccggc tacctgccca ttcgaccacc aagcgaaaca tcgcatcgag cgagcacgta   3480
ctcggatgga agccggtctt gtcgatcagg atgatctgga cgaagagcat caggggctcg   3540
cgccagccga actgttcgcc aggctcaagg cgcgcatgcc cgacggcgag gatctcgtcg   3600
tgacccatgg cgatgcctgc ttgccgaata tcatggtgga aaatggccgc ttttctggat   3660
tcatcgactg tggccggctg ggtgtggcgg accgctatca ggacatagcg ttggctaccc   3720
gtgatattgc tgaagagctt ggcggcgaat gggctgaccg cttcctcgtg ctttacggta   3780
tcgccgctcc cgattcgcag cgcatcgcct tctatcgcct tcttgacgag ttcttctgag   3840
cgggactctg gggttcgaaa tgaccgacca agcgacgccc aacctgccat cacgagattt   3900
cgattccacc gccgccttct atgaaaggtt gggcttcgga atcgttttcc gggacgccgg   3960
ctggatgatc ctccagcgcg gggatctcat gctggagttc ttcgcccacc ccaacttgtt   4020
tattgcagct tataatggtt acaaataaag caatagcatc acaaatttca caaataaagc   4080
atttttttca ctgcattcta gttgtggttt gtccaaactc atcaatgtat cttatcatgt   4140
ctgtataccg tcgacctcta gctagagctt ggcgtaatca tggtcatagc tgtttcctgt   4200
gtgaaattgt tatccgctca caattccaca caacatacga gccggaagca taaagtgtaa   4260
agcctggggt gcctaatgag tgagctaact cacattaatt gcgttgcgct cactgcccgc   4320
tttccagtcg ggaaacctgt cgtgccagct gcattaatga atcggccaac gcgcggggag   4380
aggcggtttg cgtattgggc gctcttccgc ttcctcgctc actgactcgc tgcgctcggt   4440
cgttcggctg cggcgagcgg tatcagctca ctcaaaggcg gtaatacggt tatccacaga   4500
atcaggggat aacgcaggaa agaacatgtg agcaaaaggc cagcaaaagg ccaggaaccg   4560
taaaaaggcc gcgttgctgg cgtttttcca taggctccgc ccccctgacg agcatcacaa   4620
aaatcgacgc tcaagtcaga ggtggcgaaa cccgacagga ctataaagat accaggcgtt   4680
tccccctgga agctccctcg tgcgctctcc tgttccgacc ctgccgctta ccggatacct   4740
gtccgccttt ctcccttcgg gaagcgtggc gctttctcaa tgctcacgct gtaggtatct   4800
cagttcggtg taggtcgttc gctccaagct gggctgtgtg cacgaacccc ccgttcagcc   4860
cgaccgctgc gccttatccg gtaactatcg tcttgagtcc aacccggtaa gacacgactt   4920
atcgccactg gcagcagcca ctggtaacag gattagcaga gcgaggtatg taggcggtgc   4980
tacagagttc ttgaagtggt ggcctaacta cggctacact agaaggacag tatttggtat   5040
ctgcgctctg ctgaagccag ttaccttcgg aaaaagagtt ggtagctctt gatccggcaa   5100
acaaaccacc gctggtagcg gtggtttttt tgtttgcaag cagcagatta cgcgcagaaa   5160
aaaaggatct caagaagatc tttgatcttt tctacggggt ctgacgctc agtggaacga   5220
```

-continued aaactcacgt taagggattt tggtcatgag attatcaaaa aggatcttca cctagatcct 5280
tttaaattaa aaatgaagtt ttaaatcaat ctaaagtata tatgagtaaa cttggtctga 5340
cagttaccaa tgcttaatca gtgaggcacc tatctcagcg atctgtctat ttcgttcatc 5400
catagttgcc tgactccccg tcgtgtagat aactacgata cgggagggct taccatctgg 5460
ccccagtgct gcaatgatac cgcgagaccc acgctcaccg gctccagatt tatcagcaat 5520
aaaccagcca gccggaaggg ccgagcgcag aagtggtcct gcaactttat ccgcctccat 5580
ccagtctatt aattgttgcc gggaagctag agtaagtagt tcgccagtta atagtttgcg 5640
caacgttgtt gccattgcta caggcatcgt ggtgtcacgc tcgtcgtttg gtatggcttc 5700
attcagctcc ggttcccaac gatcaaggcg agttacatga tcccccatgt tgtgcaaaaa 5760
agcggttagc tccttcggtc ctccgatcgt tgtcagaagt aagttggccg cagtgttatc 5820
actcatggtt atggcagcac tgcataattc tcttactgtc atgccatccg taagatgctt 5880
ttctgtgact ggtgagtact caaccaagtc attctgagaa tagtgtatgc ggcgaccgag 5940
ttgctcttgc ccggcgtcaa tacgggataa taccgcgcca catagcagaa ctttaaaagt 6000
gctcatcatt ggaaaacgtt cttcggggcg aaaactctca aggatcttac cgctgttgag 6060
atccagttcg atgtaaccca ctcgtgcacc caactgatct tcagcatctt ttactttcac 6120
cagcgtttct gggtgagcaa aaacaggaag gcaaaatgcc gcaaaaaagg gaataagggc 6180
gacacggaaa tgttgaatac tcatactctt cctttttcaa tattattgaa gcatttatca 6240
gggttattgt ctcatgagcg gatacatatt tgaatgtatt tagaaaaata aacaaatagg 6300
ggttccgcgc acatttcccc gaaaagtgcc acctgacgtc 6340

<210> SEQ ID NO 32
<211> LENGTH: 6607
<212> TYPE: DNA
<213> ORGANISM: Artificial Sequence
<220> FEATURE:
<223> OTHER INFORMATION: pcDNA3-2XUb-GFP construct

<400> SEQUENCE: 32
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgatatc 900

-continued

```
gaattcctgc agcccggggg atctaccatg gaaatcttcg tgaagactct gactggtaag    960

accatcactc tcgaagtgga gccgagtgac accattgaga atgtcaaggc aaagatccaa   1020

gacaaggaag gcatccctcc tgaccagcag aggttgatct ttgctgggaa acagctggaa   1080

gatggacgca ccctgtctga ctacaacatc cagaaagagt ccaccctgca cctggtactc   1140

cgtctcagag gtgtgcacca cggatctacc atggaaatct tcgtgaagac tctgactggt   1200

aagaccatca ctctcgaagt ggagccgagt gacaccattg agaatgtcaa ggcaaagatc   1260

caagacaagg aaggcatccc tcctgaccag cagaggttga tctttgctgg gaaacagctg   1320

gaagatggac gcaccctgtc tgactacaac atccagaaag agtccaccct gcacctggta   1380

ctccgtctca gaggtgtgca ccacggatcc gaattcgcca ccatggtgag caagggcgag   1440

gagctgttca ccggggtggt gcccatcctg gtcgagctgg acggcgacgt aaacggccac   1500

aagttcagcg tgtccggcga gggcgagggc gatgccacct acggcaagct gaccctgaag   1560

ttcatctgca ccaccggcaa gctgcccgtg ccctggccca ccctcgtgac caccttcacc   1620

tacggcgtgc agtgcttcgc ccgctacccc gaccacatga agcagcacga cttcttcaag   1680

tccgccatgc ccgaaggcta cgtccaggag cgcaccatct tcttcaagga cgacggcaac   1740

tacaagaccc gcgccgaggt gaagttcgag ggcgacaccc tggtgaaccg catcgagctg   1800

aagggcatcg acttcaagga ggacggcaac atcctggggc acaagctgga gtacaactac   1860

aacagccaca aggtctatat caccgccgac aagcagaaga acggcatcaa ggtgaacttc   1920

aagacccgcc acaacatcga ggacggcagc gtgcagctcg ccgaccacta ccagcagaac   1980

acccccatcg gcgacggccc cgtgctgctg cccgacaacc actacctgag cacccagtcc   2040

gccctgagca aagaccccaa cgagaagcgc gatcacatgg tcctgctgga gttcgtgacc   2100

gccgccggga tcactctcgg catggacgag ctgtacaagt aagtctagag ggccctattc   2160

tatagtgtca cctaaatgct agagctcgct gatcagcctc gactgtgcct tctagttgcc   2220

agccatctgt tgtttgcccc tcccccgtgc cttccttgac cctggaaggt gccactccca   2280

ctgtcctttc ctaataaaat gaggaaattg catcgcattg tctgagtagg tgtcattcta   2340

ttctgggggg tggggtgggg caggacagca agggggagga ttgggaagac aatagcaggc   2400

atgctgggga tgcggtgggc tctatggctt ctgaggcgga aagaaccagc tggggctcta   2460

gggggtatcc ccacgcgccc tgtagcggcg cattaagcgc ggcgggtgtg gtggttacgc   2520

gcagcgtgac cgctacactt gccagcgccc tagcgcccgc tcctttcgct ttcttccctt   2580

cctttctcgc cacgttcgcc ggctttcccc gtcaagctct aaatcggggc atccctttag   2640

ggttccgatt tagtgcttta cggcacctcg accccaaaaa acttgattag ggtgatggtt   2700

cacgtagtgg gccatcgccc tgatagacgg tttttcgccc tttgacgttg gagtccacgt   2760

tctttaatag tggactcttg ttccaaactg gaacaacact caaccctatc tcggtctatt   2820

cttttgattt ataagggatt ttggggattt cggcctattg gttaaaaaat gagctgattt   2880

aacaaaaatt taacgcgaat taattctgtg gaatgtgtgt cagttagggt gtggaaagtc   2940

cccaggctcc ccaggcaggc agaagtatgc aaagcatgca tctcaattag tcagcaacca   3000

ggtgtggaaa gtccccaggc tccccagcag gcagaagtat gcaaagcatg catctcaatt   3060

agtcagcaac catagtcccg cccctaactc cgcccatccc gcccctaact ccgcccagtt   3120

ccgcccattc tccgccccat ggctgactaa ttttttttat ttatgcagag gccgaggccg   3180

cctctgcctc tgagctattc cagaagtagt gaggaggctt ttttggaggc ctaggctttt   3240

gcaaaaagct cccgggagct tgtatatcca ttttcggatc tgatcaagag acaggatgag   3300
```

-continued

```
gatcgtttcg catgattgaa caagatggat tgcacgcagg ttctccggcc gcttgggtgg   3360
agaggctatt cggctatgac tgggcacaac agacaatcgg ctgctctgat gccgccgtgt   3420
tccggctgtc agcgcagggg cgcccggttc tttttgtcaa gaccgacctg tccggtgccc   3480
tgaatgaact gcaggacgag gcagcgcggc tatcgtggct ggccacgacg ggcgttcctt   3540
gcgcagctgt gctcgacgtt gtcactgaag cgggaaggga ctggctgcta ttgggcgaag   3600
tgccggggca ggatctcctg tcatctcacc ttgctcctgc cgagaaagta tccatcatgg   3660
ctgatgcaat gcggcggctg catacgcttg atccggctac ctgcccattc gaccaccaag   3720
cgaaacatcg catcgagcga gcacgtactc ggatggaagc cggtcttgtc gatcaggatg   3780
atctggacga agagcatcag gggctcgcgc cagccgaact gttcgccagg ctcaaggcgc   3840
gcatgcccga cggcgaggat ctcgtcgtga cccatggcga tgcctgcttg ccgaatatca   3900
tggtggaaaa tggccgcttt tctggattca tcgactgtgg ccggctgggt gtggcggacc   3960
gctatcagga catagcgttg gctacccgtg atattgctga agagcttggc ggcgaatggg   4020
ctgaccgctt cctcgtgctt tacggtatcg ccgctcccga ttcgcagcgc atcgccttct   4080
atcgccttct tgacgagttc ttctgagcgg gactctgggg ttcgaaatga ccgaccaagc   4140
gacgcccaac ctgccatcac gagatttcga ttccaccgcc gccttctatg aaaggttggg   4200
cttcggaatc gttttccggg acgccggctg gatgatcctc cagcgcgggg atctcatgct   4260
ggagttcttc gcccacccca acttgtttat tgcagcttat aatggttaca aataaagcaa   4320
tagcatcaca aatttcacaa ataaagcatt tttttcactg cattctagtt gtggtttgtc   4380
caaactcatc aatgtatctt atcatgtctg tataccgtcg acctctagct agagcttggc   4440
gtaatcatgg tcatagctgt ttcctgtgtg aaattgttat ccgctcacaa ttccacacaa   4500
catacgagcc ggaagcataa agtgtaaagc ctggggtgcc taatgagtga gctaactcac   4560
attaattgcg ttgcgctcac tgcccgcttt ccagtcggga aacctgtcgt gccagctgca   4620
ttaatgaatc ggccaacgcg cggggagagg cggtttgcgt attgggcgct cttccgcttc   4680
ctcgctcact gactcgctgc gctcggtcgt tcggctgcgg cgagcggtat cagctcactc   4740
aaaggcggta atacggttat ccacagaatc aggggataac gcaggaaaga acatgtgagc   4800
aaaaggccag caaaaggcca ggaaccgtaa aaaggccgcg ttgctggcgt ttttccatag   4860
gctccgcccc cctgacgagc atcacaaaaa tcgacgctca agtcagaggt ggcgaaaccc   4920
gacaggacta taaagatacc aggcgtttcc ccctggaagc tccctcgtgc gctctcctgt   4980
tccgaccctg ccgcttaccg gatacctgtc cgcctttctc ccttcgggaa gcgtggcgct   5040
ttctcaatgc tcacgctgta ggtatctcag ttcggtgtag gtcgttcgct ccaagctggg   5100
ctgtgtgcac gaaccccccg ttcagcccga ccgctgcgcc ttatccggta actatcgtct   5160
tgagtccaac ccggtaagac acgacttatc gccactggca gcagccactg gtaacaggat   5220
tagcagagcg aggtatgtag gcggtgctac agagttcttg aagtggtggc ctaactacgg   5280
ctacactaga aggacagtat ttggtatctg cgctctgctg aagccagtta ccttcggaaa   5340
aagagttggt agctcttgat ccggcaaaca aaccaccgct ggtagcggtg gtttttttgt   5400
ttgcaagcag cagattacgc gcagaaaaaa aggatctcaa gaagatcctt tgatcttttc   5460
tacggggtct gacgctcagt ggaacgaaaa ctcacgttaa gggattttgg tcatgagatt   5520
atcaaaaagg atcttcacct agatcctttt aaattaaaaa tgaagtttta aatcaatcta   5580
aagtatatat gagtaaactt ggtctgacag ttaccaatgc ttaatcagtg aggcacctat   5640
```

-continued ctcagcgatc tgtctatttc gttcatccat agttgcctga ctccccgtcg tgtagataac 5700
tacgatacgg gagggcttac catctggccc cagtgctgca atgataccgc gagacccacg 5760
ctcaccggct ccagatttat cagcaataaa ccagccagcc ggaagggccg agcgcagaag 5820
tggtcctgca actttatccg cctccatcca gtctattaat tgttgccggg aagctagagt 5880
aagtagttcg ccagttaata gtttgcgcaa cgttgttgcc attgctacag gcatcgtggt 5940
gtcacgctcg tcgtttggta tggcttcatt cagctccggt tcccaacgat caaggcgagt 6000
tacatgatcc cccatgttgt gcaaaaaagc ggttagctcc ttcggtcctc cgatcgttgt 6060
cagaagtaag ttggccgcag tgttatcact catggttatg gcagcactgc ataattctct 6120
tactgtcatg ccatccgtaa gatgcttttc tgtgactggt gagtactcaa ccaagtcatt 6180
ctgagaatag tgtatgcggc gaccgagttg ctcttgcccg gcgtcaatac gggataatac 6240
cgcgccacat agcagaactt taaaagtgct catcattgga aaacgttctt cggggcgaaa 6300
actctcaagg atcttaccgc tgttgagatc cagttcgatg taacccactc gtgcacccaa 6360
ctgatcttca gcatctttta ctttcaccag cgtttctggg tgagcaaaaa caggaaggca 6420
aaatgccgca aaaaagggaa taagggcgac acggaaatgt tgaatactca tactcttcct 6480
ttttcaatat tattgaagca tttatcaggg ttattgtctc atgagcggat acatatttga 6540
atgtatttag aaaaataaac aaataggggt tccgcgcaca tttccccgaa aagtgccacc 6600
tgacgtc 6607

<210> SEQ ID NO 33
<211> LENGTH: 6850
<212> TYPE: DNA
<213> ORGANISM: Artificial Sequence
<220> FEATURE:
<223> OTHER INFORMATION: pcDNA3-3XUb-GFP construct

<400> SEQUENCE: 33
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgatatc 900
gaattcctgc agcccggggg atctaccatg gaaatcttcg tgaagactct gactggtaag 960
accatcactc tcgaagtgga gccgagtgac accattgaga atgtcaaggc aaagatccaa 1020
gacaaggaag gcatccctcc tgaccagcag aggttgatct ttgctgggaa acagctggaa 1080

-continued

```
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccgaattcg ccaccatggt gagcaagggc   1680
gaggagctgt tcaccggggt ggtgcccatc ctggtcgagc tggacggcga cgtaaacggc   1740
cacaagttca gcgtgtccgg cgagggcgag ggcgatgcca cctacggcaa gctgaccctg   1800
aagttcatct gcaccaccgg caagctgccc gtgccctggc ccaccctcgt gaccaccttc   1860
acctacggcg tgcagtgctt cgcccgctac cccgaccaca tgaagcagca cgacttcttc   1920
aagtccgcca tgcccgaagg ctacgtccag gagcgcacca tcttcttcaa ggacgacggc   1980
aactacaaga cccgcgccga ggtgaagttc gagggcgaca ccctggtgaa ccgcatcgag   2040
ctgaagggca tcgacttcaa ggaggacggc aacatcctgg ggcacaagct ggagtacaac   2100
tacaacagcc acaaggtcta tatcaccgcc gacaagcaga agaacggcat caaggtgaac   2160
ttcaagaccc gccacaacat cgaggacggc agcgtgcagc tcgccgacca ctaccagcag   2220
aacaccccca tcggcgacgg ccccgtgctg ctgcccgaca accactacct gagcacccag   2280
tccgccctga gcaaagaccc caacgagaag cgcgatcaca tggtcctgct ggagttcgtg   2340
accgccgccg ggatcactct cggcatggac gagctgtaca agtaagtcta gagggcccta   2400
ttctatagtg tcacctaaat gctagagctc gctgatcagc ctcgactgtg ccttctagtt   2460
gccagccatc tgttgtttgc ccctcccccg tgccttcctt gaccctggaa ggtgccactc   2520
ccactgtcct ttcctaataa aatgaggaaa ttgcatcgca ttgtctgagt aggtgtcatt   2580
ctattctggg gggtggggtg gggcaggaca gcaaggggga ggattgggaa gacaatagca   2640
ggcatgctgg ggatgcggtg ggctctatgg cttctgaggc ggaaagaacc agctggggct   2700
ctagggggta tccccacgcg ccctgtagcg gcgcattaag cgcggcgggt gtggtggtta   2760
cgcgcagcgt gaccgctaca cttgccagcg ccctagcgcc cgctcctttc gctttcttcc   2820
cttcctttct cgccacgttc gccggctttc cccgtcaagc tctaaatcgg ggcatccctt   2880
tagggttccg atttagtgct ttacggcacc tcgaccccaa aaaacttgat tagggtgatg   2940
gttcacgtag tgggccatcg ccctgataga cggtttttcg ccctttgacg ttggagtcca   3000
cgttctttaa tagtggactc ttgttccaaa ctggaacaac actcaaccct atctcggtct   3060
attcttttga tttataaggg attttgggga tttcggccta ttggttaaaa aatgagctga   3120
tttaacaaaa atttaacgcg aattaattct gtggaatgtg tgtcagttag ggtgtggaaa   3180
gtccccaggc tccccaggca ggcagaagta tgcaaagcat gcatctcaat tagtcagcaa   3240
ccaggtgtgg aaagtcccca ggctccccag caggcagaag tatgcaaagc atgcatctca   3300
attagtcagc aaccatagtc ccgcccctaa ctccgcccat cccgccccta actccgccca   3360
gttccgccca ttctccgccc catggctgac taattttttt tatttatgca gaggccgagg   3420
```

-continued

```
ccgcctctgc ctctgagcta ttccagaagt agtgaggagg ctttttgga ggcctaggct   3480
tttgcaaaaa gctcccggga gcttgtatat ccattttcgg atctgatcaa gagacaggat   3540
gaggatcgtt tcgcatgatt gaacaagatg gattgcacgc aggttctccg gccgcttggg   3600
tggagaggct attcggctat gactgggcac aacagacaat cggctgctct gatgccgccg   3660
tgttccggct gtcagcgcag gggcgcccgg ttctttttgt caagaccgac ctgtccggtg   3720
ccctgaatga actgcaggac gaggcagcgc ggctatcgtg gctggccacg acgggcgttc   3780
cttgcgcagc tgtgctcgac gttgtcactg aagcgggaag ggactggctg ctattgggcg   3840
aagtgccggg gcaggatctc ctgtcatctc accttgctcc tgccgagaaa gtatccatca   3900
tggctgatgc aatgcggcgg ctgcatacgc ttgatccggc tacctgccca ttcgaccacc   3960
aagcgaaaca tcgcatcgag cgagcacgta ctcggatgga agccggtctt gtcgatcagg   4020
atgatctgga cgaagagcat caggggctcg cgccagccga actgttcgcc aggctcaagg   4080
cgcgcatgcc cgacggcgag gatctcgtcg tgacccatgg cgatgcctgc ttgccgaata   4140
tcatggtgga aaatggccgc ttttctggat tcatcgactg tggccggctg ggtgtggcgg   4200
accgctatca ggacatagcg ttggctaccc gtgatattgc tgaagagctt ggcggcgaat   4260
gggctgaccg cttcctcgtg ctttacggta tcgccgctcc cgattcgcag cgcatcgcct   4320
tctatcgcct tcttgacgag ttcttctgag cgggactctg gggttcgaaa tgaccgacca   4380
agcgacgccc aacctgccat cacgagattt cgattccacc gccgccttct atgaaaggtt   4440
gggcttcgga atcgttttcc gggacgccgg ctggatgatc ctccagcgcg gggatctcat   4500
gctggagttc ttcgcccacc ccaacttgtt tattgcagct tataatggtt acaaataaag   4560
caatagcatc acaaatttca caaataaagc atttttttca ctgcattcta gttgtggttt   4620
gtccaaactc atcaatgtat cttatcatgt ctgtataccg tcgacctcta gctagagctt   4680
ggcgtaatca tggtcatagc tgtttcctgt gtgaaattgt tatccgctca caattccaca   4740
caacatacga gccggaagca taaagtgtaa agcctggggt gcctaatgag tgagctaact   4800
cacattaatt gcgttgcgct cactgcccgc tttccagtcg ggaaacctgt cgtgccagct   4860
gcattaatga atcggccaac gcgcggggag aggcggtttg cgtattgggc gctcttccgc   4920
ttcctcgctc actgactcgc tgcgctcggt cgttcggctg cggcgagcgg tatcagctca   4980
ctcaaaggcg gtaatacggt tatccacaga atcaggggat aacgcaggaa agaacatgtg   5040
agcaaaaggc cagcaaaagg ccaggaaccg taaaaaggcc gcgttgctgg cgtttttcca   5100
taggctccgc ccccctgacg agcatcacaa aaatcgacgc tcaagtcaga ggtggcgaaa   5160
cccgacagga ctataaagat accaggcgtt tccccctgga agctccctcg tgcgctctcc   5220
tgttccgacc ctgccgctta ccggatacct gtccgccttt ctcccttcgg gaagcgtggc   5280
gctttctcaa tgctcacgct gtaggtatct cagttcggtg taggtcgttc gctccaagct   5340
gggctgtgtg cacgaacccc ccgttcagcc cgaccgctgc gccttatccg gtaactatcg   5400
tcttgagtcc aacccggtaa gacacgactt atcgccactg gcagcagcca ctggtaacag   5460
gattagcaga gcgaggtatg taggcggtgc tacagagttc ttgaagtggt ggcctaacta   5520
cggctacact agaaggacag tatttggtat ctgcgctctg ctgaagccag ttaccttcgg   5580
aaaaagagtt ggtagctctt gatccggcaa acaaaccacc gctggtagcg gtggtttttt   5640
tgtttgcaag cagcagatta cgcgcagaaa aaaaggatct caagaagatc ctttgatctt   5700
ttctacgggg tctgacgctc agtggaacga aaactcacgt taagggattt tggtcatgag   5760
attatcaaaa aggatcttca cctagatcct tttaaattaa aaatgaagtt ttaaatcaat   5820
```

-continued

```
ctaaagtata tatgagtaaa cttggtctga cagttaccaa tgcttaatca gtgaggcacc   5880

tatctcagcg atctgtctat ttcgttcatc catagttgcc tgactccccg tcgtgtagat   5940

aactacgata cgggagggct taccatctgg ccccagtgct gcaatgatac cgcgagaccc   6000

acgctcaccg gctccagatt tatcagcaat aaaccagcca gccggaaggg ccgagcgcag   6060

aagtggtcct gcaactttat ccgcctccat ccagtctatt aattgttgcc gggaagctag   6120

agtaagtagt tcgccagtta atagtttgcg caacgttgtt gccattgcta caggcatcgt   6180

ggtgtcacgc tcgtcgtttg gtatggcttc attcagctcc ggttcccaac gatcaaggcg   6240

agttacatga tcccccatgt tgtgcaaaaa agcggttagc tccttcggtc ctccgatcgt   6300

tgtcagaagt aagttggccg cagtgttatc actcatggtt atggcagcac tgcataattc   6360

tcttactgtc atgccatccg taagatgctt ttctgtgact ggtgagtact caaccaagtc   6420

attctgagaa tagtgtatgc ggcgaccgag ttgctcttgc ccggcgtcaa tacgggataa   6480

taccgcgcca catagcagaa ctttaaaagt gctcatcatt ggaaaacgtt cttcggggcg   6540

aaaactctca aggatcttac cgctgttgag atccagttcg atgtaaccca ctcgtgcacc   6600

caactgatct tcagcatctt ttactttcac cagcgtttct gggtgagcaa aaacaggaag   6660

gcaaaatgcc gcaaaaaagg gaataagggc gacacggaaa tgttgaatac tcatactctt   6720

cctttttcaa tattattgaa gcatttatca gggttattgt ctcatgagcg gatacatatt   6780

tgaatgtatt tagaaaaata aacaaatagg ggttccgcgc acatttcccc gaaaagtgcc   6840

acctgacgtc                                                          6850
```

```
<210> SEQ ID NO 34
<211> LENGTH: 7093
<212> TYPE: DNA
<213> ORGANISM: Artificial Sequence
<220> FEATURE:
<223> OTHER INFORMATION: pcDNA3-4XUb-GFP construct

<400> SEQUENCE: 34

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgatatc    900

gaattcctgc agcccggggg atctaccatg gaaatcttcg tgaagactct gactggtaag    960
```

-continued

```
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tctaccatgg aaatcttcgt gaagactctg   1680
actggtaaga ccatcactct cgaagtggag ccgagtgaca ccattgagaa tgtcaaggca   1740
aagatccaag acaaggaagg catccctcct gaccagcaga ggttgatctt tgctgggaaa   1800
cagctggaag atggacgcac cctgtctgac tacaacatcc agaaagagtc caccctgcac   1860
ctggtactcc gtctcagagg tgtgcaccac ggatccgaat tcgccaccat ggtgagcaag   1920
ggcgaggagc tgttcaccgg ggtggtgccc atcctggtcg agctggacgg cgacgtaaac   1980
ggccacaagt tcagcgtgtc cggcgagggc gagggcgatg ccacctacgg caagctgacc   2040
ctgaagttca tctgcaccac cggcaagctg cccgtgccct ggcccaccct cgtgaccacc   2100
ttcacctacg gcgtgcagtg cttcgcccgc taccccgacc acatgaagca gcacgacttc   2160
ttcaagtccg ccatgcccga aggctacgtc caggagcgca ccatcttctt caaggacgac   2220
ggcaactaca agacccgcgc cgaggtgaag ttcgagggcg acaccctggt gaaccgcatc   2280
gagctgaagg gcatcgactt caaggaggac ggcaacatcc tggggcacaa gctggagtac   2340
aactacaaca gccacaaggt ctatatcacc gccgacaagc agaagaacgg catcaaggtg   2400
aacttcaaga cccgccacaa catcgaggac ggcagcgtgc agctcgccga ccactaccag   2460
cagaacaccc ccatcggcga cggccccgtg ctgctgcccg acaaccacta cctgagcacc   2520
cagtccgccc tgagcaaaga ccccaacgag aagcgcgatc acatggtcct gctggagttc   2580
gtgaccgccg ccgggatcac tctcggcatg gacgagctgt acaagtaagt ctagagggcc   2640
ctattctata gtgtcaccta aatgctagag ctcgctgatc agcctcgact gtgccttcta   2700
gttgccagcc atctgttgtt tgcccctccc ccgtgccttc cttgaccctg gaaggtgcca   2760
ctcccactgt cctttcctaa taaaatgagg aaattgcatc gcattgtctg agtaggtgtc   2820
attctattct ggggggtggg gtggggcagg acagcaaggg ggaggattgg gaagacaata   2880
gcaggcatgc tggggatgcg gtgggctcta tggcttctga ggcggaaaga accagctggg   2940
gctctagggg gtatccccac gcgccctgta gcggcgcatt aagcgcggcg ggtgtggtgg   3000
ttacgcgcag cgtgaccgct acacttgcca gcgccctagc gcccgctcct ttcgctttct   3060
tcccttcctt tctcgccacg ttcgccggct ttccccgtca agctctaaat cggggcatcc   3120
ctttagggtt ccgatttagt gctttacggc acctcgaccc caaaaaactt gattagggtg   3180
atggttcacg tagtgggcca tcgccctgat agacggtttt tcgccctttg acgttggagt   3240
ccacgttctt taatagtgga ctcttgttcc aaactggaac aacactcaac cctatctcgg   3300
tctattcttt tgatttataa gggattttgg ggatttcggc ctattggtta aaaaatgagc   3360
```

-continued

```
tgatttaaca aaaatttaac gcgaattaat tctgtggaat gtgtgtcagt tagggtgtgg   3420
aaagtcccca ggctccccag gcaggcagaa gtatgcaaag catgcatctc aattagtcag   3480
caaccaggtg tggaaagtcc ccaggctccc cagcaggcag aagtatgcaa agcatgcatc   3540
tcaattagtc agcaaccata gtcccgcccc taactccgcc catcccgccc ctaactccgc   3600
ccagttccgc ccattctccg ccccatggct gactaatttt ttttatttat gcagaggccg   3660
aggccgcctc tgcctctgag ctattccaga agtagtgagg aggctttttt ggaggcctag   3720
gcttttgcaa aaagctcccg ggagcttgta tatccatttt cggatctgat caagagacag   3780
gatgaggatc gtttcgcatg attgaacaag atggattgca cgcaggttct ccggccgctt   3840
gggtggagag gctattcggc tatgactggg cacaacagac aatcggctgc tctgatgccg   3900
ccgtgttccg gctgtcagcg caggggcgcc cggttctttt tgtcaagacc gacctgtccg   3960
gtgccctgaa tgaactgcag gacgaggcag cgcggctatc gtggctggcc acgacgggcg   4020
ttccttgcgc agctgtgctc gacgttgtca ctgaagcggg aagggactgg ctgctattgg   4080
gcgaagtgcc ggggcaggat ctcctgtcat ctcaccttgc tcctgccgag aaagtatcca   4140
tcatggctga tgcaatgcgg cggctgcata cgcttgatcc ggctacctgc ccattcgacc   4200
accaagcgaa acatcgcatc gagcgagcac gtactcggat ggaagccggt cttgtcgatc   4260
aggatgatct ggacgaagag catcaggggc tcgcgccagc cgaactgttc gccaggctca   4320
aggcgcgcat gcccgacggc gaggatctcg tcgtgaccca tggcgatgcc tgcttgccga   4380
atatcatggt ggaaaatggc cgcttttctg gattcatcga ctgtggccgg ctgggtgtgg   4440
cggaccgcta tcaggacata gcgttggcta cccgtgatat tgctgaagag cttggcggcg   4500
aatgggctga ccgcttcctc gtgctttacg gtatcgccgc tcccgattcg cagcgcatcg   4560
ccttctatcg ccttcttgac gagttcttct gagcgggact ctggggttcg aaatgaccga   4620
ccaagcgacg cccaacctgc catcacgaga tttcgattcc accgccgcct tctatgaaag   4680
gttgggcttc ggaatcgttt tccgggacgc cggctggatg atcctccagc gcggggatct   4740
catgctggag ttcttcgccc accccaactt gtttattgca gcttataatg gttacaaata   4800
aagcaatagc atcacaaatt tcacaaataa agcatttttt tcactgcatt ctagttgtgg   4860
tttgtccaaa ctcatcaatg tatcttatca tgtctgtata ccgtcgacct ctagctagag   4920
cttggcgtaa tcatggtcat agctgtttcc tgtgtgaaat tgttatccgc tcacaattcc   4980
acacaacata cgagccggaa gcataaagtg taaagcctgg ggtgcctaat gagtgagcta   5040
actcacatta attgcgttgc gctcactgcc cgctttccag tcgggaaacc tgtcgtgcca   5100
gctgcattaa tgaatcggcc aacgcgcggg gagaggcggt ttgcgtattg ggcgctcttc   5160
cgcttcctcg ctcactgact cgctgcgctc ggtcgttcgg ctgcggcgag cggtatcagc   5220
tcactcaaag gcggtaatac ggttatccac agaatcaggg gataacgcag gaaagaacat   5280
gtgagcaaaa ggccagcaaa aggccaggaa ccgtaaaaag gccgcgttgc tggcgttttt   5340
ccataggctc cgcccccctg acgagcatca caaaaatcga cgctcaagtc agaggtggcg   5400
aaacccgaca ggactataaa gataccaggc gtttccccct ggaagctccc tcgtgcgctc   5460
tcctgttccg accctgccgc ttaccggata cctgtccgcc tttctccctt cgggaagcgt   5520
ggcgctttct caatgctcac gctgtaggta tctcagttcg gtgtaggtcg ttcgctccaa   5580
gctgggctgt gtgcacgaac cccccgttca gcccgaccgc tgcgccttat ccggtaacta   5640
tcgtcttgag tccaacccgg taagacacga cttatcgcca ctggcagcag ccactggtaa   5700
```

-continued

```
caggattagc agagcgaggt atgtaggcgg tgctacagag ttcttgaagt ggtggcctaa   5760

ctacggctac actagaagga cagtatttgg tatctgcgct ctgctgaagc cagttacctt   5820

cggaaaaaga gttggtagct cttgatccgg caaacaaacc accgctggta gcggtggttt   5880

ttttgtttgc aagcagcaga ttacgcgcag aaaaaaagga tctcaagaag atcctttgat   5940

cttttctacg gggtctgacg ctcagtggaa cgaaaactca cgttaaggga ttttggtcat   6000

gagattatca aaaaggatct tcacctagat ccttttaaat taaaaatgaa gttttaaatc   6060

aatctaaagt atatatgagt aaacttggtc tgacagttac caatgcttaa tcagtgaggc   6120

acctatctca gcgatctgtc tatttcgttc atccatagtt gcctgactcc ccgtcgtgta   6180

gataactacg atacgggagg gcttaccatc tggccccagt gctgcaatga taccgcgaga   6240

cccacgctca ccggctccag atttatcagc aataaaccag ccagccggaa gggccgagcg   6300

cagaagtggt cctgcaactt tatccgcctc catccagtct attaattgtt gccgggaagc   6360

tagagtaagt agttcgccag ttaatagttt gcgcaacgtt gttgccattg ctacaggcat   6420

cgtggtgtca cgctcgtcgt ttggtatggc ttcattcagc tccggttccc aacgatcaag   6480

gcgagttaca tgatccccca tgttgtgcaa aaaagcggtt agctccttcg gtcctccgat   6540

cgttgtcaga agtaagttgg ccgcagtgtt atcactcatg gttatggcag cactgcataa   6600

ttctcttact gtcatgccat ccgtaagatg cttttctgtg actggtgagt actcaaccaa   6660

gtcattctga gaatagtgta tgcggcgacc gagttgctct tgcccggcgt caatacggga   6720

taataccgcg ccacatagca gaactttaaa agtgctcatc attggaaaac gttcttcggg   6780

gcgaaaactc tcaaggatct taccgctgtt gagatccagt tcgatgtaac ccactcgtgc   6840

acccaactga tcttcagcat cttttacttt caccagcgtt tctgggtgag caaaaacagg   6900

aaggcaaaat gccgcaaaaa agggaataag ggcgacacgg aaatgttgaa tactcatact   6960

cttccttttt caatattatt gaagcattta tcagggttat tgtctcatga gcggatacat   7020

atttgaatgt atttagaaaa ataaacaaat aggggttccg cgcacatttc cccgaaaagt   7080

gccacctgac gtc                                                      7093
```

```
<210> SEQ ID NO 35
<211> LENGTH: 834
<212> TYPE: DNA
<213> ORGANISM: Homo sapiens

<400> SEQUENCE: 35

atggagaaca ctgaaaactc agtggattca aaatccatta aaaatttgga accaaagatc     60

atacatggaa gcgaatcaat ggactctgga atatccctgg acaacagtta taaaatggat    120

tatcctgaga tgggtttatg tataataatt aataataaga attttcataa aagcactgga    180

atgacatctc ggtctggtac agatgtcgat gcagcaaacc tcagggaaac attcagaaac    240

ttgaaatatg aagtcaggaa taaaaatgat cttacacgtg aagaaattgt ggaattgatg    300

cgtgatgttt ctaaagaaga tcacagcaaa aggagcagtt ttgtttgtgt gcttctgagc    360

catggtgaag aaggaataat ttttggaaca aatggacctg ttgacctgaa aaaaataaca    420

aactttttca gaggggatcg ttgtagaagt ctaactggaa aacccaaact tttcattatt    480

caggcctgcc gtggtacaga actggactgt ggcattgaga cagacagtgg tgttgatgat    540

gacatggcgt gtcataaaat accagtggag gccgacttct tgtatgcata ctccacagca    600

cctggttatt attcttggcg aaattcaaag gatggctcct ggttcatcca gtcgctttgt    660

gccatgctga aacagtatgc cgacaagctt gaatttatgc acattcttac ccgggttaac    720
```

cgaaaggtgg caacagaatt tgagtccttt tcctttgacg ctacttttca tgcaaagaaa 780
cagattccat gtattgtttc catgctcaca aaagaactct atttttatca ctaa 834

<210> SEQ ID NO 36
<211> LENGTH: 50
<212> TYPE: DNA
<213> ORGANISM: Artificial Sequence
<220> FEATURE:
<223> OTHER INFORMATION: primer for PCR

<400> SEQUENCE: 36
cggatccaac actgaaaact cagtggattc aaaatccatt aaaaatttgg 50

<210> SEQ ID NO 37
<211> LENGTH: 48
<212> TYPE: DNA
<213> ORGANISM: Artificial Sequence
<220> FEATURE:
<223> OTHER INFORMATION: primer for PCR

<400> SEQUENCE: 37
cggatccgtg ataaaaatag agttcttttg tgagcatgga aacaatac 48

<210> SEQ ID NO 38
<211> LENGTH: 6436
<212> TYPE: DNA
<213> ORGANISM: Artificial Sequence
<220> FEATURE:
<223> OTHER INFORMATION: pcDNA3-1XUb-C3 construct

<400> SEQUENCE: 38
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
accatggaga tcttcgtgaa gactctgact ggtaagacca tcactctcga agtggagccg 960
agtgacacca ttgagaatgt caaggcaaag atccaagaca aggaaggcat ccctcctgac 1020
cagcagaggt tgatctttgc tgggaaacag ctggaagatg gacgcaccct gtctgactac 1080
aacatccaga aagagtccac cctgcacctg gtactccgtc tcagaggtgt gcaccacgga 1140
tccaacactg aaaactcagt ggattcaaaa tccattaaaa atttggaacc aaagatcata 1200

-continued

```
catggaagcg aatcaatgga ctctggaata tccctggaca acagttataa aatggattat   1260
cctgagatgg gtttatgtat aataattaat aataagaatt ttcataaaag cactggaatg   1320
acatctcggt ctggtacaga tgtcgatgca gcaaacctca gggaaacatt cagaaacttg   1380
aaatatgaag tcaggaataa aaatgatctt acacgtgaag aaattgtgga attgatgcgt   1440
gatgtttcta aagaagatca cagcaaaagg agcagttttg tttgtgtgct tctgagccat   1500
ggtgaagaag gaataatttt tggaacaaat ggacctgttg acctgaaaaa aataacaaac   1560
tttttcagag ggggatcgttg tagaagtcta actggaaaac ccaaactttt cattattcag   1620
gcctgccgtg gtacagaact ggactgtggc attgagacag acagtggtgt tgatgatgac   1680
atggcgtgtc ataaaatacc agtggaggcc gacttcttgt atgcatactc cacagcacct   1740
ggttattatt cttggcgaaa ttcaaaggat ggctcctggt tcatccagtc gctttgtgcc   1800
atgctgaaac agtatgccga caagcttgaa tttatgcaca ttcttacccg ggttaaccga   1860
aaggtggcaa cagaatttga gtccttttcc tttgacgcta cttttcatgc aaagaaacag   1920
attccatgta ttgtttccat gctcacaaaa gaactctatt tttatcacgg atcctagagg   1980
gccctattct atagtgtcac ctaaatgcta gagctcgctg atcagcctcg actgtgcctt   2040
ctagttgcca gccatctgtt gtttgcccct cccccgtgcc ttccttgacc ctggaaggtg   2100
ccactcccac tgtcctttcc taataaaatg aggaaattgc atcgcattgt ctgagtaggt   2160
gtcattctat tctggggggt ggggtggggc aggacagcaa gggggaggat tgggaagaca   2220
atagcaggca tgctggggat gcggtgggct ctatggcttc tgaggcggaa agaaccagct   2280
ggggctctag ggggtatccc cacgcgccct gtagcggcgc attaagcgcg gcgggtgtgg   2340
tggttacgcg cagcgtgacc gctacacttg ccagcgccct agcgcccgct cctttcgctt   2400
tcttcccttc ctttctcgcc acgttcgccg gctttccccg tcaagctcta aatcggggca   2460
tccctttagg gttccgattt agtgctttac ggcacctcga ccccaaaaaa cttgattagg   2520
gtgatggttc acgtagtggg ccatcgccct gatagacggt ttttcgccct ttgacgttgg   2580
agtccacgtt ctttaatagt ggactcttgt tccaaactgg aacaacactc aaccctatct   2640
cggtctattc ttttgattta taagggattt tggggatttc ggcctattgg ttaaaaaatg   2700
agctgattta acaaaaattt aacgcgaatt aattctgtgg aatgtgtgtc agttagggtg   2760
tggaaagtcc ccaggctccc caggcaggca gaagtatgca aagcatgcat ctcaattagt   2820
cagcaaccag gtgtggaaag tccccaggct ccccagcagg cagaagtatg caaagcatgc   2880
atctcaatta gtcagcaacc atagtcccgc ccctaactcc gcccatcccg cccctaactc   2940
cgcccagttc cgcccattct ccgccccatg gctgactaat tttttttatt tatgcagagg   3000
ccgaggccgc ctctgcctct gagctattcc agaagtagtg aggaggcttt tttggaggcc   3060
taggcttttg caaaaagctc ccgggagctt gtatatccat tttcggatct gatcaagaga   3120
caggatgagg atcgtttcgc atgattgaac aagatggatt gcacgcaggt tctccggccg   3180
cttgggtgga gaggctattc ggctatgact gggcacaaca gacaatcggc tgctctgatg   3240
ccgccgtgtt ccggctgtca gcgcaggggc gcccggttct ttttgtcaag accgacctgt   3300
ccggtgccct gaatgaactg caggacgagg cagcgcggct atcgtggctg gccacgacgg   3360
gcgttccttg cgcagctgtg ctcgacgttg tcactgaagc gggaagggac tggctgctat   3420
tgggcgaagt gccggggcag gatctcctgt catctcacct tgctcctgcc gagaaagtat   3480
ccatcatggc tgatgcaatg cggcggctgc atacgcttga tccggctacc tgcccattcg   3540
accaccaagc gaaacatcgc atcgagcgag cacgtactcg gatggaagcc ggtcttgtcg   3600
```

-continued

```
atcaggatga tctggacgaa gagcatcagg ggctcgcgcc agccgaactg ttcgccaggc   3660
tcaaggcgcg catgcccgac ggcgaggatc tcgtcgtgac ccatggcgat gcctgcttgc   3720
cgaatatcat ggtggaaaat ggccgctttt ctggattcat cgactgtggc cggctgggtg   3780
tggcggaccg ctatcaggac atagcgttgg ctacccgtga tattgctgaa gagcttggcg   3840
gcgaatgggc tgaccgcttc ctcgtgcttt acggtatcgc cgctcccgat tcgcagcgca   3900
tcgccttcta tcgccttctt gacgagttct tctgagcggg actctggggt tcgaaatgac   3960
cgaccaagcg acgcccaacc tgccatcacg agatttcgat tccaccgccg ccttctatga   4020
aaggttgggc ttcggaatcg ttttccggga cgccggctgg atgatcctcc agcgcgggga   4080
tctcatgctg gagttcttcg cccaccccaa cttgtttatt gcagcttata atggttacaa   4140
ataaagcaat agcatcacaa atttcacaaa taaagcattt ttttcactgc attctagttg   4200
tggtttgtcc aaactcatca atgtatctta tcatgtctgt ataccgtcga cctctagcta   4260
gagcttggcg taatcatggt catagctgtt tcctgtgtga aattgttatc cgctcacaat   4320
tccacacaac atacgagccg gaagcataaa gtgtaaagcc tggggtgcct aatgagtgag   4380
ctaactcaca ttaattgcgt tgcgctcact gcccgctttc cagtcgggaa acctgtcgtg   4440
ccagctgcat taatgaatcg gccaacgcgc ggggagaggc ggtttgcgta ttgggcgctc   4500
ttccgcttcc tcgctcactg actcgctgcg ctcggtcgtt cggctgcggc gagcggtatc   4560
agctcactca aaggcggtaa tacggttatc cacagaatca ggggataacg caggaaagaa   4620
catgtgagca aaaggccagc aaaaggccag gaaccgtaaa aaggccgcgt tgctggcgtt   4680
tttccatagg ctccgccccc ctgacgagca tcacaaaaat cgacgctcaa gtcagaggtg   4740
gcgaaacccg acaggactat aaagatacca ggcgtttccc cctggaagct ccctcgtgcg   4800
ctctcctgtt ccgaccctgc cgcttaccgg atacctgtcc gcctttctcc cttcgggaag   4860
cgtggcgctt tctcaatgct cacgctgtag gtatctcagt tcggtgtagg tcgttcgctc   4920
caagctgggc tgtgtgcacg aaccccccgt tcagcccgac cgctgcgcct tatccggtaa   4980
ctatcgtctt gagtccaacc cggtaagaca cgacttatcg ccactggcag cagccactgg   5040
taacaggatt agcagagcga ggtatgtagg cggtgctaca gagttcttga agtggtggcc   5100
taactacggc tacactagaa ggacagtatt tggtatctgc gctctgctga agccagttac   5160
cttcggaaaa agagttggta gctcttgatc cggcaaacaa accaccgctg gtagcggtgg   5220
tttttttgtt tgcaagcagc agattacgcg cagaaaaaaa ggatctcaag aagatccttt   5280
gatcttttct acggggtctg acgctcagtg gaacgaaaac tcacgttaag ggattttggt   5340
catgagatta tcaaaaagga tcttcaccta gatcctttta aattaaaaat gaagttttaa   5400
atcaatctaa agtatatatg agtaaacttg gtctgacagt taccaatgct taatcagtga   5460
ggcacctatc tcagcgatct gtctatttcg ttcatccata gttgcctgac tccccgtcgt   5520
gtagataact acgatacggg agggcttacc atctggcccc agtgctgcaa tgataccgcg   5580
agacccacgc tcaccggctc cagatttatc agcaataaac cagccagccg gaagggccga   5640
gcgcagaagt ggtcctgcaa ctttatccgc ctccatccag tctattaatt gttgccggga   5700
agctagagta agtagttcgc cagttaatag tttgcgcaac gttgttgcca ttgctacagg   5760
catcgtggtg tcacgctcgt cgtttggtat ggcttcattc agctccggtt cccaacgatc   5820
aaggcgagtt acatgatccc ccatgttgtg caaaaaagcg gttagctcct tcggtcctcc   5880
gatcgttgtc agaagtaagt tggccgcagt gttatcactc atggttatgg cagcactgca   5940
```

-continued

```
taattctctt actgtcatgc catccgtaag atgcttttct gtgactggtg agtactcaac   6000

caagtcattc tgagaatagt gtatgcggcg accgagttgc tcttgcccgg cgtcaatacg   6060

ggataatacc gcgccacata gcagaacttt aaaagtgctc atcattggaa aacgttcttc   6120

ggggcgaaaa ctctcaagga tcttaccgct gttgagatcc agttcgatgt aacccactcg   6180

tgcacccaac tgatcttcag catcttttac tttcaccagc gtttctgggt gagcaaaaac   6240

aggaaggcaa aatgccgcaa aaaagggaat aagggcgaca cggaaatgtt gaatactcat   6300

actcttcctt tttcaatatt attgaagcat ttatcagggt tattgtctca tgagcggata   6360

catatttgaa tgtatttaga aaaataaaca aataggggtt ccgcgcacat ttccccgaaa   6420

agtgccacct gacgtc                                                   6436
```

```
<210> SEQ ID NO 39
<211> LENGTH: 6703
<212> TYPE: DNA
<213> ORGANISM: Artificial Sequence
<220> FEATURE:
<223> OTHER INFORMATION: pcDNA3-2XUb-C3 construct

<400> SEQUENCE: 39

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgatatc    900

gaattcctgc agcccggggg atctaccatg gaaatcttcg tgaagactct gactggtaag    960

accatcactc tcgaagtgga gccgagtgac accattgaga atgtcaaggc aaagatccaa   1020

gacaaggaag gcatccctcc tgaccagcag aggttgatct ttgctgggaa acagctggaa   1080

gatggacgca ccctgtctga ctacaacatc cagaaagagt ccaccctgca cctggtactc   1140

cgtctcagag gtgtgcacca cggatctacc atggaaatct tcgtgaagac tctgactggt   1200

aagaccatca ctctcgaagt ggagccgagt gacaccattg agaatgtcaa ggcaaagatc   1260

caagacaagg aaggcatccc tcctgaccag cagaggttga tctttgctgg gaaacagctg   1320

gaagatggac gcaccctgtc tgactacaac atccagaaag agtccaccct gcacctggta   1380

ctccgtctca gaggtgtgca ccacggatcc aacactgaaa actcagtgga ttcaaaatcc   1440

attaaaaatt tggaaccaaa gatcatacat ggaagcgaat caatggactc tggaatatcc   1500

ctggacaaca gttataaaat ggattatcct gagatgggtt tatgtataat aattaataat   1560
```

-continued

```
aagaattttc ataaaagcac tggaatgaca tctcggtctg gtacagatgt cgatgcagca   1620
aacctcaggg aaacattcag aaacttgaaa tatgaagtca ggaataaaaa tgatcttaca   1680
cgtgaagaaa ttgtggaatt gatgcgtgat gtttctaaag aagatcacag caaaaggagc   1740
agttttgttt gtgtgcttct gagccatggt gaagaaggaa taatttttgg aacaaatgga   1800
cctgttgacc tgaaaaaaat aacaaacttt ttcagagggg atcgttgtag aagtctaact   1860
ggaaaaccca aacttttcat tattcaggcc tgccgtggta cagaactgga ctgtggcatt   1920
gagacagaca gtggtgttga tgatgacatg gcgtgtcata aaataccagt ggaggccgac   1980
ttcttgtatg catactccac agcacctggt tattattctt ggcgaaattc aaaggatggc   2040
tcctggttca tccagtcgct ttgtgccatg ctgaaacagt atgccgacaa gcttgaattt   2100
atgcacattc ttacccgggt taaccgaaag gtggcaacag aatttgagtc cttttccttt   2160
gacgctactt ttcatgcaaa gaaacagatt ccatgtattg tttccatgct cacaaaagaa   2220
ctctattttt atcacggatc ctagagggcc ctattctata gtgtcaccta aatgctagag   2280
ctcgctgatc agcctcgact gtgccttcta gttgccagcc atctgttgtt tgcccctccc   2340
ccgtgccttc cttgaccctg gaaggtgcca ctcccactgt cctttcctaa taaaatgagg   2400
aaattgcatc gcattgtctg agtaggtgtc attctattct ggggggtggg gtggggcagg   2460
acagcaaggg ggaggattgg gaagacaata gcaggcatgc tggggatgcg gtgggctcta   2520
tggcttctga ggcggaaaga accagctggg gctctagggg gtatccccac gcgccctgta   2580
gcggcgcatt aagcgcggcg ggtgtggtgg ttacgcgcag cgtgaccgct acacttgcca   2640
gcgccctagc gcccgctcct ttcgctttct tcccttcctt tctcgccacg ttcgccggct   2700
ttccccgtca agctctaaat cggggcatcc ctttagggtt ccgatttagt gctttacggc   2760
acctcgaccc caaaaaactt gattagggtg atggttcacg tagtgggcca tcgccctgat   2820
agacggtttt tcgccctttg acgttggagt ccacgttctt taatagtgga ctcttgttcc   2880
aaactggaac aacactcaac cctatctcgg tctattcttt tgatttataa gggattttgg   2940
ggatttcggc ctattggtta aaaaatgagc tgatttaaca aaaatttaac gcgaattaat   3000
tctgtggaat gtgtgtcagt tagggtgtgg aaagtcccca ggctccccag gcaggcagaa   3060
gtatgcaaag catgcatctc aattagtcag caaccaggtg tggaaagtcc ccaggctccc   3120
cagcaggcag aagtatgcaa agcatgcatc tcaattagtc agcaaccata gtcccgcccc   3180
taactccgcc catcccgccc ctaactccgc ccagttccgc ccattctccg ccccatggct   3240
gactaatttt ttttatttat gcagaggccg aggccgcctc tgcctctgag ctattccaga   3300
agtagtgagg aggctttttt ggaggcctag gcttttgcaa aaagctcccg ggagcttgta   3360
tatccatttt cggatctgat caagagacag gatgaggatc gtttcgcatg attgaacaag   3420
atggattgca cgcaggttct ccggccgctt gggtggagag gctattcggc tatgactggg   3480
cacaacagac aatcggctgc tctgatgccg ccgtgttccg gctgtcagcg caggggcgcc   3540
cggttctttt tgtcaagacc gacctgtccg gtgccctgaa tgaactgcag gacgaggcag   3600
cgcggctatc gtggctggcc acgacgggcg ttccttgcgc agctgtgctc gacgttgtca   3660
ctgaagcggg aagggactgg ctgctattgg gcgaagtgcc ggggcaggat ctcctgtcat   3720
ctcaccttgc tcctgccgag aaagtatcca tcatggctga tgcaatgcgg cggctgcata   3780
cgcttgatcc ggctacctgc ccattcgacc accaagcgaa acatcgcatc gagcgagcac   3840
gtactcggat ggaagccggt cttgtcgatc aggatgatct ggacgaagag catcaggggc   3900
```

-continued

```
tcgcgccagc cgaactgttc gccaggctca aggcgcgcat gcccgacggc gaggatctcg   3960
tcgtgaccca tggcgatgcc tgcttgccga atatcatggt ggaaaatggc cgcttttctg   4020
gattcatcga ctgtggccgg ctgggtgtgg cggaccgcta tcaggacata gcgttggcta   4080
cccgtgatat tgctgaagag cttggcggcg aatgggctga ccgcttcctc gtgctttacg   4140
gtatcgccgc tcccgattcg cagcgcatcg ccttctatcg ccttcttgac gagttcttct   4200
gagcgggact ctggggttcg aaatgaccga ccaagcgacg cccaacctgc catcacgaga   4260
tttcgattcc accgccgcct tctatgaaag gttgggcttc ggaatcgttt tccgggacgc   4320
cggctggatg atcctccagc gcggggatct catgctggag ttcttcgccc accccaactt   4380
gtttattgca gcttataatg gttacaaata aagcaatagc atcacaaatt tcacaaataa   4440
agcatttttt tcactgcatt ctagttgtgg tttgtccaaa ctcatcaatg tatcttatca   4500
tgtctgtata ccgtcgacct ctagctagag cttggcgtaa tcatggtcat agctgtttcc   4560
tgtgtgaaat tgttatccgc tcacaattcc acacaacata cgagccggaa gcataaagtg   4620
taaagcctgg ggtgcctaat gagtgagcta actcacatta attgcgttgc gctcactgcc   4680
cgctttccag tcgggaaacc tgtcgtgcca gctgcattaa tgaatcggcc aacgcgcggg   4740
gagaggcggt ttgcgtattg ggcgctcttc cgcttcctcg ctcactgact cgctgcgctc   4800
ggtcgttcgg ctgcggcgag cggtatcagc tcactcaaag gcggtaatac ggttatccac   4860
agaatcaggg gataacgcag gaaagaacat gtgagcaaaa ggccagcaaa aggccaggaa   4920
ccgtaaaaag gccgcgttgc tggcgttttt ccataggctc cgcccccctg acgagcatca   4980
caaaaatcga cgctcaagtc agaggtggcg aaacccgaca ggactataaa gataccaggc   5040
gtttccccct ggaagctccc tcgtgcgctc tcctgttccg accctgccgc ttaccggata   5100
cctgtccgcc tttctccctt cgggaagcgt ggcgctttct caatgctcac gctgtaggta   5160
tctcagttcg gtgtaggtcg ttcgctccaa gctgggctgt gtgcacgaac cccccgttca   5220
gcccgaccgc tgcgccttat ccggtaacta tcgtcttgag tccaacccgg taagacacga   5280
cttatcgcca ctggcagcag ccactggtaa caggattagc agagcgaggt atgtaggcgg   5340
tgctacagag ttcttgaagt ggtggcctaa ctacggctac actagaagga cagtatttgg   5400
tatctgcgct ctgctgaagc cagttacctt cggaaaaaga gttggtagct cttgatccgg   5460
caaacaaacc accgctggta gcggtggttt ttttgtttgc aagcagcaga ttacgcgcag   5520
aaaaaaagga tctcaagaag atcctttgat cttttctacg gggtctgacg ctcagtggaa   5580
cgaaaactca cgttaaggga ttttggtcat gagattatca aaaaggatct tcacctagat   5640
ccttttaaat taaaaatgaa gttttaaatc aatctaaagt atatatgagt aaacttggtc   5700
tgacagttac caatgcttaa tcagtgaggc acctatctca gcgatctgtc tatttcgttc   5760
atccatagtt gcctgactcc ccgtcgtgta gataactacg atacgggagg gcttaccatc   5820
tggccccagt gctgcaatga taccgcgaga cccacgctca ccggctccag atttatcagc   5880
aataaaccag ccagccggaa gggccgagcg cagaagtggt cctgcaactt tatccgcctc   5940
catccagtct attaattgtt gccgggaagc tagagtaagt agttcgccag ttaatagttt   6000
gcgcaacgtt gttgccattg ctacaggcat cgtggtgtca cgctcgtcgt ttggtatggc   6060
ttcattcagc tccggttccc aacgatcaag gcgagttaca tgatccccca tgttgtgcaa   6120
aaaagcggtt agctccttcg gtcctccgat cgttgtcaga agtaagttgg ccgcagtgtt   6180
atcactcatg gttatggcag cactgcataa ttctcttact gtcatgccat ccgtaagatg   6240
cttttctgtg actggtgagt actcaaccaa gtcattctga gaatagtgta tgcggcgacc   6300
```

-continued

```
gagttgctct tgcccggcgt caatacggga taataccgcg ccacatagca gaactttaaa   6360

agtgctcatc attggaaaac gttcttcggg gcgaaaactc tcaaggatct taccgctgtt   6420

gagatccagt tcgatgtaac ccactcgtgc acccaactga tcttcagcat cttttacttt   6480

caccagcgtt tctgggtgag caaaaacagg aaggcaaaat gccgcaaaaa agggaataag   6540

ggcgacacgg aaatgttgaa tactcatact cttccttttt caatattatt gaagcattta   6600

tcagggttat tgtctcatga gcggatacat atttgaatgt atttagaaaa ataaacaaat   6660

aggggttccg cgcacatttc cccgaaaagt gccacctgac gtc                     6703
```

<210> SEQ ID NO 40
<211> LENGTH: 6946
<212> TYPE: DNA
<213> ORGANISM: Artificial Sequence
<220> FEATURE:
<223> OTHER INFORMATION: pcDNA3-3XUb-C3 construct

<400> SEQUENCE: 40

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgatatc    900

gaattcctgc agcccggggg atctaccatg gaaatcttcg tgaagactct gactggtaag    960

accatcactc tcgaagtgga gccgagtgac accattgaga atgtcaaggc aaagatccaa   1020

gacaaggaag gcatccctcc tgaccagcag aggttgatct ttgctgggaa acagctggaa   1080

gatggacgca ccctgtctga ctacaacatc cagaaagagt ccaccctgca cctggtactc   1140

cgtctcagag gtgtgcacca cggatctacc atggaaatct tcgtgaagac tctgactggt   1200

aagaccatca ctctcgaagt ggagccgagt gacaccattg agaatgtcaa ggcaaagatc   1260

caagacaagg aaggcatccc tcctgaccag cagaggttga tctttgctgg gaaacagctg   1320

gaagatggac gcaccctgtc tgactacaac atccagaaag agtccaccct gcacctggta   1380

ctccgtctca gaggtgtgca ccacggatct accatggaaa tcttcgtgaa gactctgact   1440

ggtaagacca tcactctcga agtggagccg agtgacacca ttgagaatgt caaggcaaag   1500

atccaagaca aggaaggcat ccctcctgac cagcagaggt tgatctttgc tgggaaacag   1560

ctggaagatg gacgcaccct gtctgactac aacatccaga aagagtccac cctgcacctg   1620
```

-continued

```
gtactccgtc tcagaggtgt gcaccacgga tccaacactg aaaactcagt ggattcaaaa   1680
tccattaaaa atttggaacc aaagatcata catggaagcg aatcaatgga ctctggaata   1740
tccctggaca acagttataa aatggattat cctgagatgg gtttatgtat aataattaat   1800
aataagaatt ttcataaaag cactggaatg acatctcggt ctggtacaga tgtcgatgca   1860
gcaaacctca gggaaacatt cagaaacttg aaatatgaag tcaggaataa aaatgatctt   1920
acacgtgaag aaattgtgga attgatgcgt gatgtttcta aagaagatca cagcaaaagg   1980
agcagttttg tttgtgtgct tctgagccat ggtgaagaag gaataatttt tggaacaaat   2040
ggacctgttg acctgaaaaa aataacaaac tttttcagag gggatcgttg tagaagtcta   2100
actggaaaac ccaaactttt cattattcag gcctgccgtg gtacagaact ggactgtggc   2160
attgagacag acagtggtgt tgatgatgac atggcgtgtc ataaaatacc agtggaggcc   2220
gacttcttgt atgcatactc cacagcacct ggttattatt cttggcgaaa ttcaaaggat   2280
ggctcctggt tcatccagtc gctttgtgcc atgctgaaac agtatgccga caagcttgaa   2340
tttatgcaca ttcttacccg ggttaaccga aaggtggcaa cagaatttga gtccttttcc   2400
tttgacgcta cttttcatgc aaagaaacag attccatgta ttgtttccat gctcacaaaa   2460
gaactctatt tttatcacgg atcctagagg gccctattct atagtgtcac ctaaatgcta   2520
gagctcgctg atcagcctcg actgtgcctt ctagttgcca gccatctgtt gtttgcccct   2580
cccccgtgcc ttccttgacc ctggaaggtg ccactcccac tgtcctttcc taataaaatg   2640
aggaaattgc atcgcattgt ctgagtaggt gtcattctat tctggggggt ggggtggggc   2700
aggacagcaa gggggaggat tgggaagaca atagcaggca tgctggggat gcggtgggct   2760
ctatggcttc tgaggcggaa agaaccagct ggggctctag ggggtatccc cacgcgccct   2820
gtagcggcgc attaagcgcg gcgggtgtgg tggttacgcg cagcgtgacc gctacacttg   2880
ccagcgccct agcgcccgct cctttcgctt tcttcccttc ctttctcgcc acgttcgccg   2940
gctttccccg tcaagctcta aatcggggca tccctttagg gttccgattt agtgctttac   3000
ggcacctcga ccccaaaaaa cttgattagg gtgatggttc acgtagtggg ccatcgccct   3060
gatagacggt ttttcgccct ttgacgttgg agtccacgtt ctttaatagt ggactcttgt   3120
tccaaactgg aacaacactc aaccctatct cggtctattc ttttgattta taagggattt   3180
tggggatttc ggcctattgg ttaaaaaatg agctgattta acaaaaattt aacgcgaatt   3240
aattctgtgg aatgtgtgtc agttagggtg tggaaagtcc ccaggctccc caggcaggca   3300
gaagtatgca aagcatgcat ctcaattagt cagcaaccag gtgtggaaag tccccaggct   3360
ccccagcagg cagaagtatg caaagcatgc atctcaatta gtcagcaacc atagtcccgc   3420
ccctaactcc gcccatcccg cccctaactc cgcccagttc cgcccattct ccgccccatg   3480
gctgactaat tttttttatt tatgcagagg ccgaggccgc ctctgcctct gagctattcc   3540
agaagtagtg aggaggcttt tttggaggcc taggcttttg caaaaagctc ccgggagctt   3600
gtatatccat tttcggatct gatcaagaga caggatgagg atcgtttcgc atgattgaac   3660
aagatggatt gcacgcaggt tctccggccg cttgggtgga gaggctattc ggctatgact   3720
gggcacaaca gacaatcggc tgctctgatg ccgccgtgtt ccggctgtca gcgcaggggc   3780
gcccggttct ttttgtcaag accgacctgt ccggtgccct gaatgaactg caggacgagg   3840
cagcgcggct atcgtggctg gccacgacgg gcgttccttg cgcagctgtg ctcgacgttg   3900
tcactgaagc gggaagggac tggctgctat tgggcgaagt gccggggcag gatctcctgt   3960
catctcacct tgctcctgcc gagaaagtat ccatcatggc tgatgcaatg cggcggctgc   4020
```

-continued

```
atacgcttga tccggctacc tgcccattcg accaccaagc gaaacatcgc atcgagcgag   4080
cacgtactcg gatggaagcc ggtcttgtcg atcaggatga tctggacgaa gagcatcagg   4140
ggctcgcgcc agccgaactg ttcgccaggc tcaaggcgcg catgcccgac ggcgaggatc   4200
tcgtcgtgac ccatggcgat gcctgcttgc cgaatatcat ggtggaaaat ggccgctttt   4260
ctggattcat cgactgtggc cggctgggtg tggcggaccg ctatcaggac atagcgttgg   4320
ctacccgtga tattgctgaa gagcttggcg gcgaatgggc tgaccgcttc ctcgtgcttt   4380
acggtatcgc cgctcccgat tcgcagcgca tcgccttcta tcgccttctt gacgagttct   4440
tctgagcggg actctggggt tcgaaatgac cgaccaagcg acgcccaacc tgccatcacg   4500
agatttcgat tccaccgccg ccttctatga aaggttgggc ttcggaatcg ttttccggga   4560
cgccggctgg atgatcctcc agcgcgggga tctcatgctg gagttcttcg cccaccccaa   4620
cttgtttatt gcagcttata atggttacaa ataaagcaat agcatcacaa atttcacaaa   4680
taaagcattt ttttcactgc attctagttg tggtttgtcc aaactcatca atgtatctta   4740
tcatgtctgt ataccgtcga cctctagcta gagcttggcg taatcatggt catagctgtt   4800
tcctgtgtga aattgttatc cgctcacaat tccacacaac atacgagccg gaagcataaa   4860
gtgtaaagcc tggggtgcct aatgagtgag ctaactcaca ttaattgcgt tgcgctcact   4920
gcccgctttc cagtcgggaa acctgtcgtg ccagctgcat taatgaatcg gccaacgcgc   4980
ggggagaggc ggtttgcgta ttgggcgctc ttccgcttcc tcgctcactg actcgctgcg   5040
ctcggtcgtt cggctgcggc gagcggtatc agctcactca aaggcggtaa tacggttatc   5100
cacagaatca ggggataacg caggaaagaa catgtgagca aaaggccagc aaaaggccag   5160
gaaccgtaaa aaggccgcgt tgctggcgtt tttccatagg ctccgccccc ctgacgagca   5220
tcacaaaaat cgacgctcaa gtcagaggtg gcgaaacccg acaggactat aaagatacca   5280
ggcgtttccc cctggaagct ccctcgtgcg ctctcctgtt ccgaccctgc cgcttaccgg   5340
atacctgtcc gcctttctcc cttcgggaag cgtggcgctt tctcaatgct cacgctgtag   5400
gtatctcagt tcggtgtagg tcgttcgctc caagctgggc tgtgtgcacg aaccccccgt   5460
tcagcccgac cgctgcgcct tatccggtaa ctatcgtctt gagtccaacc cggtaagaca   5520
cgacttatcg ccactggcag cagccactgg taacaggatt agcagagcga ggtatgtagg   5580
cggtgctaca gagttcttga agtggtggcc taactacggc tacactagaa ggacagtatt   5640
tggtatctgc gctctgctga agccagttac cttcggaaaa agagttggta gctcttgatc   5700
cggcaaacaa accaccgctg gtagcggtgg tttttttgtt tgcaagcagc agattacgcg   5760
cagaaaaaaa ggatctcaag aagatccttt gatcttttct acggggtctg acgctcagtg   5820
gaacgaaaac tcacgttaag ggattttggt catgagatta tcaaaaagga tcttcaccta   5880
gatcctttta aattaaaaat gaagttttaa atcaatctaa agtatatatg agtaaacttg   5940
gtctgacagt taccaatgct taatcagtga ggcacctatc tcagcgatct gtctatttcg   6000
ttcatccata gttgcctgac tccccgtcgt gtagataact acgatacggg agggcttacc   6060
atctggcccc agtgctgcaa tgataccgcg agacccacgc tcaccggctc cagatttatc   6120
agcaataaac cagccagccg gaagggccga gcgcagaagt ggtcctgcaa ctttatccgc   6180
ctccatccag tctattaatt gttgccggga agctagagta agtagttcgc cagttaatag   6240
tttgcgcaac gttgttgcca ttgctacagg catcgtggtg tcacgctcgt cgtttggtat   6300
ggcttcattc agctccggtt cccaacgatc aaggcgagtt acatgatccc ccatgttgtg   6360
```

-continued

```
caaaaaagcg gttagctcct tcggtcctcc gatcgttgtc agaagtaagt tggccgcagt   6420

gttatcactc atggttatgg cagcactgca taattctctt actgtcatgc catccgtaag   6480

atgcttttct gtgactggtg agtactcaac caagtcattc tgagaatagt gtatgcggcg   6540

accgagttgc tcttgcccgg cgtcaatacg ggataatacc gcgccacata gcagaacttt   6600

aaaagtgctc atcattggaa aacgttcttc ggggcgaaaa ctctcaagga tcttaccgct   6660

gttgagatcc agttcgatgt aacccactcg tgcacccaac tgatcttcag catcttttac   6720

tttcaccagc gtttctgggt gagcaaaaac aggaaggcaa aatgccgcaa aaaagggaat   6780

aagggcgaca cggaaatgtt gaatactcat actcttcctt tttcaatatt attgaagcat   6840

ttatcagggt tattgtctca tgagcggata catatttgaa tgtatttaga aaaataaaca   6900

aataggggtt ccgcgcacat ttccccgaaa agtgccacct gacgtc                  6946
```

<210> SEQ ID NO 41
<211> LENGTH: 7189
<212> TYPE: DNA
<213> ORGANISM: Artificial Sequence
<220> FEATURE:
<223> OTHER INFORMATION: pcDNA3-4XUb-C3 construct

<400> SEQUENCE: 41

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgatatc    900

gaattcctgc agcccggggg atctaccatg gaaatcttcg tgaagactct gactggtaag    960

accatcactc tcgaagtgga gccgagtgac accattgaga atgtcaaggc aaagatccaa   1020

gacaaggaag gcatccctcc tgaccagcag aggttgatct ttgctgggaa acagctggaa   1080

gatggacgca ccctgtctga ctacaacatc cagaaagagt ccaccctgca cctggtactc   1140

cgtctcagag gtgtgcacca cggatctacc atggaaatct tcgtgaagac tctgactggt   1200

aagaccatca ctctcgaagt ggagccgagt gacaccattg agaatgtcaa ggcaaagatc   1260

caagacaagg aaggcatccc tcctgaccag cagaggttga tctttgctgg gaaacagctg   1320

gaagatggac gcaccctgtc tgactacaac atccagaaag agtccaccct gcacctggta   1380

ctccgtctca gaggtgtgca ccacggatct accatggaaa tcttcgtgaa gactctgact   1440

ggtaagacca tcactctcga agtggagccg agtgacacca ttgagaatgt caaggcaaag   1500
```

-continued

```
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tctaccatgg aaatcttcgt gaagactctg   1680
actggtaaga ccatcactct cgaagtggag ccgagtgaca ccattgagaa tgtcaaggca   1740
aagatccaag acaaggaagg catccctcct gaccagcaga ggttgatctt tgctgggaaa   1800
cagctggaag atggacgcac cctgtctgac tacaacatcc agaaagagtc caccctgcac   1860
ctggtactcc gtctcagagg tgtgcaccac ggatccaaca ctgaaaactc agtggattca   1920
aaatccatta aaaatttgga accaaagatc atacatggaa gcgaatcaat ggactctgga   1980
atatccctgg acaacagtta taaaatggat tatcctgaga tgggtttatg tataataatt   2040
aataataaga attttcataa aagcactgga atgacatctc ggtctggtac agatgtcgat   2100
gcagcaaacc tcagggaaac attcagaaac ttgaaatatg aagtcaggaa taaaaatgat   2160
cttacacgtg aagaaattgt ggaattgatg cgtgatgttt ctaaagaaga tcacagcaaa   2220
aggagcagtt ttgtttgtgt gcttctgagc catggtgaag aaggaataat tttggaaca    2280
aatggacctg ttgacctgaa aaaaataaca aacttttca gaggggatcg ttgtagaagt    2340
ctaactggaa aacccaaact tttcattatt caggcctgcc gtggtacaga actggactgt   2400
ggcattgaga cagacagtgg tgttgatgat gacatggcgt gtcataaaat accagtggag   2460
gccgacttct tgtatgcata ctccacagca cctggttatt attcttggcg aaattcaaag   2520
gatggctcct ggttcatcca gtcgctttgt gccatgctga aacagtatgc cgacaagctt   2580
gaatttatgc acattcttac ccgggttaac cgaaaggtgg caacagaatt tgagtccttt   2640
tcctttgacg ctacttttca tgcaaagaaa cagattccat gtattgtttc catgctcaca   2700
aaagaactct atttttatca cggatcctag agggccctat tctatagtgt cacctaaatg   2760
ctagagctcg ctgatcagcc tcgactgtgc cttctagttg ccagccatct gttgtttgcc   2820
cctcccccgt gccttccttg accctggaag gtgccactcc cactgtcctt tcctaataaa   2880
atgaggaaat tgcatcgcat tgtctgagta ggtgtcattc tattctgggg ggtggggtgg   2940
ggcaggacag caagggggag gattgggaag acaatagcag gcatgctggg gatgcggtgg   3000
gctctatggc ttctgaggcg gaaagaacca gctggggctc taggggtat ccccacgcgc    3060
cctgtagcgg cgcattaagc gcggcgggtg tggtggttac gcgcagcgtg accgctacac   3120
ttgccagcgc cctagcgccc gctcctttcg ctttcttccc ttcctttctc gccacgttcg   3180
ccggctttcc ccgtcaagct ctaaatcggg gcatcccttt agggttccga tttagtgctt   3240
tacggcacct cgaccccaaa aaacttgatt agggtgatgg ttcacgtagt gggccatcgc   3300
cctgatagac ggtttttcgc cctttgacgt tggagtccac gttctttaat agtggactct   3360
tgttccaaac tggaacaaca ctcaacccta tctcggtcta ttcttttgat ttataaggga   3420
ttttggggat ttcggcctat tggttaaaaa atgagctgat ttaacaaaaa tttaacgcga   3480
attaattctg tggaatgtgt gtcagttagg gtgtggaaag tccccaggct ccccaggcag   3540
gcagaagtat gcaaagcatg catctcaatt agtcagcaac caggtgtgga aagtccccag   3600
gctccccagc aggcagaagt atgcaaagca tgcatctcaa ttagtcagca accatagtcc   3660
cgcccctaac tccgcccatc ccgcccctaa ctccgcccag ttccgcccat tctccgcccc   3720
atggctgact aattttttt atttatgcag aggccgaggc cgcctctgcc tctgagctat    3780
tccagaagta gtgaggaggc ttttttggag gcctaggctt ttgcaaaaag ctcccgggag   3840
```

-continued

```
cttgtatatc cattttcgga tctgatcaag agacaggatg aggatcgttt cgcatgattg   3900
aacaagatgg attgcacgca ggttctccgg ccgcttgggt ggagaggcta ttcggctatg   3960
actgggcaca acagacaatc ggctgctctg atgccgccgt gttccggctg tcagcgcagg   4020
ggcgcccggt tctttttgtc aagaccgacc tgtccggtgc cctgaatgaa ctgcaggacg   4080
aggcagcgcg gctatcgtgg ctggccacga cgggcgttcc ttgcgcagct gtgctcgacg   4140
ttgtcactga agcgggaagg gactggctgc tattgggcga agtgccgggg caggatctcc   4200
tgtcatctca ccttgctcct gccgagaaag tatccatcat ggctgatgca atgcggcggc   4260
tgcatacgct tgatccggct acctgcccat tcgaccacca agcgaaacat cgcatcgagc   4320
gagcacgtac tcggatggaa gccggtcttg tcgatcagga tgatctggac gaagagcatc   4380
aggggctcgc gccagccgaa ctgttcgcca ggctcaaggc gcgcatgccc gacggcgagg   4440
atctcgtcgt gacccatggc gatgcctgct tgccgaatat catggtggaa aatggccgct   4500
tttctggatt catcgactgt ggccggctgg gtgtggcgga ccgctatcag gacatagcgt   4560
tggctacccg tgatattgct gaagagcttg gcggcgaatg ggctgaccgc ttcctcgtgc   4620
tttacggtat cgccgctccc gattcgcagc gcatcgcctt ctatcgcctt cttgacgagt   4680
tcttctgagc gggactctgg ggttcgaaat gaccgaccaa gcgacgccca acctgccatc   4740
acgagatttc gattccaccg ccgccttcta tgaaaggttg ggcttcggaa tcgttttccg   4800
ggacgccggc tggatgatcc tccagcgcgg ggatctcatg ctggagttct tcgcccaccc   4860
caacttgttt attgcagctt ataatggtta caaataaagc aatagcatca caaatttcac   4920
aaataaagca tttttttcac tgcattctag ttgtggtttg tccaaactca tcaatgtatc   4980
ttatcatgtc tgtataccgt cgacctctag ctagagcttg gcgtaatcat ggtcatagct   5040
gtttcctgtg tgaaattgtt atccgctcac aattccacac aacatacgag ccggaagcat   5100
aaagtgtaaa gcctggggtg cctaatgagt gagctaactc acattaattg cgttgcgctc   5160
actgcccgct ttccagtcgg gaaacctgtc gtgccagctg cattaatgaa tcggccaacg   5220
cgcgggggaga ggcggtttgc gtattgggcg ctcttccgct tcctcgctca ctgactcgct   5280
gcgctcggtc gttcggctgc ggcgagcggt atcagctcac tcaaaggcgg taatacggtt   5340
atccacagaa tcaggggata acgcaggaaa gaacatgtga gcaaaaggcc agcaaaaggc   5400
caggaaccgt aaaaaggccg cgttgctggc gtttttccat aggctccgcc cccctgacga   5460
gcatcacaaa aatcgacgct caagtcagag gtggcgaaac ccgacaggac tataaagata   5520
ccaggcgttt ccccctggaa gctccctcgt gcgctctcct gttccgaccc tgccgcttac   5580
cggatacctg tccgcctttc tcccttcggg aagcgtggcg ctttctcaat gctcacgctg   5640
taggtatctc agttcggtgt aggtcgttcg ctccaagctg ggctgtgtgc acgaaccccc   5700
cgttcagccc gaccgctgcg ccttatccgg taactatcgt cttgagtcca acccggtaag   5760
acacgactta tcgccactgg cagcagccac tggtaacagg attagcagag cgaggtatgt   5820
aggcggtgct acagagttct tgaagtggtg gcctaactac ggctacacta gaaggacagt   5880
atttggtatc tgcgctctgc tgaagccagt taccttcgga aaaagagttg gtagctcttg   5940
atccggcaaa caaaccaccg ctggtagcgg tggttttttt gtttgcaagc agcagattac   6000
gcgcagaaaa aaaggatctc aagaagatcc tttgatcttt tctacggggt ctgacgctca   6060
gtggaacgaa aactcacgtt aagggatttt ggtcatgaga ttatcaaaaa ggatcttcac   6120
ctagatcctt ttaaattaaa aatgaagttt taaatcaatc taaagtatat atgagtaaac   6180
ttggtctgac agttaccaat gcttaatcag tgaggcacct atctcagcga tctgtctatt   6240
```

-continued

```
tcgttcatcc atagttgcct gactccccgt cgtgtagata actacgatac gggagggctt   6300

accatctggc cccagtgctg caatgatacc gcgagaccca cgctcaccgg ctccagattt   6360

atcagcaata aaccagccag ccggaagggc cgagcgcaga agtggtcctg caactttatc   6420

cgcctccatc cagtctatta attgttgccg ggaagctaga gtaagtagtt cgccagttaa   6480

tagtttgcgc aacgttgttg ccattgctac aggcatcgtg gtgtcacgct cgtcgtttgg   6540

tatggcttca ttcagctccg gttcccaacg atcaaggcga gttacatgat cccccatgtt   6600

gtgcaaaaaa gcggttagct ccttcggtcc tccgatcgtt gtcagaagta agttggccgc   6660

agtgttatca ctcatggtta tggcagcact gcataattct cttactgtca tgccatccgt   6720

aagatgcttt tctgtgactg gtgagtactc aaccaagtca ttctgagaat agtgtatgcg   6780

gcgaccgagt tgctcttgcc cggcgtcaat acgggataat accgcgccac atagcagaac   6840

tttaaaagtg ctcatcattg gaaaacgttc ttcggggcga aaactctcaa ggatcttacc   6900

gctgttgaga tccagttcga tgtaacccac tcgtgcaccc aactgatctt cagcatcttt   6960

tactttcacc agcgtttctg ggtgagcaaa aacaggaagg caaaatgccg caaaaaaggg   7020

aataagggcg acacggaaat gttgaatact catactcttc ctttttcaat attattgaag   7080

catttatcag ggttattgtc tcatgagcgg atacatattt gaatgtattt agaaaaataa   7140

acaaataggg gttccgcgca catttccccg aaaagtgcca cctgacgtc              7189
```

<210> SEQ ID NO 42
<211> LENGTH: 53
<212> TYPE: DNA
<213> ORGANISM: Artificial Sequence
<220> FEATURE:
<223> OTHER INFORMATION: primer for PCR

<400> SEQUENCE: 42

```
cggatccatg aacactgaaa actcagtgga ttcaaaatcc attaaaaatt tgg            53
```

<210> SEQ ID NO 43
<211> LENGTH: 48
<212> TYPE: DNA
<213> ORGANISM: Artificial Sequence
<220> FEATURE:
<223> OTHER INFORMATION: primer for PCR

<400> SEQUENCE: 43

```
cggatccgtg ataaaaatag agttcttttg tgagcatgga aacaatac                  48
```

<210> SEQ ID NO 44
<211> LENGTH: 7248
<212> TYPE: DNA
<213> ORGANISM: Artificial Sequence
<220> FEATURE:
<223> OTHER INFORMATION: pcDNA3-Ub-Met-C3 construct

<400> SEQUENCE: 44

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360
```

-continued

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
accatggaga tcttcgtgaa gactctgact ggtaagacca tcactctcga agtggagccg    960
agtgacacca ttgagaatgt caaggcaaag atccaagaca aggaaggcat ccctcctgac   1020
cagcagaggt tgatctttgc tgggaaacag ctggaagatg gacgcaccct gtctgactac   1080
aacatccaga aagagtccac cctgcacctg gtactccgtc tcagaggtgg gatgcacgga   1140
tcccacatca acactgaaaa ctcagtggcc tcaaaatcca ttaaaaattt ggaaccaaag   1200
atcatacatg gaagcgaatc aatggactct ggaatatccc tggacaacag ttataaaatg   1260
gattatcctg agatgggttt atgtataata attaataata agaattttca taaaagcact   1320
ggaatgacat ctcggtctgg tacagatgtc gatgcagcaa acctcaggga aacattcaga   1380
aacttgaaat atgaagtcag gaataaaaat gatcttacac gtgaagaaat tgtggaattg   1440
atgcgtgatg tttctaaaga agatcacagc aaaaggagca gttttgtttg tgtgcttctg   1500
agccatggtg aagaaggaat aatttttgga acaaatggac ctgttgacct gaaaaaaata   1560
acaaactttt tcagagggga tcgttgtaga agtctaactg gaaaacccaa acttttcatt   1620
attcaggcct gccgtggtac agaactggac tgtggcattg agacagacag tggtgttgat   1680
gatgacatgg cgtgtcataa aataccagtg gatgccgact tcttgtatgc atactccaca   1740
gcacctggtt attattcttg gcgaaattca aaggatggct cctggttcat ccagtcgctt   1800
tgtgccatgc tgaaacagta tgccgacaag cttgaattta tgcacattct tacccgggtt   1860
aaccgaaagg tggcaacaga atttgagtcc ttttcctttg acgctacttt tcatgcaaag   1920
aaacagattc catgtattgt ttccatgctc acaaaagaac tctattttta tcacggatcc   1980
ggggcgtggc tgcacccaga aacgctggtg aaagtaaaag atgctgaaga tcagttgggt   2040
gcacgagtgg gttacatcga actggatctc aacagcggta agatccttga gagttttcgc   2100
cccgaagaac gttttccaat gatgagcact tttaaagttc tgctatgtgg cgcggtatta   2160
tcccgtattg acgccgggca agagcaactc ggtcgccgca tacactattc tcagaatgac   2220
ttggttgagt actcaccagt cacagaaaag catcttacgg atggcatgac agtaagagaa   2280
ttatgcagtg ctgccataac catgagtgat aacactgcgg ccaacttact tctgacaacg   2340
atcggaggac cgaaggagct aaccgctttt ttgcacaaca tgggggatca tgtaactcgc   2400
cttgatcgtt gggaaccgga gctgaatgaa gccataccaa acgacgagcg tgacaccacg   2460
atgcctgtag caatggcaac aacgttgcgc aaactattaa ctggcgaact acttactcta   2520
gcttcccggc aacaattaat agactggatg gaggcggata aagttgcagg accacttctg   2580
cgctcggccc ttccggctgg ctggtttatt gctgataaat ctggagccgg tgagcgtggg   2640
tctcgcggta tcattgcagc actggggcca gatggtaagc cctcccgtat cgtagttatc   2700
tacacgacgg ggagtcaggc aactatggat gaacgaaata gacagatcgc tgagataggt   2760
```

-continued

```
gcctcactga ttaagcattg gtaatctaga gggccctatt ctatagtgtc acctaaatgc   2820
tagagctcgc tgatcagcct cgactgtgcc ttctagttgc cagccatctg ttgtttgccc   2880
ctcccccgtg ccttccttga ccctggaagg tgccactccc actgtccttt cctaataaaa   2940
tgaggaaatt gcatcgcatt gtctgagtag gtgtcattct attctggggg gtggggtggg   3000
gcaggacagc aagggggagg attgggaaga caatagcagg catgctgggg atgcggtggg   3060
ctctatggct tctgaggcgg aaagaaccag ctggggctct agggggtatc cccacgcgcc   3120
ctgtagcggc gcattaagcg cggcgggtgt ggtggttacg cgcagcgtga ccgctacact   3180
tgccagcgcc ctagcgcccg ctcctttcgc tttcttccct tcctttctcg ccacgttcgc   3240
cggctttccc cgtcaagctc taaatcgggg catcccttta gggttccgat ttagtgcttt   3300
acggcacctc gaccccaaaa aacttgatta gggtgatggt tcacgtagtg ggccatcgcc   3360
ctgatagacg gtttttcgcc ctttgacgtt ggagtccacg ttctttaata gtggactctt   3420
gttccaaact ggaacaacac tcaaccctat ctcggtctat tcttttgatt tataagggat   3480
tttggggatt tcggcctatt ggttaaaaaa tgagctgatt taacaaaaat ttaacgcgaa   3540
ttaattctgt ggaatgtgtg tcagttaggg tgtggaaagt ccccaggctc cccaggcagg   3600
cagaagtatg caaagcatgc atctcaatta gtcagcaacc aggtgtggaa agtccccagg   3660
ctccccagca ggcagaagta tgcaaagcat gcatctcaat tagtcagcaa ccatagtccc   3720
gcccctaact ccgcccatcc cgcccctaac tccgcccagt tccgcccatt ctccgcccca   3780
tggctgacta attttttta tttatgcaga ggccgaggcc gcctctgcct ctgagctatt   3840
ccagaagtag tgaggaggct tttttggagg cctaggcttt tgcaaaaagc tcccgggagc   3900
ttgtatatcc attttcggat ctgatcaaga gacaggatga ggatcgtttc gcatgattga   3960
acaagatgga ttgcacgcag gttctccggc cgcttgggtg gagaggctat tcggctatga   4020
ctgggcacaa cagacaatcg gctgctctga tgccgccgtg ttccggctgt cagcgcaggg   4080
gcgcccggtt ctttttgtca agaccgacct gtccggtgcc ctgaatgaac tgcaggacga   4140
ggcagcgcgg ctatcgtggc tggccacgac gggcgttcct tgcgcagctg tgctcgacgt   4200
tgtcactgaa gcgggaaggg actggctgct attgggcgaa gtgccggggc aggatctcct   4260
gtcatctcac cttgctcctg ccgagaaagt atccatcatg gctgatgcaa tgcggcggct   4320
gcatacgctt gatccggcta cctgcccatt cgaccaccaa gcgaaacatc gcatcgagcg   4380
agcacgtact cggatggaag ccggtcttgt cgatcaggat gatctggacg aagagcatca   4440
ggggctcgcg ccagccgaac tgttcgccag gctcaaggcg cgcatgcccg acggcgagga   4500
tctcgtcgtg acccatggcg atgcctgctt gccgaatatc atggtggaaa atggccgctt   4560
ttctggattc atcgactgtg gccggctggg tgtggcggac cgctatcagg acatagcgtt   4620
ggctacccgt gatattgctg aagagcttgg cggcgaatgg gctgaccgct tcctcgtgct   4680
ttacggtatc gccgctcccg attcgcagcg catcgccttc tatcgccttc ttgacgagtt   4740
cttctgagcg ggactctggg gttcgaaatg accgaccaag cgacgcccaa cctgccatca   4800
cgagatttcg attccaccgc cgccttctat gaaaggttgg gcttcggaat cgttttccgg   4860
gacgccggct ggatgatcct ccagcgcggg gatctcatgc tggagttctt cgcccacccc   4920
aacttgttta ttgcagctta taatggttac aaataaagca atagcatcac aaatttcaca   4980
aataaagcat ttttttcact gcattctagt tgtggtttgt ccaaactcat caatgtatct   5040
tatcatgtct gtataccgtc gacctctagc tagagcttgg cgtaatcatg gtcatagctg   5100
```

-continued

```
tttcctgtgt gaaattgtta tccgctcaca attccacaca acatacgagc cggaagcata   5160

aagtgtaaag cctggggtgc ctaatgagtg agctaactca cattaattgc gttgcgctca   5220

ctgcccgctt tccagtcggg aaacctgtcg tgccagctgc attaatgaat cggccaacgc   5280

gcggggagag gcggtttgcg tattgggcgc tcttccgctt cctcgctcac tgactcgctg   5340

cgctcggtcg ttcggctgcg gcgagcggta tcagctcact caaaggcggt aatacggtta   5400

tccacagaat caggggataa cgcaggaaag aacatgtgag caaaaggcca gcaaaaggcc   5460

aggaaccgta aaaaggccgc gttgctggcg tttttccata ggctccgccc ccctgacgag   5520

catcacaaaa atcgacgctc aagtcagagg tggcgaaacc cgacaggact ataaagatac   5580

caggcgtttc cccctggaag ctccctcgtg cgctctcctg ttccgaccct gccgcttacc   5640

ggatacctgt ccgcctttct cccttcggga agcgtggcgc tttctcaatg ctcacgctgt   5700

aggtatctca gttcggtgta ggtcgttcgc tccaagctgg gctgtgtgca cgaacccccc   5760

gttcagcccg accgctgcgc cttatccggt aactatcgtc ttgagtccaa cccggtaaga   5820

cacgacttat cgccactggc agcagccact ggtaacagga ttagcagagc gaggtatgta   5880

ggcggtgcta cagagttctt gaagtggtgg cctaactacg gctacactag aaggacagta   5940

tttggtatct gcgctctgct gaagccagtt accttcggaa aaagagttgg tagctcttga   6000

tccggcaaac aaaccaccgc tggtagcggt ggtttttttg tttgcaagca gcagattacg   6060

cgcagaaaaa aaggatctca agaagatcct ttgatctttt ctacggggtc tgacgctcag   6120

tggaacgaaa actcacgtta agggattttg gtcatgagat tatcaaaaag gatcttcacc   6180

tagatccttt taaattaaaa atgaagtttt aaatcaatct aaagtatata tgagtaaact   6240

tggtctgaca gttaccaatg cttaatcagt gaggcaccta tctcagcgat ctgtctattt   6300

cgttcatcca tagttgcctg actccccgtc gtgtagataa ctacgatacg ggagggctta   6360

ccatctggcc ccagtgctgc aatgataccg cgagacccac gctcaccggc tccagattta   6420

tcagcaataa accagccagc cggaagggcc gagcgcagaa gtggtcctgc aactttatcc   6480

gcctccatcc agtctattaa ttgttgccgg gaagctagag taagtagttc gccagttaat   6540

agtttgcgca acgttgttgc cattgctaca ggcatcgtgg tgtcacgctc gtcgtttggt   6600

atggcttcat tcagctccgg ttcccaacga tcaaggcgag ttacatgatc ccccatgttg   6660

tgcaaaaaag cggttagctc cttcggtcct ccgatcgttg tcagaagtaa gttggccgca   6720

gtgttatcac tcatggttat ggcagcactg cataattctc ttactgtcat gccatccgta   6780

agatgctttt ctgtgactgg tgagtactca accaagtcat tctgagaata gtgtatgcgg   6840

cgaccgagtt gctcttgccc ggcgtcaata cgggataata ccgcgccaca tagcagaact   6900

ttaaaagtgc tcatcattgg aaaacgttct tcggggcgaa aactctcaag gatcttaccg   6960

ctgttgagat ccagttcgat gtaacccact cgtgcaccca actgatcttc agcatctttt   7020

actttcacca gcgtttctgg gtgagcaaaa acaggaaggc aaaatgccgc aaaaaaggga   7080

ataagggcga cacggaaatg ttgaatactc atactcttcc tttttcaata ttattgaagc   7140

atttatcagg gttattgtct catgagcgga tacatatttg aatgtattta gaaaaataaa   7200

caaatagggg ttccgcgcac atttccccga aaagtgccac ctgacgtc                7248
```

<210> SEQ ID NO 45
<211> LENGTH: 48
<212> TYPE: DNA
<213> ORGANISM: Artificial Sequence
<220> FEATURE:
<223> OTHER INFORMATION: oligonucleotide cassette -continued

<400> SEQUENCE: 45
gatccgtcgg cgctgtcggc agcgtcggcg acgaggtcga cggcgtcg 48

<210> SEQ ID NO 46
<211> LENGTH: 48
<212> TYPE: DNA
<213> ORGANISM: Artificial Sequence
<220> FEATURE:
<223> OTHER INFORMATION: oligonucleotide cassette

<400> SEQUENCE: 46
gatccgacgc cgtcgacctc gtcgccgacg ctgccgacag cgccgacg 48

<210> SEQ ID NO 47
<211> LENGTH: 6459
<212> TYPE: DNA
<213> ORGANISM: Artificial Sequence
<220> FEATURE:
<223> OTHER INFORMATION: pcDNA3-1XUb-DEVD-Bla construct

<400> SEQUENCE: 47
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
accatggaga tcttcgtgaa gactctgact ggtaagacca tcactctcga agtggagccg 960
agtgacacca ttgagaatgt caaggcaaag atccaagaca aggaaggcat ccctcctgac 1020
cagcagaggt tgatctttgc tgggaaacag ctggaagatg gacgcaccct gtctgactac 1080
aacatccaga aagagtccac cctgcacctg gtactccgtc tcagaggtgt gcaccacgga 1140
tccgtcggcg ctgtcggcag cgtcggcgac gaggtcgacg gcgtcggatc cggggcgtgg 1200
ctgcacccag aaacgctggt gaaagtaaaa gatgctgaag atcagttggg tgcacgagtg 1260
ggttacatcg aactggatct caacagcggt aagatccttg agagttttcg ccccgaagaa 1320
cgttttccaa tgatgagcac ttttaaagtt ctgctatgtg gcgcggtatt atcccgtatt 1380
gacgccgggc aagagcaact cggtcgccgc atacactatt ctcagaatga cttggttgag 1440
tactcaccag tcacagaaaa gcatcttacg gatggcatga cagtaagaga attatgcagt 1500
gctgccataa ccatgagtga taacactgcg gccaacttac ttctgacaac gatcggagga 1560

-continued

```
ccgaaggagc taaccgcttt tttgcacaac atgggggatc atgtaactcg ccttgatcgt   1620
tgggaaccgg agctgaatga agccatacca aacgacgagc gtgacaccac gatgcctgta   1680
gcaatggcaa caacgttgcg caaactatta actggcgaac tacttactct agcttcccgg   1740
caacaattaa tagactggat ggaggcggat aaagttgcag gaccacttct gcgctcggcc   1800
cttccggctg gctggtttat tgctgataaa tctggagccg gtgagcgtgg gtctcgcggt   1860
atcattgcag cactggggcc agatggtaag ccctcccgta tcgtagttat ctacacgacg   1920
gggagtcagg caactatgga tgaacgaaat agacagatcg ctgagatagg tgcctcactg   1980
attaagcatt ggtaatctag agggccctat tctatagtgt cacctaaatg ctagagctcg   2040
ctgatcagcc tcgactgtgc cttctagttg ccagccatct gttgtttgcc cctcccccgt   2100
gccttccttg accctggaag gtgccactcc cactgtcctt tcctaataaa atgaggaaat   2160
tgcatcgcat tgtctgagta ggtgtcattc tattctgggg ggtggggtgg ggcaggacag   2220
caagggggag gattgggaag acaatagcag gcatgctggg gatgcggtgg gctctatggc   2280
ttctgaggcg gaaagaacca gctggggctc taggggggat ccccacgcgc cctgtagcgg   2340
cgcattaagc gcggcgggtg tggtggttac gcgcagcgtg accgctacac ttgccagcgc   2400
cctagcgccc gctcctttcg ctttcttccc ttcctttctc gccacgttcg ccggctttcc   2460
ccgtcaagct ctaaatcggg gcatcccttt agggttccga tttagtgctt tacggcacct   2520
cgaccccaaa aaacttgatt agggtgatgg ttcacgtagt gggccatcgc cctgatagac   2580
ggtttttcgc cctttgacgt tggagtccac gttctttaat agtggactct tgttccaaac   2640
tggaacaaca ctcaacccta tctcggtcta ttcttttgat ttataaggga ttttggggat   2700
ttcggcctat tggttaaaaa atgagctgat ttaacaaaaa tttaacgcga attaattctg   2760
tggaatgtgt gtcagttagg gtgtggaaag tccccaggct ccccaggcag gcagaagtat   2820
gcaaagcatg catctcaatt agtcagcaac caggtgtgga aagtccccag gctccccagc   2880
aggcagaagt atgcaaagca tgcatctcaa ttagtcagca accatagtcc cgcccctaac   2940
tccgcccatc ccgcccctaa ctccgcccag ttccgcccat tctccgcccc atggctgact   3000
aattttttttt atttatgcag aggccgaggc cgcctctgcc tctgagctat tccagaagta   3060
gtgaggaggc ttttttggag gcctaggctt ttgcaaaaag ctcccgggag cttgtatatc   3120
cattttcgga tctgatcaag agacaggatg aggatcgttt cgcatgattg aacaagatgg   3180
attgcacgca ggttctccgg ccgcttgggt ggagaggcta ttcggctatg actgggcaca   3240
acagacaatc ggctgctctg atgccgccgt gttccggctg tcagcgcagg ggcgcccggt   3300
tctttttgtc aagaccgacc tgtccggtgc cctgaatgaa ctgcaggacg aggcagcgcg   3360
gctatcgtgg ctggccacga cgggcgttcc ttgcgcagct gtgctcgacg ttgtcactga   3420
agcgggaagg gactggctgc tattgggcga agtgccgggg caggatctcc tgtcatctca   3480
ccttgctcct gccgagaaag tatccatcat ggctgatgca atgcggcggc tgcatacgct   3540
tgatccggct acctgcccat tcgaccacca agcgaaacat cgcatcgagc gagcacgtac   3600
tcggatggaa gccggtcttg tcgatcagga tgatctggac gaagagcatc aggggctcgc   3660
gccagccgaa ctgttcgcca ggctcaaggc gcgcatgccc gacggcgagg atctcgtcgt   3720
gacccatggc gatgcctgct tgccgaatat catggtggaa aatggccgct tttctggatt   3780
catcgactgt ggccggctgg gtgtggcgga ccgctatcag gacatagcgt tggctacccg   3840
tgatattgct gaagagcttg gcggcgaatg ggctgaccgc ttcctcgtgc tttacggtat   3900
cgccgctccc gattcgcagc gcatcgcctt ctatcgcctt cttgacgagt tcttctgagc   3960
```

-continued

```
gggactctgg ggttcgaaat gaccgaccaa gcgacgccca acctgccatc acgagatttc   4020
gattccaccg ccgccttcta tgaaaggttg ggcttcggaa tcgttttccg ggacgccggc   4080
tggatgatcc tccagcgcgg ggatctcatg ctggagttct tcgcccaccc caacttgttt   4140
attgcagctt ataatggtta caaataaagc aatagcatca caaatttcac aaataaagca   4200
tttttttcac tgcattctag ttgtggtttg tccaaactca tcaatgtatc ttatcatgtc   4260
tgtataccgt cgacctctag ctagagcttg gcgtaatcat ggtcatagct gtttcctgtg   4320
tgaaattgtt atccgctcac aattccacac aacatacgag ccggaagcat aaagtgtaaa   4380
gcctggggtg cctaatgagt gagctaactc acattaattg cgttgcgctc actgcccgct   4440
ttccagtcgg gaaacctgtc gtgccagctg cattaatgaa tcggccaacg cgcgggggaga   4500
ggcggtttgc gtattgggcg ctcttccgct tcctcgctca ctgactcgct gcgctcggtc   4560
gttcggctgc ggcgagcggt atcagctcac tcaaaggcgg taatacggtt atccacagaa   4620
tcaggggata acgcaggaaa gaacatgtga gcaaaaggcc agcaaaaggc caggaaccgt   4680
aaaaaggccg cgttgctggc gtttttccat aggctccgcc cccctgacga gcatcacaaa   4740
aatcgacgct caagtcagag gtggcgaaac ccgacaggac tataaagata ccaggcgttt   4800
ccccctggaa gctccctcgt gcgctctcct gttccgaccc tgccgcttac cggatacctg   4860
tccgcctttc tcccttcggg aagcgtggcg ctttctcaat gctcacgctg taggtatctc   4920
agttcggtgt aggtcgttcg ctccaagctg ggctgtgtgc acgaaccccc cgttcagccc   4980
gaccgctgcg ccttatccgg taactatcgt cttgagtcca acccggtaag acacgactta   5040
tcgccactgg cagcagccac tggtaacagg attagcagag cgaggtatgt aggcggtgct   5100
acagagttct tgaagtggtg gcctaactac ggctacacta gaaggacagt atttggtatc   5160
tgcgctctgc tgaagccagt taccttcgga aaaagagttg gtagctcttg atccggcaaa   5220
caaaccaccg ctggtagcgg tggttttttt gtttgcaagc agcagattac gcgcagaaaa   5280
aaaggatctc aagaagatcc tttgatcttt tctacggggt ctgacgctca gtggaacgaa   5340
aactcacgtt aagggatttt ggtcatgaga ttatcaaaaa ggatcttcac ctagatcctt   5400
ttaaattaaa aatgaagttt taaatcaatc taaagtatat atgagtaaac ttggtctgac   5460
agttaccaat gcttaatcag tgaggcacct atctcagcga tctgtctatt tcgttcatcc   5520
atagttgcct gactccccgt cgtgtagata actacgatac gggagggctt accatctggc   5580
cccagtgctg caatgatacc gcgagaccca cgctcaccgg ctccagattt atcagcaata   5640
aaccagccag ccggaagggc cgagcgcaga agtggtcctg caactttatc cgcctccatc   5700
cagtctatta attgttgccg ggaagctaga gtaagtagtt cgccagttaa tagtttgcgc   5760
aacgttgttg ccattgctac aggcatcgtg gtgtcacgct cgtcgtttgg tatggcttca   5820
ttcagctccg gttcccaacg atcaaggcga gttacatgat cccccatgtt gtgcaaaaaa   5880
gcggttagct ccttcggtcc tccgatcgtt gtcagaagta agttggccgc agtgttatca   5940
ctcatggtta tggcagcact gcataattct cttactgtca tgccatccgt aagatgcttt   6000
tctgtgactg gtgagtactc aaccaagtca ttctgagaat agtgtatgcg gcgaccgagt   6060
tgctcttgcc cggcgtcaat acgggataat accgcgccac atagcagaac tttaaaagtg   6120
ctcatcattg gaaaacgttc ttcggggcga aaactctcaa ggatcttacc gctgttgaga   6180
tccagttcga tgtaacccac tcgtgcaccc aactgatctt cagcatcttt tactttcacc   6240
agcgtttctg ggtgagcaaa aacaggaagg caaaatgccg caaaaaaggg aataagggcg   6300
```

-continued acacggaaat gttgaatact catactcttc ctttttcaat attattgaag catttatcag 6360
ggttattgtc tcatgagcgg atacatattt gaatgtattt agaaaaataa acaaataggg 6420
gttccgcgca catttccccg aaaagtgcca cctgacgtc 6459

<210> SEQ ID NO 48
<211> LENGTH: 6726
<212> TYPE: DNA
<213> ORGANISM: Artificial Sequence
<220> FEATURE:
<223> OTHER INFORMATION: pcDNA3-2XUb-DEVD-Bla construct

<400> SEQUENCE: 48
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgatatc 900
gaattcctgc agcccggggg atctaccatg gaaatcttcg tgaagactct gactggtaag 960
accatcactc tcgaagtgga gccgagtgac accattgaga atgtcaaggc aaagatccaa 1020
gacaaggaag gcatccctcc tgaccagcag aggttgatct ttgctgggaa acagctggaa 1080
gatggacgca ccctgtctga ctacaacatc cagaaagagt ccaccctgca cctggtactc 1140
cgtctcagag gtgtgcacca cggatctacc atggaaatct tcgtgaagac tctgactggt 1200
aagaccatca ctctcgaagt ggagccgagt gacaccattg agaatgtcaa ggcaaagatc 1260
caagacaagg aaggcatccc tcctgaccag cagaggttga tctttgctgg gaaacagctg 1320
gaagatggac gcaccctgtc tgactacaac atccagaaag agtccaccct gcacctggta 1380
ctccgtctca gaggtgtgca ccacggatcc gtcggcgctg tcggcagcgt cggcgacgag 1440
gtcgacggcg tcggatccgg ggcgtggctg cacccagaaa cgctggtgaa agtaaaagat 1500
gctgaagatc agttgggtgc acgagtgggt tacatcgaac tggatctcaa cagcggtaag 1560
atccttgaga gttttcgccc cgaagaacgt tttccaatga tgagcacttt taaagttctg 1620
ctatgtggcg cggtattatc ccgtattgac gccgggcaag agcaactcgg tcgccgcata 1680
cactattctc agaatgactt ggttgagtac tcaccagtca cagaaaagca tcttacggat 1740
ggcatgacag taagagaatt atgcagtgct gccataacca tgagtgataa cactgcggcc 1800
aacttacttc tgacaacgat cggaggaccg aaggagctaa ccgctttttt gcacaacatg 1860
ggggatcatg taactcgcct tgatcgttgg gaaccggagc tgaatgaagc cataccaaac 1920

-continued

```
gacgagcgtg acaccacgat gcctgtagca atggcaacaa cgttgcgcaa actattaact   1980
ggcgaactac ttactctagc ttcccggcaa caattaatag actggatgga ggcggataaa   2040
gttgcaggac cacttctgcg ctcggccctt ccggctggct ggtttattgc tgataaatct   2100
ggagccggtg agcgtgggtc tcgcggtatc attgcagcac tggggccaga tggtaagccc   2160
tcccgtatcg tagttatcta cacgacgggg agtcaggcaa ctatggatga acgaaataga   2220
cagatcgctg agataggtgc ctcactgatt aagcattggt aatctagagg gccctattct   2280
atagtgtcac ctaaatgcta gagctcgctg atcagcctcg actgtgcctt ctagttgcca   2340
gccatctgtt gtttgcccct cccccgtgcc ttccttgacc ctggaaggtg ccactcccac   2400
tgtcctttcc taataaaatg aggaaattgc atcgcattgt ctgagtaggt gtcattctat   2460
tctggggggt ggggtggggc aggacagcaa gggggaggat tgggaagaca atagcaggca   2520
tgctggggat gcggtgggct ctatggcttc tgaggcggaa agaaccagct ggggctctag   2580
ggggtatccc cacgcgccct gtagcggcgc attaagcgcg gcgggtgtgg tggttacgcg   2640
cagcgtgacc gctacacttg ccagcgccct agcgcccgct cctttcgctt tcttcccttc   2700
ctttctcgcc acgttcgccg gctttccccg tcaagctcta aatcggggca tccctttagg   2760
gttccgattt agtgctttac ggcacctcga ccccaaaaaa cttgattagg gtgatggttc   2820
acgtagtggg ccatcgccct gatagacggt ttttcgccct ttgacgttgg agtccacgtt   2880
ctttaatagt ggactcttgt tccaaactgg aacaacactc aaccctatct cggtctattc   2940
ttttgattta taagggattt tggggatttc ggcctattgg ttaaaaaatg agctgattta   3000
acaaaaattt aacgcgaatt aattctgtgg aatgtgtgtc agttagggtg tggaaagtcc   3060
ccaggctccc caggcaggca gaagtatgca aagcatgcat ctcaattagt cagcaaccag   3120
gtgtggaaag tccccaggct ccccagcagg cagaagtatg caaagcatgc atctcaatta   3180
gtcagcaacc atagtcccgc ccctaactcc gcccatcccg cccctaactc cgcccagttc   3240
cgcccattct ccgccccatg gctgactaat tttttttatt tatgcagagg ccgaggccgc   3300
ctctgcctct gagctattcc agaagtagtg aggaggcttt tttggaggcc taggcttttg   3360
caaaaagctc ccgggagctt gtatatccat tttcggatct gatcaagaga caggatgagg   3420
atcgtttcgc atgattgaac aagatggatt gcacgcaggt tctccggccg cttgggtgga   3480
gaggctattc ggctatgact gggcacaaca gacaatcggc tgctctgatg ccgccgtgtt   3540
ccggctgtca gcgcaggggc gcccggttct ttttgtcaag accgacctgt ccggtgccct   3600
gaatgaactg caggacgagg cagcgcggct atcgtggctg gccacgacgg gcgttccttg   3660
cgcagctgtg ctcgacgttg tcactgaagc gggaagggac tggctgctat tgggcgaagt   3720
gccggggcag gatctcctgt catctcacct tgctcctgcc gagaaagtat ccatcatggc   3780
tgatgcaatg cggcggctgc atacgcttga tccggctacc tgcccattcg accaccaagc   3840
gaaacatcgc atcgagcgag cacgtactcg gatggaagcc ggtcttgtcg atcaggatga   3900
tctggacgaa gagcatcagg ggctcgcgcc agccgaactg ttcgccaggc tcaaggcgcg   3960
catgcccgac ggcgaggatc tcgtcgtgac ccatggcgat gcctgcttgc cgaatatcat   4020
ggtggaaaat ggccgctttt ctggattcat cgactgtggc cggctgggtg tggcggaccg   4080
ctatcaggac atagcgttgg ctacccgtga tattgctgaa gagcttggcg gcgaatgggc   4140
tgaccgcttc ctcgtgcttt acggtatcgc cgctcccgat tcgcagcgca tcgccttcta   4200
tcgccttctt gacgagttct tctgagcggg actctggggt tcgaaatgac cgaccaagcg   4260
```

-continued

```
acgcccaacc tgccatcacg agatttcgat tccaccgccg ccttctatga aaggttgggc   4320
ttcggaatcg ttttccggga cgccggctgg atgatcctcc agcgcgggga tctcatgctg   4380
gagttcttcg cccaccccaa cttgtttatt gcagcttata atggttacaa ataaagcaat   4440
agcatcacaa atttcacaaa taaagcattt ttttcactgc attctagttg tggtttgtcc   4500
aaactcatca atgtatctta tcatgtctgt ataccgtcga cctctagcta gagcttggcg   4560
taatcatggt catagctgtt tcctgtgtga aattgttatc cgctcacaat tccacacaac   4620
atacgagccg gaagcataaa gtgtaaagcc tggggtgcct aatgagtgag ctaactcaca   4680
ttaattgcgt tgcgctcact gcccgctttc cagtcgggaa acctgtcgtg ccagctgcat   4740
taatgaatcg gccaacgcgc ggggagaggc ggtttgcgta ttgggcgctc ttccgcttcc   4800
tcgctcactg actcgctgcg ctcggtcgtt cggctgcggc gagcggtatc agctcactca   4860
aaggcggtaa tacggttatc cacagaatca ggggataacg caggaaagaa catgtgagca   4920
aaaggccagc aaaaggccag gaaccgtaaa aaggccgcgt tgctggcgtt tttccatagg   4980
ctccgccccc ctgacgagca tcacaaaaat cgacgctcaa gtcagaggtg gcgaaacccg   5040
acaggactat aaagatacca ggcgtttccc cctggaagct ccctcgtgcg ctctcctgtt   5100
ccgaccctgc cgcttaccgg atacctgtcc gcctttctcc cttcgggaag cgtggcgctt   5160
tctcaatgct cacgctgtag gtatctcagt tcggtgtagg tcgttcgctc caagctgggc   5220
tgtgtgcacg aaccccccgt tcagcccgac cgctgcgcct tatccggtaa ctatcgtctt   5280
gagtccaacc cggtaagaca cgacttatcg ccactggcag cagccactgg taacaggatt   5340
agcagagcga ggtatgtagg cggtgctaca gagttcttga agtggtggcc taactacggc   5400
tacactagaa ggacagtatt tggtatctgc gctctgctga agccagttac cttcggaaaa   5460
agagttggta gctcttgatc cggcaaacaa accaccgctg gtagcggtgg tttttttgtt   5520
tgcaagcagc agattacgcg cagaaaaaaa ggatctcaag aagatccttt gatcttttct   5580
acggggtctg acgctcagtg gaacgaaaac tcacgttaag ggattttggt catgagatta   5640
tcaaaaagga tcttcaccta gatcctttta aattaaaaat gaagttttaa atcaatctaa   5700
agtatatatg agtaaacttg gtctgacagt taccaatgct taatcagtga ggcacctatc   5760
tcagcgatct gtctatttcg ttcatccata gttgcctgac tccccgtcgt gtagataact   5820
acgatacggg agggcttacc atctggcccc agtgctgcaa tgataccgcg agacccacgc   5880
tcaccggctc cagatttatc agcaataaac cagccagccg gaagggccga gcgcagaagt   5940
ggtcctgcaa ctttatccgc ctccatccag tctattaatt gttgccggga agctagagta   6000
agtagttcgc cagttaatag tttgcgcaac gttgttgcca ttgctacagg catcgtggtg   6060
tcacgctcgt cgtttggtat ggcttcattc agctccggtt cccaacgatc aaggcgagtt   6120
acatgatccc ccatgttgtg caaaaaagcg gttagctcct tcggtcctcc gatcgttgtc   6180
agaagtaagt tggccgcagt gttatcactc atggttatgg cagcactgca taattctctt   6240
actgtcatgc catccgtaag atgcttttct gtgactggtg agtactcaac caagtcattc   6300
tgagaatagt gtatgcggcg accgagttgc tcttgcccgg cgtcaatacg ggataatacc   6360
gcgccacata gcagaacttt aaaagtgctc atcattggaa aacgttcttc ggggcgaaaa   6420
ctctcaagga tcttaccgct gttgagatcc agttcgatgt aacccactcg tgcacccaac   6480
tgatcttcag catcttttac tttcaccagc gtttctgggt gagcaaaaac aggaaggcaa   6540
aatgccgcaa aaaagggaat aagggcgaca cggaaatgtt gaatactcat actcttcctt   6600
tttcaatatt attgaagcat ttatcagggt tattgtctca tgagcggata catatttgaa   6660
```

-continued

```
tgtatttaga aaaataaaca aataggggtt ccgcgcacat ttccccgaaa agtgccacct   6720

gacgtc                                                               6726
```

<210> SEQ ID NO 49
<211> LENGTH: 6969
<212> TYPE: DNA
<213> ORGANISM: Artificial Sequence
<220> FEATURE:
<223> OTHER INFORMATION: pcDNA3-3XUb-DEVD-Bla construct

<400> SEQUENCE: 49

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccgtcggcg ctgtcggcag cgtcggcgac   1680
gaggtcgacg gcgtcggatc cggggcgtgg ctgcacccag aaacgctggt gaaagtaaaa   1740
gatgctgaag atcagttggg tgcacgagtg ggttacatcg aactggatct caacagcggt   1800
aagatccttg agagttttcg ccccgaagaa cgttttccaa tgatgagcac ttttaaagtt   1860
ctgctatgtg gcgcggtatt atcccgtatt gacgccgggc aagagcaact cggtcgccgc   1920
```

-continued

```
atacactatt ctcagaatga cttggttgag tactcaccag tcacagaaaa gcatcttacg   1980
gatggcatga cagtaagaga attatgcagt gctgccataa ccatgagtga taacactgcg   2040
gccaacttac ttctgacaac gatcggagga ccgaaggagc taaccgcttt tttgcacaac   2100
atgggggatc atgtaactcg ccttgatcgt tgggaaccgg agctgaatga agccatacca   2160
aacgacgagc gtgacaccac gatgcctgta gcaatggcaa caacgttgcg caaactatta   2220
actggcgaac tacttactct agcttcccgg caacaattaa tagactggat ggaggcggat   2280
aaagttgcag gaccacttct gcgctcggcc cttccggctg gctggtttat tgctgataaa   2340
tctggagccg gtgagcgtgg gtctcgcggt atcattgcag cactggggcc agatggtaag   2400
ccctcccgta tcgtagttat ctacacgacg gggagtcagg caactatgga tgaacgaaat   2460
agacagatcg ctgagatagg tgcctcactg attaagcatt ggtaatctag agggccctat   2520
tctatagtgt cacctaaatg ctagagctcg ctgatcagcc tcgactgtgc cttctagttg   2580
ccagccatct gttgtttgcc cctcccccgt gccttccttg accctggaag gtgccactcc   2640
cactgtcctt tcctaataaa atgaggaaat tgcatcgcat tgtctgagta ggtgtcattc   2700
tattctgggg ggtggggtgg ggcaggacag caagggggag gattgggaag acaatagcag   2760
gcatgctggg gatgcggtgg gctctatggc ttctgaggcg gaaagaacca gctggggctc   2820
taggggggtat ccccacgcgc cctgtagcgg cgcattaagc gcggcgggtg tggtggttac   2880
gcgcagcgtg accgctacac ttgccagcgc cctagcgccc gctcctttcg ctttcttccc   2940
ttcctttctc gccacgttcg ccggctttcc ccgtcaagct ctaaatcggg gcatcccttt   3000
agggttccga tttagtgctt tacggcacct cgaccccaaa aaacttgatt agggtgatgg   3060
ttcacgtagt gggccatcgc cctgatagac ggtttttcgc cctttgacgt tggagtccac   3120
gttctttaat agtggactct tgttccaaac tggaacaaca ctcaacccta tctcggtcta   3180
ttcttttgat ttataaggga ttttggggat ttcggcctat tggttaaaaa atgagctgat   3240
ttaacaaaaa tttaacgcga attaattctg tggaatgtgt gtcagttagg gtgtggaaag   3300
tccccaggct ccccaggcag gcagaagtat gcaaagcatg catctcaatt agtcagcaac   3360
caggtgtgga aagtccccag gctccccagc aggcagaagt atgcaaagca tgcatctcaa   3420
ttagtcagca accatagtcc cgcccctaac tccgcccatc ccgcccctaa ctccgcccag   3480
ttccgcccat tctccgcccc atggctgact aatttttttt atttatgcag aggccgaggc   3540
cgcctctgcc tctgagctat tccagaagta gtgaggaggc ttttttggag gcctaggctt   3600
ttgcaaaaag ctcccgggag cttgtatatc cattttcgga tctgatcaag agacaggatg   3660
aggatcgttt cgcatgattg aacaagatgg attgcacgca ggttctccgg ccgcttgggt   3720
ggagaggcta ttcggctatg actgggcaca acagacaatc ggctgctctg atgccgccgt   3780
gttccggctg tcagcgcagg ggcgcccggt tctttttgtc aagaccgacc tgtccggtgc   3840
cctgaatgaa ctgcaggacg aggcagcgcg gctatcgtgg ctggccacga cgggcgttcc   3900
ttgcgcagct gtgctcgacg ttgtcactga agcgggaagg gactggctgc tattgggcga   3960
agtgccgggg caggatctcc tgtcatctca ccttgctcct gccgagaaag tatccatcat   4020
ggctgatgca atgcggcggc tgcatacgct tgatccggct acctgcccat tcgaccacca   4080
agcgaaacat cgcatcgagc gagcacgtac tcggatggaa gccggtcttg tcgatcagga   4140
tgatctggac gaagagcatc aggggctcgc gccagccgaa ctgttcgcca ggctcaaggc   4200
gcgcatgccc gacggcgagg atctcgtcgt gacccatggc gatgcctgct tgccgaatat   4260
catggtggaa aatggccgct tttctggatt catcgactgt ggccggctgg gtgtggcgga   4320
```

-continued ccgctatcag gacatagcgt tggctacccg tgatattgct gaagagcttg gcggcgaatg 4380
ggctgaccgc ttcctcgtgc tttacggtat cgccgctccc gattcgcagc gcatcgcctt 4440
ctatcgcctt cttgacgagt tcttctgagc gggactctgg ggttcgaaat gaccgaccaa 4500
gcgacgccca acctgccatc acgagatttc gattccaccg ccgccttcta tgaaaggttg 4560
ggcttcggaa tcgttttccg ggacgccggc tggatgatcc tccagcgcgg ggatctcatg 4620
ctggagttct tcgcccaccc caacttgttt attgcagctt ataatggtta caaataaagc 4680
aatagcatca caaatttcac aaataaagca tttttttcac tgcattctag ttgtggtttg 4740
tccaaactca tcaatgtatc ttatcatgtc tgtataccgt cgacctctag ctagagcttg 4800
gcgtaatcat ggtcatagct gtttcctgtg tgaaattgtt atccgctcac aattccacac 4860
aacatacgag ccggaagcat aaagtgtaaa gcctggggtg cctaatgagt gagctaactc 4920
acattaattg cgttgcgctc actgcccgct ttccagtcgg gaaacctgtc gtgccagctg 4980
cattaatgaa tcggccaacg cgcggggaga ggcggtttgc gtattgggcg ctcttccgct 5040
tcctcgctca ctgactcgct gcgctcggtc gttcggctgc ggcgagcggt atcagctcac 5100
tcaaaggcgg taatacggtt atccacagaa tcaggggata acgcaggaaa gaacatgtga 5160
gcaaaaggcc agcaaaaggc caggaaccgt aaaaaggccg cgttgctggc gtttttccat 5220
aggctccgcc cccctgacga gcatcacaaa aatcgacgct caagtcagag gtggcgaaac 5280
ccgacaggac tataaagata ccaggcgttt ccccctggaa gctccctcgt gcgctctcct 5340
gttccgaccc tgccgcttac cggatacctg tccgcctttc tcccttcggg aagcgtggcg 5400
ctttctcaat gctcacgctg taggtatctc agttcggtgt aggtcgttcg ctccaagctg 5460
ggctgtgtgc acgaaccccc cgttcagccc gaccgctgcg ccttatccgg taactatcgt 5520
cttgagtcca acccggtaag acacgactta tcgccactgg cagcagccac tggtaacagg 5580
attagcagag cgaggtatgt aggcggtgct acagagttct tgaagtggtg gcctaactac 5640
ggctacacta gaaggacagt atttggtatc tgcgctctgc tgaagccagt taccttcgga 5700
aaaagagttg gtagctcttg atccggcaaa caaaccaccg ctggtagcgg tggttttttt 5760
gtttgcaagc agcagattac gcgcagaaaa aaaggatctc aagaagatcc tttgatcttt 5820
tctacggggt ctgacgctca gtggaacgaa aactcacgtt aagggatttt ggtcatgaga 5880
ttatcaaaaa ggatcttcac ctagatcctt ttaaattaaa aatgaagttt taaatcaatc 5940
taaagtatat atgagtaaac ttggtctgac agttaccaat gcttaatcag tgaggcacct 6000
atctcagcga tctgtctatt tcgttcatcc atagttgcct gactccccgt cgtgtagata 6060
actacgatac gggagggctt accatctggc cccagtgctg caatgatacc gcgagaccca 6120
cgctcaccgg ctccagattt atcagcaata aaccagccag ccggaagggc cgagcgcaga 6180
agtggtcctg caactttatc cgcctccatc cagtctatta attgttgccg ggaagctaga 6240
gtaagtagtt cgccagttaa tagtttgcgc aacgttgttg ccattgctac aggcatcgtg 6300
gtgtcacgct cgtcgtttgg tatggcttca ttcagctccg gttcccaacg atcaaggcga 6360
gttacatgat cccccatgtt gtgcaaaaaa gcggttagct ccttcggtcc tccgatcgtt 6420
gtcagaagta agttggccgc agtgttatca ctcatggtta tggcagcact gcataattct 6480
cttactgtca tgccatccgt aagatgcttt tctgtgactg gtgagtactc aaccaagtca 6540
ttctgagaat agtgtatgcg gcgaccgagt tgctcttgcc cggcgtcaat acgggataat 6600
accgcgccac atagcagaac tttaaaagtg ctcatcattg gaaaacgttc ttcggggcga 6660

-continued aaactctcaa ggatcttacc gctgttgaga tccagttcga tgtaacccac tcgtgcaccc 6720
aactgatctt cagcatcttt tactttcacc agcgtttctg ggtgagcaaa aacaggaagg 6780
caaaatgccg caaaaaaggg aataagggcg acacggaaat gttgaatact catactcttc 6840
ctttttcaat attattgaag catttatcag ggttattgtc tcatgagcgg atacatattt 6900
gaatgtattt agaaaaataa acaaataggg gttccgcgca catttccccg aaaagtgcca 6960
cctgacgtc 6969

<210> SEQ ID NO 50
<211> LENGTH: 7212
<212> TYPE: DNA
<213> ORGANISM: Artificial Sequence
<220> FEATURE:
<223> OTHER INFORMATION: pcDNA3-4XUb-DEVD-Bla construct

<400> SEQUENCE: 50
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgatatc 900
gaattcctgc agcccggggg atctaccatg gaaatcttcg tgaagactct gactggtaag 960
accatcactc tcgaagtgga gccgagtgac accattgaga atgtcaaggc aaagatccaa 1020
gacaaggaag gcatccctcc tgaccagcag aggttgatct ttgctgggaa acagctggaa 1080
gatggacgca ccctgtctga ctacaacatc cagaaagagt ccaccctgca cctggtactc 1140
cgtctcagag gtgtgcacca cggatctacc atggaaatct tcgtgaagac tctgactggt 1200
aagaccatca ctctcgaagt ggagccgagt gacaccattg agaatgtcaa ggcaaagatc 1260
caagacaagg aaggcatccc tcctgaccag cagaggttga tctttgctgg gaaacagctg 1320
gaagatggac gcaccctgtc tgactacaac atccagaaag agtccaccct gcacctggta 1380
ctccgtctca gaggtgtgca ccacggatct accatggaaa tcttcgtgaa gactctgact 1440
ggtaagacca tcactctcga agtggagccg agtgacacca ttgagaatgt caaggcaaag 1500
atccaagaca aggaaggcat ccctcctgac cagcagaggt tgatctttgc tgggaaacag 1560
ctggaagatg gacgcaccct gtctgactac aacatccaga aagagtccac cctgcacctg 1620
gtactccgtc tcagaggtgt gcaccacgga tctaccatgg aaatcttcgt gaagactctg 1680
actggtaaga ccatcactct cgaagtggag ccgagtgaca ccattgagaa tgtcaaggca 1740

-continued

```
aagatccaag acaaggaagg catccctcct gaccagcaga ggttgatctt tgctgggaaa   1800
cagctggaag atggacgcac cctgtctgac tacaacatcc agaaagagtc caccctgcac   1860
ctggtactcc gtctcagagg tgtgcaccac ggatccgtcg gcgctgtcgg cagcgtcggc   1920
gacgaggtcg acggcgtcgg atccggggcg tggctgcacc cagaaacgct ggtgaaagta   1980
aaagatgctg aagatcagtt gggtgcacga gtgggttaca tcgaactgga tctcaacagc   2040
ggtaagatcc ttgagagttt tcgccccgaa gaacgttttc caatgatgag cacttttaaa   2100
gttctgctat gtggcgcggt attatcccgt attgacgccg ggcaagagca actcggtcgc   2160
cgcatacact attctcagaa tgacttggtt gagtactcac cagtcacaga aaagcatctt   2220
acggatggca tgacagtaag agaattatgc agtgctgcca taaccatgag tgataacact   2280
gcggccaact tacttctgac aacgatcgga ggaccgaagg agctaaccgc ttttttgcac   2340
aacatggggg atcatgtaac tcgccttgat cgttgggaac cggagctgaa tgaagccata   2400
ccaaacgacg agcgtgacac cacgatgcct gtagcaatgg caacaacgtt gcgcaaacta   2460
ttaactggcg aactacttac tctagcttcc cggcaacaat taatagactg gatggaggcg   2520
gataaagttg caggaccact tctgcgctcg gcccttccgg ctggctggtt tattgctgat   2580
aaatctggag ccggtgagcg tgggtctcgc ggtatcattg cagcactggg gccagatggt   2640
aagccctccc gtatcgtagt tatctacacg acggggagtc aggcaactat ggatgaacga   2700
aatagacaga tcgctgagat aggtgcctca ctgattaagc attggtaatc tagagggccc   2760
tattctatag tgtcacctaa atgctagagc tcgctgatca gcctcgactg tgccttctag   2820
ttgccagcca tctgttgttt gcccctcccc cgtgccttcc ttgaccctgg aaggtgccac   2880
tcccactgtc ctttcctaat aaaatgagga aattgcatcg cattgtctga gtaggtgtca   2940
ttctattctg gggggtgggg tggggcagga cagcaagggg gaggattggg aagacaatag   3000
caggcatgct ggggatgcgg tgggctctat ggcttctgag gcggaaagaa ccagctgggg   3060
ctctaggggg tatccccacg cgccctgtag cggcgcatta agcgcggcgg gtgtggtggt   3120
tacgcgcagc gtgaccgcta cacttgccag cgccctagcg cccgctcctt tcgctttctt   3180
cccttccttt ctcgccacgt tcgccggctt tccccgtcaa gctctaaatc ggggcatccc   3240
tttagggttc cgatttagtg ctttacggca cctcgacccc aaaaaacttg attagggtga   3300
tggttcacgt agtgggccat cgccctgata gacggttttt cgccctttga cgttggagtc   3360
cacgttcttt aatagtggac tcttgttcca aactggaaca acactcaacc ctatctcggt   3420
ctattctttt gatttataag ggattttggg gatttcggcc tattggttaa aaaatgagct   3480
gatttaacaa aaatttaacg cgaattaatt ctgtggaatg tgtgtcagtt agggtgtgga   3540
aagtccccag gctccccagg caggcagaag tatgcaaagc atgcatctca attagtcagc   3600
aaccaggtgt ggaaagtccc caggctcccc agcaggcaga agtatgcaaa gcatgcatct   3660
caattagtca gcaaccatag tcccgcccct aactccgccc atcccgcccc taactccgcc   3720
cagttccgcc cattctccgc cccatggctg actaattttt tttatttatg cagaggccga   3780
ggccgcctct gcctctgagc tattccagaa gtagtgagga ggcttttttg gaggcctagg   3840
cttttgcaaa aagctcccgg gagcttgtat atccattttc ggatctgatc aagagacagg   3900
atgaggatcg tttcgcatga ttgaacaaga tggattgcac gcaggttctc cggccgcttg   3960
ggtggagagg ctattcggct atgactgggc acaacagaca atcggctgct ctgatgccgc   4020
cgtgttccgg ctgtcagcgc aggggcgccc ggttcttttt gtcaagaccg acctgtccgg   4080
```

-continued

```
tgccctgaat gaactgcagg acgaggcagc gcggctatcg tggctggcca cgacgggcgt   4140
tccttgcgca gctgtgctcg acgttgtcac tgaagcggga agggactggc tgctattggg   4200
cgaagtgccg gggcaggatc tcctgtcatc tcaccttgct cctgccgaga aagtatccat   4260
catggctgat gcaatgcggc ggctgcatac gcttgatccg gctacctgcc cattcgacca   4320
ccaagcgaaa catcgcatcg agcgagcacg tactcggatg gaagccggtc ttgtcgatca   4380
ggatgatctg gacgaagagc atcaggggct cgcgccagcc gaactgttcg ccaggctcaa   4440
ggcgcgcatg cccgacggcg aggatctcgt cgtgacccat ggcgatgcct gcttgccgaa   4500
tatcatggtg gaaaatggcc gcttttctgg attcatcgac tgtggccggc tgggtgtggc   4560
ggaccgctat caggacatag cgttggctac ccgtgatatt gctgaagagc ttggcggcga   4620
atgggctgac cgcttcctcg tgctttacgg tatcgccgct cccgattcgc agcgcatcgc   4680
cttctatcgc cttcttgacg agttcttctg agcgggactc tggggttcga aatgaccgac   4740
caagcgacgc ccaacctgcc atcacgagat ttcgattcca ccgccgcctt ctatgaaagg   4800
ttgggcttcg gaatcgtttt ccgggacgcc ggctggatga tcctccagcg cggggatctc   4860
atgctggagt tcttcgccca ccccaacttg tttattgcag cttataatgg ttacaaataa   4920
agcaatagca tcacaaattt cacaaataaa gcattttttt cactgcattc tagttgtggt   4980
ttgtccaaac tcatcaatgt atcttatcat gtctgtatac cgtcgacctc tagctagagc   5040
ttggcgtaat catggtcata gctgtttcct gtgtgaaatt gttatccgct cacaattcca   5100
cacaacatac gagccggaag cataaagtgt aaagcctggg gtgcctaatg agtgagctaa   5160
ctcacattaa ttgcgttgcg ctcactgccc gctttccagt cgggaaacct gtcgtgccag   5220
ctgcattaat gaatcggcca acgcgcgggg agaggcggtt tgcgtattgg gcgctcttcc   5280
gcttcctcgc tcactgactc gctgcgctcg gtcgttcggc tgcggcgagc ggtatcagct   5340
cactcaaagg cggtaatacg gttatccaca gaatcagggg ataacgcagg aaagaacatg   5400
tgagcaaaag gccagcaaaa ggccaggaac cgtaaaaagg ccgcgttgct ggcgtttttc   5460
cataggctcc gcccccctga cgagcatcac aaaaatcgac gctcaagtca gaggtggcga   5520
aacccgacag gactataaag ataccaggcg tttccccctg gaagctccct cgtgcgctct   5580
cctgttccga ccctgccgct taccggatac ctgtccgcct ttctcccttc gggaagcgtg   5640
gcgctttctc aatgctcacg ctgtaggtat ctcagttcgg tgtaggtcgt tcgctccaag   5700
ctgggctgtg tgcacgaacc ccccgttcag cccgaccgct gcgccttatc cggtaactat   5760
cgtcttgagt ccaacccggt aagacacgac ttatcgccac tggcagcagc cactggtaac   5820
aggattagca gagcgaggta tgtaggcggt gctacagagt tcttgaagtg gtggcctaac   5880
tacggctaca ctagaaggac agtatttggt atctgcgctc tgctgaagcc agttaccttc   5940
ggaaaaagag ttggtagctc ttgatccggc aaacaaacca ccgctggtag cggtggtttt   6000
tttgtttgca agcagcagat tacgcgcaga aaaaaaggat ctcaagaaga tcctttgatc   6060
ttttctacgg ggtctgacgc tcagtggaac gaaaactcac gttaagggat tttggtcatg   6120
agattatcaa aaaggatctt cacctagatc cttttaaatt aaaaatgaag ttttaaatca   6180
atctaaagta tatatgagta aacttggtct gacagttacc aatgcttaat cagtgaggca   6240
cctatctcag cgatctgtct atttcgttca tccatagttg cctgactccc cgtcgtgtag   6300
ataactacga tacgggaggg cttaccatct ggccccagtg ctgcaatgat accgcgagac   6360
ccacgctcac cggctccaga tttatcagca ataaaccagc cagccggaag ggccgagcgc   6420
agaagtggtc ctgcaacttt atccgcctcc atccagtcta ttaattgttg ccgggaagct   6480
```

agagtaagta gttcgccagt taatagtttg cgcaacgttg ttgccattgc tacaggcatc 6540
gtggtgtcac gctcgtcgtt tggtatggct tcattcagct ccggttccca acgatcaagg 6600
cgagttacat gatcccccat gttgtgcaaa aaagcggtta gctccttcgg tcctccgatc 6660
gttgtcagaa gtaagttggc cgcagtgtta tcactcatgg ttatggcagc actgcataat 6720
tctcttactg tcatgccatc cgtaagatgc ttttctgtga ctggtgagta ctcaaccaag 6780
tcattctgag aatagtgtat gcggcgaccg agttgctctt gcccggcgtc aatacgggat 6840
aataccgcgc cacatagcag aactttaaaa gtgctcatca ttggaaaacg ttcttcgggg 6900
cgaaaactct caaggatctt accgctgttg agatccagtt cgatgtaacc cactcgtgca 6960
cccaactgat cttcagcatc ttttactttc accagcgttt ctgggtgagc aaaaacagga 7020
aggcaaaatg ccgcaaaaaa gggaataagg gcgacacgga aatgttgaat actcatactc 7080
ttcctttttc aatattattg aagcatttat cagggttatt gtctcatgag cggatacata 7140
tttgaatgta tttagaaaaa taaacaaata ggggttccgc gcacatttcc ccgaaaagtg 7200
ccacctgacg tc 7212

<210> SEQ ID NO 51
<211> LENGTH: 48
<212> TYPE: DNA
<213> ORGANISM: Artificial Sequence
<220> FEATURE:
<223> OTHER INFORMATION: oligonucleotide cassette

<400> SEQUENCE: 51
gatccgtcgg cgctgtcggc agcgtcggcg acgaggtcgc tggcgtcg 48

<210> SEQ ID NO 52
<211> LENGTH: 48
<212> TYPE: DNA
<213> ORGANISM: Artificial Sequence
<220> FEATURE:
<223> OTHER INFORMATION: oligonucleotide cassette

<400> SEQUENCE: 52
gatccgacgc cagcgacctc gtcgccgacg ctgccgacag cgccgacg 48

<210> SEQ ID NO 53
<211> LENGTH: 6459
<212> TYPE: DNA
<213> ORGANISM: Artificial Sequence
<220> FEATURE:
<223> OTHER INFORMATION: pcDNA3-1XUb-DEVA-Bla construct

<400> SEQUENCE: 53
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540

-continued

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
accatggaga tcttcgtgaa gactctgact ggtaagacca tcactctcga agtggagccg    960
agtgacacca ttgagaatgt caaggcaaag atccaagaca aggaaggcat ccctcctgac   1020
cagcagaggt tgatctttgc tgggaaacag ctggaagatg gacgcaccct gtctgactac   1080
aacatccaga aagagtccac cctgcacctg gtactccgtc tcagaggtgt gcaccacgga   1140
tccgtcggcg ctgtcggcag cgtcggcgac gaggtcgctg gcgtcggatc cggggcgtgg   1200
ctgcacccag aaacgctggt gaaagtaaaa gatgctgaag atcagttggg tgcacgagtg   1260
ggttacatcg aactggatct caacagcggt aagatccttg agagttttcg ccccgaagaa   1320
cgttttccaa tgatgagcac ttttaaagtt ctgctatgtg gcgcggtatt atcccgtatt   1380
gacgccgggc aagagcaact cggtcgccgc atacactatt ctcagaatga cttggttgag   1440
tactcaccag tcacagaaaa gcatcttacg gatggcatga cagtaagaga attatgcagt   1500
gctgccataa ccatgagtga taacactgcg gccaacttac ttctgacaac gatcggagga   1560
ccgaaggagc taaccgcttt tttgcacaac atgggggatc atgtaactcg ccttgatcgt   1620
tgggaaccgg agctgaatga agccatacca aacgacgagc gtgacaccac gatgcctgta   1680
gcaatggcaa caacgttgcg caaactatta actggcgaac tacttactct agcttcccgg   1740
caacaattaa tagactggat ggaggcggat aaagttgcag gaccacttct gcgctcggcc   1800
cttccggctg gctggtttat tgctgataaa tctggagccg gtgagcgtgg gtctcgcggt   1860
atcattgcag cactggggcc agatggtaag ccctcccgta tcgtagttat ctacacgacg   1920
gggagtcagg caactatgga tgaacgaaat agacagatcg ctgagatagg tgcctcactg   1980
attaagcatt ggtaatctag agggccctat tctatagtgt cacctaaatg ctagagctcg   2040
ctgatcagcc tcgactgtgc cttctagttg ccagccatct gttgtttgcc cctcccccgt   2100
gccttccttg accctggaag gtgccactcc cactgtcctt tcctaataaa atgaggaaat   2160
tgcatcgcat tgtctgagta ggtgtcattc tattctgggg ggtggggtgg ggcaggacag   2220
caagggggag gattgggaag acaatagcag gcatgctggg gatgcggtgg gctctatggc   2280
ttctgaggcg gaaagaacca gctggggctc tagggggtat ccccacgcgc cctgtagcgg   2340
cgcattaagc gcggcgggtg tggtggttac gcgcagcgtg accgctacac ttgccagcgc   2400
cctagcgccc gctcctttcg ctttcttccc ttcctttctc gccacgttcg ccggctttcc   2460
ccgtcaagct ctaaatcggg gcatcccttt agggttccga tttagtgctt tacggcacct   2520
cgaccccaaa aaacttgatt agggtgatgg ttcacgtagt gggccatcgc cctgatagac   2580
ggtttttcgc cctttgacgt tggagtccac gttctttaat agtggactct tgttccaaac   2640
tggaacaaca ctcaacccta tctcggtcta ttcttttgat ttataaggga ttttggggat   2700
ttcggcctat tggttaaaaa atgagctgat ttaacaaaaa tttaacgcga attaattctg   2760
tggaatgtgt gtcagttagg gtgtggaaag tccccaggct ccccaggcag gcagaagtat   2820
gcaaagcatg catctcaatt agtcagcaac caggtgtgga aagtccccag gctccccagc   2880
aggcagaagt atgcaaagca tgcatctcaa ttagtcagca accatagtcc cgcccctaac   2940
```

-continued

```
tccgcccatc ccgcccctaa ctccgcccag ttccgcccat tctccgcccc atggctgact   3000
aatttttttt atttatgcag aggccgaggc cgcctctgcc tctgagctat tccagaagta   3060
gtgaggaggc ttttttggag gcctaggctt ttgcaaaaag ctcccgggag cttgtatatc   3120
cattttcgga tctgatcaag agacaggatg aggatcgttt cgcatgattg aacaagatgg   3180
attgcacgca ggttctccgg ccgcttgggt ggagaggcta ttcggctatg actgggcaca   3240
acagacaatc ggctgctctg atgccgccgt gttccggctg tcagcgcagg ggcgcccggt   3300
tctttttgtc aagaccgacc tgtccggtgc cctgaatgaa ctgcaggacg aggcagcgcg   3360
gctatcgtgg ctggccacga cgggcgttcc ttgcgcagct gtgctcgacg ttgtcactga   3420
agcgggaagg gactggctgc tattgggcga agtgccgggg caggatctcc tgtcatctca   3480
ccttgctcct gccgagaaag tatccatcat ggctgatgca atgcggcggc tgcatacgct   3540
tgatccggct acctgcccat tcgaccacca agcgaaacat cgcatcgagc gagcacgtac   3600
tcggatggaa gccggtcttg tcgatcagga tgatctggac gaagagcatc aggggctcgc   3660
gccagccgaa ctgttcgcca ggctcaaggc gcgcatgccc gacggcgagg atctcgtcgt   3720
gacccatggc gatgcctgct tgccgaatat catggtggaa aatggccgct tttctggatt   3780
catcgactgt ggccggctgg gtgtggcgga ccgctatcag gacatagcgt tggctacccg   3840
tgatattgct gaagagcttg gcggcgaatg ggctgaccgc ttcctcgtgc tttacggtat   3900
cgccgctccc gattcgcagc gcatcgcctt ctatcgcctt cttgacgagt tcttctgagc   3960
gggactctgg ggttcgaaat gaccgaccaa gcgacgccca acctgccatc acgagatttc   4020
gattccaccg ccgccttcta tgaaaggttg ggcttcggaa tcgttttccg ggacgccggc   4080
tggatgatcc tccagcgcgg ggatctcatg ctggagttct tcgcccaccc caacttgttt   4140
attgcagctt ataatggtta caaataaagc aatagcatca caaatttcac aaataaagca   4200
tttttttcac tgcattctag ttgtggtttg tccaaactca tcaatgtatc ttatcatgtc   4260
tgtataccgt cgacctctag ctagagcttg gcgtaatcat ggtcatagct gtttcctgtg   4320
tgaaattgtt atccgctcac aattccacac aacatacgag ccggaagcat aaagtgtaaa   4380
gcctggggtg cctaatgagt gagctaactc acattaattg cgttgcgctc actgcccgct   4440
ttccagtcgg gaaacctgtc gtgccagctg cattaatgaa tcggccaacg cgcggggaga   4500
ggcggtttgc gtattgggcg ctcttccgct tcctcgctca ctgactcgct gcgctcggtc   4560
gttcggctgc ggcgagcggt atcagctcac tcaaaggcgg taatacggtt atccacagaa   4620
tcaggggata acgcaggaaa gaacatgtga gcaaaaggcc agcaaaaggc caggaaccgt   4680
aaaaaggccg cgttgctggc gtttttccat aggctccgcc cccctgacga gcatcacaaa   4740
aatcgacgct caagtcagag gtggcgaaac ccgacaggac tataaagata ccaggcgttt   4800
ccccctggaa gctccctcgt gcgctctcct gttccgaccc tgccgcttac cggatacctg   4860
tccgcctttc tcccttcggg aagcgtggcg ctttctcaat gctcacgctg taggtatctc   4920
agttcggtgt aggtcgttcg ctccaagctg ggctgtgtgc acgaaccccc cgttcagccc   4980
gaccgctgcg ccttatccgg taactatcgt cttgagtcca acccggtaag acacgactta   5040
tcgccactgg cagcagccac tggtaacagg attagcagag cgaggtatgt aggcggtgct   5100
acagagttct tgaagtggtg gcctaactac ggctacacta gaaggacagt atttggtatc   5160
tgcgctctgc tgaagccagt taccttcgga aaaagagttg gtagctcttg atccggcaaa   5220
caaaccaccg ctggtagcgg tggttttttt gtttgcaagc agcagattac gcgcagaaaa   5280
```

-continued

```
aaaggatctc aagaagatcc tttgatcttt tctacggggt ctgacgctca gtggaacgaa   5340

aactcacgtt aagggatttt ggtcatgaga ttatcaaaaa ggatcttcac ctagatcctt   5400

ttaaattaaa aatgaagttt taaatcaatc taaagtatat atgagtaaac ttggtctgac   5460

agttaccaat gcttaatcag tgaggcacct atctcagcga tctgtctatt tcgttcatcc   5520

atagttgcct gactccccgt cgtgtagata actacgatac gggagggctt accatctggc   5580

cccagtgctg caatgatacc gcgagaccca cgctcaccgg ctccagattt atcagcaata   5640

aaccagccag ccggaagggc cgagcgcaga agtggtcctg caactttatc cgcctccatc   5700

cagtctatta attgttgccg ggaagctaga gtaagtagtt cgccagttaa tagtttgcgc   5760

aacgttgttg ccattgctac aggcatcgtg gtgtcacgct cgtcgtttgg tatggcttca   5820

ttcagctccg gttcccaacg atcaaggcga gttacatgat cccccatgtt gtgcaaaaaa   5880

gcggttagct ccttcggtcc tccgatcgtt gtcagaagta agttggccgc agtgttatca   5940

ctcatggtta tggcagcact gcataattct cttactgtca tgccatccgt aagatgcttt   6000

tctgtgactg gtgagtactc aaccaagtca ttctgagaat agtgtatgcg gcgaccgagt   6060

tgctcttgcc cggcgtcaat acgggataat accgcgccac atagcagaac tttaaaagtg   6120

ctcatcattg gaaaacgttc ttcggggcga aaactctcaa ggatcttacc gctgttgaga   6180

tccagttcga tgtaacccac tcgtgcaccc aactgatctt cagcatcttt tactttcacc   6240

agcgtttctg ggtgagcaaa aacaggaagg caaaatgccg caaaaaaggg aataagggcg   6300

acacggaaat gttgaatact catactcttc ctttttcaat attattgaag catttatcag   6360

ggttattgtc tcatgagcgg atacatattt gaatgtattt agaaaaataa acaaataggg   6420

gttccgcgca catttccccg aaaagtgcca cctgacgtc                          6459
```

<210> SEQ ID NO 54
<211> LENGTH: 6726
<212> TYPE: DNA
<213> ORGANISM: Artificial Sequence
<220> FEATURE:
<223> OTHER INFORMATION: pcDNA3-2XUb-DEVA-Bla construct

<400> SEQUENCE: 54

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgatatc    900
```

-continued

```
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatcc gtcggcgctg tcggcagcgt cggcgacgag   1440
gtcgctggcg tcggatccgg ggcgtggctg cacccagaaa cgctggtgaa agtaaaagat   1500
gctgaagatc agttgggtgc acgagtgggt tacatcgaac tggatctcaa cagcggtaag   1560
atccttgaga gttttcgccc cgaagaacgt tttccaatga tgagcacttt taaagttctg   1620
ctatgtggcg cggtattatc ccgtattgac gccgggcaag agcaactcgg tcgccgcata   1680
cactattctc agaatgactt ggttgagtac tcaccagtca cagaaaagca tcttacggat   1740
ggcatgacag taagagaatt atgcagtgct gccataacca tgagtgataa cactgcggcc   1800
aacttacttc tgacaacgat cggaggaccg aaggagctaa ccgctttttt gcacaacatg   1860
ggggatcatg taactcgcct tgatcgttgg gaaccggagc tgaatgaagc cataccaaac   1920
gacgagcgtg acaccacgat gcctgtagca atggcaacaa cgttgcgcaa actattaact   1980
ggcgaactac ttactctagc ttcccggcaa caattaatag actggatgga ggcggataaa   2040
gttgcaggac cacttctgcg ctcggccctt ccggctggct ggtttattgc tgataaatct   2100
ggagccggtg agcgtgggtc tcgcggtatc attgcagcac tggggccaga tggtaagccc   2160
tcccgtatcg tagttatcta cacgacgggg agtcaggcaa ctatggatga acgaaataga   2220
cagatcgctg agataggtgc ctcactgatt aagcattggt aatctagagg gccctattct   2280
atagtgtcac ctaaatgcta gagctcgctg atcagcctcg actgtgcctt ctagttgcca   2340
gccatctgtt gtttgcccct cccccgtgcc ttccttgacc ctggaaggtg ccactcccac   2400
tgtcctttcc taataaaatg aggaaattgc atcgcattgt ctgagtaggt gtcattctat   2460
tctggggggt ggggtggggc aggacagcaa gggggaggat tgggaagaca atagcaggca   2520
tgctggggat gcggtgggct ctatggcttc tgaggcggaa agaaccagct ggggctctag   2580
ggggtatccc cacgcgccct gtagcggcgc attaagcgcg gcgggtgtgg tggttacgcg   2640
cagcgtgacc gctacacttg ccagcgccct agcgcccgct cctttcgctt tcttcccttc   2700
ctttctcgcc acgttcgccg gctttccccg tcaagctcta aatcggggca tccctttagg   2760
gttccgattt agtgctttac ggcacctcga ccccaaaaaa cttgattagg gtgatggttc   2820
acgtagtggg ccatcgccct gatagacggt ttttcgccct ttgacgttgg agtccacgtt   2880
ctttaatagt ggactcttgt tccaaactgg aacaacactc aaccctatct cggtctattc   2940
ttttgattta taagggattt tggggatttc ggcctattgg ttaaaaaatg agctgattta   3000
acaaaaattt aacgcgaatt aattctgtgg aatgtgtgtc agttagggtg tggaaagtcc   3060
ccaggctccc caggcaggca gaagtatgca aagcatgcat ctcaattagt cagcaaccag   3120
gtgtggaaag tccccaggct ccccagcagg cagaagtatg caaagcatgc atctcaatta   3180
gtcagcaacc atagtcccgc ccctaactcc gcccatcccg cccctaactc cgcccagttc   3240
```

-continued

```
cgcccattct ccgccccatg gctgactaat tttttttatt tatgcagagg ccgaggccgc   3300

ctctgcctct gagctattcc agaagtagtg aggaggcttt tttggaggcc taggcttttg   3360

caaaaagctc ccgggagctt gtatatccat tttcggatct gatcaagaga caggatgagg   3420

atcgtttcgc atgattgaac aagatggatt gcacgcaggt tctccggccg cttgggtgga   3480

gaggctattc ggctatgact gggcacaaca gacaatcggc tgctctgatg ccgccgtgtt   3540

ccggctgtca gcgcaggggc gcccggttct ttttgtcaag accgacctgt ccggtgccct   3600

gaatgaactg caggacgagg cagcgcggct atcgtggctg gccacgacgg gcgttccttg   3660

cgcagctgtg ctcgacgttg tcactgaagc gggaagggac tggctgctat tgggcgaagt   3720

gccggggcag gatctcctgt catctcacct tgctcctgcc gagaaagtat ccatcatggc   3780

tgatgcaatg cggcggctgc atacgcttga tccggctacc tgcccattcg accaccaagc   3840

gaaacatcgc atcgagcgag cacgtactcg gatggaagcc ggtcttgtcg atcaggatga   3900

tctggacgaa gagcatcagg ggctcgcgcc agccgaactg ttcgccaggc tcaaggcgcg   3960

catgcccgac ggcgaggatc tcgtcgtgac ccatggcgat gcctgcttgc cgaatatcat   4020

ggtggaaaat ggccgctttt ctggattcat cgactgtggc cggctgggtg tggcggaccg   4080

ctatcaggac atagcgttgg ctacccgtga tattgctgaa gagcttggcg gcgaatgggc   4140

tgaccgcttc ctcgtgcttt acggtatcgc cgctcccgat tcgcagcgca tcgccttcta   4200

tcgccttctt gacgagttct tctgagcggg actctggggt tcgaaatgac cgaccaagcg   4260

acgcccaacc tgccatcacg agatttcgat tccaccgccg ccttctatga aaggttgggc   4320

ttcggaatcg ttttccggga cgccggctgg atgatcctcc agcgcgggga tctcatgctg   4380

gagttcttcg cccaccccaa cttgtttatt gcagcttata atggttacaa ataaagcaat   4440

agcatcacaa atttcacaaa taaagcattt ttttcactgc attctagttg tggtttgtcc   4500

aaactcatca atgtatctta tcatgtctgt ataccgtcga cctctagcta gagcttggcg   4560

taatcatggt catagctgtt tcctgtgtga aattgttatc cgctcacaat tccacacaac   4620

atacgagccg gaagcataaa gtgtaaagcc tggggtgcct aatgagtgag ctaactcaca   4680

ttaattgcgt tgcgctcact gcccgctttc cagtcgggaa acctgtcgtg ccagctgcat   4740

taatgaatcg gccaacgcgc ggggagaggc ggtttgcgta ttgggcgctc ttccgcttcc   4800

tcgctcactg actcgctgcg ctcggtcgtt cggctgcggc gagcggtatc agctcactca   4860

aaggcggtaa tacggttatc cacagaatca ggggataacg caggaaagaa catgtgagca   4920

aaaggccagc aaaaggccag gaaccgtaaa aaggccgcgt tgctggcgtt tttccatagg   4980

ctccgccccc ctgacgagca tcacaaaaat cgacgctcaa gtcagaggtg gcgaaacccg   5040

acaggactat aaagatacca ggcgtttccc cctggaagct ccctcgtgcg ctctcctgtt   5100

ccgaccctgc cgcttaccgg atacctgtcc gcctttctcc cttcgggaag cgtggcgctt   5160

tctcaatgct cacgctgtag gtatctcagt tcggtgtagg tcgttcgctc caagctgggc   5220

tgtgtgcacg aaccccccgt tcagcccgac cgctgcgcct tatccggtaa ctatcgtctt   5280

gagtccaacc cggtaagaca cgacttatcg ccactggcag cagccactgg taacaggatt   5340

agcagagcga ggtatgtagg cggtgctaca gagttcttga agtggtggcc taactacggc   5400

tacactagaa ggacagtatt tggtatctgc gctctgctga agccagttac cttcggaaaa   5460

agagttggta gctcttgatc cggcaaacaa accaccgctg gtagcggtgg tttttttgtt   5520

tgcaagcagc agattacgcg cagaaaaaaa ggatctcaag aagatccttt gatcttttct   5580

acggggtctg acgctcagtg gaacgaaaac tcacgttaag ggattttggt catgagatta   5640
```

-continued

```
tcaaaaagga tcttcaccta gatcctttta aattaaaaat gaagttttaa atcaatctaa   5700

agtatatatg agtaaacttg gtctgacagt taccaatgct taatcagtga ggcacctatc   5760

tcagcgatct gtctatttcg ttcatccata gttgcctgac tccccgtcgt gtagataact   5820

acgatacggg agggcttacc atctggcccc agtgctgcaa tgataccgcg agacccacgc   5880

tcaccggctc cagatttatc agcaataaac cagccagccg gaagggccga gcgcagaagt   5940

ggtcctgcaa ctttatccgc ctccatccag tctattaatt gttgccggga agctagagta   6000

agtagttcgc cagttaatag tttgcgcaac gttgttgcca ttgctacagg catcgtggtg   6060

tcacgctcgt cgtttggtat ggcttcattc agctccggtt cccaacgatc aaggcgagtt   6120

acatgatccc ccatgttgtg caaaaaagcg gttagctcct tcggtcctcc gatcgttgtc   6180

agaagtaagt tggccgcagt gttatcactc atggttatgg cagcactgca taattctctt   6240

actgtcatgc catccgtaag atgcttttct gtgactggtg agtactcaac caagtcattc   6300

tgagaatagt gtatgcggcg accgagttgc tcttgcccgg cgtcaatacg ggataatacc   6360

gcgccacata gcagaacttt aaaagtgctc atcattggaa aacgttcttc ggggcgaaaa   6420

ctctcaagga tcttaccgct gttgagatcc agttcgatgt aacccactcg tgcacccaac   6480

tgatcttcag catcttttac tttcaccagc gtttctgggt gagcaaaaac aggaaggcaa   6540

aatgccgcaa aaaagggaat aagggcgaca cggaaatgtt gaatactcat actcttcctt   6600

tttcaatatt attgaagcat ttatcagggt tattgtctca tgagcggata catatttgaa   6660

tgtatttaga aaaataaaca aataggggtt ccgcgcacat ttccccgaaa agtgccacct   6720

gacgtc                                                              6726
```

<210> SEQ ID NO 55
<211> LENGTH: 6969
<212> TYPE: DNA
<213> ORGANISM: Artificial Sequence
<220> FEATURE:
<223> OTHER INFORMATION: pcDNA3-3XUb-DEVA-Bla construct

<400> SEQUENCE: 55

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgatatc    900
```

-continued

```
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccgtcggcg ctgtcggcag cgtcggcgac   1680
gaggtcgctg gcgtcggatc cggggcgtgg ctgcacccag aaacgctggt gaaagtaaaa   1740
gatgctgaag atcagttggg tgcacgagtg ggttacatcg aactggatct caacagcggt   1800
aagatccttg agagttttcg ccccgaagaa cgttttccaa tgatgagcac ttttaaagtt   1860
ctgctatgtg gcgcggtatt atcccgtatt gacgccgggc aagagcaact cggtcgccgc   1920
atacactatt ctcagaatga cttggttgag tactcaccag tcacagaaaa gcatcttacg   1980
gatggcatga cagtaagaga attatgcagt gctgccataa ccatgagtga taacactgcg   2040
gccaacttac ttctgacaac gatcggagga ccgaaggagc taaccgcttt tttgcacaac   2100
atgggggatc atgtaactcg ccttgatcgt tgggaaccgg agctgaatga agccatacca   2160
aacgacgagc gtgacaccac gatgcctgta gcaatggcaa caacgttgcg caaactatta   2220
actggcgaac tacttactct agcttcccgg caacaattaa tagactggat ggaggcggat   2280
aaagttgcag gaccacttct gcgctcggcc cttccggctg gctggtttat tgctgataaa   2340
tctggagccg gtgagcgtgg gtctcgcggt atcattgcag cactggggcc agatggtaag   2400
ccctcccgta tcgtagttat ctacacgacg gggagtcagg caactatgga tgaacgaaat   2460
agacagatcg ctgagatagg tgcctcactg attaagcatt ggtaatctag agggccctat   2520
tctatagtgt cacctaaatg ctagagctcg ctgatcagcc tcgactgtgc cttctagttg   2580
ccagccatct gttgtttgcc cctcccccgt gccttccttg accctggaag gtgccactcc   2640
cactgtcctt tcctaataaa atgaggaaat tgcatcgcat tgtctgagta ggtgtcattc   2700
tattctgggg ggtggggtgg ggcaggacag caagggggag gattgggaag acaatagcag   2760
gcatgctggg gatgcggtgg gctctatggc ttctgaggcg gaaagaacca gctggggctc   2820
taggggggtat ccccacgcgc cctgtagcgg cgcattaagc gcggcgggtg tggtggttac  2880
gcgcagcgtg accgctacac ttgccagcgc cctagcgccc gctcctttcg ctttcttccc   2940
ttcctttctc gccacgttcg ccggctttcc ccgtcaagct ctaaatcggg gcatcccttt   3000
agggttccga tttagtgctt tacggcacct cgaccccaaa aaacttgatt agggtgatgg   3060
ttcacgtagt gggccatcgc cctgatagac ggtttttcgc cctttgacgt tggagtccac   3120
gttctttaat agtggactct tgttccaaac tggaacaaca ctcaacccta tctcggtcta   3180
ttcttttgat ttataaggga ttttggggat ttcggcctat tggttaaaaa atgagctgat   3240
ttaacaaaaa tttaacgcga attaattctg tggaatgtgt gtcagttagg gtgtggaaag   3300
```

-continued

```
tccccaggct ccccaggcag gcagaagtat gcaaagcatg catctcaatt agtcagcaac   3360
caggtgtgga aagtccccag gctccccagc aggcagaagt atgcaaagca tgcatctcaa   3420
ttagtcagca accatagtcc cgcccctaac tccgcccatc ccgcccctaa ctccgcccag   3480
ttccgcccat tctccgcccc atggctgact aatttttttt atttatgcag aggccgaggc   3540
cgcctctgcc tctgagctat tccagaagta gtgaggaggc ttttttggag gcctaggctt   3600
ttgcaaaaag ctcccgggag cttgtatatc cattttcgga tctgatcaag agacaggatg   3660
aggatcgttt cgcatgattg aacaagatgg attgcacgca ggttctccgg ccgcttgggt   3720
ggagaggcta ttcggctatg actgggcaca acagacaatc ggctgctctg atgccgccgt   3780
gttccggctg tcagcgcagg ggcgcccggt tctttttgtc aagaccgacc tgtccggtgc   3840
cctgaatgaa ctgcaggacg aggcagcgcg gctatcgtgg ctggccacga cgggcgttcc   3900
ttgcgcagct gtgctcgacg ttgtcactga agcgggaagg gactggctgc tattgggcga   3960
agtgccgggg caggatctcc tgtcatctca ccttgctcct gccgagaaag tatccatcat   4020
ggctgatgca atgcggcggc tgcatacgct tgatccggct acctgcccat tcgaccacca   4080
agcgaaacat cgcatcgagc gagcacgtac tcggatggaa gccggtcttg tcgatcagga   4140
tgatctggac gaagagcatc aggggctcgc gccagccgaa ctgttcgcca ggctcaaggc   4200
gcgcatgccc gacggcgagg atctcgtcgt gacccatggc gatgcctgct tgccgaatat   4260
catggtggaa aatggccgct tttctggatt catcgactgt ggccggctgg gtgtggcgga   4320
ccgctatcag gacatagcgt tggctacccg tgatattgct gaagagcttg gcggcgaatg   4380
ggctgaccgc ttcctcgtgc tttacggtat cgccgctccc gattcgcagc gcatcgcctt   4440
ctatcgcctt cttgacgagt tcttctgagc gggactctgg ggttcgaaat gaccgaccaa   4500
gcgacgccca acctgccatc acgagatttc gattccaccg ccgccttcta tgaaaggttg   4560
ggcttcggaa tcgttttccg ggacgccggc tggatgatcc tccagcgcgg ggatctcatg   4620
ctggagttct tcgcccaccc caacttgttt attgcagctt ataatggtta caaataaagc   4680
aatagcatca caaatttcac aaataaagca tttttttcac tgcattctag ttgtggtttg   4740
tccaaactca tcaatgtatc ttatcatgtc tgtataccgt cgacctctag ctagagcttg   4800
gcgtaatcat ggtcatagct gtttcctgtg tgaaattgtt atccgctcac aattccacac   4860
aacatacgag ccggaagcat aaagtgtaaa gcctggggtg cctaatgagt gagctaactc   4920
acattaattg cgttgcgctc actgcccgct ttccagtcgg gaaacctgtc gtgccagctg   4980
cattaatgaa tcggccaacg cgcgggggaga ggcggtttgc gtattgggcg ctcttccgct   5040
tcctcgctca ctgactcgct gcgctcggtc gttcggctgc ggcgagcggt atcagctcac   5100
tcaaaggcgg taatacggtt atccacagaa tcaggggata acgcaggaaa gaacatgtga   5160
gcaaaaggcc agcaaaaggc caggaaccgt aaaaaggccg cgttgctggc gtttttccat   5220
aggctccgcc cccctgacga gcatcacaaa aatcgacgct caagtcagag gtggcgaaac   5280
ccgacaggac tataaagata ccaggcgttt ccccctggaa gctccctcgt gcgctctcct   5340
gttccgaccc tgccgcttac cggatacctg tccgcctttc tcccttcggg aagcgtggcg   5400
ctttctcaat gctcacgctg taggtatctc agttcggtgt aggtcgttcg ctccaagctg   5460
ggctgtgtgc acgaaccccc cgttcagccc gaccgctgcg ccttatccgg taactatcgt   5520
cttgagtcca acccggtaag acacgactta tcgccactgg cagcagccac tggtaacagg   5580
attagcagag cgaggtatgt aggcggtgct acagagttct tgaagtggtg gcctaactac   5640
```

-continued

```
ggctacacta gaaggacagt atttggtatc tgcgctctgc tgaagccagt taccttcgga   5700

aaaagagttg gtagctcttg atccggcaaa caaaccaccg ctggtagcgg tggttttttt   5760

gtttgcaagc agcagattac gcgcagaaaa aaaggatctc aagaagatcc tttgatcttt   5820

tctacggggt ctgacgctca gtggaacgaa aactcacgtt aagggatttt ggtcatgaga   5880

ttatcaaaaa ggatcttcac ctagatcctt ttaaattaaa aatgaagttt taaatcaatc   5940

taaagtatat atgagtaaac ttggtctgac agttaccaat gcttaatcag tgaggcacct   6000

atctcagcga tctgtctatt tcgttcatcc atagttgcct gactccccgt cgtgtagata   6060

actacgatac gggagggctt accatctggc cccagtgctg caatgatacc gcgagaccca   6120

cgctcaccgg ctccagattt atcagcaata aaccagccag ccggaagggc cgagcgcaga   6180

agtggtcctg caactttatc cgcctccatc cagtctatta attgttgccg ggaagctaga   6240

gtaagtagtt cgccagttaa tagtttgcgc aacgttgttg ccattgctac aggcatcgtg   6300

gtgtcacgct cgtcgtttgg tatggcttca ttcagctccg gttcccaacg atcaaggcga   6360

gttacatgat cccccatgtt gtgcaaaaaa gcggttagct ccttcggtcc tccgatcgtt   6420

gtcagaagta agttggccgc agtgttatca ctcatggtta tggcagcact gcataattct   6480

cttactgtca tgccatccgt aagatgcttt tctgtgactg gtgagtactc aaccaagtca   6540

ttctgagaat agtgtatgcg gcgaccgagt tgctcttgcc cggcgtcaat acgggataat   6600

accgcgccac atagcagaac tttaaaagtg ctcatcattg gaaaacgttc ttcggggcga   6660

aaactctcaa ggatcttacc gctgttgaga tccagttcga tgtaacccac tcgtgcaccc   6720

aactgatctt cagcatcttt tactttcacc agcgtttctg ggtgagcaaa aacaggaagg   6780

caaaatgccg caaaaaaggg aataagggcg acacggaaat gttgaatact catactcttc   6840

ctttttcaat attattgaag catttatcag ggttattgtc tcatgagcgg atacatattt   6900

gaatgtattt agaaaaataa acaaataggg gttccgcgca catttccccg aaaagtgcca   6960

cctgacgtc                                                           6969
```

<210> SEQ ID NO 56
<211> LENGTH: 7212
<212> TYPE: DNA
<213> ORGANISM: Artificial Sequence
<220> FEATURE:
<223> OTHER INFORMATION: pcDNA3-4XUb-DEVA-Bla construct

<400> SEQUENCE: 56

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720
```

-continued

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tctaccatgg aaatcttcgt gaagactctg   1680
actggtaaga ccatcactct cgaagtggag ccgagtgaca ccattgagaa tgtcaaggca   1740
aagatccaag acaaggaagg catccctcct gaccagcaga ggttgatctt tgctgggaaa   1800
cagctggaag atggacgcac cctgtctgac tacaacatcc agaaagagtc caccctgcac   1860
ctggtactcc gtctcagagg tgtgcaccac ggatccgtcg gcgctgtcgg cagcgtcggc   1920
gacgaggtcg ctggcgtcgg atccggggcg tggctgcacc cagaaacgct ggtgaaagta   1980
aaagatgctg aagatcagtt gggtgcacga gtgggttaca tcgaactgga tctcaacagc   2040
ggtaagatcc ttgagagttt tcgccccgaa gaacgttttc caatgatgag cacttttaaa   2100
gttctgctat gtggcgcggt attatcccgt attgacgccg ggcaagagca actcggtcgc   2160
cgcatacact attctcagaa tgacttggtt gagtactcac cagtcacaga aaagcatctt   2220
acggatggca tgacagtaag agaattatgc agtgctgcca taaccatgag tgataacact   2280
gcggccaact tacttctgac aacgatcgga ggaccgaagg agctaaccgc ttttttgcac   2340
aacatggggg atcatgtaac tcgccttgat cgttgggaac cggagctgaa tgaagccata   2400
ccaaacgacg agcgtgacac cacgatgcct gtagcaatgg caacaacgtt gcgcaaacta   2460
ttaactggcg aactacttac tctagcttcc cggcaacaat taatagactg gatggaggcg   2520
gataaagttg caggaccact tctgcgctcg gcccttccgg ctggctggtt tattgctgat   2580
aaatctggag ccggtgagcg tgggtctcgc ggtatcattg cagcactggg gccagatggt   2640
aagccctccc gtatcgtagt tatctacacg acggggagtc aggcaactat ggatgaacga   2700
aatagacaga tcgctgagat aggtgcctca ctgattaagc attggtaatc tagagggccc   2760
tattctatag tgtcacctaa atgctagagc tcgctgatca gcctcgactg tgccttctag   2820
ttgccagcca tctgttgttt gcccctcccc cgtgccttcc ttgaccctgg aaggtgccac   2880
tcccactgtc ctttcctaat aaaatgagga aattgcatcg cattgtctga gtaggtgtca   2940
ttctattctg gggggtgggg tggggcagga cagcaagggg gaggattggg aagacaatag   3000
caggcatgct ggggatgcgg tgggctctat ggcttctgag gcggaaagaa ccagctgggg   3060
```

-continued

```
ctctaggggg tatccccacg cgccctgtag cggcgcatta agcgcggcgg gtgtggtggt   3120
tacgcgcagc gtgaccgcta cacttgccag cgccctagcg cccgctcctt tcgctttctt   3180
cccttccttt ctcgccacgt tcgccggctt tccccgtcaa gctctaaatc ggggcatccc   3240
tttagggttc cgatttagtg ctttacggca cctcgacccc aaaaaacttg attagggtga   3300
tggttcacgt agtgggccat cgccctgata gacggttttt cgccctttga cgttggagtc   3360
cacgttcttt aatagtggac tcttgttcca aactggaaca acactcaacc ctatctcggt   3420
ctattctttt gatttataag ggattttggg gatttcggcc tattggttaa aaaatgagct   3480
gatttaacaa aaatttaacg cgaattaatt ctgtggaatg tgtgtcagtt agggtgtgga   3540
aagtccccag gctccccagg caggcagaag tatgcaaagc atgcatctca attagtcagc   3600
aaccaggtgt ggaaagtccc caggctcccc agcaggcaga agtatgcaaa gcatgcatct   3660
caattagtca gcaaccatag tcccgcccct aactccgccc atcccgcccc taactccgcc   3720
cagttccgcc cattctccgc cccatggctg actaattttt tttatttatg cagaggccga   3780
ggccgcctct gcctctgagc tattccagaa gtagtgagga ggcttttttg gaggcctagg   3840
cttttgcaaa aagctcccgg gagcttgtat atccattttc ggatctgatc aagagacagg   3900
atgaggatcg tttcgcatga ttgaacaaga tggattgcac gcaggttctc cggccgcttg   3960
ggtggagagg ctattcggct atgactgggc acaacagaca atcggctgct ctgatgccgc   4020
cgtgttccgg ctgtcagcgc aggggcgccc ggttcttttt gtcaagaccg acctgtccgg   4080
tgccctgaat gaactgcagg acgaggcagc gcggctatcg tggctggcca cgacgggcgt   4140
tccttgcgca gctgtgctcg acgttgtcac tgaagcggga agggactggc tgctattggg   4200
cgaagtgccg gggcaggatc tcctgtcatc tcaccttgct cctgccgaga aagtatccat   4260
catggctgat gcaatgcggc ggctgcatac gcttgatccg gctacctgcc cattcgacca   4320
ccaagcgaaa catcgcatcg agcgagcacg tactcggatg gaagccggtc ttgtcgatca   4380
ggatgatctg gacgaagagc atcaggggct cgcgccagcc gaactgttcg ccaggctcaa   4440
ggcgcgcatg cccgacggcg aggatctcgt cgtgacccat ggcgatgcct gcttgccgaa   4500
tatcatggtg gaaaatggcc gcttttctgg attcatcgac tgtggccggc tgggtgtggc   4560
ggaccgctat caggacatag cgttggctac ccgtgatatt gctgaagagc ttggcggcga   4620
atgggctgac cgcttcctcg tgctttacgg tatcgccgct cccgattcgc agcgcatcgc   4680
cttctatcgc cttcttgacg agttcttctg agcgggactc tggggttcga aatgaccgac   4740
caagcgacgc ccaacctgcc atcacgagat ttcgattcca ccgccgcctt ctatgaaagg   4800
ttgggcttcg gaatcgtttt ccgggacgcc ggctggatga tcctccagcg cggggatctc   4860
atgctggagt tcttcgccca ccccaacttg tttattgcag cttataatgg ttacaaataa   4920
agcaatagca tcacaaattt cacaaataaa gcattttttt cactgcattc tagttgtggt   4980
ttgtccaaac tcatcaatgt atcttatcat gtctgtatac cgtcgacctc tagctagagc   5040
ttggcgtaat catggtcata gctgtttcct gtgtgaaatt gttatccgct cacaattcca   5100
cacaacatac gagccggaag cataaagtgt aaagcctggg gtgcctaatg agtgagctaa   5160
ctcacattaa ttgcgttgcg ctcactgccc gctttccagt cgggaaacct gtcgtgccag   5220
ctgcattaat gaatcggcca acgcgcgggg agaggcggtt tgcgtattgg gcgctcttcc   5280
gcttcctcgc tcactgactc gctgcgctcg gtcgttcggc tgcggcgagc ggtatcagct   5340
cactcaaagg cggtaatacg gttatccaca gaatcagggg ataacgcagg aaagaacatg   5400
tgagcaaaag gccagcaaaa ggccaggaac cgtaaaaagg ccgcgttgct ggcgtttttc   5460
```

-continued

```
cataggctcc gccccccctga cgagcatcac aaaaatcgac gctcaagtca gaggtggcga   5520

aacccgacag gactataaag ataccaggcg tttccccctg gaagctccct cgtgcgctct   5580

cctgttccga ccctgccgct taccggatac ctgtccgcct ttctcccttc gggaagcgtg   5640

gcgctttctc aatgctcacg ctgtaggtat ctcagttcgg tgtaggtcgt tcgctccaag   5700

ctgggctgtg tgcacgaacc ccccgttcag cccgaccgct gcgccttatc cggtaactat   5760

cgtcttgagt ccaacccggt aagacacgac ttatcgccac tggcagcagc cactggtaac   5820

aggattagca gagcgaggta tgtaggcggt gctacagagt tcttgaagtg gtggcctaac   5880

tacggctaca ctagaaggac agtatttggt atctgcgctc tgctgaagcc agttaccttc   5940

ggaaaaagag ttggtagctc ttgatccggc aaacaaacca ccgctggtag cggtggtttt   6000

tttgtttgca agcagcagat tacgcgcaga aaaaaaggat ctcaagaaga tcctttgatc   6060

ttttctacgg ggtctgacgc tcagtggaac gaaaactcac gttaagggat tttggtcatg   6120

agattatcaa aaaggatctt cacctagatc cttttaaatt aaaaatgaag ttttaaatca   6180

atctaaagta tatatgagta aacttggtct gacagttacc aatgcttaat cagtgaggca   6240

cctatctcag cgatctgtct atttcgttca tccatagttg cctgactccc cgtcgtgtag   6300

ataactacga tacgggaggg cttaccatct ggccccagtg ctgcaatgat accgcgagac   6360

ccacgctcac cggctccaga tttatcagca ataaaccagc cagccggaag ggccgagcgc   6420

agaagtggtc ctgcaacttt atccgcctcc atccagtcta ttaattgttg ccgggaagct   6480

agagtaagta gttcgccagt taatagtttg cgcaacgttg ttgccattgc tacaggcatc   6540

gtggtgtcac gctcgtcgtt tggtatggct tcattcagct ccggttccca acgatcaagg   6600

cgagttacat gatcccccat gttgtgcaaa aaagcggtta gctccttcgg tcctccgatc   6660

gttgtcagaa gtaagttggc cgcagtgtta tcactcatgg ttatggcagc actgcataat   6720

tctcttactg tcatgccatc cgtaagatgc ttttctgtga ctggtgagta ctcaaccaag   6780

tcattctgag aatagtgtat gcggcgaccg agttgctctt gcccggcgtc aatacgggat   6840

aataccgcgc cacatagcag aactttaaaa gtgctcatca ttggaaaacg ttcttcgggg   6900

cgaaaactct caaggatctt accgctgttg agatccagtt cgatgtaacc cactcgtgca   6960

cccaactgat cttcagcatc ttttactttc accagcgttt ctgggtgagc aaaaacagga   7020

aggcaaaatg ccgcaaaaaa gggaataagg gcgacacgga aatgttgaat actcatactc   7080

ttcctttttc aatattattg aagcatttat cagggttatt gtctcatgag cggatacata   7140

tttgaatgta tttagaaaaa taaacaaata ggggttccgc gcacatttcc ccgaaaagtg   7200

ccacctgacg tc                                                        7212
```

<210> SEQ ID NO 57
<211> LENGTH: 1095
<212> TYPE: DNA
<213> ORGANISM: Human rhinovirus 14

<400> SEQUENCE: 57

```
ttgggtcgtg cagcttgtgt gcatgtaact gaaatacaaa acaaagatgc tactggaata     60

gataatcaca gagaagcaaa attgttcaat gattggaaaa tcaacctgtc cagccttgtc    120

caacttagaa agaaactgga actcttcact tatgttaggt ttgattctga gtataccata    180

ctggccactg catctcaacc tgattcagca aactattcaa gcaatttggt ggtccaagcc    240

atgtatgttc cacatggtgc ccgaaatcc aaaaagagtgg gcgattacac atggcaaagt    300
```

-continued

```
gcttcaaacc ccagtgtatt cttcaaggtg ggggatacat caaggtttag tgtgccttat    360

gtaggattgg catcagcata taattgtttt tatgatggtt actcacatga tgatgcagaa    420

actcagtatg gcataactgt tctaaaccat atgggtagta tggcattcag aatagtaaat    480

gaacatgatg aacacaaaac tcttgtcaag atcagagttt atcacagggc aaagctcgtt    540

gaagcatgga ttccaagagc acccagagca ctaccctaca catcaatagg gcgcacaaat    600

tatcctaaga atacagaacc agtaattaag aagaggaaag gtgacattaa atcctatggt    660

ttaggaccta ggtacggtgg gatttataca tcaaatgtta aaataatgaa ttaccacttg    720

atgacaccag aagaccacca taatctgata gcaccctatc caaatagaga tttagcaata    780

gtctcaacag gaggacatgg tgcagaaaca ataccacact gtaaccgtac atcaggtgtt    840

tactattcca catattacag aaagtattac cccataattt gcgaaaagcc caccaacatc    900

tggattgaag gaagccctta ttacccaagt agatttcaag caggagtgat gaaaggggtt    960

gggccggcag agctaggaga ctgcggtggg attttgagat gcatacatgg tcccattgga   1020

ttgttaacag ctgaaggtag tggatatgtt tgttttgctg acatacgaca gttggagtgt   1080

atcgcagagg aacag                                                   1095
```

<210> SEQ ID NO 58
<211> LENGTH: 29
<212> TYPE: DNA
<213> ORGANISM: Artificial Sequence
<220> FEATURE:
<223> OTHER INFORMATION: oligonucleotide for RT-PCR

<400> SEQUENCE: 58

```
taggatcctt gggtcgtgca gcttgtgtg                                      29
```

<210> SEQ ID NO 59
<211> LENGTH: 29
<212> TYPE: DNA
<213> ORGANISM: Artificial Sequence
<220> FEATURE:
<223> OTHER INFORMATION: oligonucleotide for RT-PCR

<400> SEQUENCE: 59

```
aaggatccct gttcctctgc catacactc                                      29
```

<210> SEQ ID NO 60
<211> LENGTH: 8022
<212> TYPE: DNA
<213> ORGANISM: Artificial Sequence
<220> FEATURE:
<223> OTHER INFORMATION: pcDNA3-3XUb-Bla HRV 14 construct

<400> SEQUENCE: 60

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540
```

-continued

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccttgggtc gtgcagcttg tgtgcatgta   1680
actgaaatac aaaacaaaga tgctactgga atagataatc acagagaagc aaaattgttc   1740
aatgattgga aatcaacct gtccagcctt gtccaactta gaaagaaact ggaactcttc   1800
acttatgtta ggtttgattc tgagtatacc atactggcca ctgcatctca acctgattca   1860
gcaaactatt caagcaattt ggtggtccaa gccatgtatg ttccacatgg tgccccgaaa   1920
tccaaaagag tgggcgatta cacatggcaa agtgcttcaa accccagtgt attcttcaag   1980
gtgggggata catcaaggtt tagtgtgcct tatgtaggat tggcatcagc atataattgt   2040
ttttatgatg gttactcaca tgatgatgca gaaactcagt atggcataac tgttctaaac   2100
catatgggta gtatggcatt cagaatagta aatgaacatg atgaacacaa aactcttgtc   2160
aagatcagag tttatcacag ggcaaagctc gttgaagcat ggattccaag agcacccaga   2220
gcactaccct acacatcaat agggcgcaca aattatccta agaatacaga accagtaatt   2280
aagaagagga aaggtgacat taaatcctat ggtttaggac ctaggtacgg tgggatttat   2340
acatcaaatg ttaaaataat gaattaccac ttgatgacac cagaagacca ccataatctg   2400
atagcaccct atccaaatag agatttagca atagtctcaa caggaggaca tggtgcagaa   2460
acaataccac actgtaaccg tacatcaggt gtttactatt ccacatatta cagaaagtat   2520
taccccataa tttgcgaaaa gcccaccaac atctggattg aaggaagccc ttattaccca   2580
agtagatttc aagcaggagt gatgaaaggg gttgggccgg cagagctagg agactgcggt   2640
gggattttga gatgcataca tggtcccatt ggattgttaa cagctgaagg tagtggatat   2700
gtttgttttg ctgacatacg acagttggag tgtatcgcag aggaacaggg atccggggcg   2760
tggctgcacc cagaaacgct ggtgaaagta aaagatgctg aagatcagtt gggtgcacga   2820
gtgggttaca tcgaactgga tctcaacagc ggtaagatcc ttgagagttt tcgccccgaa   2880
```

-continued

```
gaacgttttc caatgatgag cacttttaaa gttctgctat gtggcgcggt attatcccgt   2940
attgacgccg ggcaagagca actcggtcgc cgcatacact attctcagaa tgacttggtt   3000
gagtactcac cagtcacaga aaagcatctt acggatggca tgacagtaag agaattatgc   3060
agtgctgcca taaccatgag tgataacact gcggccaact tacttctgac aacgatcgga   3120
ggaccgaagg agctaaccgc ttttttgcac aacatggggg atcatgtaac tcgccttgat   3180
cgttgggaac cggagctgaa tgaagccata ccaaacgacg agcgtgacac cacgatgcct   3240
gtagcaatgg caacaacgtt gcgcaaacta ttaactggcg aactacttac tctagcttcc   3300
cggcaacaat taatagactg gatggaggcg gataaagttg caggaccact tctgcgctcg   3360
gcccttccgg ctggctggtt tattgctgat aaatctggag ccggtgagcg tgggtctcgc   3420
ggtatcattg cagcactggg gccagatggt aagccctccc gtatcgtagt tatctacacg   3480
acggggagtc aggcaactat ggatgaacga aatagacaga tcgctgagat aggtgcctca   3540
ctgattaagc attggtaatc tagagggccc tattctatag tgtcacctaa atgctagagc   3600
tcgctgatca gcctcgactg tgccttctag ttgccagcca tctgttgttt gcccctcccc   3660
cgtgccttcc ttgaccctgg aaggtgccac tcccactgtc ctttcctaat aaaatgagga   3720
aattgcatcg cattgtctga gtaggtgtca ttctattctg gggggtgggg tggggcagga   3780
cagcaagggg gaggattggg aagacaatag caggcatgct ggggatgcgg tgggctctat   3840
ggcttctgag gcggaaagaa ccagctgggg ctctaggggg tatccccacg cgccctgtag   3900
cggcgcatta agcgcggcgg gtgtggtggt tacgcgcagc gtgaccgcta cacttgccag   3960
cgccctagcg cccgctcctt tcgctttctt cccttccttt ctcgccacgt tcgccggctt   4020
tccccgtcaa gctctaaatc ggggcatccc tttagggttc cgatttagtg ctttacggca   4080
cctcgacccc aaaaaacttg attagggtga tggttcacgt agtgggccat cgccctgata   4140
gacggttttt cgccctttga cgttggagtc cacgttcttt aatagtggac tcttgttcca   4200
aactggaaca acactcaacc ctatctcggt ctattctttt gatttataag ggattttggg   4260
gatttcggcc tattggttaa aaaatgagct gatttaacaa aaatttaacg cgaattaatt   4320
ctgtggaatg tgtgtcagtt agggtgtgga aagtccccag gctccccagg caggcagaag   4380
tatgcaaagc atgcatctca attagtcagc aaccaggtgt ggaaagtccc caggctcccc   4440
agcaggcaga agtatgcaaa gcatgcatct caattagtca gcaaccatag tcccgcccct   4500
aactccgccc atcccgcccc taactccgcc cagttccgcc cattctccgc cccatggctg   4560
actaattttt tttatttatg cagaggccga ggccgcctct gcctctgagc tattccagaa   4620
gtagtgagga ggcttttttg gaggcctagg cttttgcaaa aagctcccgg gagcttgtat   4680
atccattttc ggatctgatc aagagacagg atgaggatcg tttcgcatga ttgaacaaga   4740
tggattgcac gcaggttctc cggccgcttg ggtggagagg ctattcggct atgactgggc   4800
acaacagaca atcggctgct ctgatgccgc cgtgttccgg ctgtcagcgc aggggcgccc   4860
ggttcttttt gtcaagaccg acctgtccgg tgccctgaat gaactgcagg acgaggcagc   4920
gcggctatcg tggctggcca cgacgggcgt tccttgcgca gctgtgctcg acgttgtcac   4980
tgaagcggga agggactggc tgctattggg cgaagtgccg gggcaggatc tcctgtcatc   5040
tcaccttgct cctgccgaga aagtatccat catggctgat gcaatgcggc ggctgcatac   5100
gcttgatccg gctacctgcc cattcgacca ccaagcgaaa catcgcatcg agcgagcacg   5160
tactcggatg gaagccggtc ttgtcgatca ggatgatctg gacgaagagc atcaggggct   5220
cgcgccagcc gaactgttcg ccaggctcaa ggcgcgcatg cccgacggcg aggatctcgt   5280
```

-continued

```
cgtgacccat ggcgatgcct gcttgccgaa tatcatggtg gaaaatggcc gcttttctgg   5340
attcatcgac tgtggccggc tgggtgtggc ggaccgctat caggacatag cgttggctac   5400
ccgtgatatt gctgaagagc ttggcggcga atgggctgac cgcttcctcg tgctttacgg   5460
tatcgccgct cccgattcgc agcgcatcgc cttctatcgc cttcttgacg agttcttctg   5520
agcgggactc tggggttcga aatgaccgac caagcgacgc ccaacctgcc atcacgagat   5580
ttcgattcca ccgccgcctt ctatgaaagg ttgggcttcg gaatcgtttt ccgggacgcc   5640
ggctggatga tcctccagcg cggggatctc atgctggagt tcttcgccca ccccaacttg   5700
tttattgcag cttataatgg ttacaaataa agcaatagca tcacaaattt cacaaataaa   5760
gcattttttt cactgcattc tagttgtggt ttgtccaaac tcatcaatgt atcttatcat   5820
gtctgtatac cgtcgacctc tagctagagc ttggcgtaat catggtcata gctgtttcct   5880
gtgtgaaatt gttatccgct cacaattcca cacaacatac gagccggaag cataaagtgt   5940
aaagcctggg gtgcctaatg agtgagctaa ctcacattaa ttgcgttgcg ctcactgccc   6000
gctttccagt cgggaaacct gtcgtgccag ctgcattaat gaatcggcca acgcgcgggg   6060
agaggcggtt tgcgtattgg gcgctcttcc gcttcctcgc tcactgactc gctgcgctcg   6120
gtcgttcggc tgcggcgagc ggtatcagct cactcaaagg cggtaatacg gttatccaca   6180
gaatcagggg ataacgcagg aaagaacatg tgagcaaaag gccagcaaaa ggccaggaac   6240
cgtaaaaagg ccgcgttgct ggcgtttttc cataggctcc gcccccctga cgagcatcac   6300
aaaaatcgac gctcaagtca gaggtggcga aacccgacag gactataaag ataccaggcg   6360
tttccccctg gaagctccct cgtgcgctct cctgttccga ccctgccgct taccggatac   6420
ctgtccgcct ttctcccttc gggaagcgtg gcgctttctc aatgctcacg ctgtaggtat   6480
ctcagttcgg tgtaggtcgt tcgctccaag ctgggctgtg tgcacgaacc ccccgttcag   6540
cccgaccgct gcgccttatc cggtaactat cgtcttgagt ccaacccggt aagacacgac   6600
ttatcgccac tggcagcagc cactggtaac aggattagca gagcgaggta tgtaggcggt   6660
gctacagagt tcttgaagtg gtggcctaac tacggctaca ctagaaggac agtatttggt   6720
atctgcgctc tgctgaagcc agttaccttc ggaaaaagag ttggtagctc ttgatccggc   6780
aaacaaacca ccgctggtag cggtggtttt tttgtttgca agcagcagat tacgcgcaga   6840
aaaaaaggat ctcaagaaga tcctttgatc ttttctacgg ggtctgacgc tcagtggaac   6900
gaaaactcac gttaagggat tttggtcatg agattatcaa aaaggatctt cacctagatc   6960
cttttaaatt aaaaatgaag ttttaaatca atctaaagta tatatgagta aacttggtct   7020
gacagttacc aatgcttaat cagtgaggca cctatctcag cgatctgtct atttcgttca   7080
tccatagttg cctgactccc cgtcgtgtag ataactacga tacgggaggg cttaccatct   7140
ggccccagtg ctgcaatgat accgcgagac ccacgctcac cggctccaga tttatcagca   7200
ataaaccagc cagccggaag ggccgagcgc agaagtggtc ctgcaacttt atccgcctcc   7260
atccagtcta ttaattgttg ccgggaagct agagtaagta gttcgccagt taatagtttg   7320
cgcaacgttg ttgccattgc tacaggcatc gtggtgtcac gctcgtcgtt tggtatggct   7380
tcattcagct ccggttccca acgatcaagg cgagttacat gatcccccat gttgtgcaaa   7440
aaagcggtta gctccttcgg tcctccgatc gttgtcagaa gtaagttggc cgcagtgtta   7500
tcactcatgg ttatggcagc actgcataat tctcttactg tcatgccatc cgtaagatgc   7560
ttttctgtga ctggtgagta ctcaaccaag tcattctgag aatagtgtat gcggcgaccg   7620
```

-continued agttgctctt gcccggcgtc aatacgggat aataccgcgc cacatagcag aactttaaaa 7680
gtgctcatca ttggaaaacg ttcttcgggg cgaaaactct caaggatctt accgctgttg 7740
agatccagtt cgatgtaacc cactcgtgca cccaactgat cttcagcatc ttttactttc 7800
accagcgttt ctgggtgagc aaaaacagga aggcaaaatg ccgcaaaaaa gggaataagg 7860
gcgacacgga aatgttgaat actcatactc ttcctttttc aatattattg aagcatttat 7920
cagggttatt gtctcatgag cggatacata tttgaatgta tttagaaaaa taaacaaata 7980
ggggttccgc gcacatttcc ccgaaaagtg ccacctgacg tc 8022

<210> SEQ ID NO 61
<211> LENGTH: 636
<212> TYPE: DNA
<213> ORGANISM: Human rhinovirus 16

<400> SEQUENCE: 61
atgggaactt tgtgttcgcg tattgtgacc agtgagcaat tacacaaagt caaagtggta 60
acaaggatat atcacaaagc caaacacacc aaagcttggt gcccaagacc acccagagct 120
gttcaatact cacatacaca taccaccaac tacaaattga gttcagaagt acacaatgat 180
gtggctataa gacctagaac aaatctaaca actgttgggc ctagtgacat gtatgtgcat 240
gttggtaatc taatatacag aaatctacat ttatttaact ctgacataca tgattccatt 300
ttagtgtctt attcatcaga tttaatcata taccgaacaa gcacacaagg tgatggttat 360
attccaacat gtaattgcac tgaagctaca tattactgca aacacaaaaa caggtactac 420
ccaattaatg tcacacctca tgactggtat gagatacaag agagtgaata ttatccaaaa 480
catatccagt acaatttact aataggtgaa ggaccatgtg aaccaggtga ttgtggtggg 540
aaattattat gcaaacatgg agtgataggt attattacag caggtggtga gggccatgtt 600
gcattcatag atcttagaca ctttcactgt gctgaa 636

<210> SEQ ID NO 62
<211> LENGTH: 29
<212> TYPE: DNA
<213> ORGANISM: Artificial Sequence
<220> FEATURE:
<223> OTHER INFORMATION: oligonucleotide for PCR

<400> SEQUENCE: 62
aaggatccat gggaactttg tgttcgcgt 29

<210> SEQ ID NO 63
<211> LENGTH: 31
<212> TYPE: DNA
<213> ORGANISM: Artificial Sequence
<220> FEATURE:
<223> OTHER INFORMATION: oligonucleotide for PCR

<400> SEQUENCE: 63
ttggatcctt cttcagcaca gtgaaagtgt c 31

<210> SEQ ID NO 64
<211> LENGTH: 7563
<212> TYPE: DNA
<213> ORGANISM: Artificial Sequence
<220> FEATURE:
<223> OTHER INFORMATION: pcDNA3-3XUb-Bla HRV16 construct

<400> SEQUENCE: 64
gacggatcgg gagatctccc gatcccctat ggtcgactct cagtacaatc tgctctgatg 60

-continued

```
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccatgggaa ctttgtgttc gcgtattgtg   1680
accagtgagc aattacacaa agtcaaagtg gtaacaagga tatatcacaa agccaaacac   1740
accaaagctt ggtgcccaag accacccaga gctgttcaat actcacatac acataccacc   1800
aactacaaat tgagttcaga agtacacaat gatgtggcta taagacctag aacaaatcta   1860
acaactgttg ggcctagtga catgtatgtg catgttggta atctaatata cagaaatcta   1920
catttattta actctgacat acatgattcc attttagtgt cttattcatc agatttaatc   1980
atataccgaa caagcacaca aggtgatggt tatattccaa catgtaattg cactgaagct   2040
acatattact gcaaacacaa aaacaggtac tacccaatta atgtcacacc tcatgactgg   2100
tatgagatac aagagagtga atattatcca aaacatatcc agtacaattt actaataggt   2160
gaaggaccat gtgaaccagg tgattgtggt gggaaattat tatgcaaaca tggagtgata   2220
ggtattatta cagcaggtgg tgagggccat gttgcattca tagatcttag acactttcac   2280
tgtgctgaag gatccggggc gtggctgcac ccagaaacgc tggtgaaagt aaaagatgct   2340
gaagatcagt tgggtgcacg agtgggttac atcgaactgg atctcaacag cggtaagatc   2400
```

-continued

```
cttgagagtt ttcgccccga agaacgtttt ccaatgatga gcacttttaa agttctgcta   2460
tgtggcgcgg tattatcccg tattgacgcc gggcaagagc aactcggtcg ccgcatacac   2520
tattctcaga atgacttggt tgagtactca ccagtcacag aaaagcatct tacggatggc   2580
atgacagtaa gagaattatg cagtgctgcc ataaccatga gtgataacac tgcggccaac   2640
ttacttctga caacgatcgg aggaccgaag gagctaaccg cttttttgca caacatgggg   2700
gatcatgtaa ctcgccttga tcgttgggaa ccggagctga atgaagccat accaaacgac   2760
gagcgtgaca ccacgatgcc tgtagcaatg gcaacaacgt tgcgcaaact attaactggc   2820
gaactactta ctctagcttc ccggcaacaa ttaatagact ggatggaggc ggataaagtt   2880
gcaggaccac ttctgcgctc ggcccttccg gctggctggt ttattgctga taaatctgga   2940
gccggtgagc gtgggtctcg cggtatcatt gcagcactgg ggccagatgg taagccctcc   3000
cgtatcgtag ttatctacac gacggggagt caggcaacta tggatgaacg aaatagacag   3060
atcgctgaga taggtgcctc actgattaag cattggtaat ctagagggcc ctattctata   3120
gtgtcaccta aatgctagag ctcgctgatc agcctcgact gtgccttcta gttgccagcc   3180
atctgttgtt tgcccctccc ccgtgccttc cttgaccctg gaaggtgcca ctcccactgt   3240
cctttcctaa taaaatgagg aaattgcatc gcattgtctg agtaggtgtc attctattct   3300
ggggggtggg gtggggcagg acagcaaggg ggaggattgg gaagacaata gcaggcatgc   3360
tggggatgcg gtgggctcta tggcttctga ggcggaaaga accagctggg gctctagggg   3420
gtatccccac gcgccctgta gcggcgcatt aagcgcggcg ggtgtggtgg ttacgcgcag   3480
cgtgaccgct acacttgcca gcgccctagc gcccgctcct ttcgctttct tcccttcctt   3540
tctcgccacg ttcgccggct ttccccgtca agctctaaat cggggcatcc ctttagggtt   3600
ccgatttagt gctttacggc acctcgaccc caaaaaactt gattagggtg atggttcacg   3660
tagtgggcca tcgccctgat agacggtttt tcgccctttg acgttggagt ccacgttctt   3720
taatagtgga ctcttgttcc aaactggaac aacactcaac cctatctcgg tctattcttt   3780
tgatttataa gggattttgg ggatttcggc ctattggtta aaaaatgagc tgatttaaca   3840
aaaatttaac gcgaattaat tctgtggaat gtgtgtcagt tagggtgtgg aaagtcccca   3900
ggctccccag gcaggcagaa gtatgcaaag catgcatctc aattagtcag caaccaggtg   3960
tggaaagtcc ccaggctccc cagcaggcag aagtatgcaa agcatgcatc tcaattagtc   4020
agcaaccata gtcccgcccc taactccgcc catcccgccc ctaactccgc ccagttccgc   4080
ccattctccg ccccatggct gactaatttt ttttatttat gcagaggccg aggccgcctc   4140
tgcctctgag ctattccaga agtagtgagg aggctttttt ggaggcctag gcttttgcaa   4200
aaagctcccg ggagcttgta tatccatttt cggatctgat caagagacag gatgaggatc   4260
gtttcgcatg attgaacaag atggattgca cgcaggttct ccggccgctt gggtggagag   4320
gctattcggc tatgactggg cacaacagac aatcggctgc tctgatgccg ccgtgttccg   4380
gctgtcagcg caggggcgcc cggttctttt tgtcaagacc gacctgtccg gtgccctgaa   4440
tgaactgcag gacgaggcag cgcggctatc gtggctggcc acgacgggcg ttccttgcgc   4500
agctgtgctc gacgttgtca ctgaagcggg aagggactgg ctgctattgg gcgaagtgcc   4560
ggggcaggat ctcctgtcat ctcaccttgc tcctgccgag aaagtatcca tcatggctga   4620
tgcaatgcgg cggctgcata cgcttgatcc ggctacctgc ccattcgacc accaagcgaa   4680
acatcgcatc gagcgagcac gtactcggat ggaagccggt cttgtcgatc aggatgatct   4740
ggacgaagag catcaggggc tcgcgccagc cgaactgttc gccaggctca aggcgcgcat   4800
```

-continued

```
gcccgacggc gaggatctcg tcgtgaccca tggcgatgcc tgcttgccga atatcatggt   4860
ggaaaatggc cgcttttctg gattcatcga ctgtggccgg ctgggtgtgg cggaccgcta   4920
tcaggacata gcgttggcta cccgtgatat tgctgaagag cttggcggcg aatgggctga   4980
ccgcttcctc gtgctttacg gtatcgccgc tcccgattcg cagcgcatcg ccttctatcg   5040
ccttcttgac gagttcttct gagcgggact ctggggttcg aaatgaccga ccaagcgacg   5100
cccaacctgc catcacgaga tttcgattcc accgccgcct tctatgaaag gttgggcttc   5160
ggaatcgttt tccgggacgc cggctggatg atcctccagc gcggggatct catgctggag   5220
ttcttcgccc accccaactt gtttattgca gcttataatg gttacaaata aagcaatagc   5280
atcacaaatt tcacaaataa agcatttttt tcactgcatt ctagttgtgg tttgtccaaa   5340
ctcatcaatg tatcttatca tgtctgtata ccgtcgacct ctagctagag cttggcgtaa   5400
tcatggtcat agctgtttcc tgtgtgaaat tgttatccgc tcacaattcc acacaacata   5460
cgagccggaa gcataaagtg taaagcctgg ggtgcctaat gagtgagcta actcacatta   5520
attgcgttgc gctcactgcc cgctttccag tcgggaaacc tgtcgtgcca gctgcattaa   5580
tgaatcggcc aacgcgcggg gagaggcggt ttgcgtattg ggcgctcttc cgcttcctcg   5640
ctcactgact cgctgcgctc ggtcgttcgg ctgcggcgag cggtatcagc tcactcaaag   5700
gcggtaatac ggttatccac agaatcaggg gataacgcag gaaagaacat gtgagcaaaa   5760
ggccagcaaa aggccaggaa ccgtaaaaag gccgcgttgc tggcgttttt ccataggctc   5820
cgcccccctg acgagcatca caaaaatcga cgctcaagtc agaggtggcg aaacccgaca   5880
ggactataaa gataccaggc gtttccccct ggaagctccc tcgtgcgctc tcctgttccg   5940
accctgccgc ttaccggata cctgtccgcc tttctccctt cgggaagcgt ggcgctttct   6000
caatgctcac gctgtaggta tctcagttcg gtgtaggtcg ttcgctccaa gctgggctgt   6060
gtgcacgaac cccccgttca gcccgaccgc tgcgccttat ccggtaacta tcgtcttgag   6120
tccaacccgg taagacacga cttatcgcca ctggcagcag ccactggtaa caggattagc   6180
agagcgaggt atgtaggcgg tgctacagag ttcttgaagt ggtggcctaa ctacggctac   6240
actagaagga cagtatttgg tatctgcgct ctgctgaagc cagttacctt cggaaaaaga   6300
gttggtagct cttgatccgg caaacaaacc accgctggta gcggtggttt ttttgtttgc   6360
aagcagcaga ttacgcgcag aaaaaaagga tctcaagaag atcctttgat cttttctacg   6420
gggtctgacg ctcagtggaa cgaaaactca cgttaaggga ttttggtcat gagattatca   6480
aaaaggatct tcacctagat ccttttaaat taaaaatgaa gttttaaatc aatctaaagt   6540
atatatgagt aaacttggtc tgacagttac caatgcttaa tcagtgaggc acctatctca   6600
gcgatctgtc tatttcgttc atccatagtt gcctgactcc ccgtcgtgta gataactacg   6660
atacgggagg gcttaccatc tggccccagt gctgcaatga taccgcgaga cccacgctca   6720
ccggctccag atttatcagc aataaaccag ccagccggaa gggccgagcg cagaagtggt   6780
cctgcaactt tatccgcctc catccagtct attaattgtt gccgggaagc tagagtaagt   6840
agttcgccag ttaatagttt gcgcaacgtt gttgccattg ctacaggcat cgtggtgtca   6900
cgctcgtcgt ttggtatggc ttcattcagc tccggttccc aacgatcaag gcgagttaca   6960
tgatccccca tgttgtgcaa aaaagcggtt agctccttcg gtcctccgat cgttgtcaga   7020
agtaagttgg ccgcagtgtt atcactcatg gttatggcag cactgcataa ttctcttact   7080
gtcatgccat ccgtaagatg cttttctgtg actggtgagt actcaaccaa gtcattctga   7140
```

-continued gaatagtgta tgcggcgacc gagttgctct tgcccggcgt caatacggga taataccgcg 7200
ccacatagca gaactttaaa agtgctcatc attggaaaac gttcttcggg gcgaaaactc 7260
tcaaggatct taccgctgtt gagatccagt tcgatgtaac ccactcgtgc acccaactga 7320
tcttcagcat cttttacttt caccagcgtt tctgggtgag caaaaacagg aaggcaaaat 7380
gccgcaaaaa agggaataag ggcgacacgg aaatgttgaa tactcatact cttccttttt 7440
caatattatt gaagcattta tcagggttat tgtctcatga gcggatacat atttgaatgt 7500
atttagaaaa ataaacaaat aggggttccg cgcacatttc cccgaaaagt gccacctgac 7560
gtc 7563

<210> SEQ ID NO 65
<211> LENGTH: 7053
<212> TYPE: DNA
<213> ORGANISM: Artificial Sequence
<220> FEATURE:
<223> OTHER INFORMATION: pcDNA3-Ub-Met-Bla HRV16 construct

<400> SEQUENCE: 65
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttggtacc 900
accatggaga tcttcgtgaa gactctgact ggtaagacca tcactctcga agtggagccg 960
agtgacacca ttgagaatgt caaggcaaag atccaagaca aggaaggcat ccctcctgac 1020
cagcagaggt tgatctttgc tgggaaacag ctggaagatg gacgcaccct gtctgactac 1080
aacatccaga aagagtccac cctgcacctg gtactccgtc tcagaggtgg gatgcacgga 1140
tccatgggaa ctttgtgttc gcgtattgtg accagtgagc aattacacaa agtcaaagtg 1200
gtaacaagga tatatcacaa agccaaacac accaaagctt ggtgcccaag accacccaga 1260
gctgttcaat actcacatac acataccacc aactacaaat tgagttcaga agtacacaat 1320
gatgtggcta taagacctag aacaaatcta acaactgttg ggcctagtga catgtatgtg 1380
catgttggta atctaatata cagaaatcta catttattta actctgacat acatgattcc 1440
attttagtgt cttattcatc agatttaatc atataccgaa caagcacaca aggtgatggt 1500
tatattccaa catgtaattg cactgaagct acatattact gcaaacacaa aaacaggtac 1560
tacccaatta atgtcacacc tcatgactgg tatgagatac aagagagtga atattatcca 1620

-continued

```
aaacatatcc agtacaattt actaataggt gaaggaccat gtgaaccagg tgattgtggt   1680
gggaaattat tatgcaaaca tggagtgata ggtattatta cagcaggtgg tgagggccat   1740
gttgcattca tagatcttag acactttcac tgtgctgaag gatccggggc gtggctgcac   1800
ccagaaacgc tggtgaaagt aaaagatgct gaagatcagt tgggtgcacg agtgggttac   1860
atcgaactgg atctcaacag cggtaagatc cttgagagtt ttcgccccga agaacgtttt   1920
ccaatgatga gcacttttaa agttctgcta tgtggcgcgg tattatcccg tattgacgcc   1980
gggcaagagc aactcggtcg ccgcatacac tattctcaga atgacttggt tgagtactca   2040
ccagtcacag aaaagcatct tacggatggc atgacagtaa gagaattatg cagtgctgcc   2100
ataaccatga gtgataacac tgcggccaac ttacttctga caacgatcgg aggaccgaag   2160
gagctaaccg cttttttgca caacatgggg gatcatgtaa ctcgccttga tcgttgggaa   2220
ccggagctga atgaagccat accaaacgac gagcgtgaca ccacgatgcc tgtagcaatg   2280
gcaacaacgt tgcgcaaact attaactggc gaactactta ctctagcttc ccggcaacaa   2340
ttaatagact ggatggaggc ggataaagtt gcaggaccac ttctgcgctc ggcccttccg   2400
gctggctggt ttattgctga taaatctgga gccggtgagc gtgggtctcg cggtatcatt   2460
gcagcactgg ggccagatgg taagccctcc cgtatcgtag ttatctacac gacggggagt   2520
caggcaacta tggatgaacg aaatagacag atcgctgaga taggtgcctc actgattaag   2580
cattggtaat ctagagggcc ctattctata gtgtcaccta aatgctagag ctcgctgatc   2640
agcctcgact gtgccttcta gttgccagcc atctgttgtt tgcccctccc ccgtgccttc   2700
cttgaccctg gaaggtgcca ctcccactgt cctttcctaa taaaatgagg aaattgcatc   2760
gcattgtctg agtaggtgtc attctattct ggggggtggg gtggggcagg acagcaaggg   2820
ggaggattgg gaagacaata gcaggcatgc tggggatgcg gtgggctcta tggcttctga   2880
ggcggaaaga accagctggg gctctagggg gtatccccac gcgccctgta gcggcgcatt   2940
aagcgcggcg ggtgtggtgg ttacgcgcag cgtgaccgct acacttgcca gcgccctagc   3000
gcccgctcct ttcgctttct tcccttcctt tctcgccacg ttcgccggct ttccccgtca   3060
agctctaaat cggggcatcc ctttagggtt ccgatttagt gctttacggc acctcgaccc   3120
caaaaaactt gattagggtg atggttcacg tagtgggcca tcgccctgat agacggtttt   3180
tcgccctttg acgttggagt ccacgttctt taatagtgga ctcttgttcc aaactggaac   3240
aacactcaac cctatctcgg tctattcttt tgatttataa gggattttgg ggatttcggc   3300
ctattggtta aaaaatgagc tgatttaaca aaaatttaac gcgaattaat tctgtggaat   3360
gtgtgtcagt tagggtgtgg aaagtcccca ggctccccag gcaggcagaa gtatgcaaag   3420
catgcatctc aattagtcag caaccaggtg tggaaagtcc ccaggctccc cagcaggcag   3480
aagtatgcaa agcatgcatc tcaattagtc agcaaccata gtcccgcccc taactccgcc   3540
catcccgccc ctaactccgc ccagttccgc ccattctccg ccccatggct gactaatttt   3600
ttttatttat gcagaggccg aggccgcctc tgcctctgag ctattccaga agtagtgagg   3660
aggctttttt ggaggcctag gcttttgcaa aaagctcccg ggagcttgta tatccatttt   3720
cggatctgat caagagacag gatgaggatc gtttcgcatg attgaacaag atggattgca   3780
cgcaggttct ccggccgctt gggtggagag gctattcggc tatgactggg cacaacagac   3840
aatcggctgc tctgatgccg ccgtgttccg gctgtcagcg caggggcgcc cggttctttt   3900
tgtcaagacc gacctgtccg gtgccctgaa tgaactgcag gacgaggcag cgcggctatc   3960
```

-continued

```
gtggctggcc acgacgggcg ttccttgcgc agctgtgctc gacgttgtca ctgaagcggg   4020
aagggactgg ctgctattgg gcgaagtgcc ggggcaggat ctcctgtcat ctcaccttgc   4080
tcctgccgag aaagtatcca tcatggctga tgcaatgcgg cggctgcata cgcttgatcc   4140
ggctacctgc ccattcgacc accaagcgaa acatcgcatc gagcgagcac gtactcggat   4200
ggaagccggt cttgtcgatc aggatgatct ggacgaagag catcaggggc tcgcgccagc   4260
cgaactgttc gccaggctca aggcgcgcat gcccgacggc gaggatctcg tcgtgaccca   4320
tggcgatgcc tgcttgccga atatcatggt ggaaaatggc cgcttttctg gattcatcga   4380
ctgtggccgg ctgggtgtgg cggaccgcta tcaggacata gcgttggcta cccgtgatat   4440
tgctgaagag cttggcggcg aatgggctga ccgcttcctc gtgctttacg gtatcgccgc   4500
tcccgattcg cagcgcatcg ccttctatcg ccttcttgac gagttcttct gagcgggact   4560
ctggggttcg aaatgaccga ccaagcgacg cccaacctgc catcacgaga tttcgattcc   4620
accgccgcct tctatgaaag gttgggcttc ggaatcgttt tccgggacgc cggctggatg   4680
atcctccagc gcggggatct catgctggag ttcttcgccc accccaactt gtttattgca   4740
gcttataatg gttacaaata aagcaatagc atcacaaatt tcacaaataa agcatttttt   4800
tcactgcatt ctagttgtgg tttgtccaaa ctcatcaatg tatcttatca tgtctgtata   4860
ccgtcgacct ctagctagag cttggcgtaa tcatggtcat agctgtttcc tgtgtgaaat   4920
tgttatccgc tcacaattcc acacaacata cgagccggaa gcataaagtg taaagcctgg   4980
ggtgcctaat gagtgagcta actcacatta attgcgttgc gctcactgcc cgctttccag   5040
tcgggaaacc tgtcgtgcca gctgcattaa tgaatcggcc aacgcgcggg gagaggcggt   5100
ttgcgtattg ggcgctcttc cgcttcctcg ctcactgact cgctgcgctc ggtcgttcgg   5160
ctgcggcgag cggtatcagc tcactcaaag gcggtaatac ggttatccac agaatcaggg   5220
gataacgcag gaaagaacat gtgagcaaaa ggccagcaaa aggccaggaa ccgtaaaaag   5280
gccgcgttgc tggcgttttt ccataggctc cgcccccctg acgagcatca caaaaatcga   5340
cgctcaagtc agaggtggcg aaacccgaca ggactataaa gataccaggc gtttccccct   5400
ggaagctccc tcgtgcgctc tcctgttccg accctgccgc ttaccggata cctgtccgcc   5460
tttctccctt cgggaagcgt ggcgctttct caatgctcac gctgtaggta tctcagttcg   5520
gtgtaggtcg ttcgctccaa gctgggctgt gtgcacgaac cccccgttca gcccgaccgc   5580
tgcgccttat ccggtaacta tcgtcttgag tccaacccgg taagacacga cttatcgcca   5640
ctggcagcag ccactggtaa caggattagc agagcgaggt atgtaggcgg tgctacagag   5700
ttcttgaagt ggtggcctaa ctacggctac actagaagga cagtatttgg tatctgcgct   5760
ctgctgaagc cagttacctt cggaaaaaga gttggtagct cttgatccgg caaacaaacc   5820
accgctggta gcggtggttt ttttgtttgc aagcagcaga ttacgcgcag aaaaaaagga   5880
tctcaagaag atcctttgat cttttctacg gggtctgacg ctcagtggaa cgaaaactca   5940
cgttaaggga ttttggtcat gagattatca aaaaggatct tcacctagat ccttttaaat   6000
taaaaatgaa gttttaaatc aatctaaagt atatatgagt aaacttggtc tgacagttac   6060
caatgcttaa tcagtgaggc acctatctca gcgatctgtc tatttcgttc atccatagtt   6120
gcctgactcc ccgtcgtgta gataactacg atacgggagg gcttaccatc tggccccagt   6180
gctgcaatga taccgcgaga cccacgctca ccggctccag atttatcagc aataaaccag   6240
ccagccggaa gggccgagcg cagaagtggt cctgcaactt tatccgcctc catccagtct   6300
attaattgtt gccgggaagc tagagtaagt agttcgccag ttaatagttt gcgcaacgtt   6360
```

-continued gttgccattg ctacaggcat cgtggtgtca cgctcgtcgt ttggtatggc ttcattcagc 6420
tccggttccc aacgatcaag gcgagttaca tgatccccca tgttgtgcaa aaaagcggtt 6480
agctccttcg gtcctccgat cgttgtcaga agtaagttgg ccgcagtgtt atcactcatg 6540
gttatggcag cactgcataa ttctcttact gtcatgccat ccgtaagatg cttttctgtg 6600
actggtgagt actcaaccaa gtcattctga gaatagtgta tgcggcgacc gagttgctct 6660
tgcccggcgt caatacggga taataccgcg ccacatagca gaactttaaa agtgctcatc 6720
attggaaaac gttcttcggg gcgaaaactc tcaaggatct taccgctgtt gagatccagt 6780
tcgatgtaac ccactcgtgc acccaactga tcttcagcat cttttacttt caccagcgtt 6840
tctgggtgag caaaaacagg aaggcaaaat gccgcaaaaa agggaataag ggcgacacgg 6900
aaatgttgaa tactcatact cttccttttt caatattatt gaagcattta tcagggttat 6960
tgtctcatga gcggatacat atttgaatgt atttagaaaa ataaacaaat aggggttccg 7020
cgcacatttc cccgaaaagt gccacctgac gtc 7053

<210> SEQ ID NO 66
<211> LENGTH: 32
<212> TYPE: DNA
<213> ORGANISM: Artificial Sequence
<220> FEATURE:
<223> OTHER INFORMATION: oligonucleotide for mutagenesis

<400> SEQUENCE: 66
gtgtcttatt catcagcttt aatcatatac cg 32

<210> SEQ ID NO 67
<211> LENGTH: 34
<212> TYPE: DNA
<213> ORGANISM: Artificial Sequence
<220> FEATURE:
<223> OTHER INFORMATION: oligonucleotide for mutagenesis

<400> SEQUENCE: 67
gtgaaccagg tgatgctggt gggaaattat tatg 34

<210> SEQ ID NO 68
<211> LENGTH: 7563
<212> TYPE: DNA
<213> ORGANISM: Artificial Sequence
<220> FEATURE:
<223> OTHER INFORMATION: pcDNA3-3XUb-Bla HRV16 (C106A) construct

<400> SEQUENCE: 68
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600

-continued

```
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgatatc    900
gaattcctgc agcccggggg atctaccatg gaaatcttcg tgaagactct gactggtaag    960
accatcactc tcgaagtgga gccgagtgac accattgaga atgtcaaggc aaagatccaa   1020
gacaaggaag gcatccctcc tgaccagcag aggttgatct ttgctgggaa acagctggaa   1080
gatggacgca ccctgtctga ctacaacatc cagaaagagt ccaccctgca cctggtactc   1140
cgtctcagag gtgtgcacca cggatctacc atggaaatct tcgtgaagac tctgactggt   1200
aagaccatca ctctcgaagt ggagccgagt gacaccattg agaatgtcaa ggcaaagatc   1260
caagacaagg aaggcatccc tcctgaccag cagaggttga tctttgctgg gaaacagctg   1320
gaagatggac gcaccctgtc tgactacaac atccagaaag agtccaccct gcacctggta   1380
ctccgtctca gaggtgtgca ccacggatct accatggaaa tcttcgtgaa gactctgact   1440
ggtaagacca tcactctcga agtggagccg agtgacacca ttgagaatgt caaggcaaag   1500
atccaagaca aggaaggcat ccctcctgac cagcagaggt tgatctttgc tgggaaacag   1560
ctggaagatg gacgcaccct gtctgactac aacatccaga aagagtccac cctgcacctg   1620
gtactccgtc tcagaggtgt gcaccacgga tccatgggaa ctttgtgttc gcgtattgtg   1680
accagtgagc aattacacaa agtcaaagtg gtaacaagga tatatcacaa agccaaacac   1740
accaaagctt ggtgcccaag accacccaga gctgttcaat actcacatac acataccacc   1800
aactacaaat tgagttcaga agtacacaat gatgtggcta taagacctag aacaaatcta   1860
acaactgttg ggcctagtga catgtatgtg catgttggta atctaatata cagaaatcta   1920
catttattta actctgacat acatgattcc attttagtgt cttattcatc agatttaatc   1980
atataccgaa caagcacaca aggtgatggt tatattccaa catgtaattg cactgaagct   2040
acatattact gcaaacacaa aaacaggtac tacccaatta atgtcacacc tcatgactgg   2100
tatgagatac aagagagtga atattatcca aaacatatcc agtacaattt actaataggt   2160
gaaggaccat gtgaaccagg tgatgctggt gggaaattat tatgcaaaca tggagtgata   2220
ggtattatta cagcaggtgg tgagggccat gttgcattca tagatcttag acactttcac   2280
tgtgctgaag gatccggggc gtggctgcac ccagaaacgc tggtgaaagt aaaagatgct   2340
gaagatcagt tgggtgcacg agtgggttac atcgaactgg atctcaacag cggtaagatc   2400
cttgagagtt ttcgccccga agaacgtttt ccaatgatga gcacttttaa agttctgcta   2460
tgtggcgcgg tattatcccg tattgacgcc gggcaagagc aactcggtcg ccgcatacac   2520
tattctcaga atgacttggt tgagtactca ccagtcacag aaaagcatct tacggatggc   2580
atgacagtaa gagaattatg cagtgctgcc ataaccatga gtgataacac tgcggccaac   2640
ttacttctga caacgatcgg aggaccgaag gagctaaccg cttttttgca caacatgggg   2700
gatcatgtaa ctcgccttga tcgttgggaa ccggagctga atgaagccat accaaacgac   2760
gagcgtgaca ccacgatgcc tgtagcaatg gcaacaacgt tgcgcaaact attaactggc   2820
gaactactta ctctagcttc ccggcaacaa ttaatagact ggatggaggc ggataaagtt   2880
gcaggaccac ttctgcgctc ggcccttccg gctggctggt ttattgctga taaatctgga   2940
gccggtgagc gtgggtctcg cggtatcatt gcagcactgg ggccagatgg taagccctcc   3000
```

-continued

```
cgtatcgtag ttatctacac gacggggagt caggcaacta tggatgaacg aaatagacag   3060
atcgctgaga taggtgcctc actgattaag cattggtaat ctagagggcc ctattctata   3120
gtgtcaccta aatgctagag ctcgctgatc agcctcgact gtgccttcta gttgccagcc   3180
atctgttgtt tgcccctccc ccgtgccttc cttgaccctg gaaggtgcca ctcccactgt   3240
cctttcctaa taaaatgagg aaattgcatc gcattgtctg agtaggtgtc attctattct   3300
ggggggtggg gtggggcagg acagcaaggg ggaggattgg gaagacaata gcaggcatgc   3360
tggggatgcg gtgggctcta tggcttctga ggcggaaaga accagctggg gctctagggg   3420
gtatccccac gcgccctgta gcggcgcatt aagcgcggcg ggtgtggtgg ttacgcgcag   3480
cgtgaccgct acacttgcca gcgccctagc gcccgctcct ttcgctttct tcccttcctt   3540
tctcgccacg ttcgccggct ttccccgtca agctctaaat cggggcatcc ctttagggtt   3600
ccgatttagt gctttacggc acctcgaccc caaaaaactt gattagggtg atggttcacg   3660
tagtgggcca tcgccctgat agacggtttt tcgccctttg acgttggagt ccacgttctt   3720
taatagtgga ctcttgttcc aaactggaac aacactcaac cctatctcgg tctattcttt   3780
tgatttataa gggattttgg ggatttcggc ctattggtta aaaaatgagc tgatttaaca   3840
aaaatttaac gcgaattaat tctgtggaat gtgtgtcagt tagggtgtgg aaagtcccca   3900
ggctccccag gcaggcagaa gtatgcaaag catgcatctc aattagtcag caaccaggtg   3960
tggaaagtcc ccaggctccc cagcaggcag aagtatgcaa agcatgcatc tcaattagtc   4020
agcaaccata gtcccgcccc taactccgcc catcccgccc ctaactccgc ccagttccgc   4080
ccattctccg ccccatggct gactaatttt ttttatttat gcagaggccg aggccgcctc   4140
tgcctctgag ctattccaga agtagtgagg aggctttttt ggaggcctag gcttttgcaa   4200
aaagctcccg ggagcttgta tatccatttt cggatctgat caagagacag gatgaggatc   4260
gtttcgcatg attgaacaag atggattgca cgcaggttct ccggccgctt gggtggagag   4320
gctattcggc tatgactggg cacaacagac aatcggctgc tctgatgccg ccgtgttccg   4380
gctgtcagcg caggggcgcc cggttctttt tgtcaagacc gacctgtccg gtgccctgaa   4440
tgaactgcag gacgaggcag cgcggctatc gtggctggcc acgacgggcg ttccttgcgc   4500
agctgtgctc gacgttgtca ctgaagcggg aagggactgg ctgctattgg gcgaagtgcc   4560
ggggcaggat ctcctgtcat ctcaccttgc tcctgccgag aaagtatcca tcatggctga   4620
tgcaatgcgg cggctgcata cgcttgatcc ggctacctgc ccattcgacc accaagcgaa   4680
acatcgcatc gagcgagcac gtactcggat ggaagccggt cttgtcgatc aggatgatct   4740
ggacgaagag catcaggggc tcgcgccagc cgaactgttc gccaggctca aggcgcgcat   4800
gcccgacggc gaggatctcg tcgtgaccca tggcgatgcc tgcttgccga atatcatggt   4860
ggaaaatggc cgcttttctg gattcatcga ctgtggccgg ctgggtgtgg cggaccgcta   4920
tcaggacata gcgttggcta cccgtgatat tgctgaagag cttggcggcg aatgggctga   4980
ccgcttcctc gtgctttacg gtatcgccgc tcccgattcg cagcgcatcg ccttctatcg   5040
ccttcttgac gagttcttct gagcgggact ctggggttcg aaatgaccga ccaagcgacg   5100
cccaacctgc catcacgaga tttcgattcc accgccgcct tctatgaaag gttgggcttc   5160
ggaatcgttt tccgggacgc cggctggatg atcctccagc gcggggatct catgctggag   5220
ttcttcgccc accccaactt gtttattgca gcttataatg gttacaaata aagcaatagc   5280
atcacaaatt tcacaaataa agcatttttt tcactgcatt ctagttgtgg tttgtccaaa   5340
```

-continued

```
ctcatcaatg tatcttatca tgtctgtata ccgtcgacct ctagctagag cttggcgtaa   5400
tcatggtcat agctgtttcc tgtgtgaaat tgttatccgc tcacaattcc acacaacata   5460
cgagccggaa gcataaagtg taaagcctgg ggtgcctaat gagtgagcta actcacatta   5520
attgcgttgc gctcactgcc cgctttccag tcgggaaacc tgtcgtgcca gctgcattaa   5580
tgaatcggcc aacgcgcggg gagaggcggt ttgcgtattg ggcgctcttc cgcttcctcg   5640
ctcactgact cgctgcgctc ggtcgttcgg ctgcggcgag cggtatcagc tcactcaaag   5700
gcggtaatac ggttatccac agaatcaggg gataacgcag gaaagaacat gtgagcaaaa   5760
ggccagcaaa aggccaggaa ccgtaaaaag gccgcgttgc tggcgttttt ccataggctc   5820
cgcccccctg acgagcatca caaaaatcga cgctcaagtc agaggtggcg aaacccgaca   5880
ggactataaa gataccaggc gtttccccct ggaagctccc tcgtgcgctc tcctgttccg   5940
accctgccgc ttaccggata cctgtccgcc tttctccctt cgggaagcgt ggcgctttct   6000
caatgctcac gctgtaggta tctcagttcg gtgtaggtcg ttcgctccaa gctgggctgt   6060
gtgcacgaac cccccgttca gcccgaccgc tgcgccttat ccggtaacta tcgtcttgag   6120
tccaacccgg taagacacga cttatcgcca ctggcagcag ccactggtaa caggattagc   6180
agagcgaggt atgtaggcgg tgctacagag ttcttgaagt ggtggcctaa ctacggctac   6240
actagaagga cagtatttgg tatctgcgct ctgctgaagc cagttacctt cggaaaaaga   6300
gttggtagct cttgatccgg caaacaaacc accgctggta gcggtggttt ttttgtttgc   6360
aagcagcaga ttacgcgcag aaaaaaagga tctcaagaag atcctttgat cttttctacg   6420
gggtctgacg ctcagtggaa cgaaaactca cgttaaggga ttttggtcat gagattatca   6480
aaaaggatct tcacctagat ccttttaaat taaaaatgaa gttttaaatc aatctaaagt   6540
atatatgagt aaacttggtc tgacagttac caatgcttaa tcagtgaggc acctatctca   6600
gcgatctgtc tatttcgttc atccatagtt gcctgactcc ccgtcgtgta gataactacg   6660
atacgggagg gcttaccatc tggccccagt gctgcaatga taccgcgaga cccacgctca   6720
ccggctccag atttatcagc aataaaccag ccagccggaa gggccgagcg cagaagtggt   6780
cctgcaactt tatccgcctc catccagtct attaattgtt gccgggaagc tagagtaagt   6840
agttcgccag ttaatagttt gcgcaacgtt gttgccattg ctacaggcat cgtggtgtca   6900
cgctcgtcgt ttggtatggc ttcattcagc tccggttccc aacgatcaag gcgagttaca   6960
tgatccccca tgttgtgcaa aaaagcggtt agctccttcg gtcctccgat cgttgtcaga   7020
agtaagttgg ccgcagtgtt atcactcatg gttatggcag cactgcataa ttctcttact   7080
gtcatgccat ccgtaagatg cttttctgtg actggtgagt actcaaccaa gtcattctga   7140
gaatagtgta tgcggcgacc gagttgctct tgcccggcgt caatacggga taataccgcg   7200
ccacatagca gaactttaaa agtgctcatc attggaaaac gttcttcggg gcgaaaactc   7260
tcaaggatct taccgctgtt gagatccagt tcgatgtaac ccactcgtgc acccaactga   7320
tcttcagcat cttttacttt caccagcgtt tctgggtgag caaaaacagg aaggcaaaat   7380
gccgcaaaaa agggaataag ggcgacacgg aaatgttgaa tactcatact cttccttttt   7440
caatattatt gaagcattta tcagggttat tgtctcatga gcggatacat atttgaatgt   7500
atttagaaaa ataaacaaat aggggttccg cgcacatttc cccgaaaagt gccacctgac   7560
gtc                                                                 7563
```

<210> SEQ ID NO 69
<211> LENGTH: 7563

-continued

<212> TYPE: DNA
<213> ORGANISM: Artificial Sequence
<220> FEATURE:
<223> OTHER INFORMATION: pcDNA3-3XUb-Bla HRV16 (D35A) construct

<400> SEQUENCE: 69
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgatatc 900
gaattcctgc agcccggggg atctaccatg gaaatcttcg tgaagactct gactggtaag 960
accatcactc tcgaagtgga gccgagtgac accattgaga atgtcaaggc aaagatccaa 1020
gacaaggaag gcatccctcc tgaccagcag aggttgatct ttgctgggaa acagctggaa 1080
gatggacgca ccctgtctga ctacaacatc cagaaagagt ccaccctgca cctggtactc 1140
cgtctcagag gtgtgcacca cggatctacc atggaaatct tcgtgaagac tctgactggt 1200
aagaccatca ctctcgaagt ggagccgagt gacaccattg agaatgtcaa ggcaaagatc 1260
caagacaagg aaggcatccc tcctgaccag cagaggttga tctttgctgg gaaacagctg 1320
gaagatggac gcaccctgtc tgactacaac atccagaaag agtccaccct gcacctggta 1380
ctccgtctca gaggtgtgca ccacggatct accatggaaa tcttcgtgaa gactctgact 1440
ggtaagacca tcactctcga agtggagccg agtgacacca ttgagaatgt caaggcaaag 1500
atccaagaca aggaaggcat ccctcctgac cagcagaggt tgatctttgc tgggaaacag 1560
ctggaagatg gacgcaccct gtctgactac aacatccaga aagagtccac cctgcacctg 1620
gtactccgtc tcagaggtgt gcaccacgga tccatgggaa ctttgtgttc gcgtattgtg 1680
accagtgagc aattacacaa agtcaaagtg gtaacaagga tatatcacaa agccaaacac 1740
accaaagctt ggtgcccaag accacccaga gctgttcaat actcacatac acataccacc 1800
aactacaaat tgagttcaga agtacacaat gatgtggcta taagacctag aacaaatcta 1860
acaactgttg ggcctagtga catgtatgtg catgttggta atctaatata cagaaatcta 1920
catttattta actctgacat acatgattcc attttagtgt cttattcatc agctttaatc 1980
atataccgaa caagcacaca aggtgatggt tatattccaa catgtaattg cactgaagct 2040
acatattact gcaaacacaa aaacaggtac tacccaatta atgtcacacc tcatgactgg 2100
tatgagatac aagagagtga atattatcca aaacatatcc agtacaattt actaataggt 2160

-continued

```
gaaggaccat gtgaaccagg tgattgtggt gggaaattat tatgcaaaca tggagtgata   2220
ggtattatta cagcaggtgg tgagggccat gttgcattca tagatcttag acactttcac   2280
tgtgctgaag gatccggggc gtggctgcac ccagaaacgc tggtgaaagt aaaagatgct   2340
gaagatcagt tgggtgcacg agtgggttac atcgaactgg atctcaacag cggtaagatc   2400
cttgagagtt ttcgccccga agaacgtttt ccaatgatga gcacttttaa agttctgcta   2460
tgtggcgcgg tattatcccg tattgacgcc gggcaagagc aactcggtcg ccgcatacac   2520
tattctcaga atgacttggt tgagtactca ccagtcacag aaaagcatct tacggatggc   2580
atgacagtaa gagaattatg cagtgctgcc ataaccatga gtgataacac tgcggccaac   2640
ttacttctga caacgatcgg aggaccgaag gagctaaccg cttttttgca caacatgggg   2700
gatcatgtaa ctcgccttga tcgttgggaa ccggagctga atgaagccat accaaacgac   2760
gagcgtgaca ccacgatgcc tgtagcaatg gcaacaacgt tgcgcaaact attaactggc   2820
gaactactta ctctagcttc ccggcaacaa ttaatagact ggatggaggc ggataaagtt   2880
gcaggaccac ttctgcgctc ggcccttccg gctggctggt ttattgctga taaatctgga   2940
gccggtgagc gtgggtctcg cggtatcatt gcagcactgg ggccagatgg taagccctcc   3000
cgtatcgtag ttatctacac gacggggagt caggcaacta tggatgaacg aaatagacag   3060
atcgctgaga taggtgcctc actgattaag cattggtaat ctagagggcc ctattctata   3120
gtgtcaccta aatgctagag ctcgctgatc agcctcgact gtgccttcta gttgccagcc   3180
atctgttgtt tgcccctccc ccgtgccttc cttgaccctg gaaggtgcca ctcccactgt   3240
cctttcctaa taaaatgagg aaattgcatc gcattgtctg agtaggtgtc attctattct   3300
ggggggtggg gtggggcagg acagcaaggg ggaggattgg gaagacaata gcaggcatgc   3360
tggggatgcg gtgggctcta tggcttctga ggcggaaaga accagctggg gctctagggg   3420
gtatccccac gcgccctgta gcggcgcatt aagcgcggcg ggtgtggtgg ttacgcgcag   3480
cgtgaccgct acacttgcca gcgccctagc gcccgctcct ttcgctttct tcccttcctt   3540
tctcgccacg ttcgccggct ttccccgtca agctctaaat cggggcatcc ctttagggtt   3600
ccgatttagt gctttacggc acctcgaccc caaaaaactt gattagggtg atggttcacg   3660
tagtgggcca tcgccctgat agacggtttt tcgccctttg acgttggagt ccacgttctt   3720
taatagtgga ctcttgttcc aaactggaac aacactcaac cctatctcgg tctattcttt   3780
tgatttataa gggattttgg ggatttcggc ctattggtta aaaaatgagc tgatttaaca   3840
aaaatttaac gcgaattaat tctgtggaat gtgtgtcagt tagggtgtgg aaagtcccca   3900
ggctccccag gcaggcagaa gtatgcaaag catgcatctc aattagtcag caaccaggtg   3960
tggaaagtcc ccaggctccc cagcaggcag aagtatgcaa agcatgcatc tcaattagtc   4020
agcaaccata gtcccgcccc taactccgcc catcccgccc ctaactccgc ccagttccgc   4080
ccattctccg ccccatggct gactaatttt ttttatttat gcagaggccg aggccgcctc   4140
tgcctctgag ctattccaga agtagtgagg aggctttttt ggaggcctag gcttttgcaa   4200
aaagctcccg ggagcttgta tatccatttt cggatctgat caagagacag gatgaggatc   4260
gtttcgcatg attgaacaag atggattgca cgcaggttct ccggccgctt gggtggagag   4320
gctattcggc tatgactggg cacaacagac aatcggctgc tctgatgccg ccgtgttccg   4380
gctgtcagcg caggggcgcc cggttctttt tgtcaagacc gacctgtccg gtgccctgaa   4440
tgaactgcag gacgaggcag cgcggctatc gtggctggcc acgacgggcg ttccttgcgc   4500
agctgtgctc gacgttgtca ctgaagcggg aagggactgg ctgctattgg gcgaagtgcc   4560
```

-continued

```
ggggcaggat ctcctgtcat ctcaccttgc tcctgccgag aaagtatcca tcatggctga   4620
tgcaatgcgg cggctgcata cgcttgatcc ggctacctgc ccattcgacc accaagcgaa   4680
acatcgcatc gagcgagcac gtactcggat ggaagccggt cttgtcgatc aggatgatct   4740
ggacgaagag catcaggggc tcgcgccagc cgaactgttc gccaggctca aggcgcgcat   4800
gcccgacggc gaggatctcg tcgtgaccca tggcgatgcc tgcttgccga atatcatggt   4860
ggaaaatggc cgcttttctg gattcatcga ctgtggccgg ctgggtgtgg cggaccgcta   4920
tcaggacata gcgttggcta cccgtgatat tgctgaagag cttggcggcg aatgggctga   4980
ccgcttcctc gtgctttacg gtatcgccgc tcccgattcg cagcgcatcg ccttctatcg   5040
ccttcttgac gagttcttct gagcgggact ctggggttcg aaatgaccga ccaagcgacg   5100
cccaacctgc catcacgaga tttcgattcc accgccgcct tctatgaaag gttgggcttc   5160
ggaatcgttt tccgggacgc cggctggatg atcctccagc gcggggatct catgctggag   5220
ttcttcgccc accccaactt gtttattgca gcttataatg gttacaaata aagcaatagc   5280
atcacaaatt tcacaaataa agcatttttt tcactgcatt ctagttgtgg tttgtccaaa   5340
ctcatcaatg tatcttatca tgtctgtata ccgtcgacct ctagctagag cttggcgtaa   5400
tcatggtcat agctgtttcc tgtgtgaaat tgttatccgc tcacaattcc acacaacata   5460
cgagccggaa gcataaagtg taaagcctgg ggtgcctaat gagtgagcta actcacatta   5520
attgcgttgc gctcactgcc cgctttccag tcgggaaacc tgtcgtgcca gctgcattaa   5580
tgaatcggcc aacgcgcggg gagaggcggt ttgcgtattg ggcgctcttc cgcttcctcg   5640
ctcactgact cgctgcgctc ggtcgttcgg ctgcggcgag cggtatcagc tcactcaaag   5700
gcggtaatac ggttatccac agaatcaggg gataacgcag gaaagaacat gtgagcaaaa   5760
ggccagcaaa aggccaggaa ccgtaaaaag gccgcgttgc tggcgttttt ccataggctc   5820
cgcccccctg acgagcatca caaaaatcga cgctcaagtc agaggtggcg aaacccgaca   5880
ggactataaa gataccaggc gtttccccct ggaagctccc tcgtgcgctc tcctgttccg   5940
accctgccgc ttaccggata cctgtccgcc tttctccctt cgggaagcgt ggcgctttct   6000
caatgctcac gctgtaggta tctcagttcg gtgtaggtcg ttcgctccaa gctgggctgt   6060
gtgcacgaac cccccgttca gcccgaccgc tgcgccttat ccggtaacta tcgtcttgag   6120
tccaacccgg taagacacga cttatcgcca ctggcagcag ccactggtaa caggattagc   6180
agagcgaggt atgtaggcgg tgctacagag ttcttgaagt ggtggcctaa ctacggctac   6240
actagaagga cagtatttgg tatctgcgct ctgctgaagc cagttacctt cggaaaaaga   6300
gttggtagct cttgatccgg caaacaaacc accgctggta gcggtggttt ttttgtttgc   6360
aagcagcaga ttacgcgcag aaaaaaagga tctcaagaag atcctttgat cttttctacg   6420
gggtctgacg ctcagtggaa cgaaaactca cgttaaggga ttttggtcat gagattatca   6480
aaaaggatct tcacctagat ccttttaaat taaaaatgaa gttttaaatc aatctaaagt   6540
atatatgagt aaacttggtc tgacagttac caatgcttaa tcagtgaggc acctatctca   6600
gcgatctgtc tatttcgttc atccatagtt gcctgactcc ccgtcgtgta gataactacg   6660
atacgggagg gcttaccatc tggccccagt gctgcaatga taccgcgaga cccacgctca   6720
ccggctccag atttatcagc aataaaccag ccagccggaa gggccgagcg cagaagtggt   6780
cctgcaactt tatccgcctc catccagtct attaattgtt gccgggaagc tagagtaagt   6840
agttcgccag ttaatagttt gcgcaacgtt gttgccattg ctacaggcat cgtggtgtca   6900
```

-continued

```
cgctcgtcgt ttggtatggc ttcattcagc tccggttccc aacgatcaag gcgagttaca   6960

tgatccccca tgttgtgcaa aaaagcggtt agctccttcg gtcctccgat cgttgtcaga   7020

agtaagttgg ccgcagtgtt atcactcatg gttatggcag cactgcataa ttctcttact   7080

gtcatgccat ccgtaagatg cttttctgtg actggtgagt actcaaccaa gtcattctga   7140

gaatagtgta tgcggcgacc gagttgctct tgcccggcgt caatacggga taataccgcg   7200

ccacatagca gaactttaaa agtgctcatc attggaaaac gttcttcggg gcgaaaactc   7260

tcaaggatct taccgctgtt gagatccagt tcgatgtaac ccactcgtgc acccaactga   7320

tcttcagcat cttttacttt caccagcgtt tctgggtgag caaaaacagg aaggcaaaat   7380

gccgcaaaaa agggaataag ggcgacacgg aaatgttgaa tactcatact cttccttttt   7440

caatattatt gaagcattta tcagggttat tgtctcatga gcggatacat atttgaatgt   7500

atttagaaaa ataaacaaat aggggttccg cgcacatttc cccgaaaagt gccacctgac   7560

gtc                                                                 7563
```

<210> SEQ ID NO 70
<211> LENGTH: 7053
<212> TYPE: DNA
<213> ORGANISM: Artificial Sequence
<220> FEATURE:
<223> OTHER INFORMATION: pcDNA3-Ub-Met-Bla HRV16 (C106A) construct

<400> SEQUENCE: 70

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

accatggaga tcttcgtgaa gactctgact ggtaagacca tcactctcga agtggagccg    960

agtgacacca ttgagaatgt caaggcaaag atccaagaca aggaaggcat ccctcctgac   1020

cagcagaggt tgatctttgc tgggaaacag ctggaagatg gacgcaccct gtctgactac   1080

aacatccaga aagagtccac cctgcacctg gtactccgtc tcagaggtgg gatgcacgga   1140

tccatgggaa ctttgtgttc gcgtattgtg accagtgagc aattacacaa agtcaaagtg   1200

gtaacaagga tatatcacaa agccaaacac accaaagctt ggtgcccaag accacccaga   1260

gctgttcaat actcacatac acataccacc aactacaaat tgagttcaga agtacacaat   1320

gatgtggcta taagacctag aacaaatcta acaactgttg ggcctagtga catgtatgtg   1380
```

-continued catgttggta atctaatata cagaaatcta catttattta actctgacat acatgattcc 1440
attttagtgt cttattcatc agatttaatc atataccgaa caagcacaca aggtgatggt 1500
tatattccaa catgtaattg cactgaagct acatattact gcaaacacaa aaacaggtac 1560
tacccaatta atgtcacacc tcatgactgg tatgagatac aagagagtga atattatcca 1620
aaacatatcc agtacaattt actaataggt gaaggaccat gtgaaccagg tgatgctggt 1680
gggaaattat tatgcaaaca tggagtgata ggtattatta cagcaggtgg tgagggccat 1740
gttgcattca tagatcttag acactttcac tgtgctgaag gatccggggc gtggctgcac 1800
ccagaaacgc tggtgaaagt aaaagatgct gaagatcagt tgggtgcacg agtgggttac 1860
atcgaactgg atctcaacag cggtaagatc cttgagagtt ttcgccccga agaacgtttt 1920
ccaatgatga gcacttttaa agttctgcta tgtggcgcgg tattatcccg tattgacgcc 1980
gggcaagagc aactcggtcg ccgcatacac tattctcaga atgacttggt tgagtactca 2040
ccagtcacag aaaagcatct tacggatggc atgacagtaa gagaattatg cagtgctgcc 2100
ataaccatga gtgataacac tgcggccaac ttacttctga caacgatcgg aggaccgaag 2160
gagctaaccg cttttttgca caacatgggg gatcatgtaa ctcgccttga tcgttgggaa 2220
ccggagctga atgaagccat accaaacgac gagcgtgaca ccacgatgcc tgtagcaatg 2280
gcaacaacgt tgcgcaaact attaactggc gaactactta ctctagcttc ccggcaacaa 2340
ttaatagact ggatggaggc ggataaagtt gcaggaccac ttctgcgctc ggcccttccg 2400
gctggctggt ttattgctga taaatctgga gccggtgagc gtgggtctcg cggtatcatt 2460
gcagcactgg ggccagatgg taagccctcc cgtatcgtag ttatctacac gacggggagt 2520
caggcaacta tggatgaacg aaatagacag atcgctgaga taggtgcctc actgattaag 2580
cattggtaat ctagagggcc ctattctata gtgtcaccta aatgctagag ctcgctgatc 2640
agcctcgact gtgccttcta gttgccagcc atctgttgtt tgcccctccc ccgtgccttc 2700
cttgaccctg gaaggtgcca ctcccactgt cctttcctaa taaaatgagg aaattgcatc 2760
gcattgtctg agtaggtgtc attctattct ggggggtggg gtggggcagg acagcaaggg 2820
ggaggattgg gaagacaata gcaggcatgc tggggatgcg gtgggctcta tggcttctga 2880
ggcggaaaga accagctggg gctctagggg gtatccccac gcgccctgta gcggcgcatt 2940
aagcgcggcg ggtgtggtgg ttacgcgcag cgtgaccgct acacttgcca gcgccctagc 3000
gcccgctcct ttcgctttct tcccttcctt tctcgccacg ttcgccggct ttccccgtca 3060
agctctaaat cggggcatcc ctttagggtt ccgatttagt gctttacggc acctcgaccc 3120
caaaaaactt gattagggtg atggttcacg tagtgggcca tcgccctgat agacggtttt 3180
tcgccctttg acgttggagt ccacgttctt taatagtgga ctcttgttcc aaactggaac 3240
aacactcaac cctatctcgg tctattcttt tgatttataa gggattttgg ggatttcggc 3300
ctattggtta aaaaatgagc tgatttaaca aaaatttaac gcgaattaat tctgtggaat 3360
gtgtgtcagt tagggtgtgg aaagtcccca ggctccccag gcaggcagaa gtatgcaaag 3420
catgcatctc aattagtcag caaccaggtg tggaaagtcc ccaggctccc cagcaggcag 3480
aagtatgcaa agcatgcatc tcaattagtc agcaaccata gtcccgcccc taactccgcc 3540
catcccgccc ctaactccgc ccagttccgc ccattctccg ccccatggct gactaatttt 3600
ttttatttat gcagaggccg aggccgcctc tgcctctgag ctattccaga agtagtgagg 3660
aggctttttt ggaggcctag gcttttgcaa aaagctcccg ggagcttgta tatccatttt 3720

-continued

```
cggatctgat caagagacag gatgaggatc gtttcgcatg attgaacaag atggattgca   3780
cgcaggttct ccggccgctt gggtggagag gctattcggc tatgactggg cacaacagac   3840
aatcggctgc tctgatgccg ccgtgttccg gctgtcagcg caggggcgcc cggttctttt   3900
tgtcaagacc gacctgtccg gtgccctgaa tgaactgcag gacgaggcag cgcggctatc   3960
gtggctggcc acgacgggcg ttccttgcgc agctgtgctc gacgttgtca ctgaagcggg   4020
aagggactgg ctgctattgg gcgaagtgcc ggggcaggat ctcctgtcat ctcaccttgc   4080
tcctgccgag aaagtatcca tcatggctga tgcaatgcgg cggctgcata cgcttgatcc   4140
ggctacctgc ccattcgacc accaagcgaa acatcgcatc gagcgagcac gtactcggat   4200
ggaagccggt cttgtcgatc aggatgatct ggacgaagag catcaggggc tcgcgccagc   4260
cgaactgttc gccaggctca aggcgcgcat gcccgacggc gaggatctcg tcgtgaccca   4320
tggcgatgcc tgcttgccga atatcatggt ggaaaatggc cgcttttctg gattcatcga   4380
ctgtggccgg ctgggtgtgg cggaccgcta tcaggacata gcgttggcta cccgtgatat   4440
tgctgaagag cttggcggcg aatgggctga ccgcttcctc gtgctttacg gtatcgccgc   4500
tcccgattcg cagcgcatcg ccttctatcg ccttcttgac gagttcttct gagcgggact   4560
ctggggttcg aaatgaccga ccaagcgacg cccaacctgc catcacgaga tttcgattcc   4620
accgccgcct tctatgaaag gttgggcttc ggaatcgttt tccgggacgc cggctggatg   4680
atcctccagc gcggggatct catgctggag ttcttcgccc accccaactt gtttattgca   4740
gcttataatg gttacaaata aagcaatagc atcacaaatt tcacaaataa agcatttttt   4800
tcactgcatt ctagttgtgg tttgtccaaa ctcatcaatg tatcttatca tgtctgtata   4860
ccgtcgacct ctagctagag cttggcgtaa tcatggtcat agctgtttcc tgtgtgaaat   4920
tgttatccgc tcacaattcc acacaacata cgagccggaa gcataaagtg taaagcctgg   4980
ggtgcctaat gagtgagcta actcacatta attgcgttgc gctcactgcc cgctttccag   5040
tcgggaaacc tgtcgtgcca gctgcattaa tgaatcggcc aacgcgcggg gagaggcggt   5100
ttgcgtattg ggcgctcttc cgcttcctcg ctcactgact cgctgcgctc ggtcgttcgg   5160
ctgcggcgag cggtatcagc tcactcaaag gcggtaatac ggttatccac agaatcaggg   5220
gataacgcag gaaagaacat gtgagcaaaa ggccagcaaa aggccaggaa ccgtaaaaag   5280
gccgcgttgc tggcgttttt ccataggctc cgcccccctg acgagcatca caaaaatcga   5340
cgctcaagtc agaggtggcg aaacccgaca ggactataaa gataccaggc gtttccccct   5400
ggaagctccc tcgtgcgctc tcctgttccg accctgccgc ttaccggata cctgtccgcc   5460
tttctccctt cgggaagcgt ggcgctttct caatgctcac gctgtaggta tctcagttcg   5520
gtgtaggtcg ttcgctccaa gctgggctgt gtgcacgaac cccccgttca gcccgaccgc   5580
tgcgccttat ccggtaacta tcgtcttgag tccaacccgg taagacacga cttatcgcca   5640
ctggcagcag ccactggtaa caggattagc agagcgaggt atgtaggcgg tgctacagag   5700
ttcttgaagt ggtggcctaa ctacggctac actagaagga cagtatttgg tatctgcgct   5760
ctgctgaagc cagttacctt cggaaaaaga gttggtagct cttgatccgg caaacaaacc   5820
accgctggta gcggtggttt ttttgtttgc aagcagcaga ttacgcgcag aaaaaaagga   5880
tctcaagaag atcctttgat cttttctacg gggtctgacg ctcagtggaa cgaaaactca   5940
cgttaaggga ttttggtcat gagattatca aaaaggatct tcacctagat ccttttaaat   6000
taaaaatgaa gttttaaatc aatctaaagt atatatgagt aaacttggtc tgacagttac   6060
caatgcttaa tcagtgaggc acctatctca gcgatctgtc tatttcgttc atccatagtt   6120
```

-continued

```
gcctgactcc ccgtcgtgta gataactacg atacgggagg gcttaccatc tggccccagt   6180

gctgcaatga taccgcgaga cccacgctca ccggctccag atttatcagc aataaaccag   6240

ccagccggaa gggccgagcg cagaagtggt cctgcaactt tatccgcctc catccagtct   6300

attaattgtt gccgggaagc tagagtaagt agttcgccag ttaatagttt gcgcaacgtt   6360

gttgccattg ctacaggcat cgtggtgtca cgctcgtcgt ttggtatggc ttcattcagc   6420

tccggttccc aacgatcaag gcgagttaca tgatccccca tgttgtgcaa aaaagcggtt   6480

agctccttcg gtcctccgat cgttgtcaga agtaagttgg ccgcagtgtt atcactcatg   6540

gttatggcag cactgcataa ttctcttact gtcatgccat ccgtaagatg cttttctgtg   6600

actggtgagt actcaaccaa gtcattctga gaatagtgta tgcggcgacc gagttgctct   6660

tgcccggcgt caatacggga taataccgcg ccacatagca gaactttaaa agtgctcatc   6720

attggaaaac gttcttcggg gcgaaaactc tcaaggatct taccgctgtt gagatccagt   6780

tcgatgtaac ccactcgtgc acccaactga tcttcagcat cttttacttt caccagcgtt   6840

tctgggtgag caaaaacagg aaggcaaaat gccgcaaaaa agggaataag ggcgacacgg   6900

aaatgttgaa tactcatact cttccttttt caatattatt gaagcattta tcagggttat   6960

tgtctcatga gcggatacat atttgaatgt atttagaaaa ataaacaaat aggggttccg   7020

cgcacatttc cccgaaaagt gccacctgac gtc                                7053
```

<210> SEQ ID NO 71
<211> LENGTH: 7053
<212> TYPE: DNA
<213> ORGANISM: Artificial Sequence
<220> FEATURE:
<223> OTHER INFORMATION: pcDNA3-Ub-Met-Bla HRV16 (D35A) construct

<400> SEQUENCE: 71

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

accatggaga tcttcgtgaa gactctgact ggtaagacca tcactctcga agtggagccg    960

agtgacacca ttgagaatgt caaggcaaag atccaagaca aggaaggcat ccctcctgac   1020

cagcagaggt tgatctttgc tgggaaacag ctggaagatg gacgcaccct gtctgactac   1080
```

-continued

```
aacatccaga aagagtccac cctgcacctg gtactccgtc tcagaggtgg gatgcacgga   1140
tccatgggaa ctttgtgttc gcgtattgtg accagtgagc aattacacaa agtcaaagtg   1200
gtaacaagga tatatcacaa agccaaacac accaaagctt ggtgcccaag accacccaga   1260
gctgttcaat actcacatac acataccacc aactacaaat tgagttcaga agtacacaat   1320
gatgtggcta taagacctag aacaaatcta acaactgttg ggcctagtga catgtatgtg   1380
catgttggta atctaatata cagaaatcta catttattta actctgacat acatgattcc   1440
attttagtgt cttattcatc agctttaatc atataccgaa caagcacaca aggtgatggt   1500
tatattccaa catgtaattg cactgaagct acatattact gcaaacacaa aaacaggtac   1560
tacccaatta atgtcacacc tcatgactgg tatgagatac aagagagtga atattatcca   1620
aaacatatcc agtacaattt actaataggt gaaggaccat gtgaaccagg tgattgtggt   1680
gggaaattat tatgcaaaca tggagtgata ggtattatta cagcaggtgg tgagggccat   1740
gttgcattca tagatcttag acactttcac tgtgctgaag gatccggggc gtggctgcac   1800
ccagaaacgc tggtgaaagt aaaagatgct gaagatcagt tgggtgcacg agtgggttac   1860
atcgaactgg atctcaacag cggtaagatc cttgagagtt ttcgccccga agaacgtttt   1920
ccaatgatga gcacttttaa agttctgcta tgtggcgcgg tattatcccg tattgacgcc   1980
gggcaagagc aactcggtcg ccgcatacac tattctcaga atgacttggt tgagtactca   2040
ccagtcacag aaaagcatct tacggatggc atgacagtaa gagaattatg cagtgctgcc   2100
ataaccatga gtgataacac tgcggccaac ttacttctga caacgatcgg aggaccgaag   2160
gagctaaccg cttttttgca caacatgggg gatcatgtaa ctcgccttga tcgttgggaa   2220
ccggagctga atgaagccat accaaacgac gagcgtgaca ccacgatgcc tgtagcaatg   2280
gcaacaacgt tgcgcaaact attaactggc gaactactta ctctagcttc ccggcaacaa   2340
ttaatagact ggatggaggc ggataaagtt gcaggaccac ttctgcgctc ggcccttccg   2400
gctggctggt ttattgctga taaatctgga gccggtgagc gtgggtctcg cggtatcatt   2460
gcagcactgg ggccagatgg taagccctcc cgtatcgtag ttatctacac gacggggagt   2520
caggcaacta tggatgaacg aaatagacag atcgctgaga taggtgcctc actgattaag   2580
cattggtaat ctagagggcc ctattctata gtgtcaccta aatgctagag ctcgctgatc   2640
agcctcgact gtgccttcta gttgccagcc atctgttgtt tgcccctccc ccgtgccttc   2700
cttgaccctg gaaggtgcca ctcccactgt cctttcctaa taaaatgagg aaattgcatc   2760
gcattgtctg agtaggtgtc attctattct ggggggtggg gtggggcagg acagcaaggg   2820
ggaggattgg gaagacaata gcaggcatgc tggggatgcg gtgggctcta tggcttctga   2880
ggcggaaaga accagctggg gctctagggg gtatccccac gcgccctgta gcggcgcatt   2940
aagcgcggcg ggtgtggtgg ttacgcgcag cgtgaccgct acacttgcca gcgccctagc   3000
gcccgctcct ttcgctttct tcccttcctt tctcgccacg ttcgccggct ttccccgtca   3060
agctctaaat cggggcatcc ctttagggtt ccgatttagt gctttacggc acctcgaccc   3120
caaaaaactt gattagggtg atggttcacg tagtgggcca tcgccctgat agacggtttt   3180
tcgccctttg acgttggagt ccacgttctt taatagtgga ctcttgttcc aaactggaac   3240
aacactcaac cctatctcgg tctattcttt tgatttataa gggattttgg ggatttcggc   3300
ctattggtta aaaaatgagc tgatttaaca aaaatttaac gcgaattaat tctgtggaat   3360
gtgtgtcagt tagggtgtgg aaagtcccca ggctccccag gcaggcagaa gtatgcaaag   3420
catgcatctc aattagtcag caaccaggtg tggaaagtcc ccaggctccc cagcaggcag   3480
```

-continued

```
aagtatgcaa agcatgcatc tcaattagtc agcaaccata gtcccgcccc taactccgcc   3540
catcccgccc ctaactccgc ccagttccgc ccattctccg ccccatggct gactaatttt   3600
ttttatttat gcagaggccg aggccgcctc tgcctctgag ctattccaga agtagtgagg   3660
aggctttttt ggaggcctag gcttttgcaa aaagctcccg ggagcttgta tatccatttt   3720
cggatctgat caagagacag gatgaggatc gtttcgcatg attgaacaag atggattgca   3780
cgcaggttct ccggccgctt gggtggagag gctattcggc tatgactggg cacaacagac   3840
aatcggctgc tctgatgccg ccgtgttccg gctgtcagcg caggggcgcc cggttctttt   3900
tgtcaagacc gacctgtccg gtgccctgaa tgaactgcag gacgaggcag cgcggctatc   3960
gtggctggcc acgacgggcg ttccttgcgc agctgtgctc gacgttgtca ctgaagcggg   4020
aagggactgg ctgctattgg gcgaagtgcc ggggcaggat ctcctgtcat ctcaccttgc   4080
tcctgccgag aaagtatcca tcatggctga tgcaatgcgg cggctgcata cgcttgatcc   4140
ggctacctgc ccattcgacc accaagcgaa acatcgcatc gagcgagcac gtactcggat   4200
ggaagccggt cttgtcgatc aggatgatct ggacgaagag catcaggggc tcgcgccagc   4260
cgaactgttc gccaggctca aggcgcgcat gcccgacggc gaggatctcg tcgtgaccca   4320
tggcgatgcc tgcttgccga atatcatggt ggaaaatggc cgcttttctg gattcatcga   4380
ctgtggccgg ctgggtgtgg cggaccgcta tcaggacata gcgttggcta cccgtgatat   4440
tgctgaagag cttggcggcg aatgggctga ccgcttcctc gtgctttacg gtatcgccgc   4500
tcccgattcg cagcgcatcg ccttctatcg ccttcttgac gagttcttct gagcgggact   4560
ctggggttcg aaatgaccga ccaagcgacg cccaacctgc catcacgaga tttcgattcc   4620
accgccgcct tctatgaaag gttgggcttc ggaatcgttt tccgggacgc cggctggatg   4680
atcctccagc gcggggatct catgctggag ttcttcgccc accccaactt gtttattgca   4740
gcttataatg gttacaaata aagcaatagc atcacaaatt tcacaaataa agcatttttt   4800
tcactgcatt ctagttgtgg tttgtccaaa ctcatcaatg tatcttatca tgtctgtata   4860
ccgtcgacct ctagctagag cttggcgtaa tcatggtcat agctgtttcc tgtgtgaaat   4920
tgttatccgc tcacaattcc acacaacata cgagccggaa gcataaagtg taaagcctgg   4980
ggtgcctaat gagtgagcta actcacatta attgcgttgc gctcactgcc cgctttccag   5040
tcgggaaacc tgtcgtgcca gctgcattaa tgaatcggcc aacgcgcggg gagaggcggt   5100
ttgcgtattg ggcgctcttc cgcttcctcg ctcactgact cgctgcgctc ggtcgttcgg   5160
ctgcggcgag cggtatcagc tcactcaaag gcggtaatac ggttatccac agaatcaggg   5220
gataacgcag gaaagaacat gtgagcaaaa ggccagcaaa aggccaggaa ccgtaaaaag   5280
gccgcgttgc tggcgttttt ccataggctc cgcccccctg acgagcatca caaaaatcga   5340
cgctcaagtc agaggtggcg aaacccgaca ggactataaa gataccaggc gtttccccct   5400
ggaagctccc tcgtgcgctc tcctgttccg accctgccgc ttaccggata cctgtccgcc   5460
tttctccctt cgggaagcgt ggcgctttct caatgctcac gctgtaggta tctcagttcg   5520
gtgtaggtcg ttcgctccaa gctgggctgt gtgcacgaac cccccgttca gcccgaccgc   5580
tgcgccttat ccggtaacta tcgtcttgag tccaacccgg taagacacga cttatcgcca   5640
ctggcagcag ccactggtaa caggattagc agagcgaggt atgtaggcgg tgctacagag   5700
ttcttgaagt ggtggcctaa ctacggctac actagaagga cagtatttgg tatctgcgct   5760
ctgctgaagc cagttacctt cggaaaaaga gttggtagct cttgatccgg caaacaaacc   5820
```

-continued accgctggta gcggtggttt ttttgtttgc aagcagcaga ttacgcgcag aaaaaaagga 5880
tctcaagaag atcctttgat cttttctacg gggtctgacg ctcagtggaa cgaaaactca 5940
cgttaaggga ttttggtcat gagattatca aaaaggatct tcacctagat ccttttaaat 6000
taaaaatgaa gttttaaatc aatctaaagt atatatgagt aaacttggtc tgacagttac 6060
caatgcttaa tcagtgaggc acctatctca gcgatctgtc tatttcgttc atccatagtt 6120
gcctgactcc ccgtcgtgta gataactacg atacgggagg gcttaccatc tggccccagt 6180
gctgcaatga taccgcgaga cccacgctca ccggctccag atttatcagc aataaaccag 6240
ccagccggaa gggccgagcg cagaagtggt cctgcaactt tatccgcctc catccagtct 6300
attaattgtt gccgggaagc tagagtaagt agttcgccag ttaatagttt gcgcaacgtt 6360
gttgccattg ctacaggcat cgtggtgtca cgctcgtcgt ttggtatggc ttcattcagc 6420
tccggttccc aacgatcaag gcgagttaca tgatccccca tgttgtgcaa aaaagcggtt 6480
agctccttcg gtcctccgat cgttgtcaga agtaagttgg ccgcagtgtt atcactcatg 6540
gttatggcag cactgcataa ttctcttact gtcatgccat ccgtaagatg cttttctgtg 6600
actggtgagt actcaaccaa gtcattctga gaatagtgta tgcggcgacc gagttgctct 6660
tgcccggcgt caatacggga taataccgcg ccacatagca gaactttaaa agtgctcatc 6720
attggaaaac gttcttcggg gcgaaaactc tcaaggatct taccgctgtt gagatccagt 6780
tcgatgtaac ccactcgtgc acccaactga tcttcagcat cttttacttt caccagcgtt 6840
tctgggtgag caaaaacagg aaggcaaaat gccgcaaaaa agggaataag ggcgacacgg 6900
aaatgttgaa tactcatact cttccttttt caatattatt gaagcattta tcagggttat 6960
tgtctcatga gcggatacat atttgaatgt atttagaaaa ataaacaaat aggggttccg 7020
cgcacatttc cccgaaaagt gccacctgac gtc 7053

<210> SEQ ID NO 72
<211> LENGTH: 7512
<212> TYPE: DNA
<213> ORGANISM: Artificial Sequence
<220> FEATURE:
<223> OTHER INFORMATION: pcDNA3-MetUb-Bla HR14 construct

<400> SEQUENCE: 72
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840

-continued

```
ctgcttactg gcttatcgaa attaatacga ctcactatag ggagacccaa gcttggtacc    900
accatggaga tcttcgtgaa gactctgact ggtaagacca tcactctcga agtggagccg    960
agtgacacca ttgagaatgt caaggcaaag atccaagaca aggaaggcat ccctcctgac   1020
cagcagaggt tgatctttgc tgggaaacag ctggaagatg gacgcaccct gtctgactac   1080
aacatccaga aagagtccac cctgcacctg gtactccgtc tcagaggtgg gatgcacgga   1140
tccttgggtc gtgcagcttg tgtgcatgta actgaaatac aaaacaaaga tgctactgga   1200
atagataatc acagagaagc aaaattgttc aatgattgga aatcaacct gtccagcctt   1260
gtccaactta gaaagaaact ggaactcttc acttatgtta ggtttgattc tgagtatacc   1320
atactggcca ctgcatctca acctgattca gcaaactatt caagcaattt ggtggtccaa   1380
gccatgtatg ttccacatgg tgccccgaaa tccaaaagag tgggcgatta cacatggcaa   1440
agtgcttcaa accccagtgt attcttcaag gtgggggata catcaaggtt tagtgtgcct   1500
tatgtaggat tggcatcagc atataattgt ttttatgatg gttactcaca tgatgatgca   1560
gaaactcagt atggcataac tgttctaaac catatgggta gtatggcatt cagaatagta   1620
aatgaacatg atgaacacaa aactcttgtc aagatcagag tttatcacag ggcaaagctc   1680
gttgaagcat ggattccaag agcacccaga gcactaccct acacatcaat agggcgcaca   1740
aattatccta agaatacaga accagtaatt aagaagagga aaggtgacat taaatcctat   1800
ggtttaggac ctaggtacgg tgggatttat acatcaaatg ttaaaataat gaattaccac   1860
ttgatgacac cagaagacca ccataatctg atagcaccct atccaaatag agatttagca   1920
atagtctcaa caggaggaca tggtgcagaa acaataccac actgtaaccg tacatcaggt   1980
gtttactatt ccacatatta cagaaagtat taccccataa tttgcgaaaa gcccaccaac   2040
atctggattg aaggaagccc ttattaccca agtagatttc aagcaggagt gatgaaaggg   2100
gttgggccgg cagagctagg agactgcggt gggattttga gatgcataca tggtcccatt   2160
ggattgttaa cagctgaagg tagtggatat gtttgttttg ctgacatacg acagttggag   2220
tgtatcgcag aggaacaggg atccggggcg tggctgcacc cagaaacgct ggtgaaagta   2280
aaagatgctg aagatcagtt gggtgcacga gtgggttaca tcgaactgga tctcaacagc   2340
ggtaagatcc ttgagagttt tcgccccgaa gaacgttttc caatgatgag cacttttaaa   2400
gttctgctat gtggcgcggt attatcccgt attgacgccg ggcaagagca actcggtcgc   2460
cgcatacact attctcagaa tgacttggtt gagtactcac cagtcacaga aaagcatctt   2520
acggatggca tgacagtaag agaattatgc agtgctgcca taaccatgag tgataacact   2580
gcggccaact tacttctgac aacgatcgga ggaccgaagg agctaaccgc ttttttgcac   2640
aacatggggg atcatgtaac tcgccttgat cgttgggaac cggagctgaa tgaagccata   2700
ccaaacgacg agcgtgacac cacgatgcct gtagcaatgg caacaacgtt gcgcaaacta   2760
ttaactggcg aactacttac tctagcttcc cggcaacaat taatagactg gatggaggcg   2820
gataaagttg caggaccact tctgcgctcg gcccttccgg ctggctggtt tattgctgat   2880
aaatctggag ccggtgagcg tgggtctcgc ggtatcattg cagcactggg gccagatggt   2940
aagccctccc gtatcgtagt tatctacacg acggggagtc aggcaactat ggatgaacga   3000
aatagacaga tcgctgagat aggtgcctca ctgattaagc attggtaatc tagagggccc   3060
tattctatag tgtcacctaa atgctagagc tcgctgatca gcctcgactg tgccttctag   3120
ttgccagcca tctgttgttt gcccctcccc cgtgccttcc ttgaccctgg aaggtgccac   3180
```

-continued

```
tcccactgtc ctttcctaat aaaatgagga aattgcatcg cattgtctga gtaggtgtca   3240
ttctattctg gggggtgggg tggggcagga cagcaagggg gaggattggg aagacaatag   3300
caggcatgct ggggatgcgg tgggctctat ggcttctgag gcggaaagaa ccagctgggg   3360
ctctaggggg tatccccacg cgccctgtag cggcgcatta agcgcggcgg gtgtggtggt   3420
tacgcgcagc gtgaccgcta cacttgccag cgccctagcg cccgctcctt tcgctttctt   3480
cccttccttt ctcgccacgt tcgccggctt tccccgtcaa gctctaaatc ggggcatccc   3540
tttagggttc cgatttagtg ctttacggca cctcgacccc aaaaaacttg attagggtga   3600
tggttcacgt agtgggccat cgccctgata gacggttttt cgccctttga cgttggagtc   3660
cacgttcttt aatagtggac tcttgttcca aactggaaca acactcaacc ctatctcggt   3720
ctattctttt gatttataag ggattttggg gatttcggcc tattggttaa aaaatgagct   3780
gatttaacaa aaatttaacg cgaattaatt ctgtggaatg tgtgtcagtt agggtgtgga   3840
aagtccccag gctccccagg caggcagaag tatgcaaagc atgcatctca attagtcagc   3900
aaccaggtgt ggaaagtccc caggctcccc agcaggcaga agtatgcaaa gcatgcatct   3960
caattagtca gcaaccatag tcccgcccct aactccgccc atcccgcccc taactccgcc   4020
cagttccgcc cattctccgc cccatggctg actaattttt tttatttatg cagaggccga   4080
ggccgcctct gcctctgagc tattccagaa gtagtgagga ggcttttttg gaggcctagg   4140
cttttgcaaa aagctcccgg gagcttgtat atccattttc ggatctgatc aagagacagg   4200
atgaggatcg tttcgcatga ttgaacaaga tggattgcac gcaggttctc cggccgcttg   4260
ggtggagagg ctattcggct atgactgggc acaacagaca atcggctgct ctgatgccgc   4320
cgtgttccgg ctgtcagcgc aggggcgccc ggttcttttt gtcaagaccg acctgtccgg   4380
tgccctgaat gaactgcagg acgaggcagc gcggctatcg tggctggcca cgacgggcgt   4440
tccttgcgca gctgtgctcg acgttgtcac tgaagcggga agggactggc tgctattggg   4500
cgaagtgccg gggcaggatc tcctgtcatc tcaccttgct cctgccgaga aagtatccat   4560
catggctgat gcaatgcggc ggctgcatac gcttgatccg gctacctgcc cattcgacca   4620
ccaagcgaaa catcgcatcg agcgagcacg tactcggatg gaagccggtc ttgtcgatca   4680
ggatgatctg gacgaagagc atcaggggct cgcgccagcc gaactgttcg ccaggctcaa   4740
ggcgcgcatg cccgacggcg aggatctcgt cgtgacccat ggcgatgcct gcttgccgaa   4800
tatcatggtg gaaaatggcc gcttttctgg attcatcgac tgtggccggc tgggtgtggc   4860
ggaccgctat caggacatag cgttggctac ccgtgatatt gctgaagagc ttggcggcga   4920
atgggctgac cgcttcctcg tgctttacgg tatcgccgct cccgattcgc agcgcatcgc   4980
cttctatcgc cttcttgacg agttcttctg agcgggactc tggggttcga aatgaccgac   5040
caagcgacgc ccaacctgcc atcacgagat ttcgattcca ccgccgcctt ctatgaaagg   5100
ttgggcttcg gaatcgtttt ccgggacgcc ggctggatga tcctccagcg cggggatctc   5160
atgctggagt tcttcgccca ccccaacttg tttattgcag cttataatgg ttacaaataa   5220
agcaatagca tcacaaattt cacaaataaa gcattttttt cactgcattc tagttgtggt   5280
ttgtccaaac tcatcaatgt atcttatcat gtctgtatac cgtcgacctc tagctagagc   5340
ttggcgtaat catggtcata gctgtttcct gtgtgaaatt gttatccgct cacaattcca   5400
cacaacatac gagccggaag cataaagtgt aaagcctggg gtgcctaatg agtgagctaa   5460
ctcacattaa ttgcgttgcg ctcactgccc gctttccagt cgggaaacct gtcgtgccag   5520
ctgcattaat gaatcggcca acgcgcgggg agaggcggtt tgcgtattgg gcgctcttcc   5580
```

-continued

```
gcttcctcgc tcactgactc gctgcgctcg gtcgttcggc tgcggcgagc ggtatcagct   5640

cactcaaagg cggtaatacg gttatccaca gaatcagggg ataacgcagg aaagaacatg   5700

tgagcaaaag gccagcaaaa ggccaggaac cgtaaaaagg ccgcgttgct ggcgtttttc   5760

cataggctcc gcccccctga cgagcatcac aaaaatcgac gctcaagtca gaggtggcga   5820

aacccgacag gactataaag ataccaggcg tttccccctg gaagctccct cgtgcgctct   5880

cctgttccga ccctgccgct taccggatac ctgtccgcct ttctcccttc gggaagcgtg   5940

gcgctttctc aatgctcacg ctgtaggtat ctcagttcgg tgtaggtcgt tcgctccaag   6000

ctgggctgtg tgcacgaacc ccccgttcag cccgaccgct gcgccttatc cggtaactat   6060

cgtcttgagt ccaacccggt aagacacgac ttatcgccac tggcagcagc cactggtaac   6120

aggattagca gagcgaggta tgtaggcggt gctacagagt tcttgaagtg gtggcctaac   6180

tacggctaca ctagaaggac agtatttggt atctgcgctc tgctgaagcc agttaccttc   6240

ggaaaaagag ttggtagctc ttgatccggc aaacaaacca ccgctggtag cggtggtttt   6300

tttgtttgca agcagcagat tacgcgcaga aaaaaaggat ctcaagaaga tcctttgatc   6360

ttttctacgg ggtctgacgc tcagtggaac gaaaactcac gttaagggat tttggtcatg   6420

agattatcaa aaaggatctt cacctagatc cttttaaatt aaaaatgaag ttttaaatca   6480

atctaaagta tatatgagta aacttggtct gacagttacc aatgcttaat cagtgaggca   6540

cctatctcag cgatctgtct atttcgttca tccatagttg cctgactccc cgtcgtgtag   6600

ataactacga tacgggaggg cttaccatct ggccccagtg ctgcaatgat accgcgagac   6660

ccacgctcac cggctccaga tttatcagca ataaaccagc cagccggaag ggccgagcgc   6720

agaagtggtc ctgcaacttt atccgcctcc atccagtcta ttaattgttg ccgggaagct   6780

agagtaagta gttcgccagt taatagtttg cgcaacgttg ttgccattgc tacaggcatc   6840

gtggtgtcac gctcgtcgtt tggtatggct tcattcagct ccggttccca acgatcaagg   6900

cgagttacat gatcccccat gttgtgcaaa aaagcggtta gctccttcgg tcctccgatc   6960

gttgtcagaa gtaagttggc cgcagtgtta tcactcatgg ttatggcagc actgcataat   7020

tctcttactg tcatgccatc cgtaagatgc ttttctgtga ctggtgagta ctcaaccaag   7080

tcattctgag aatagtgtat gcggcgaccg agttgctctt gcccggcgtc aatacgggat   7140

aataccgcgc cacatagcag aactttaaaa gtgctcatca ttggaaaacg ttcttcgggg   7200

cgaaaactct caaggatctt accgctgttg agatccagtt cgatgtaacc cactcgtgca   7260

cccaactgat cttcagcatc ttttactttc accagcgttt ctgggtgagc aaaaacagga   7320

aggcaaaatg ccgcaaaaaa gggaataagg gcgacacgga aatgttgaat actcatactc   7380

ttcctttttc aatattattg aagcatttat cagggttatt gtctcatgag cggatacata   7440

tttgaatgta tttagaaaaa taaacaaata ggggttccgc gcacatttcc ccgaaaagtg   7500

ccacctgacg tc                                                        7512
```

<210> SEQ ID NO 73
<211> LENGTH: 16
<212> TYPE: PRT
<213> ORGANISM: Artificial Sequence
<220> FEATURE:
<223> OTHER INFORMATION: fusion protein

<400> SEQUENCE: 73

```
His Gly Ser Gly Ala Trp Leu His Pro Glu Thr Leu Val Lys Val Lys
 1               5                  10                  15
```

-continued

```
<210> SEQ ID NO 74
<211> LENGTH: 36
<212> TYPE: PRT
<213> ORGANISM: Artificial Sequence
<220> FEATURE:
<223> OTHER INFORMATION: fusion protein

<400> SEQUENCE: 74

Leu Val Leu Arg Leu Arg Gly Val Gly Ser Val Gly Ala Val Gly Ser
 1              5                   10                  15

Val Gly Asp Glu Val Asp Gly Ser Gly Ala Trp Leu His Pro Glu Thr
            20                  25                  30

Leu Val Lys Val
        35
```

METHODS OF PROTEIN DESTABILIZATION AND USES THEREOF

FIELD OF THE INVENTION

The present invention is in the field of protein analysis and more particularly methods of destabilizing proteins and using the destabilized proteins for novel cell based assays.

BACKGROUND OF THE INVENTION

While genomic programs provide ever more sophisticated information on the sequence and patterns of expression of mammalian genes, it is increasingly recognized that integrating this information into a functional model of how a cell works requires an understanding of how the protein products of expressed genes interact within the cell. Although we have made significant improvements in our ability to clone, sequence and analyze DNA sequences, our reciprocal abilities for studying RNA and protein molecules are significantly less facile or advanced. Furthermore, proteins themselves represent significantly more complex molecules in terms of composition, shape and activity compared to double stranded DNA. A central challenge facing workers in the field today is to understand out how a protein's activity and function within a cell are regulated and coordinated within the native physiological context.

Traditionally, genetic analysis has been used for determining the function of gene products and how they interact with other proteins within a common pathway. Unfortunately genetic analysis in vertebrate organisms is extremely time consuming and expensive. An alternative approach is to devise an assay system for a given protein and then screen for compounds that activate or inhibit its function. These compounds can be used to dissect the cellular pathways the protein functions in, as well as serving as potential compounds of therapeutic value.

Although there is tremendous interest in understanding the regulation and interactions of proteins within cells there are relatively few methods that are robust, simple to use, amenable to high throughput screening or can be used effectively within living cells. Furthermore in many cases where specific assays do exist these are restricted in scope to individual enzymatic steps or to one or two defined pathways.

A need thus exists for sensitive methods of interfacing the functional modifications of proteins with optical signals that can be used detect and monitor these changes, for example for use in high throughput screening. In drug screening applications these assays can be applied to find useful compounds that are specific and selective for a particular protein or signal transduction or metabolic pathway.

Proteins may undergo a huge variety of post-translational modifications subsequent to their synthesis in the cell. In many cases these modifications can play critical roles in the functioning and stability of the modified proteins. For example, proteolysis, phosphorylation, covalent attachment of a lipid or lipid derivative, disulfide bond formation, glycosylation and oxidation all can have important functional effects. Many other examples also exist and may play important functional roles within a cell for defined proteins.

One approach to developing a generic assay capable of detecting these myriad post-translational modifications is to operatively couple these activities through a central pathway of protein modification that can be sensitively measured with a common reporter system. In the present invention, the inventors have recognized that by coupling post-translational activities to the stability of a high sensitivity reporter moiety it is possible to develop uniform cell based assays for a range of activities. Importantly these measurements are robust enough for high throughput screening applications, readily adaptable to a range of activities and provide cellular assays that provide information within a living cell.

In the present invention, post-translational activities can be measured by providing one or more constructs in which the activity to be measured influences the stability of a reporter moiety. In one embodiment, this may be achieved by providing a reporter moiety that is operatively coupled to a multimerized destabilization domain via a linking moiety. The linking moiety comprises a recognition motif for the target activity such that modification of the linker by the activity results in altered stability of the reporter moiety. If the reporter moiety is an enzymatic reporter gene the method provides a high sensitivity readout that is generally applicable to a range of activities which are otherwise difficult to measure within living cells. The multimerized destabilization domain described herein provides a key advantage in the method because it enables the degree of destabilization to be predictably tuned to any activity level or intrinsic stability of the target protein or reporter moiety.

The regulation of protein stability is an area of particular interest because of its increased recognition as a key regulator of a protein's concentration and function in the cell. Although our knowledge of the factors that control protein stability have grown dramatically in recent years, it is clear that a variety of cellular pathways and environmental cues participate in and control a protein's fate. For example, mis-folding, proteolysis, oxidation and some conformational changes that expose significant surface hydrophobicity readily contribute to the recognition of a protein by the cellular machinery for protein degradation. The majority of cytoplasmic protein degradation involves the ubiquitination of the target protein followed by binding and degradation by the proteasome. (For review see Hershko and Ciechanover (1998) Annu. Rev. Biochem. 67 425-79)

A key step in protein ubiquitination, and degradation, is recognition of the target protein by ubiquitin protein ligase or E3 enzyme. This class of enzymes is responsible for the covalent attachment of ubiquitin to the target protein via an amide isopeptide linkage to an $\epsilon$-amino group of one of the substrate protein's lysine residues. There are currently believed to be multiple families of E3 enzymes, additionally there is increasing evidence that some E3 proteins exist as multi-subunit protein complexes (Laney and Hochstrasser (1999) Cell 97 427-430). E3 proteins and their associated complexes are believed to be largely responsible for recognizing and ubiquitinating damaged proteins as well as specific destabilization domains present in target proteins. Once recognized, a protein target that has been modified by the addition of a single ubiquitin domain, becomes a substrate for further ubiquitination, either at different sites in the substrate protein, or through extension of the conjugated ubiquitin. This process can thus lead to a poly-ubiquitinated protein with numerous branched ubiquitin domains attached. Once poly-ubiquitinated, the protein is recognized with high affinity by the proteasome where it is degraded.

The addition of specific destabilization domains to a target protein has in some cases been demonstrated to destabilize that target protein. A key challenge in this area has been to provide a predictable way of creating graded levels of destabilization for a given protein that that can be utilized in manipulating the steady state levels or dynamic temporal regulation of that protein. The present inventors have discovered for the first time that by providing stable multimerized linear chains of individual destabilization domains, such as ubiquitin, it is possible to create a generic method of protein destabilization that is widely applicable to virtually any protein. Importantly, this approach has the advantage that the degree of destabilization can be accurately controlled by varying the number of destabilization domains added to the target protein. As a result, the actual cellular concentration and half-life of an exogenously expressed protein in a cell or living organism can be accurately and reproducibly controlled. By coupling 1, 2, 3, 4 or more copies of ubiquitin to the reporter gene β-lactamase it has been possible to regulate the protein concentration of this protein in the cell over a 10-fold range compared to the native protein. The present inventors have applied this discovery to create an assay technology that is broadly capable of measuring a wide range of post-translational activities.

SUMMARY OF THE INVENTION

This invention provides a fluorescent, bioluminescent or enzymatic substrate useful as an optical probe or sensor of post-translational modifications, such as proteolysis. In one embodiment, the invention comprises a reporter moiety that is functionally coupled to one or more destabilizing domains via a linker. The linker typically contains a recognition motif for an activity. Modification of the linker by the activity results in uncoupling of the reporter moiety from the destabilizing domain(s) with a corresponding change in the stability of the reporter moiety. The level of activity within a sample is sensed by a measurable change in the level of the reporter moiety, for example by detecting at least one optical property of the reporter moiety, or by detecting at least one optical property of detectable product of the reporter moiety. FIG. 1.

In one embodiment the reporter moiety is an enzymatic reporter such as alkaline phosphatase, β-galactosidase, chloramphenicol acetyltransferase, β-glucuronidase, peroxidase, β-lactamase, bioluminescent proteins, luciferases and catalytic antibodies. In another embodiment the reporter moiety is a naturally fluorescent protein, epitope or structural protein.

In one aspect the linker moiety is an amino acid sequence that covalently couples the reporter moiety to the multimerized destabilization domain. In another aspect, the linker moiety comprises two separate amino acid sequences, one of which is covalently coupled to the reporter moiety, and one of which is coupled to the multimerized destabilization domain. Coupling of the reporter moiety to the destabilization domains occurs through the non-covalent interaction or binding of the two amino acid sequences of the linker together. In either case, modification of the linker by the activity results in a modulation of the coupling of the reporter moiety to the multimerized destabilization domains. In one aspect of this method the activity is selected from the group consisting of a protease activity, a protein kinase activity and a phosphoprotein phosphatase activity.

In one aspect the multimerized destabilization domain comprises two, three, four, or more copies of the destabilization domain covalently coupled together in a linear chain. In one embodiment, the destabilization domains comprise ubiquitin, or a homolog thereof. In a preferred embodiment the multimerized copies of ubiquitin are not cleavable by α-NH-ubiquitin protein endoproteases. In one embodiment the ubiquitin domains comprise a mutation that prevents cleavage by α-NH-ubiquitin protein endoproteases. In one aspect of this embodiment the mutation represents the mutation of glycine 76 to a larger or more bulky amino acid.

In another aspect the invention comprises a method of regulating the concentration of one or more target proteins in a cell. The method involves the creation of a fusion protein containing the protein of interest coupled to one or more destabilization domains. In different embodiments the protein of interest may be coupled to a multimerized destabilization domain comprising two or more copies of the destabilization domain. In one embodiment, the destabilization domains comprise ubiquitin, or a homolog thereof. In a preferred embodiment the multimerized copies of ubiquitin are not cleavable by α-NH-ubiquitin protein endoproteases. In one embodiment the ubiquitin domains comprise a mutation that prevents cleavage by α-NH-ubiquitin protein endoproteases. In one aspect of this embodiment the mutation represents the mutation of glycine 76 to a larger or more bulky amino acid.

In one aspect of this method, the fusion protein may additionally comprise a linker that couples the protein of interest to one or more destabilization domains. The linker typically comprises a protease cleavage site for a protease. Cleavage of the linker by the protease modulates the coupling of the multimerized destabilization domain to the protein of interest, thereby providing a method of rapidly modulating the stability of one or more proteins of interest in the cell simultaneously. The protease may be introduced into the cell, or its activity regulated by the presence of a membrane permeant small molecule inhibitor. In one embodiment of this method, the protease does not naturally occur in the target cell.

In another aspect the invention includes a recombinant DNA molecule, comprising a nucleic acid sequence encoding for one or more destabilization domains, a target protein, and a linker moiety that operatively couples the destabilization domain(s) to the target protein. In different embodiments the protein of interest may be coupled to one, two, three, four or more copies of the destabilization domain. In one embodiment, the destabilization domains comprise ubiquitin, or a homolog thereof. In a preferred embodiment the multimerized copies of ubiquitin are not cleavable by α-NH-ubiquitin protein endoproteases. In one embodiment the ubiquitin domains comprise a mutation that prevents cleavage by α-NH-ubiquitin protein endoproteases. In one aspect of this embodiment the mutation represents the mutation of glycine 76 to a larger or more bulky amino acid.

In another embodiment the invention includes a recombinant protein molecule, comprising an amino acid sequence encoding for one or more destabilization domains, a target protein, and a linker moiety that operatively couples the multimerized destabilization domain to the target protein.

In another aspect the invention includes a cell or transgenic organism comprising a nucleic acid sequence encoding for a one or more destabilization domains, a target protein, and a linker moiety that operatively couples the destabilization domain(s) to the target protein. In different embodiments the protein of interest may be coupled to one, two, three, four or more copies of the destabilization domain. In one embodiment, the destabilization domains comprise ubiquitin, or a homolog thereof. In a preferred embodiment the multimerized copies of ubiquitin are not cleavable by α-NH-ubiquitin protein endoproteases. In one embodiment the ubiquitin domains comprise a mutation that prevents cleavage by α-NH-ubiquitin protein endoproteases. In one aspect of this embodiment the mutation represents the mutation of glycine 76 to a larger or more bulky amino acid.

In another embodiment the invention includes a method for identifying a modulator of an activity, comprising the use of the inventions cells or transgenic organisms. The method includes contacting the cells with a test chemical and detecting the activity of the reporter moiety. Additional claims involve the steps of contacting the cell with an activator of the activity prior to the addition said test chemical, and of in parallel determining the cell viability of the cell in the presence of the test chemical.

In another embodiment the invention is directed to the test chemical and a pharmaceutical composition comprising a test chemical identified by the methods of the present invention.

The accompanying drawings, which are incorporated in and form part of the specification, merely illustrate embodiments of the present invention. Together with the remainder of the specification, they are meant to serve to explain certain principles of the invention to those of skill in the art.

DETAILED DESCRIPTION

Definitions

Figure 1:
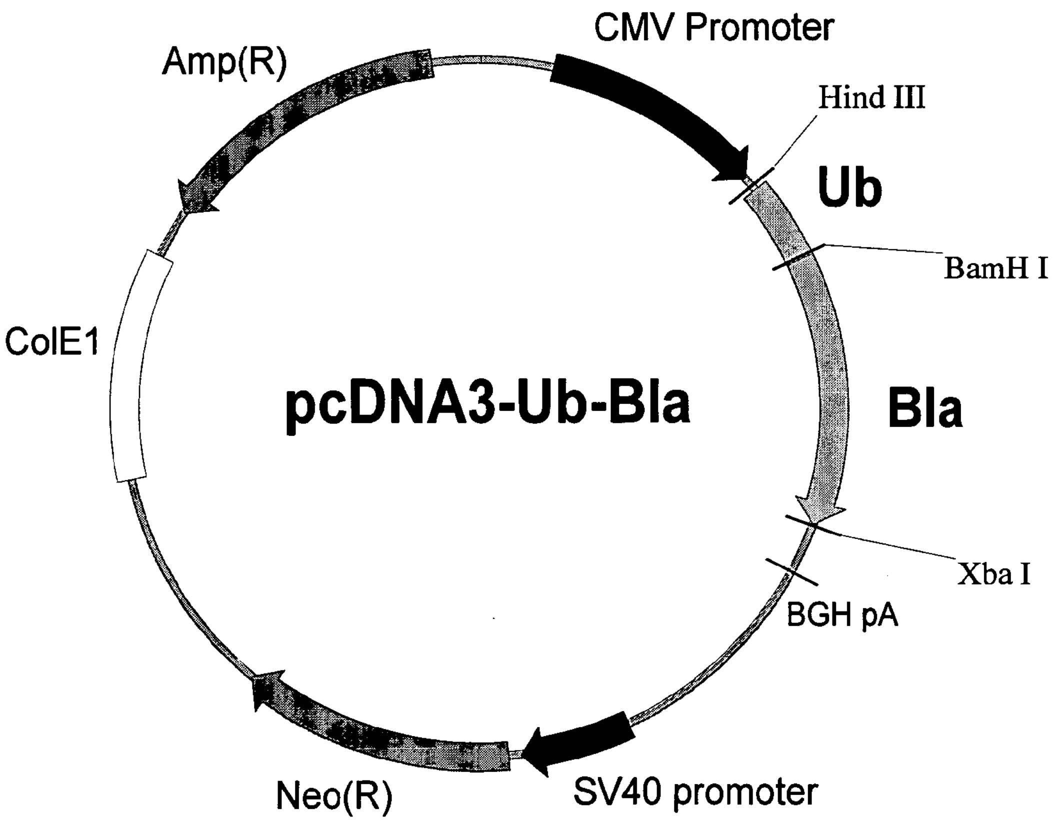
FIG. 1 General schematic overview of parent construct pcDNA3-UbiquitinG76V-B1a. Shown are important coding regions including the ubiquitin-β-lactamase fusion coding region, various promoters and important restriction sites used in the cloning of derivative constructs.

The techniques and procedures are generally performed according to conventional methods in the art and various general references. (Lakowicz, J. R. Topics in Fluorescence Spectroscopy, (3 volumes) New York: Plenum Press (1991), and Lakowicz, J. R. (1996) Scanning Microsc Suppl. 10 213-24, for fluorescence techniques; Sambrook et al. (1989) Molecular Cloning: A Laboratory Manual, $2^{nd}$ ed. Cold Spring Harbor Laboratory Press, Cold Spring Harbor, N.Y., for molecular biology methods; Cells: A Laboratory Manual, $1^{st}$ edition (1998) Cold Spring Harbor Laboratory Press, Cold Spring Harbor, N.Y., for cell biology methods; Optics Guide 5 Melles Griot® Irvine Calif., and Optical Waveguide Theory, Snyder & Love published by Chapman & Hall for general optical methods, which are incorporated herein by reference which are provided throughout this document).

"Activity" refers to the enzymatic or non-enzymatic activity capable of modifying an amino acid residue or peptide bond (preferably enzymatic). Such covalent modifications include proteolysis, phosphorylation, dephosphorylation, glycosylation, methylation, sulfation, prenylation and ADP-ribsoylation. The term includes non-covalent modifications including protein-protein interactions, and the binding of allosteric, or other modulators or second messengers such as calcium, or cAMP or inositol phosphates to a polypeptide.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the gene sequence using recombinant DNA techniques.

"Animal" as used herein may be defined to include human, domestic (cats, dogs, etc), agricultural (cows, horses, sheep, goats, chicken, fish, etc) or test species (frogs, mice, rats, rabbits, simians, etc).

"Chimeric" molecules are polynucleotides or polypeptides which are created by combining one or more of nucleotide sequences of this invention (or their parts) with additional nucleic acid sequence(s). Such combined sequences may be introduced into an appropriate vector and expressed to give rise to a chimeric polypeptide which may be expected to be different from the native molecule in one or more of the following characteristics: cellular location, distribution, ligand-binding affinities, interchain affinities, degradation/turnover rate, signaling, etc.

The terms "cleavage site" or "protease site" refers to the bond cleaved by the protease (e.g. a scissile bond) and typically the surrounding three to four amino acids of either side of the bond.

"Control elements" or "regulatory sequences" are those non-translated regions of the gene or DNA such as enhancers, promoters, introns and 3' untranslated regions which interact with cellular proteins to carry out replication, transcription, and translation. They may occur as boundary sequences or even split the gene. They function at the molecular level and along with regulatory genes are very important in development, growth, differentiation and aging processes.

"Corresponds to" refers to a polynucleotide sequence that is homologous (i.e., is identical, not strictly evolutionarily related) to all or a portion of a reference polynucleotide sequence, or that a polypeptide sequence is identical to all or a portion of a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

"Derivative" refers to those polypeptides which have been chemically modified by such techniques as ubiquitination, labeling, pegylation (derivatization with polyethylene glycol), and chemical insertion or substitution of amino acids such as ornithine which do not normally occur in human proteins.

A "destabilization domain" refers to a protein, polypeptide or amino acid sequence that is capable of modulating the stability of a protein of interest when functionally coupled to the protein of interest. Examples of destabilizing domains include ubiquitin, PEST sequences, cyclin destruction boxes and hydrophobic stretches of amino acids. Preferred destabilization domains include ubiquitin and homologs thereof, particularly those comprising mutations that prevent, or significantly reduce, the cleavage of ubiquitin multimers by α-NH-ubiquitin protein endoproteases. Examples of such mutations include the mutation of glycine 76 to another amino acid, particularly an amino acid selected from the group consisting of Ala, Leu, Ile, Phe, Tyr, Val, Met, Cys, His, Trp, Pro, Arg, Lys, Thr and Ser. Preferred is UbiquitinG76V.

A "detectable product" is a chemical moiety used for detecting a reporter moiety. They include, but are not limited to, radionuclides, enzymes, fluorescent, chemi-luminescent, or chromogenic agents. Detectable products associate with, establish the presence of, and may allow quantification of a particular nucleic sequence, amino acid sequence or reporter moiety. Preferred detectable products are retained within living cells and provide a fluorescence readout that is compatible with fluorescent activated cell sorting (FACS) analysis.

The term "engineered protease site" refers to a protease site that has been modified from the naturally existing sequence by at least one amino acid substitution.

The term "homolog" refers to two sequences or parts thereof, that are greater than, or equal to 85% identical when optimally aligned using the ALIGN program. Homology or sequence identity refers to the following. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., (1972) in Atlas of Protein Sequence and Structure 5, National Biomedical Research Foundation, 101-110, and Supplement 2 to this volume, pp. 1-10.

An "inhibitor" is a substance that retards or prevents a chemical or physiological reaction or response. Common inhibitors include but are not limited to antisense molecules, antibodies, antagonists and their derivatives.

"Isolated" refers to material removed from its original environment (e.g. the natural environment if it is naturally occurring), and thus is altered from its natural state. For example, an isolated polynucleotide could be part of a vector or a composition of matter, or could be contained within a cell, and still be "isolated" because that vector, composition of matter, or particular cell is not the original environment of the polynucleotide.

The term "linker" or "linker moiety" refers to an amino acid, polypeptide or protein sequence that serves to operatively couple a reporter moiety to one or more destabilization domains. Linkers may comprise a single polypeptide chain that covalently couples the reporter moiety to the multimerized destabilization domain. Alternatively the linker may comprise two separate polypeptides. Typically the first polypeptide is covalently coupled to the reporter moiety, and the second polypeptide is covalently coupled to the multimerized destabilization domain. Generally the first and second polypeptides comprising the linker moiety in this embodiment are capable of interacting or associating such that the interaction or association operatively couples the reporter moiety to the multimerized destabilization domain. Preferably the linker moiety is non-cleavable by α-NH-ubiquitin protein endoproteases. Linkers may be of any size.

The term "modulates" refers to, either the partial or complete, enhancement or inhibition (e.g. attenuation of the rate or efficiency) of an activity or process.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian, including human) cells or tissues. Modulators are evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

The term "multimerized destabilization domain" refers to at least two destabilization domains that are linearly coupled together. Preferred multimerized domains are non-cleavable by α-NH-ubiquitin protein endoproteases. The term does not include naturally occurring poly-ubiquitin chains in which the ubiquitin monomers are coupled together via isopeptide bonds attached to the ε-amino group of lysine. The term also does not include naturally occurring multi-ubiquitin genes, are cleavable by α-NH-ubiquitin protein endoproteases to create ubiquitin monomers. The destabilization domains present in the multimerized destabilization domain are typically the same, but need not necessarily be identical.

"Naturally fluorescent protein" refers to proteins capable of forming a highly fluorescent, intrinsic chromophore either through the cyclization and oxidation of internal amino acids within the protein or via the enzymatic addition of a fluorescent co-factor. Typically such chromophores can be spectrally resolved from weakly fluorescent amino acids such as tryptophan and tyrosine.

"Naturally occurring" refers to a polypeptide produced by cells which have not been genetically engineered or which have been genetically engineered to produce the same sequence as that naturally produced. Specifically contemplated are various polypeptides that arise from post-transnational modifications. Such modifications of the polypeptide include but are not limited to acetylation, carboxylation, glycosylation, phosphorylation, lipidation, proteolytic cleavage and acylation.

An "oligonucleotide" or "oligomer" is a stretch of nucleotide residues which has a sufficient number of bases to be used in a polymerase chain reaction (PCR), a site directed mutagenesis reaction or a cassette to create a desired sequence element. These short sequences are based on (or designed from) genomic or cDNA sequences and are used to amplify, mutate or create particular sequence elements. Oligonucleotides or oligomers comprise portions of a DNA sequence having at least about 10 nucleotides and as many as about 50 nucleotides, preferably about 15 to 30 nucleotides. They are chemically synthesized and may also be used as probes.

An "oligopeptide" is a short stretch of amino acid residues and may be expressed from an oligonucleotide. It may be functionally equivalent to and either the same length as or considerably shorter than a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biologic and/or immunogenic activity.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "operably coupled" refers to a juxtaposition wherein the components so described are either directly or indirectly coupled. Examples of directly coupled components include proteins that are translationally fused together. Examples of indirectly coupled components include proteins that can functionally associate either transiently, or persistently, through a binding interaction.

The term "polynucleotide" refers to a polymeric form of nucleotides of at least 10 bases in length, either ribonucleotides or deoxynucleotides. Modified forms and analogs of either type of nucleotide are also included, as are ribonucleotides or deoxynucleotides linked via novel bonds such as those described in U.S. Pat. No. 5,532,130, European Patent Applications EP 0 839 830, EP 0 742 287, EP 0 285 057 and EP 0 694 559. The term includes single and double stranded forms of nucleotides, or a mixture of single and double stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine, as well as other chemical or enzymatic modifications.

The term "polypeptide" refers to a amino acids joined to each other by peptide bonds or modified peptide bonds, i.e. peptide isosteres, and may contain amino acids other than the 20 gene-encoded amino acids. The polypeptides may be modified by either natural processes, such as posttranslational processing, or by chemical modification techniques which are well known in the art. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Modification include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, transfer-RNA mediated addition of amino acids to protein such as arginylation. (See Proteins-Structure and Molecular Properties $2^{nd}$ Ed., T. E. Creighton, W.H. Freeman and Company, New York (1993); Posttranslational Covalent Modification of Proteins, B. C. Johnson, Ed., Academic Pres, New York, pp. 1-12 (1983).

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labeled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Probes" are nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

The term "recognition motif" refers to all or part of a polypeptide sequence recognized by a post-translational modification activity to enable a polypeptide to become modified by that post-translational modification activity. Typically, the affinity of a protein, e.g. enzyme, for the recognition motif is about 1 mM (apparent $K_d$), preferably a greater affinity of about 10 μM, more preferably, 1 μM or most preferably has an apparent $K_d$ of about 0.1 μM. The term is not meant to be limited to optimal or preferred recognition motifs, but encompasses all sequences that can specifically confer substrate recognition to a peptide. In some embodiments the recognition motif is a phosphorylated recognition motif (e.g. includes a phosphate group), or comprises other post-translationally modified residues.

"Recombinant nucleotide variants" are polynucleotides that encode a protein. They may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Recombinant polypeptide variant" refers to any polypeptide which differs from a naturally occurring polypeptide by amino acid insertions, deletions and/or substitutions, created using recombinant DNA techniques. Guidance in determining which amino acid residues may be replaced, added or deleted without abolishing characteristics of interest may be found by comparing the sequence of a polypeptide with that of related polypeptides and minimizing the number of amino acid sequence changes made in highly conserved regions.

A "reporter moiety" includes any protein that directly or indirectly produces a specific detectable product, or cellular phenotype, such as drug resistance that can be used to monitor transcription of a gene. Preferred reporter moieties include proteins with an enzymatic activity that provides enzymatic amplification of gene expression such as alkaline phosphatase, β-galactosidase, chloramphenicol acetyltransferase, β-glucuronidase, peroxidase, β-lactamase, bioluminescent proteins, luciferases and catalytic antibodies. Other reporter moieties include proteins such as naturally fluorescent proteins or homologs thereof, cell surface proteins or the native or modified forms of an endogenous protein to which a specific assay exists or can be developed in the future. Preferred reporter moieties for use in the present invention provide for a fluorescent readout that is compatible with fluorescent activated cell sorting (FACS) analysis.

A "signal or leader sequence" is a short amino acid sequence which is or can be used, when desired, to direct the polypeptide through a membrane of a cell. Such a sequence may be naturally present on the polypeptides of the present invention or provided from heterologous sources by recombinant DNA techniques.

A "standard" is a quantitative or qualitative measurement for comparison. Preferably, it is based on a statistically appropriate number of samples and is created to use as a basis of comparison when performing diagnostic assays, running clinical trials, or following patient treatment profiles. The samples of a particular standard may be normal or similarly abnormal.

The term "stringent hybridization conditions", refers to an overnight incubation at 42° C. in a solution comprising 50% formamide, 5×SSC (750 mM NaCl, 75 mM sodium citrate), 50 mM sodium phosphate (pH 7.6), 5× Denhardt's solution, 10% dextran sulfate and 20 μg/ml denatured sheared salmon sperm DNA, followed by washing the filters in 0.1×SSC at about 65° C. Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lower stringency); salt conditions, or temperature. For example, lower stringency conditions include an overnight incubation at 37° C. in a solution comprising 6×SSPE (20×SSPE=3M NaCl; 0.2M NaH2PO4; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variation in the above conditions may be accomplished through the inclusion and/or substitution of alternative blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. A polynucleotide which hybridizes only to polyA+ sequences (such as any 3' terminal polyA+ tract of a cDNA shown in the sequence listing), or to a complementary stretch of T (or U) residues would not be included in the definition of a "polynucleotide" since such a polynucleotide would hybridize to any nucleic acid molecule containing a poly (A) stretch, or the complement thereof.

The term "target" refers to a biochemical entity involved a biological process. Targets are typically proteins that play a useful role in the physiology or biology of an organism. A therapeutic chemical binds to target to alter or modulate its function. As used herein, targets can include cell surface receptors, G-proteins, kinases, ion channels, phopholipases, proteases and other proteins mentioned herein.

The term "test chemical" refers to a chemical to be tested by one or more screening method(s) of the invention as a putative modulator. A test chemical can be any chemical, such as an inorganic chemical, an organic chemical, a protein, a peptide, a carbohydrate, a lipid, or a combination thereof. Usually, various predetermined concentrations of test chemicals are used for screening, such as 0.01 micromolar, 1 micromolar and 10 micromolar. Test chemical controls can include the measurement of a signal in the absence of the test compound or comparison to a compound known to modulate the target.

The following terms are used to describe the sequence relationships between two or more polynucleotides: "reference sequence", "comparison window", "sequence identity", "percentage identical to a sequence", and "substantial identity". A "reference sequence" is a defined sequence used as a basis for a sequence comparison; a reference sequence may be a subset of a larger sequence, for example, as a segment of a full-length cDNA or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods selected. The term "sequence identity" means that two polynucleotide sequences are identical (i.e., on a nucleotide-by-nucleotide basis) over the window of comparison. The term "percentage identical to a sequence" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 30 percent sequence identity, preferably at least 40 percent sequence identity, more preferably at least 50 percent sequence identity, and most preferably at least 60 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

I. Multimerized Destabilization Domains

Destabilization domains include proteins, protein domains and amino acid sequences that when functionally coupled to a target protein effect a change in the half-life of that protein when expressed in a cell. Examples include PEST domains, stretches of hydrophobic amino acids, phosphorylation dependent degradation signals, cyclin destruction boxes and the addition of ubiquitin domains. Preferred as a destabilization domain is ubiquitin and homologs thereof, particularly mutants or homologs comprising mutations that prevent, or significantly reduce, the cleavage of ubiquitin multimers by α-NH-ubiquitin protein endoproteases. In general, destabilization domains function by causing the target protein to be recognized by one or more elements of the cellular protein degradation apparatus. Once marked for destruction, the protein is actively recruited into the 28S proteasome where the protein is degraded. Within the cell a variety of signals may target a protein for degradation. In some cases a destabilization feature may be revealed in a protein as a result of oxidation, mis-folding or proteolysis. For example, stretches of hydrophobic amino acids are often exposed in denatured or improperly folded proteins thereby targeting them for degradation. Short stretches of hydrophobic amino acids, or hydrophobic domains, also occur in correctly folded proteins and have been identified in proteins with short half lives.

For example, the Deg 1 domain of yeast mating type transcription factor α2 is a 19 residue element that forms an amphipathic helix with an exposed hydrophobic face, and is responsible for the rapid degradation of this protein (Johnson et al., (1998) Cell 94 217-227). These elements are believed to be recognized by E3 ubiquitin ligases and target the protein to degradation through the ubiquitin system described below.

PEST domains (regions rich in the amino acids proline (P), glutamic acid (E), serine (S) and threonine (T)) are often located at the C-terminal domains of relatively unstable proteins. (Rogers, et al., (1986) Science 234 (4774) 364-8). A well characterized PEST domain is located in residues 422 to 461 of ornithine decarboxylase, and has been used to successfully destabilize a number of proteins including the green fluorescent protein from *Aequorea* green fluorescent protein (Li et al. J. Biol. Chem. (1998) 273 (52) 34970-5). Certain PEST sequences are believed to be recognized by the 26S proteasome subunit directly and do not require ubiquitination.

PEST sequences may also be regulated by phosphorylation, for example multiple phosphorylation within the PEST sequences of the yeast G1 cyclins Cln3 and Cln2 are required for degradation.

Phosphorylation dependent degradation signals have also been identified in the transcription factors NF-κB and β-catenin, in addition to many cell cycle regulatory proteins such as cyclins. (Ghosh et al., (1998) Ann. Rev. Immunol. 16 225-260; Aberle et al., (1997) EMBO J. 16 3797-3804; Koepp et al., (1999) 97 431-434). These proteins include phosphorylation dependent recognition sequences that bind to one of the growing family of E3 ubiquitin ligases only when the site is phosphorylated. In NF-κB, the binding domain for the E3 ubiquitin ligase comprises the relatively short sequence DS*GLDS*, (SEQ. ID. NO.: 1) where S* denotes phosphoserine. Binding to the E3 ubiquitin ligase does not require a ubiquitination conjugation site in this case.

The cell-cycle destruction box is a partially conserved 9 amino acid sequence motif usually located approximately 40-50 amino acid residues from the N-terminus of the protein first described for the A and B type cyclins. The consensus destruction box sequence has the general structure as shown in Table 1 below.

TABLE 1

| Consensus destruction box sequence | | | | | | | | |
|---|---|---|---|---|---|---|---|---|
| R | (A/T) | (A) | L | (G) | x | (I/V) | (G/T) | (N) |
| 1 | 2 | 3 | 4 | 5 | 6 | 7 | 8 | 9 |

Amino acid residues, or combinations of two residues, that appear in parentheses in the above structure occur in more than 50% of known destruction sequences. The residues at positions 1 and 4 are conserved in all destruction boxes.

Ubiquitin (SEQ. ID. NO.: 2), a 76 amino acid polypeptide found in all eukaryotic cells, is centrally involved in the mechanism of targeting a protein for degradation by the cell. In general, the covalent attachment of a ubiquitin domain (SEQ. ID. NO.: 2), to a protein represents a primary recognition motif for binding of that protein to the proteasome. The attachment of ubiquitin (SEQ. ID. NO.: 2) to the protein typically occurs after recognition of one or more of the destabilization domains discussed above, or some other destabilizing feature of a protein. Attachment of ubiquitin (SEQ. ID. NO.: 2) occurs via the reversible isopeptide linkage of the carboxy-terminus of ubiquitin (SEQ. ID. NO.: 2) to lysine residues in the target protein. After the addition of the first ubiquitin domain (SEQ. ID. NO.: 2), further ubiquitin moieties (SEQ. ID. NO.: 2) may subsequently be added via free lysine residues in ubiquitin (SEQ. ID. NO.: 2) to create branched poly-ubiquitin chains on the substrate protein. These reactions are catalyzed by a family of enzymes that are often referred to as the ubiquitination complex. Once the target protein comprises one or more copies of ubiquitin (SEQ. ID. NO.: 2) it binds with high affinity to the proteasome where it is degraded. (See generally, Hershko et al., (1998) Annu. Rev. Biochem. 76 425-79; Laney et al., (1999) Cell 97 427-430).

The ubiquitin gene typically comprises multiple copies of the ubiquitin coding sequence (SEQ. ID. NO.: 2). Individual ubiquitin domains (SEQ. ID. NO.: 2) are post-translationally formed from the poly-ubiquitin gene by cleavage of the expressed protein by specific α-NH-ubiquitin protein endoproteases that are present within all eukaryotic cells. (Jonnalagadda et al., (1989) J. Biol. Chem. 264 10637-10642. The endoproteases will cleave either multiple ubiquitin-ubiquitin chains, or ubiquitin-fusion protein constructs, provided that the last amino acid of the ubiquitin moiety (SEQ. ID. NO.: 2) is glycine. If this last amino acid is mutated to a more bulky amino acid the ubiquitin fusion protein is not cleavable by α-NH-ubiquitin protein endoproteases.

The present inventors have recognized for the first time that the creation of multiple ubiquitin fusion proteins that are not cleavable by the α-NH-ubiquitin protein endoproteases provides for a facile and tunable method of regulating protein stability. This invention has many important applications for developing novel assays for intracellular activities, and as a regulatable method of coordinately controlling protein concentrations within the cell.

II. Reporter Moieties

Enzymatic reporter moieties include any protein capable of catalyzing the creation of a detectable product. Specific examples include alkaline phosphatase, β-galactosidase, chloramphenicol acetyltransferase, β-glucuronidase, peroxidase, β-lactamase, catalytic antibodies, luciferases and other bioluminescent proteins.

Alkaline phosphatase, including human placental and calf intestinal alkaline phosphatase (for example, GenBank Accession # U89937), can be measured using colorimetric, fluorescent and chemiluminescent substrates. (Berger, J., et al. (1988) Gene 66 1-10; Kain, S. R. (1997) Methods. Mol. Biol. 63 49-60) Alkaline phosphatase is widely used in transcriptional assays, typically by measuring secreted alkaline phosphatase (SEAP).

β-galactosidase (β-Gal) the gene product of the bacterial gene LacZ, is also widely used as a reporter gene for transcriptional analysis and may be assayed via histochemical, fluorescent or chemiluminescent substrates, either within intact, or permeabilized cells. (See, U.S. Pat. No. 5,070,012, issued Dec., 3, 1991 to Nolan et al., and Bronstein, I., et al., (1989) J. Chemilum. Biolum. 4 99-111).

β-glucuronidase (GUS) is widely used for transcriptional analysis in higher plants and may also be assayed using a variety of histochemical and fluorescent substrates. (See generally U.S. Pat. No. 5,599,670, issued Feb., 4, 1997 to Jefferson).

Chloramphenicol acetyltransferase (CAT), encoded by the bacterial Tn9 gene, is widely used for transcriptional assays and is traditionally measured using a radioisotopic assay in cell extracts (See Gorman et al., (1982) 2 1044-51).

Catalytic antibodies are also amenable for use as reporter genes, if the reaction catalyzed by the antibody results in the formation of a detectable product. Examples include the aldolase specific antibodies 38C2 and 33F12 that catalyze the synthesis of novel fluorogenic retro-aldol reactions (List et al., (1998) Proc. Natl. Acad. Sci. USA 95 15351-15355). Typical antibody substrates are cell permeant nonpolar organic molecules that are not substrates for the natural enzymes and are thus good markers of enzyme activity.

β-Lactamases

A large number of β-lactamases have been isolated and characterized, all of which would be suitable for use in accordance with the present method. Initially, β-lactamases were divided into different classes (I through V) on the basis of their substrate and inhibitor profiles and their molecular weight (Richmond, M. H. and Sykes, R. B., (1973) Adv. Microb. Physiol. 9 31-88). More recently, a classification system based on amino acid and nucleotide sequence has been introduced (Ambler, R. P., (1980) Phil. Trans. R. Soc. Lond. [Ser.B.] 289 321-331). Class A β-lactamases possess a serine in the active site and have an approximate weight of 29 kd. This class contains the plasmid-mediated TEM β-lactamases such as the RTEM enzyme of pBR322. Class B β-lactamases have an active-site zinc bound to a cysteine residue. Class C enzymes have an active site serine and a molecular weight of approximately 39 kd, but have no amino acid homology to the class A enzymes.

The coding regions of an exemplary β-lactamase employed in the methods described herein include SEQ. ID. NOs: 3 through 7. Nucleic acids encoding proteins with β-lactamase activity can be obtained by methods known in the art, for example, by polymerase chain reaction of cDNA using primers based on a DNA sequence in SEQ. ID. NO.: 3. PCR methods are described in, for example, U.S. Pat. No. 4,683,195; Mullis et al. (1987) Cold Spring Harbor Symp. Quant. Biol. 51 263; and Erlich, ed., PCR Technology, (Stockton Press, NY, 1989).

Preferably, beta-lactamase polynucleotides encode an intracellular form of a protein with beta-lactamase activity that lacks a functional signal sequence. This provides the advantage of trapping the normally secreted beta-lactamase protein within the cell, which enhances the signal to noise ratio of the signal associated with beta-lactamase activity, and enables the individual cells to be FACS™ sorted. For example, in any of the polypeptides of SEQ. ID. NO.: 3-7, the signal sequence has been replaced with the amino acids Met-Ser. Accordingly, upon expression, beta-lactamase activity remains within the cell. For expression in mammalian cells it is preferable to use beta-lactamase polynucleotides with nucleotide sequences preferred by mammalian cells. In some applications secreted forms of beta-lactamase can be used with the methods described herein.

A variety of colorimetric and fluorescent substrates of β-lactamase are available. Fluorescent substrates include those capable of changes, either individually or in combination, of total fluorescence, excitation or emission spectra or fluorescence resonance energy transfer (FRET), for example those described in U.S. Pat. No. 5,741,657, issued Apr. 21, 1998, and U.S. Pat. No. 5,955,604, issued Sep. 22, 1999. Any membrane permanent β-lactamase substrate capable of being measured inside the cell after cleavage can be used in the methods and compositions of the invention. Membrane permanent β-lactamase substrates will not require permeablizing eukaryotic cells either by hypotonic shock or by electroporation. Generally, such non-specific pore forming methods are not desirable to use in eukaryotic cells because such methods injure the cells, thereby decreasing viability and introducing additional variables into the screening assay (such as loss of ionic and biological contents of the shocked or electroplated cells). Such methods can be used in cells with cell walls or membranes that significantly prevent or retard the diffusion of such substrates. Preferably, the membrane permeant β-lactamase substrates are transformed in the cell into a β-lactamase substrate of reduced membrane permeability (usually at least five-fold less permeable) or that is membrane impermeant. Transformation inside the cell can occur via intracellular enzymes (e.g. esterases) or intracellular metabolites or organic molecules (e.g. sulfhydryl groups).

Bioluminescent Proteins

Preferred bioluminescent proteins include firefly, bacterial or click beetle luciferases, aequorins and other photoproteins, for example as described in U.S. Pat. No. 5,221,623, issued Jun. 22, 1989 to Thompson et al., U.S. Pat. No. 5,683,888 issued Nov. 4, 1997 to Campbell; U.S. Pat. No. 5,674,713 issued Sep. 7, 1997 to DeLuca et al., U.S. Pat. No. 5,650,289 issued Jul. 22, 1997 to Wood and U.S. Pat. No. 5,843,746 issued Dec. 1, 1998 to Tatsumi et al. Particularly preferred are bioluminescent proteins isolated from the ostracod Cypridina (or Vargula) hilgendorfii. (Johnson and Shimomura, (1978) Methods Enzymol 57 331-364; Thompson, Nagata & Tsuji (1989) Proc. Natl. Acad. Sci. USA 86, 6567-6571).

Beyond the availability of bioluminescent proteins (luciferases) isolated directly from the light organs of beetles, cDNAs encoding luciferases of several beetle species (including, among others, the luciferase of *P. pyralis* (firefly), the four luciferase isozymes of *P. plagiophthalamus* (click beetle), the luciferase of *L. cruciata*(firefly) and the luciferase of *L. lateralis*) (deWet et al., (1987) Molec. Cell. Biol. 7, 725-737; Masuda et al., (1989) Gene 77, 265-270; Wood et al., (1989) Science 244, 700-702; European Patent Application Publication No. 0 353 464) are available. Further, the cDNAs encoding luciferases of any other beetle species, which make bioluminescent proteins, are readily obtainable by the skilled using known techniques (de Wet et al. (1986) Meth. Enzymol. 133, 3-14; Wood et al., (1989) Science 244, 700-702).

Most firefly and click beetle luciferases are ATP- and magnesium dependent and require oxygen for light production. Typically light emission from these enzymes exhibits a rapid burst in intensity followed by a rapid decrease in the first few seconds, followed by a significantly slower sustained light emission. Relatively sustained light output at high rates has been accomplished in these systems by inclusion of coenzyme A, dithiothreitol and other reducing agents that reduce product inhibition and slows inactivation of the luciferase that occurs during catalysis of the light producing reaction, as described in U.S. Pat. No. 5,641,641, issued Jun. 24, 1997, and U.S. Pat. No. 5,650,289, issued Jul. 22, 1997. Such stable light emitting systems are preferred for use in the present invention.

Particularly preferred bioluminescent proteins are those derived from the ostracod *Cypridina* (or *Vargula*) *hilgendorfii*. The *Cypridina luciferase* (GenBank accession no. U89490) uses no cofactors other than water and oxygen, and its luminescent reaction proceeds optimally at pH 7.2 and physiological salt concentrations, (Shimomura, O., Johnson, F. H. and Saiga, Y. (1961) J. Cell. Comp. Physiol. 58 113-124). By comparison, firefly luciferase has optimal activity at low ionic strength, alkaline pH and reducing conditions, that are typically quite different to those usually found within mammalian cells. Because Cypridina luciferase has a turnover number of 1600 $min^{-1}$ and a quantum yield of 0.29, (Shimomura, O. & Johnson, F. H. and Masugi, T. (1969) Science 164 1299-1300; Shimomura, O. & Johnson, F. H. (1970) Photochem. Photobiol. 12 291-295), the Cypridina luciferase produces a specific photon flux exceeding that of the optimized firefly system by a factor of at least 50 (Miesenbock and Rothman, (1997) Proc. Natl. Acad. Sci. USA 94 3402-3407).

Naturally Fluorescent Proteins

Another preferred class of embodiments of the reporter moiety includes naturally fluorescent proteins such as the Green Fluorescent Protein (GFP) of *Aequorea Victoria* (Tsien, R. Y. (1998) Annu. Rev. Biochem. 67 509-44). Because the entire fluorophore and peptide of a naturally fluorescent protein can be expressed within intact living cells without the addition of other co-factors or fluorophores, optical probes comprising such proteins as the reporter moiety provide the ability to monitor activities, within defined cell populations, tissues or in an entire transgenic organism. For example, by the use of cell type specific promoters and subcellular targeting motifs, it is possible to selectively target the probe to a discrete location to enable highly spatially defined measurements.

Naturally fluorescent proteins have been isolated and cloned from a number of marine species including the sea pansies *Renilla reniformis, R. kollikeri* and *R. mullerei* and from the sea pens *Ptilosarcus, Stylatula* and *Acanthoptilum*, as well as from the Pacific Northwest jellyfish, *Aequorea Victoria*; Szent-Gyorgyi et al. (SPIE conference 1999); D. C. Prasher et al., (1992) Gene, 111:229-233 and several species of coral (Matz et al. (1999). Nature Biotechnology 17 969-973. These proteins are capable of forming a highly fluorescent, intrinsic chromophore through the cyclization and oxidation of internal amino acids within the protein that can be spectrally resolved from weakly fluorescent amino acids such as tryptophan and tyrosine.

Additionally naturally fluorescent proteins have also been observed in other organisms, although in most cases these require the addition of some exogenous factor to enable fluorescence development. For example, the cloning and expression of yellow fluorescent protein from *Vibrio fischeri* strain Y-1 has been described by T. O. Baldwin et al., Biochemistry (1990) 29 5509-15. This protein requires flavins as fluorescent co-factors. The cloning of Peridinin-chlorophyll a binding protein from the dinoflagellate *Symbiodinium* sp. was described by B. J. Morris et al., (1994) Plant Molecular Biology, 24 673:77. One useful aspect of this protein is that it fluoresces in red. The cloning of phycobiliproteins from marine cyanobacteria such as Synechococcus, e.g., phycoerythrin and phycocyanin, is described in S. M. Wilbanks et al., (1993) J. Biol. Chem. 268 1226-35. These proteins require phycobilins as fluorescent co-factors, whose insertion into the proteins involves auxiliary enzymes. The proteins fluoresce at yellow to red wavelengths.

A variety of mutants of the GFP from *Aequorea victoria* have been created that have distinct spectral properties, improved brightness and enhanced expression and folding in mammalian cells compared to the native GFP, (SEQ. ID. NO.: 8), Table 2. (*Green Fluorescent Proteins*, Chapter 2, pages 19 to 47, edited Sullivan and Kay, Academic Press, U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type *Aequorea* GFP and are preferred for use as reporter moieties in the present invention.

TABLE 2

Aequorea Fluorescent Proteins

| Mutations | Common Name | Quantum Yield (Φ) & Molar Extinction (ε) | Excitation & Emission Max | Relative Fluorescence At 37° C. | Sensitivity To Low pH % max F at pH 6 |
|---|---|---|---|---|---|
| S65T type | | | | | |
| S65T, S72A, N149K, M153T, I167T | Emerald (SEQ. ID. NO.: 28) | Φ = 0.68<br>ε = 57,500 | 487<br>509 | 100 | 91 |
| F64L, S65T, V163A | | Φ = 0.58<br>ε = 42,000 | 488<br>511 | 54 | 43 |
| F64L, S65T | EGFP | Φ = 0.60<br>ε = 55,900 | 488<br>507 | 20 | 57 |
| S65T | | Φ = 0.64<br>ε = 52,000 | 489<br>511 | 12 | 56 |
| Y66H type | | | | | |
| F64L, Y66H, Y145F, V163A | P4-3E | Φ = 0.27<br>ε = 22,000 | 384<br>448 | 100 | N.D. |
| F64L, Y66H, Y145F | | Φ = 0.26<br>ε = 26,300 | 383<br>447 | 82 | 57 |
| Y66H, Y145F | P4-3 | Φ = 0.3<br>ε = 22,300 | 382<br>446 | 51 | 64 |
| Y66H | BFP | Φ = 0.24<br>ε = 21,000 | 384<br>448 | 15 | 59 |
| Y66W type | | | | | |
| S65A, Y66W, S72A, N146I, M153T, V163A | W1C | Φ = 0.39<br>ε = 21,200 | 435<br>495 | 100 | 82 |
| F64L, S65T, Y66W, N146I, M153T, V163A | W1B | Φ = 0.4<br>ε = 32,500 | 434 452<br>476 (505) | 80 | 71 |
| Y66W, N146I, M153T, V163A | hW7 | Φ = 0.42<br>ε = 23,900 | 434 452<br>476 (505) | 61 | 88 |
| Y66W | | | 436<br>485 | N.D. | N.D. |
| T203Y type | | | | | |
| S65G, S72A, K79R, T203Y | Topaz | Φ = 0.60<br>ε = 94,500 | 514<br>527 | 100 | 14 |
| S65G, V68L, S72A, T203Y | 10C | Φ = 0.61<br>ε = 83,400 | 514<br>527 | 58 | 21 |
| S65G, V68L, Q69K, S72A, | h10C+ | Φ = 0.71<br>ε = 62,000 | 516<br>529 | 50 | 54 |

TABLE 2-continued

Aequorea Fluorescent Proteins

| Mutations | Common Name | Quantum Yield (Φ) & Molar Extinction (ε) | Excitation & Emission Max | Relative Fluorescence At 37° C. | Sensitivity To Low pH % max F at pH 6 |
|---|---|---|---|---|---|
| T203Y | | | | | |
| S65G, S72A, T203H | | Φ = 0.78<br>ε = 48,500 | 508<br>518 | 12 | 30 |
| S65G, S72A, T203F | | Φ = 0.70<br>ε = 65,500 | 512<br>522 | 6 | 28 |
| T203I type | | | | | |
| T203I, S72A, Y145F | Sapphire | Φ = 0.64<br>ε = 29,000 | 395<br>511 | 100 | 90 |
| T203I T202F | H9 | Φ = 0.6<br>ε = 20,000 | 395<br>511 | 13 | 80 |

Non Aequorea, naturally fluorescent proteins, for example Anthozoan fluorescent proteins, and functional engineered homologs thereof, are also suitable for use in the present invention including those shown in Table 3 below.

TABLE 3

Anthozoa Fluorescent Proteins

| Species | Protein Name | Quantum Yield (Φ) & Molar Extinction (ε) | Excitation & Emission Max | Relative Brightness | SEQ. ID. NO.: |
|---|---|---|---|---|---|
| *Anemonia majano* | amFP486 | Φ = 0.24<br>ε = 40,000 | 458<br>486 | 0.43 | SEQ. ID. NO.:9 |
| *Zoanthus* sp | zFP506 | Φ = 0.63<br>ε = 35,600 | 496, 506 | 1.02 | SEQ. ID. NO.:10 |
| | zFP538 | Φ = 0.42<br>ε = 20,200 | 528, 538 | 0.38 | SEQ. ID. NO.:11 |
| *Discosoma striata* | dsFP483 | Φ = 0.46<br>ε = 23,900 | 443<br>483 | 0.5 | SEQ. ID. NO.:12 |
| *Discosoma* sp "red" | drFP583 | Φ = 0.23<br>ε = 22,500 | 558<br>583 | 0.24 | SEQ. ID. NO.:13 |
| *Clavularia* sp | CFP484 | Φ = 0.48<br>ε = 35,300 | 456<br>484 | 0.77 | SEQ. ID. NO.:14 |

III. Linker Moieties

Generally linker moieties for measuring a post-translational activity encompass a post-translational recognition motif that contains a residue that, when modified, modulates the coupling of the reporter moiety to the multimerized destabilization domain, thus effecting a change in the stability of the reporter moiety. Typically, for measuring proteases, such linkers contain a single scissile bond (bond that is cleaved within the substrate) for a specific protease and preserve the native function and activity of the reporter moiety and destabilization domains in the intact fusion protein. The design and size of peptide sequences for specific constructs, is dependent upon the application for which the optical probe is to be used. For example, for most applications, the peptide linker separating the reporter moiety and the multimerized destabilization domains will typically be in the range of 5 to 50 amino acids in length, preferably 10 to 25 amino acids in length, or more preferably 10 to 15 amino acids in length. For certain applications, the peptide may be significantly larger, up to and including entire protein domains, for example 50 to 100 amino acids in length. Smaller peptides, in the range of 5 to 50 amino acids may also be used. Typically the protease site may be located at any position within the linker with respect to the reporter moiety and destabilization domains.

In one embodiment the linker comprises a single polypeptide chain that covalently couples the destabilization domains to the reporter moiety. Typically in this embodiment, the linker will comprise a post-translational recognition motif such as a protease recognition motif. Cleavage of the linker by the protease at the cleavage site results in uncoupling of the multimerized destabilization domains from the reporter moiety resulting in a modulation in the stability of the reporter moiety. An important feature of the linker is that it does not contain a protease recognition site for α-NH-ubiquitin protein endoproteases that would otherwise result in the post-translational processing of the construct irrespective of the presence or absence of the target post-translational activity. Any cleavage activity capable of hydrolyzing the linker moiety may be assayed with this embodiment of the present invention, provided it does not also cleave the reporter moiety thereby directly modulating its function.

In another aspect of this method, the linker may comprise distinct post-translational recognition motifs and cleavage sites for example, a phosphorylation site and a protease cleavage site, as described in commonly owned U.S. patent application Ser. No. 09/306,542 filed May 5, 1999. In this case, post-translational modification of the linker results in the modulation of the rate and efficiency of cleavage of the modified linker compared to the non-modified linker. This approach enables the present method to be used to detect a broad range of post translational activities.

In some embodiments, the linker functions to couple a target protein to one or more destabilization domains for the purpose of regulating the concentration of the target protein in the cell. In this case the linker need not contain a protease cleavage site, and may be significantly smaller, in the order of about 1 to 10 amino acids in length.

In another aspect, the linker may comprise two separate polypeptide chains that are capable of interacting with each other to functionally couple the multimerized destabilization domains to the reporter gene. This approach enables an additional range of post-translational activities to be assayed. In this embodiment, one polypeptide chain is typically covalently coupled to the multimerized destabilization domain, and a separate polypeptide chain is covalently coupled to the reporter moiety. (FIG. 1) Binding of the first polypeptide chain to the second polypeptide chain results in coupling of the destabilization domain to reporter moiety resulting in a modulation of the stability of the reporter moiety. This approach thus enables the identification and detection of protein-protein interactions between defined proteins as well as the ability to detect post-translational modifications that influence these protein-protein interactions.

Examples of suitable interaction domains include protein-protein interaction domains such as SH2, SH3, PDZ, 14-3-3, WW and PTB domains. Other interaction domains are described in for example, the database of interacting proteins available on the worldwide web at doe-mbi.ucla.edu.

To identify and characterize the interaction of two test proteins, the method would typically involve 1) the creation of a first fusion protein comprising the first test protein coupled to the reporter moiety, and a second fusion protein comprising the second test protein coupled to the multimerized destabilization domain construct. 2) The introduction of the test protein fusion proteins alone in to control cells, and in combination into test cells. 3) The measurement of the stability of the reporter moiety in the control cells and test cells. 4) Comparison of the stability of the reporter moiety in the control cells, compared to the stability of the reporter moiety in the test cells. If the cell expressing both test fusion proteins exhibits a reporter moiety with a significantly altered stability (or level of expression) compared to the control cells, then the results indicate that the two proteins do interact under the experimental conditions chosen. Conversely if the stability's of the reporter moieties in the control cells, and in the test cells are the same, then the results indicate that the proteins probably don't interact strongly under the test conditions.

The method also enables the detection and characterization of stimuli (such as receptor stimulation) that cause two proteins to alter their degree of interaction. In this case, a cell line is created that expresses the first and second fusion proteins, as described above, comprising interaction domains that exhibit, or are believed to exhibit post-translational regulated interactions. For example, post-translational modification by phosphorylation of serine or threonine residues can modulate 14-3-3 domain interactions, tyrosine phosphorylation can influence SH2 domain interactions, the redox state can influence disulfide bond formation. The cell line is then exposed to a test stimulus to determine whether the stimulus regulates the interaction of the two proteins. If the stimulus does regulate the interaction of the two proteins, then this will result in the coupling of the multimerized destabilization domain fusion protein to the reporter moiety fusion protein, subsequently resulting in a modulation of the stability of the reporter moiety in the treated cells, compared to the non-treated cells.

The invention is also readily amenable to identifying new protein-protein interactions. For example, where a first protein is known, but the protein(s) with which it interacts are unknown. In this case, a first fusion protein is made between the first protein and the reporter moiety (or destabilization domain) and cloned into a suitable expression vector. Second, a library of test proteins, for example isolated from a cDNA expression library, is fused in frame to the multimerized destabilization domains (or reporter moiety) and subcloned into a second expression vector. Typically the first fusion protein would be then be introduced into a population of test cells and single clones identified that stably expressed the reporter moiety. The library of test proteins (typically in the form of expression vectors) would be introduced into the clonal cells, stably expressing the first fusion protein. The resulting transformed cells would then be screened to identify cells with altered expression of the reporter moiety fusion compared to the control cells. Suitable clones expressing the reporter moieties with modulated stability, (i.e., reduced levels of the reporter moiety) may then be identified, isolated and characterized, for example by fluorescence activated cell sorting (FACS™). Those library members that display reporter moieties with larger relative changes in expression level may then be identified by the degree to which the stability of the reporter moiety is altered for each library member after exposure to the library of test fusion proteins.

IV. Methods of Use

Introduction of Constructs into Cells

Typically the constructs of the present invention will be introduced and expressed in target cells via the use of standard molecular biology techniques known in the art. Another approach involves the use of membrane translocating sequences, as described in U.S. Pat. No. 5,807,746, issued Sep. 15 1998 to Lin et al. to introduce the protein constructs into cells.

Nucleic acids may also be used to transfect cells with sequences coding for expression of the multimerized destabilization domain, linker and reporter moiety. Generally these will be in the form of an expression vector including expression control sequences operatively linked to a nucleotide sequence coding for expression of the polypeptide. As used, the term "nucleotide sequence coding for expression of" a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, IRES sequences (internal ribosome entry site) maintenance of the correct reading frame of that gene to permit proper translation of the mRNA, and stop codons.

Methods that are well known to those skilled in the art can be used to construct expression vectors containing the multimerized destabilization domain, linker, reporter moiety construct. These methods include in vitro recombinant DNA techniques, synthetic techniques and in vivo recombination/genetic recombination. (See, for example, the techniques described in Maniatis, et al., (1989) Cold Spring Harbor Laboratory, N.Y.). Many commercially available expression vectors are available from a variety of sources including Clontech (Palo Alto, Calif.), Stratagene (San Diego, Calif.) and Invitrogen (San Diego, Calif.) as well as and many other commercial sources.

A contemplated version of the method is to use inducible controlling nucleotide sequences to produce a sudden increase in the expression of the reporter moiety, linker and multimerized destabilization domain construct e.g., by inducing expression of the construct. Example inducible systems include the tetracycline inducible system first described by Bujard and colleagues (Gossen and Bujard (1992) Proc. Natl. Acad. Sci. USA 89 5547-5551, Gossen et al. (1995) Science 268 1766-1769) and described in U.S. Pat. No. 5,464,758.

Transformation of a host cell with recombinant DNA may be carried out by conventional techniques as are well known to those skilled in the art. Where the host is prokaryotic, such as *E. coli*, competent cells that are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the fusion polypeptide of the invention, and a second foreign DNA molecule encoding a selectable phenotype, such as the herpes simplex thymidine kinase gene. Another method is to use an eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, an eukaryotic host is utilized as the host cell as described herein.

The construction of expression vectors and the expression of genes in transfected cells involve the use of molecular cloning techniques also well known in the art. Sambrook et al., (1989) Cold Spring Harbor Laboratory, Cold Spring Harbor, N.Y., and *Current Protocols in Molecular Biology*, F. M. Ausubel et al., eds., (Current Protocols, a joint venture between Greene Publishing Associates, Inc. and John Wiley & Sons, Inc., (most recent Supplement). Nucleic acids used to transfect cells with sequences coding for expression of the polypeptide of interest generally will be in the form of an expression vector including expression control sequences operatively linked to a nucleotide sequence coding for expression of the polypeptide comprising the optical probe.

Assays for Post-Translational Activities

In one class of embodiments, the present invention can be used to measure post-translational activities, such as proteolysis, phosphorylation, dephosphorylation, glycosylation, methylation, sulfation, prenylation, disulfide bond formation and ADP-ribsoylation within cells.

The method generally involves the expression within, or introduction into a cell of a reporter moiety that is functionally coupled to one or more destabilizing domains via a linker. The linker typically contains a recognition motif that is specific for the post-translational activity to be assayed. Modification of the linker by the post-translational activity, results in uncoupling of the reporter moiety from the destabilizing domain resulting in a modulation in the stability of the reporter moiety. The level of activity within a sample is sensed by a measurable change in the level of the reporter moiety, for example by detecting at least one optical property of the reporter moiety, or by detecting at least one optical property of detectable product of the reporter moiety.

To measure protease activity, it is typically desirable to provide an expression vector in which the expressed fusion gene product comprises a reporter moiety covalently linked to the multimerized destabilization moieties via a single amino acid chain. Thus under these conditions the expressed construct is destabilized until acted upon by the target protease. Upon proteolysis, the cleaved reporter moiety exhibits significantly increased stability, resulting in its steady state accumulation within the cell to a higher level.

The choice of reporter moiety depends in part on the cellular system in which the assays are conducted, and the sensitivity and detection means at hand. For mammalian cells, the β-lactamase, β-galactosidase, and naturally fluorescent protein based reporter genes provide for intracellular fluorescent measurements, which are preferred. Preferred reporter moieties for luminescent readouts include luciferase and other bioluminescent protein based reporters. In plant studies, preferred reporters include β-glucuronidase and luciferase. For transgenic applications in whole animals or intact tissue samples, naturally fluorescent proteins are preferred because the reporter does not require the addition of any substrates or co-factors in order to produce a detectable product. For applications were high sensitivity is required, for example because the target activity has a low turnover number, enzymatic reporter moieties are preferred because they provide enzymatic amplification. That is, each reporter moiety is capable of generating hundreds or thousands of detectable products per minute. By comparison a non enzymatic reporter, such as a naturally fluorescent protein, provides for little signal amplification.

The choice of the multimerized destabilization domain, and the number of copies of the destabilization domain to use are also dependent on the reporter moiety and type of activity being measured. Preferred destabilization domains include, those based on ubiquitin (SEQ. ID. NO.: 2) and mutants and homologs thereof. Particularly preferred are mutants or homologs of ubiquitin (SEQ. ID. NO.: 2) comprising mutations that prevent, or significantly reduce, the cleavage of ubiquitin multimers by α-NH-ubiquitin protein endoproteases.

To establish the optimal number of destabilization domains one would generally start by evaluating a construct containing three copies of the destabilization domain. Depending upon the results, one would either increase or decrease the number of copies of destabilization domains. Generally one would increase the number of copies of the destabilization domain if the steady state levels of the non-protease treated samples were too high (too little degradation), and decrease the number of copies of the destabilization domain if the steady state level of the non-protease treated samples were too low (too much degradation). If the target protein was subject to excessive degradation, the steady state level of the target protein may be too low to provide for effective cleavage by the protease, particularly if that protease exhibits a relatively low affinity for that substrate.

An important advantage of the present invention is the ability to titrate the degree of destabilization, and therefore the steady state concentration, of the target protein in the cell. Since the destabilized, unmodified sensor represents the substrate for the target activity, it is preferable to provide the substrate at a physiologically relevant concentration within the cell while retaining the appropriate turnover characteristics for each individual reporter molecule.

For assays measuring protease activity, the linker generally comprises a protease recognition motif within its sequence. The protease recognition motif may be placed anywhere within the linker moiety, but is conveniently placed close to the center of the linker unless there are steric, or other reasons, to position the recognition motif at a specific location. Typically, the recognition motif will provide for relatively specific recognition of the sequence by the target protease. In some cases it may be preferable for the linker to contain a second "control" protease site for a known protease for use as a positive control.

The expression vector will normally direct expression of the sensor to the cytosol of the cell, although other cellular compartments, such as the plasma membrane are also practical. Once the expression vector is introduced in a population of cells, the cells are typically screened for reporter moiety expression level in the absence of the target protease. This can be achieved by FACS™, after addition of appropriate substrates for the reporter moieties (if required). While cells may be selected for varying levels of expression of the reporter moiety within the population of cells, observations to date suggest that cells exhibiting somewhat lower levels of reporter moiety are superior to those that initially exhibit high levels of reporter moieties under these conditions. Cells may also be selected via antibiotic resistance to provide for stable cell lines.

Once isolated and characterized, the resulting cell line represents a living sensor for the activation or expression of the target protease that enables the identification and screening of compounds that modulate the activation of the target protease. Importantly these determinations can be completed within the living cell where other issues such as membrane permeability, specificity and toxicity may be directly assessed.

In most cases, it will be preferable to start with a cell line that does not normally express high levels of the active target protease. However if this is not possible, then the initial evaluation of the cell lines may be modified in order to screen for cells initially exhibiting high levels of reporter moiety expression. For example, by using an inhibitor of the reporter moiety to inhibit basal reporter gene activity, (as discussed below). In general any types of cells may be used with the present invention, including animal, plant, insect, yeast and other eukaryotic cells or prokaryotic cells.

In whole cell studies it may be desirable to add an inhibitor of protein synthesis such as cycloheximide in order to reduce the steady state level of the destabilized reporter moiety in the cell immediately prior to the measurement of reporter activity. This approach has the advantage of improving the dynamic range of the assay because in the absence of new protein synthesis, uncleaved and therefore destabilized reporter moieties are destroyed by targeting to the proteasome leaving the cleaved and stabilized reporters intact within the cell. (i.e. the background is reduced). This results in a larger net difference in reporter moiety activity in cells containing a suitable protease compared with those lacking a suitable protease. Typically for such uses, cycloheximide is added to cell in the range of 10 to 150 μg/ml cycloheximide, preferably 50 to 100 μg/ml. Generally cells are pretreated with an appropriate stimulus to activate the target protease, and then cycloheximide is added one to two hours prior to the addition of suitable substrates for the reporter moiety.

In another aspect of this method, it sometimes may also be desirable to add an inhibitor of the enzymatic reporter moiety to reduce the activity of the reporter moiety prior to compound addition in screening applications. For example, in order to screen for inhibitors of a constitutively active protease, such inhibitors of reporter activity can be used to eliminate the pool of cleaved and stabilized reporter prior to adding compound, in effect zeroing out the cells to begin the experiment. This approach also has the advantage that the actual concentration of destabilized substrate molecules is not reduced in the cell, so that the protein substrate can be effectively degraded by the target protease. Example inhibitors include clavulanic acid for the β-lactamase reporter gene (see commonly owned U.S. patent application Ser. No. 09/067,612 filed Apr. 28, 1999) and phenylethyl-β-D-thiogalactoside for β-galactosidase (see Fiering et al., (1991) Cytometry 12 291-301). These membrane permeable inhibitors may be added prior to, simultaneously with, or after exposure of the cells to an inhibitor of protein synthesis.

To measure the degree of protein-protein interaction between two defined test proteins, it is typically desirable to separately couple one protein to one or more destabilization domains, and the second protein to the reporter moiety, and then express both fusion proteins in a test cell. This could be achieved for example by transfecting a cell with two compatible expression vectors. In one expression vector, the expressed fusion protein typically comprises a reporter moiety coupled to the first test protein, and in the second expression vector, the expressed fusion protein typically comprises the second test protein, coupled to one or more destabilization domains.

If the first polypeptide fusion protein binds to the second polypeptide fusion protein then the destabilization domain(s) are effectively coupled to the reporter moiety resulting in a modulation of its stability. Thus the relative degree of destabilization of the reporter moiety is a direct indicator of the extent to which the proteins physically interact. Typically this can be accomplished by determining the stability of the reporter moiety in a cell expressing both proteins compared to a control cell, expressing the reporter moiety fusion protein alone. If the cell expressing both constructs exhibits a reporter moiety with a significantly altered stability compared to the control cell, the results indicate that the two proteins are interacting when co-expressed within the cell.

The choice and selection of the appropriate reporter moiety and destabilization domain are determined by the same issues of sensitivity and ease of detection discussed above. Preferred reporter moieties include β-lactamase and naturally fluorescent proteins. Preferred destabilization domains include those based on ubiquitin (SEQ. ID. NO.: 2), and mutants and functional homologs thereof. Particularly preferred are mutants or homologs of ubiquitin (SEQ. ID. NO.: 2) comprising mutations that prevent, or significantly reduce, the cleavage of ubiquitin multimers by α-NH-ubiquitin protein endoproteases.

The choice of the number of copies of the destabilization domain is dependent on the affinity of the target interaction to be measured, and the degree of destabilization exerted on the reporter moiety when the proteins are associated. In many cases, the affinity of the interaction will not be known and it will be necessary to evaluate a range of multimerized constructs in order to identify the optimal assay characteristics. Ideally a multimerized construct will be selected in which both the first test protein and the second test protein are present at physiologically relevant concentrations. One way to achieve this result may be to couple both the first test protein and the second test protein with at least one ubiquitin (SEQ. ID. NO.: 2) domain. Under these circumstances both proteins are slowly degraded when separated, but more rapidly degraded when complexed together.

Induction and Regulation of Expression Levels of Target Proteins

In another embodiment, the invention provides for a generalized way of coordinately regulating the cellular concentration of a plurality of target proteins in a cell, or transgenic organism. In this method, the target proteins are operatively coupled to a multimerized destabilization domain via a linker. By varying the number of destabilization domains present in the multimerized destabilization domain, it is possible to titrate the degree of destabilization, and therefore the steady state concentration of the target protein within the cell or transgenic organism. Thus using this approach it is possible to reproducibly vary the relative stoichometery, as well as, the level of expression, of one or more target proteins.

In some embodiments the linker may comprise about 1 to 10 amino acids. Typically the linker is non-cleavable by α-NH-ubiquitin protein endoproteases.

In one embodiment the linker may contain a non-naturally occurring protease cleavage site (in that cell type), such that cleavage of the linker by the protease results in uncoupling of the target protein from the multimerized destabilization domain hence creating an increase in the stability and concentration of the target protein after protease digestion. In one aspect of this method, regulation of the activity of the protease can be achieved via regulating the concentration and exposure of the cell to an inhibitor of the protease.

This approach enables the coordinate regulation of the intracellular concentration of a number of target proteins that contain the same protease recognition sites in their linker moieties, simultaneously within a cell. The approach is particularly well suited for the engineering of organisms or cells where multiple proteins need to be induced and expressed in order to create the desired effect, for example for regulating a multi-step metabolic or signal transduction pathway.

In one embodiment the protease is a non-naturally occurring protease in the host cell, which recognizes a relatively rare recognition motif in the linker moiety, for example, including proteases such as Factor Xa (EC 3.4.21.6), Entrokinase (EC 3.4.21.9) and IgA protease (EC 3.4.21.72). Proteases that recognize defined sequences of at least 4, or preferably at least 5 or more preferably about 6 amino acid residues, are generally preferred. Viral proteases, such as a CMV protease or other non-naturally occurring proteases (for that particular cell or organism) are also preferred. If this is the case, then expression of the protease should not significantly impact the cell, and the fusion proteins should not suffer non-specific degradation via the host cells endogenous proteases. Induction or activation of the protease in the cell results in a rapid increase in protease activity within the cell that can cleave the target fusion proteins thereby increasing their stability and steady state concentration in the cell.

V. Screening Applications

The present invention is suited for use with systems and methods that utilize automated and integratable workstations for identifying modulators, and chemicals having useful activity. Such systems are described generally in the art (see, U.S. Pat. Nos. 4,000,976 to Kramer et al. (issued Jan. 4, 1977), 5,104,621 to Pfost et al. (issued Apr. 14, 1992), 5,125,748 to Bjornson et al. (issued Jun. 30, 1992), 5,139,744 to Kowalski (issued Aug. 18, 1992), 5,206,568 Bjornson et al. (issued Apr. 27, 1993), 5,350,564 to Mazza et al. (Sep. 27, 1994), 5,589,351 to Harootunian (issued Dec. 31, 1996), and PCT Application Nos: WO 93/20612 to Baxter Deutschland GMBH (published Oct. 14, 1993), WO 96/05488 to McNeil et al. (published Feb. 22, 1996), WO 93/13423 to Agong et al. (published Jul. 8, 1993) and U.S. Pat. No. 5,985,214, issued Nov. 16, 1999.

Typically, such a system includes: A) a storage and retrieval module comprising storage locations for storing a plurality of chemicals in solution in addressable chemical wells, a chemical well retriever and having programmable selection and retrieval of the addressable chemical wells and having a storage capacity for at least 100,000 addressable wells, B) a sample distribution module comprising a liquid handler to aspirate or dispense solutions from selected addressable chemical wells, the chemical distribution module having programmable selection of, and aspiration from, the selected addressable chemical wells and programmable dispensation into selected addressable sample wells (including dispensation into arrays of addressable wells with different densities of addressable wells per centimeter squared) or at locations, preferably pre-selected, on a plate, C) a sample transporter to transport the selected addressable chemical wells to the sample distribution module and optionally having programmable control of transport of the selected addressable chemical wells or locations on a plate (including adaptive routing and parallel processing), D) a reaction module comprising either a reagent dispenser to dispense reagents into the selected addressable sample wells or locations on a plate or a fluorescent detector to detect chemical reactions in the selected addressable sample wells or locations on a plate, and a data processing and integration module.

The storage and retrieval module, the sample distribution module, and the reaction module are integrated and programmably controlled by the data processing and integration module. The storage and retrieval module, the sample distribution module, the sample transporter, the reaction module and the data processing and integration module are operably linked to facilitate rapid processing of the addressable sample wells or locations on a plate. Typically, devices of the invention can process at least 100,000 addressable wells or locations on a plate in 24 hours. This type of system is described in commonly owned U.S. Pat. No. 5,985,214, issued Nov. 16, 1999. If desired, each separate module is integrated and programmably controlled to facilitate the rapid processing of liquid samples, as well as being operably linked to facilitate the rapid processing of liquid samples. In one embodiment the system provides for a reaction module that is a fluorescence detector to monitor fluorescence. The fluorescence detector is integrated to other workstations with the data processing and integration module and operably linked with the sample transporter. Preferably, the fluorescence detector is of the type described herein and can be used for epi-fluorescence. Other fluorescence detectors that are compatible with the data processing and integration module and the sample transporter, if operable linkage to the sample transporter is desired can be used as known in the art or developed in the future. For some embodiments of the invention, particularly for plates with 96, 192, 384 and 864 wells per plate, detectors are available for integration into the system. Such detectors are described in U.S. Pat. No. 5,589,351 (Harootunian), U.S. Pat. No. 5,355,215 (Schroeder), and PCT patent application WO 93/13423 (Akong). Alternatively, an entire plate may be "read" using an imager, such as a Molecular Dynamics Fluor-Imager 595 (Sunnyvale, Calif.). Multi-well platforms having greater than 864 wells, including 3,456 wells, can also be used in the present invention (see, for example, the PCT Application PCT/US98/11061, filed Jun. 2, 1998. These higher density well plates require miniaturized assay volumes that necessitate the use of highly sensitivity assays that do not require washing. The present invention provides such assays as described herein.

The screening methods described herein can be made on cells growing in or deposited on solid surfaces. A common technique is to use a microtiter plate well wherein the fluorescence measurements are made by commercially available fluorescent plate readers. One such method is to use cells in Costar 96 well microtiter plates (flat with a clear bottom) and measure fluorescent signal with CytoFluor multiwell plate reader (Perseptive Biosystems, Inc., MA) using two emission wavelengths to record fluorescent emission ratios. In another embodiment, the system comprises a microvolume liquid handling system that uses electrokinetic forces to control the movement of fluids through channels of the system, for example as described in U.S. Pat. No. 5,800,690 issued Sep. 1, 1998 to Chow et al., European patent application EP 0 810 438 A2 filed May 5, 1997, by Pelc et al. and PCT application WO 98/00231 filed 24 Jun. 1997 by Parce et al. These systems use "chip" based analysis systems to provide massively parallel miniaturized analysis. Such systems are preferred systems of spectroscopic measurements in some instances that require miniaturized analysis.

A Method for Identifying a Chemical, Modulator or a Therapeutic

The present invention can also be used for testing a therapeutic for useful therapeutic activity. A therapeutic is identified by contacting a test chemical suspected of having a modulating activity of a biological process or target with a test cell comprising the constructs of the present invention. Typically the cells are located within at least one well of a multi-well platform. The test chemical can be part of a library of test chemicals that is screened for activity, such as biological activity. The library can have individual members that are tested individually or in combination, or the library can be a combination of individual members. Such libraries can have at least two members, preferably greater than about 100 members or greater than about 1,000 members, more preferably greater than about 10,000 members, and most preferably greater than about 100,000 or 1,000,000 members. After appropriate incubation of the sample with the test cell, an inhibitor of protein synthesis may be added and a substrate for the reporter moiety added. At least one optical property (such as fluorescence or absorbance) of the sample is determined and compared to a non-treated control to determine the level of reporter gene expression or activity. If the sample having the test chemical exhibits increased or decreased reporter moiety expression or activity relative to that of the control cell then a candidate modulator has been identified.

The candidate modulator can be further characterized and monitored for structure, potency, toxicology, and pharmacology using well-known methods. The structure of a candidate modulator identified by the invention can be determined or confirmed by methods known in the art, such as mass spectroscopy. For putative modulators stored for extended periods of time, the structure, activity, and potency of the putative modulator can be confirmed.

Depending on the system used to identify a candidate modulator, the candidate modulator will have putative pharmacological activity. For example, if the candidate modulator is found to inhibit a protein tyrosine phosphatase involved, for example in T-cell proliferation in vitro, then the candidate modulator would have presumptive pharmacological properties as an immunosuppressant or anti-inflammatory (see, Suthanthiran et al., (1996) Am. J. Kidney Disease, 28 159-172) Such nexuses are known in the art for several disease states, and more are expected to be discovered over time. Based on such nexuses, appropriate confirmatory in vitro and in vivo models of pharmacological activity, as well as toxicology, can be selected. The assays, and methods of use described herein, enable rapid pharmacological profiling to assess selectivity and specificity, and toxicity. This data can subsequently be used to develop new candidates with improved characteristics.

Bioavailability and Toxicology of Candidate Modulators

Once identified, candidate modulators can be evaluated for bioavailability and toxicological effects using known methods (see, Lu, Basic Toxicology, Fundamentals, Target Organs, and Risk Assessment, Hemisphere Publishing Corp., Washington (1985); U.S. Pat. No. 5,196,313 to Culbreth (issued Mar. 23, 1993) and U.S. Pat. No. 5,567,952 to Benet (issued Oct. 22, 1996). For example, toxicology of a candidate modulator can be established by determining in vitro toxicity towards a cell line, such as a mammalian i.e. human, cell line. Candidate modulators can be treated with, for example, tissue extracts, such as preparations of liver, such as microsomal preparations, to determine increased or decreased toxicological properties of the chemical after being metabolized by a whole organism. The results of these types of studies are often predictive of toxicological properties of chemicals in animals, such as mammals, including humans.

The toxicological activity can be measured using reporter genes that are activated during toxicological activity or by cell lysis (see WO 98/13353, published Apr. 2, 1998). Preferred reporter genes produce a fluorescent or luminescent translational product (such as, for example, a Green Fluorescent Protein (see, for example, U.S. Pat. No. 5,625,048 to Tsien et al., issued Apr. 29, 1998; U.S. Pat. No. 5,777,079 to Tsien et al., issued Jul. 7, 1998; WO 96/23810 to Tsien, published Aug. 8, 1996; WO 97/28261, published Aug. 7, 1997; PCT/US97/12410, filed Jul. 16, 1997; PCT/US97/14595, filed Aug. 15, 1997)) or a translational product that can produce a fluorescent or luminescent product (such as, for example, beta-lactamase (see, for example, U.S. Pat. No. 5,741,657 to Tsien, issued Apr. 21, 1998, and WO 96/30540, published Oct. 3, 1996)), such as an enzymatic degradation product. Cell lysis can be detected in the present invention as a reduction in a fluorescence signal from at least one photon-producing agent within a cell in the presence of at least one photon reducing agent. Such toxicological determinations can be made using prokaryotic or eukaryotic cells, optionally using toxicological profiling, such as described in PCT/US94/00583, filed Jan. 21, 1994 (WO 94/17208), German Patent No 69406772.5-08, issued Nov. 25, 1997; EPC 0680517, issued Nov. 12, 1994; U.S. Pat. No. 5,589,337, issued Dec. 31, 1996; EPO 651825, issued Jan. 14, 1998; and U.S. Pat. No. 5,585,232, issued Dec. 17, 1996).

Alternatively, or in addition to these in vitro studies, the bioavailability and toxicological properties of a candidate modulator in an animal model, such as mice, rats, rabbits, or monkeys, can be determined using established methods (see, Lu, supra (1985); and Creasey, Drug Disposition in Humans, The Basis of Clinical Pharmacology, Oxford University Press, Oxford (1979), Osweiler, *Toxicology*, Williams and Wilkins, Baltimore, Md. (1995), Yang, Toxicology of Chemical Mixtures; Case Studies, Mechanisms, and Novel Approaches, Academic Press, Inc., San Diego, Calif. (1994), Burrell et al., Toxicology of the Immune System; A Human Approach, Van Nostrand Reinhld, Co. (1997), Niesink et al., Toxicology; Principles and Applications, CRC Press, Boca Raton, Fla. (1996)). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the therapeutic utility of a candidate modulator in vivo.

Efficacy of Candidate Modulators

Efficacy of a candidate modulator can be established using several art-recognized methods, such as in vitro methods, animal models, or human clinical trials (see, Creasey, supra (1979)). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS (see, Daluge et al., (1995) Antimicro. Agents Chemother. 41

1082-1093). Furthermore, the ability of cyclosporin A (CsA) to prevent proliferation of T-cells in vitro has been established as an acceptable model to identify chemicals expected to be efficacious as immunosuppressants (see, Suthanthiran et al., supra, (1996)). For nearly every class of therapeutic, disease, or condition, an acceptable in vitro or animal model is available. Such models exist, for example, for gastro-intestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis (see, Shaw and Lacy, J. (1973) Bone Joint Surg. (Br) 55 197-205. Hydrocortisone, which is approved for use in humans to treat arthritis, is efficacious in this model which confirms the validity of this model (see, McDonough, (1982) Phys. Ther. 62 835-839). When choosing an appropriate model to determine efficacy of a candidate modulator, the skilled artisan can be guided by the state of the art to choose an appropriate model, dose, and route of administration, regime, and endpoint and as such would not be unduly burdened.

In addition to animal models, human clinical trials can be used to determine the efficacy of a candidate modulator in humans. The USFDA, or equivalent governmental agencies, have established procedures for such studies (see, on the worldwide web, fda.gov).

Selectivity of Candidate Modulators

The in vitro and in vivo methods described above also establish the selectivity of a candidate modulator. It is recognized that chemicals can modulate a wide variety of biological processes or be selective. Panels of cells, each containing constructs with varying specificity, based on the present invention, can be used to determine the specificity of the candidate modulator. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies can be extended into in vivo animal model studies, including human clinical trials, to determine toxicity, efficacy, and selectivity of the candidate modulator suing art-recognized methods.

An Identified Chemical, Modulator, or Therapeutic and Compositions

The invention includes compositions, such as novel chemicals, and therapeutics identified by at least one method of the present invention as having activity by the operation of methods, systems or components described herein. Novel chemicals, as used herein, do not include chemicals already publicly known in the art as of the filing date of this application. Typically, a chemical would be identified as having activity from using the invention and then its structure revealed from a proprietary database of chemical structures or determined using analytical techniques such as mass spectroscopy.

One embodiment of the invention is a chemical with useful activity, comprising a chemical identified by the method described above. Such compositions include small organic molecules, nucleic acids, peptides and other molecules readily synthesized by techniques available in the art and developed in the future. For example, the following combinatorial compounds are suitable for screening: peptoids (PCT Publication No. WO 91/19735, 26 Dec. 1991), encoded peptides (PCT Publication No. WO 93/20242, 14 Oct. 1993), random bio-oligomers (PCT Publication WO 92/00091, 9 Jan. 1992), benzodiazepines (U.S. Pat. No. 5,288,514), diversomeres such as hydantoins, benzodiazepines and dipeptides (Hobbs DeWitt, S. et al., (1993) Proc. Nat. Acad. Sci. USA 90 6909-6913), vinylogous polypeptides (Hagihara et al., (1992) J. Amer. Chem. Soc. 114 6568), nonpeptidal peptidomimetics with a Beta-D-Glucose scaffolding (Hirschmann, R. et al., (1992) J. Amer. Chem. Soc. 114 9217-9218), analogous organic syntheses of small compound libraries (Chen, C. et al., (1994) J. Amer. Chem. Soc. 116 2661), oligocarbamates (Cho, C. Y. et al., (1993) Science 261: 1303), and/or peptidyl phosphonates (Campbell, D. A. et al., (1994) J. Org. Chem. 59 658). See, generally, Gordon, E. M. et al., (1994). J. Med. Chem. 37 1385. The contents of all of the aforementioned publications are incorporated herein by reference.

The present invention also encompasses the identified compositions in a pharmaceutical composition comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, acsorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the invention, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 mg/kg and 100 mg/kg body weight, and preferably between about 100 μg/kg and 10 mg/kg body weight. Administration is preferably oral on a daily basis.

The exact formulation, route of administration and dosage can be chosen by the individual physician in view of the patient's condition. (See e.g., Fingl et al., in The Pharmacological Basis of Therapeutics, 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, for example, by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. Nos. 5,733,888 (injectable compositions); 5,726,181 (poorly water soluble compounds); 5,707,641 (therapeutically active proteins or peptides); 5,667,809 (lipophilic agents); 5,576,012 (solubilizing polymeric agents); 5,707,615 (anti-viral formulations); 5,683,676 (particulate medicaments); 5,654,286 (topical formulations); 5,688,529 (oral suspensions); 5,445,829 (extended release formulations); 5,653,987 (liquid formulations); 5,641,515 (controlled release formulations) and 5,601,845 (spheroid formulations).

VII. Transgenic Animals

In another embodiment, the invention provides a transgenic non-human organism that expresses a nucleic acid sequence that encodes a target protein, (such as a reporter moiety, enzyme or structural protein) functionally coupled to one or more destabilization domains by a linker. Because such constructs can be expressed within intact living cells, with preset degrees of stability, the invention provides the ability to regulate the expression level of the target protein, or to monitor post translational activities within defined cell populations, tissues or in an entire transgenic organism.

In one embodiment the approach may be used to regulate the expression level of an enzyme or group of enzymes involved in a particular signal transduction, disease, or metabolic pathway. Such methods may be useful, for example, for creating transgenic model animals for certain disease states, or for modulating the intracellular concentration of enzymatic intermediates though the manipulation of the expression levels of the enzymes involved. For example, to increase the intracellular concentration of an intermediate one could increase the concentration of the enzyme(s) involved in the synthesis of the intermediate, and/or decrease the concentration of the enzyme(s) involved in degradation of the intermediate. Typically the approach would require the replacement of the native enzymes with fusion proteins of the enzymes with the multimerized destabilization domains of the present invention. For target proteins in which the desired concentration was relatively high, one would select fusion proteins with relatively few (i.e. one or two), or even no, (zero) copies of the destabilization domain. For target proteins for which a relatively low intracellular concentration was desired, one would select fusion proteins with relatively more copies of the destabilization domain (i.e. three or more).

In another embodiment, the approach can be used to identify where in specific tissues a particular activity is located, for example, by expression of a reporter moiety coupled to the multimerized destabilization domain via a linker comprising recognition and cleavage motifs for that activity, in the organism. Typically the linker would comprise a single polypeptide chain that covalently couples the destabilization domains to the reporter moiety. Typically in this embodiment, the linker will comprise a post-translational recognition motif such as a protease recognition motif. Cleavage of the linker by the protease at the cleavage site results in uncoupling of the multimerized destabilization domains from the reporter moiety resulting in a modulation in the stability of the reporter moiety, thereby resulting in an accumulation of reporter moiety in cells or tissues that exhibit protease activity.

Such non-human organisms include vertebrates such as rodents, fish such as Zebrafish, non-human primates and reptiles as well as invertebrates. Preferred non-human organisms are selected from the rodent family including rat and mouse, most preferably mouse. The transgenic non-human organisms of the invention are produced by introducing transgenes into the germline of the non-human organism. Embryonic target cells at various developmental stages can be used to introduce transgenes. Different methods are used depending on the organism and stage of development of the embryonic target cell. In vertebrates, the zygote is the best target for microinjection. In the mouse, the male pronucleus reaches the size of approximately 20 micrometers in diameter, which allows reproducible injection of 1-2 pl of DNA solution. The use of zygotes as a target for gene transfer has a major advantage in that in most cases the injected DNA will be incorporated into the host gene before the first cleavage (Brinster et al., (1985) Proc. Natl. Acad. Sci. USA 82 4438-4442,). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

A transgenic organism can be produced by cross-breeding two chimeric organisms which include exogenous genetic material within cells used in reproduction. Twenty-five percent of the resulting offspring will be transgenic i.e., organisms that include the exogenous genetic material within all of their cells in both alleles. 50% of the resulting organisms will include the exogenous genetic material within one allele and 25% will include no exogenous genetic material.

Retroviral infection can also be used to introduce transgene into a non-human organism. In vertebrates, the developing non-human embryo can be cultured in vitro to the blastocyst stage. During this time, the blastomeres can be targets for retro viral infection (Jaenich, R., (1976) Proc. Natl. Acad. Sci. USA 73 1260-1264,). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., (1985) Proc. Natl. Acad. Sci. USA 82 6927-6931; Van der Putten, et al., (1985) Proc. Natl. Acad. Sci. USA 82 6148-6152). Transfection is easily and efficiently obtained by culturing the blastomeres on a monolayer of virus-producing cells (Van der Putten, supra; Stewart, et al., (1987) EMBO J. 6 383-388).

Alternatively, infection can be performed at a later stage. Virus or virus-producing cells can be injected into the blastocoele (D. Jahner et al., (1982) Nature 298 623-628). Most of the founders will be mosaic for the transgene since incorporation occurs only in a subset of the cells that formed the transgenic nonhuman animal. Further, the founder may contain various retro viral insertions of the transgene at different positions in the genome that generally will segregate in the offspring. In addition, it is also possible to introduce transgenes into the germ line, albeit with low efficiency, by intrauterine retro viral infection of the midgestation embryo (D. Jahner et al., supra). A third type of target cell for transgene introduction for vertebrates is the embryonic stem cell (ES). ES cells are obtained from pre-implantation embryos cultured in vitro and fused with embryos (M. J. Evans et al. (1981) Nature 292 154-156; M. O. Bradley et al., (1984) Nature 309 255-258; Gossler, et al., (1986) Proc. Natl. Acad. Sci. USA 83 9065-9069; and Robertson et al., (1986) Nature 322 445-448). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., (1988) Science 240 1468-1474).

VIII Transgenic Plants

In another embodiment, the invention provides a transgenic plant that expresses a nucleic acid sequence that encodes a target protein, (such as a reporter moiety, enzyme or structural protein) functionally coupled to a multimerized destabilization domain by a linker. Because such constructs can be specifically expressed, both spatially and temporally, within intact living cells, the invention provides the ability to regulate the expression level of the target protein, within defined cell populations, tissues, or in the entire transgenic plant.

In one embodiment the approach may be used to regulate the expression level of an enzyme or group of enzymes involved in a particular signal transduction, developmental or metabolic pathway. Such methods may be useful for creating transgenic plants with improved disease resistance or other favorable traits. More particularly, plants can be genetically engineered to express various phenotypes of agronomic interest, for example by allowing for the regulated expression of agronomically important genes. Given potential concerns about the safety of transgenic plants, the ability to reduce or eliminate the expression of certain resistance genes prior to harvesting and human consumption is of particular interest. Examples of the types of genes that could be manipulated using the methods described herein, include disease resistance genes, herbicide resistance genes and genes that improve plant traits, including those shown in Table 4, below.

TABLE 4

| Gene or Gene Product | Function | Reference |
|---|---|---|
| | I. Disease Resistance Genes | |
| Tomato Cf-9 gene | Resistance to *Cladosporium fulvum* | Jones et al., Science 266 789 (1994) |
| Tomato Pto gene | Resistance to *Pseudomonassy.ringae* | Martin et al., Science 262: 1432 (1993) |
| Arabidopsis RSP2 gene | Resistance to *Pseudomonas syringae* | Mindrinos et al., Cell 78: 1089 (1994) |
| *Bacillus thuringiensis* protein | Insect resistance | Geiser et al., Gene 48: 109 (1986), |
| *Streptomyces nitrospoeus* α-amylase inhibitor | Inhibition of amylase activity. | Sumitani et al., Biosci. Biotech. Biochem. 57 1243 (1993) |
| Expression of insect-specific hormones or pheromones such as an ecdysteroid and juvenile hormone | Disruption of insect development | Hammock et al., Nature 344: 458 (1990) |
| Expression insect-specific scorpion venom | Insect resistance | Pang et al.,Gene 116: 165 (1992) |
| Altered expression of metabolic enzymes | Expression of enzymes responsible for the formation of non protein molecules with insecticidal activity | |
| Altered expression of signal transduction enzymes | Expression of enzymes responsible for the post-translational modification of biologically active molecules | See PCT application WO 93/02197, Botella et al., Plant Molec. Biol. 24: 757 (1994), |
| Expression of synthetic antimicrobial peptides, such as peptide derivatives of Tachyplesin | Improved disease resistance | |
| Altered expression of Ion channels, blockers or permeases such as cecropin-3 lytic peptide | Improved resistance to *Pseudomonas solanacearum.* | Jaynes et al., Plant Sci. 89: 43 (1993), |
| Expression of viral coat proteins or viral-invasive proteins or toxins. | Improved viral resistance to alfalfa mosaic virus, cucumber mosaic virus, tobacco streak virus, potato virus X, potato virus Y, tobacco etch virus, tobacco rattle virus and tobacco mosaic virus | See Beachy et al., Ann. Rev. Phytopathol. 28: 451 (1990). |
| Expression of insect-specific antibody or immunotoxins | Improved resistance to insects | Taylor et al., Abstract #497, SEVENTH INT'L SYMPOSIUM ON MOLECULAR PLANT- |

TABLE 4-continued

| Gene or Gene Product | Function | Reference |
|---|---|---|
| | | MICROBE INTERACTIONS (1994) |
| Expression of virus-specific antibodies. | Improved resistance to viruses | Tavladoraki et al., Nature 366: 469 (1993) |
| Expression of developmental-arrestive proteins or gene products, as endo a1,4-D-polygalacturonase, or expression of barley ribosome-inactivating gene | Increased resistance to pathogens or parasites | See Lamb et al., Biol Technology ;Q: 1436 (1992). Logemann et al.,BiolTechnology.10: 30 (1992) |
| | II. Herbicide Resistance Genes | |
| Expression of mutant ALS and AHAS enzymes | Inhibition of the growing point or meristem, increasing resistance to herbicides | Lee et al., EMBO J. 7: 1241 (1988), and Miki et al., Theor. Appl. Genet. 8 : 449 (1990), |
| Expression of mutant EPSP synthase and aroA genes, | Resistance to glyphosate and other phosphono compounds such as glufosinate | U.S. Pat. No. 4,940,835 to Shah et al., U.S. Pat. No. 4,769,061 to Comai. European patent application No. 0 333 033 to Kumada et al. and U.S. Pat. No. 4,975,374 to Goodman et al. |
| | III. Genes That Confer Or Contribute To A Value-added Trait | |
| Expression of antisense gene of stearoyl-ACP desaturase | Improved fatty acid composition | Knultzon et al., Proc. Natl. Acad. Sci.USA 89: 2624 (1992). |
| Expression of phytic acid degrading enzymes | Improved free phosphate composition | Van Hartingsveldt et al., Gene 127: 87 (1993) |
| Expression of fructosyltransferase, levansucrase, or invertase genes | Improved carbohydrate composition | See Shiroza et al., J. Bacteriol. 170: 810 (1988), Steinmetz et al., Mol. Gen. Genet. 200 220 (1985), Elliot et al., Plant Molec. Biol. 21 515 (1993) |

In another embodiment, the approach can be used to specifically identify where in specific tissues a particular activity is expressed, for example by expression of the protease sensor in specific plant tissues.

Transgenic plants may be produced by any one of a number of methods of plant transformation and regeneration. Numerous methods for plant transformation have been developed, including biological and physical, plant transformation protocols. See, for example, Miki et al., “Procedures for Introducing Foreign DNA into Plants” in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., “Vectors for Plant Transformation” in Methods in Plant Molecular Biology and Biotechnology, Glick, B. R. and Thompson, J. E. Eds. (CRC Press, Inc., Boca Raton, 1993) pages 89-119.

The most widely utilized method for introducing an expression vector into plants is based on the natural transformation system of *Agrobacterium*. See, for example, Horsch et al., (1985) Science 227 1229. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant See, for example, Kado, C. I., Crit. Rev. Plant. Sci. 10: 1 (1991). Descriptions of *Agrobacterium* vector systems and methods for *Agrobacterium*-mediated gene transfer are provided by Gruber et al., supra, Miki et al., supra, and Moloney et al., (1989) Plant Cell Reports 8 238.

Despite the fact the host range for *Agrobacterium* mediated transformation is broad, some major cereal crop species and gymnosperms have generally been recalcitrant to this mode of gene transfer, even though some success has recently been achieved in rice. Hiei et al., (1994) The Plant Journal 6 271-282. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 Am. The expression vector is introduced into plant tissues with a biolistic device that accelerates the microprojectiles to speeds of 300 to 600 m/s which is sufficient to penetrate plant cell walls and membranes. Sanford et al., (1987), Part. Sci. Technol. 5 27, Sanford, J. C., (1988) Trends Biotech. 6 299, Sanford, J. C., (1990) Physiol. Plant 79 206, Klein et al., (1992) Biotechnology 10 268.

Another method for physical delivery of DNA to plants is sonication of target cells. Zhang et al., (1991) BioTechnology 2 996. Alternatively, liposome or spheroplast fusion have been used to introduce expression vectors into plants. Deshayes et al., (1985) EMBO J., 4 2731, Christou et al., (1987) Proc Natl. Acad. Sci. U.S.A. 84 3962. Direct uptake of DNA into protoplasts using $CaCl_2$ precipitation, polyvinyl alcohol or poly-Lornithine have also been reported. Hain et al., (1985) Mol. Gen. Genet. 199 161 and Draper et al., (1982) Plant Cell Physiol. 23 451. Electroporation of protoplasts and whole cells and tissues have also been described. Donn et al., In Abstracts of VIIth International Congress on Plant Cell and Tissue Culture IAPTC, A2-38, p 53 (1990); D'Halluin et al., (1992) Plant Cell 4 1495-1505 and Spencer et al., (1994) Plant Mol. Biol. 24 51-61.

A preferred method is microprojectile-mediated bombardment of immature embryos. The embryos can be bombarded on the embryo axis side to target the meristem at a very early stage of development or bombarded on the scutellar side to target cells that typically form callus and somatic embryos. Targeting of the scutellum using projectile bombardment is well known to those in the art of cereal tissue culture. Klein et al., (1988) BioTechnol., 6 559-563; Sautter et al., Bio/Technol., 9 1080-1085 (1991); Chibbar et al., (1991) Genome, 34 435-460. The scutellar origin of regenerable callus from cereals is well known. Green et al., (1975) Crop Sci., 15 417-421; Lu et al., (1982) TAG 62 109-112; and Thomas and Scott, (1985) J. Plant Physiol. 121 159-169-Targeting the scutellum and then using chemical selection to recover transgenic plants is well established in cereals. D/Halluin et al., Plant Cell 4: 1495-1505 (1992); Perl et al., MGG 235: 279-284 (1992); Cristou et al., Bio/Technol. 9: 957-962 (1991). This literature reports DNA targeting of the scutellum and recovery of transgenic callus, plants and progeny based on a chemical selection regime. None of these references teach successful plant transformation wherein transformed cells are visualized with a screenable marker such as GUS.

A preferred transformation method involves bombardment of the scutellar surface of immature embryos to introduce the expression cassette with the gene for a bioluminescent protein, such as Aequorea Victoria GFP (See PCT publication WO 97/41228 to Gordon-Kamm et al., incorporated herein by reference). Embryos can be pretreated for 1 to 48 hours with a high osmoticum medium or left on a highosmoticum medium for 24-48 hours after bombardment to improve cell survival and transformation frequencies. Immature embryos are then cultured on typical callusinducing medium with no selective agent. At each subculture transfer, i.e., every two weeks, the culture is monitored using UV-blue light for GFP fluorescence. Fluorescing calli are separated from non-fluorescing callus, and grown to the point where plants can be regenerated through standard media progressions.

Plants can be manipulated, for example, by removal of the apical meristem, to stimulate axillary or secondary buds which can exhibit larger transgenic sectors relative to the primary shoot. Flowers above transgenic shoots are pollinated and the progeny are analyzed for transgene presence and expression. A variety of starting explants can regenerate shoots in sunflower, and thus represent alternative targets for GFP-encoding DNA delivery and transmission to progeny. These include the seedling meristem (as above), also the seedling hypocotyl, the mature cotyledon, the immature cotyledon, zygotic immature embryos, somaticembryos, and primary leaflets. See for example, respectively, Greco et al., (1984) Plant Sci. Lett. 36 73-77; Krauter et al., (1991) Helia 14 117-122; Power (1987) Am. J. Bot. 74 497503; Krauter et al., (1991) Theor. Appl. Genet. a2: 521525; Finer, (1987) Plant Cell Rep. J: 372-374, and Greco et al., (1984) Plant Sci. Lett. 36 73-77.

EXAMPLES

Example 1

Generation of Multimerized Destabilization Domains

The cDNA encoding human ubiquitin was isolated from a human genomic DNA preparation obtained from Jurkat cells by polymerase chain reaction (PCR) using the PCR primers Ubi5 (SEQ. ID. NO. 15) and Ubi3 (SEQ. ID. NO. 16) and cloned into pBluescript H vector (Stratagene). The C-terminal residue of ubiquitin was altered from glycine to valine by site-directed mutagenesis (Kunkel) in order to generate a mutant form of ubiquitin that cannot be cleaved by cellular α-NH-ubiquitin endopeptidases. This mutant is hereafter referred to as ubiquitinG76V (SEQ. ID. NO. 17). The ubiquitinG76V (SEQ. ID. NO. 17) mutant was then amplified by PCR using the oligonucleotide primers Ub5' (SEQ. ID. NO. 18) and Ub3', (SEQ. ID. NO. 19). These primers introduce a Bgl II restriction site at the 5' end of the coding sequence and a BamH I site at the 3' end of the coding sequence. The PCR fragment from the reaction was digested with Bgl II and BamH I and ligated into BamH I-digested pBluescript II vector. This plasmid was then digested with Bgl II and BamH I and the ubiquitinG76V (SEQ. ID. NO. 17) containing fragment was isolated and ligated to generate multimerized ubiquitinG76V domains. The ubiquitinG76V multimers were digested with Bgl II and BamH I to ensure that the individual ubiquitinG76V domains (SEQ. ID. NO. 17) were in the correct orientation. The digested ubiquitinG76V multimers were separated by agarose gel electrophoresis and multimers of the appropriate sizes were isolated and cloned into BamH I-digested pBluescript II. The ubiquitinG76V multimers were then excised using BamH I and Hind III and subcloned to generate a series of plasmids containing in frame fusions of from one to four copies of ubiquitinG76V (SEQ. ID. NO. 17) fused to the reporter moiety or protein of interest. These constructs are referred to as 1XUb (one copy of ubiquitinG76V (SEQ. ID. NO. 17)), 2XUb (two copies of ubiquitinG76V (SEQ. ID. NO. 17)), 3XUb (three copies of ubiquitinG76V (SEQ. ID. NO. 17)) and 4XUb (four copies of ubiquitinG76V (SEQ. ID. NO. 17)).

Example 2

Creation of Multimerized Destabilization Domain-β-Lactamase Fusion Proteins

The gene encoding the *E. coli* TEM-1 β-lactamase was isolated from the plasmid pBluescript (Stratagene) by polymerase chain reaction (PCR) amplification using the PCR primers BLA5 (SEQ. ID. NO. 20) and ABSC107, (SEQ. ID. NO. 21) resulting in the deletion of the signal sequence and introduction of a BamH I restriction site and the amino acids below at the 5' end of the coding sequence.

BamH1 HHSGAWLHPETLVKYK (SEQ. ID. NO:73)

Amino acids in bold represent original β-lactamase coding sequence, underlined amino acids represent the BamH I restriction site. An Xba I site was inserted at the 3' end of the coding sequence. The PCR fragments from these reactions were digested with BamH I and Xba I and ligated into pcDNA3 (Invitrogen) via the same sites. The resulting construct, pcDNA3-B1a (SEQ. ID. NO. 22), was then used to create in-frame fusions with the multimerized ubiquitinG76V constructs above. This was achieved by digesting the multimerized ubiquitinG76V constructs with the restriction enzymes BamH I and Hind III, and then ligating them via the same sites into the pcDNA3-B1a construct. These constructs were named pcDNA3-1XUb-B1a (SEQ. ID. NO. 23), pcDNA3-2XUb-B1a (SEQ. ID. NO. 24), pcDNA3-3XUb-B1a (SEQ. ID. NO. 25), pcDNA3-4XUb-B1a (SEQ. ID. NO. 26). To produce the wild-type β-lactamase protein, we used a construct that contains one copy of wild-type (cleavable) ubiquitin (SEQ. ID. NO. 2) fused to the β-lactamase coding region in the pcDNA3 vector; this plasmid is referred to as pcDNA3-Ub-Met-B1a (SEQ. ID. NO. 27). Upon synthesis of the Ub-Met-B1a fusion protein, ubiquitin isopeptidases efficiently cleave off the N-terminal ubiquitin (SEQ. ID. NO. 2) precisely after glycine-76, generating the wild-type β-lactamase protein with methionine at its N-terminus.

Example 3

Creation of Multimerized Destabilization Domain-Naturally Fluorescent Protein Fusions The gene encoding the GFP mutant Emerald (S65T, S72A, N149K, M153T, I167T) (SEQ. ID. NO. 28) was amplified by PCR using the oligonucleotides GFP5' (SEQ. ID. NO. 29) and GFP3', (SEQ. ID. NO. 30). The resulting PCR product had a BamH I restriction site at the 5' end of the coding sequence and a Xba I site at the 3' end of the coding sequence. The PCR fragment from this reaction was digested with BamH I and Xba I and ligated into pcDNA3 via the same sites. The resulting construct, pcDNA3-GFP was then used to create in-frame fusions with the multimerized ubiquitinG76V constructs described above. This was achieved by digesting the pcDNA3-1-4XUb-B1a constructs (SEQ. ID. NOs. 23 to 26) with the restriction enzymes BamH I and Hind III, and then ligating the fragment encoding the various multiUb destabilization domains via the same sites into the pcDNA3-GFP construct. These constructs were named pcDNA3-1XUb-GFP (SEQ. ID. NO. 31), pcDNA3-2XUb-GFP (SEQ. ID. NO. 32), pcDNA3-3XUb-GFP (SEQ. ID. NO. 33), pcDNA3-4XUb-GFP (SEQ. ID. NO. 34).

Example 4

Creation of Multimerized Destabilization Domain-Naturally Occurring Mammalian Protein Fusions Fusions between multimerized uncleavable ubiquitinG76V (SEQ. ID. NO. 17) and caspase-3 were constructed to further investigate the relationship between the degree of destabilization exerted by varying the number of copies of the destabilization domain with different target proteins.

The caspase-3 cDNA (SEQ. ID. NO. 35) was amplified by PCR using the primers C35' (SEQ. ID. NO. 36) and C33' (SEQ. ID. NO. 37) to add BamH I sites at the ends of the caspase-3 cDNA. The amplified caspase-3 cDNA was digested with BamH I then cloned into BamH I-digested pcDNA3-1-4XUb-B1a plasmids (SEQ. ID. NOs. 23 to 26), to create fusions of the different multiubiquitin destabilization domains to a caspase-3-β-lactamase fusion. The β-lactamase coding region was then removed from these plasmids by digesting to completion with Xba I followed by a partial digest with BamH I. The digests were separated by agarose gel electrophoresis and the correct size DNA band was purified from the gel. The ends of the digested plasmid were blunted with the Klenow fragment of DNA polymerase and the plasmid recircularized by ligation. The resulting plasmids contained an in-frame fusion of the ubiquitinG76V destabilization domain (with from one to four copies of ubiquitinG76V (SEQ. ID. NO. 17)) to the caspase-3 coding region. These plasmids were designated pcDNA3-1-4XUb-C3 (SEQ. ID. NO. 38 to 41). To produce the wild-type caspase-3 protein, the caspase-3 cDNA was amplified by PCR with primers C35Met (SEQ. ID. NO. 42) and C33' (SEQ. ID. NO. 43) and cloned directly into pcDNA3-Ub-Met-B1a (SEQ. ID. NO. 27). The resulting plasmid was then digested with BamH I and Xba I and recircularized as described above to create the wild-type caspase-3 control construct; this plasmid was designated as pcDNA3-Ub-Met-C3 (SEQ. ID. NO. 44). Upon synthesis of the Ub-Met-caspase-3 fusion protein, ubiquitin isopeptidases efficiently cleave off the N-terminal ubiquitin precisely after glycine-76, generating the wild-type caspase-3 protein with methionine at its N-terminus (data not shown).

Example 5

Characterization of Multimerized Destabilization Domain-β-Lactamase Fusion Proteins In Vitro $^{35}$S-Labeled multimerized destabilization domain-β-lactamase fusion protein molecules were produced using a coupled in vitro transcription/translation system based on a rabbit reticulocyte lysate (TNT T7 Quick; Promega). Constructs containing from one to four copies of the destabilization domain (pcDNA3-1-4XUb-B1a (SEQ. ID. NOs. 23 to 26) from Example 2) were incubated in the TNT lysate essentially as described in the manufacturer's directions in the presence of 0.25 mCi/ml $^{35}$S-methionine (10 mCi/ml, 1175 Ci/mmol; New England Nuclear) to generate $^{35}$S-labeled fusion proteins.

Figure 2A:
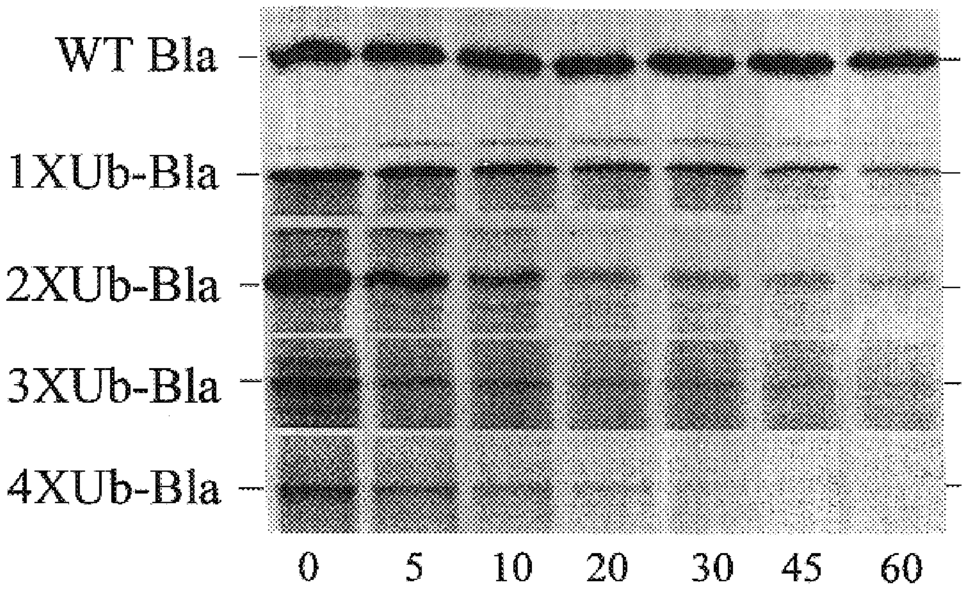
FIG. 2 TNT in vitro synthesis and degradation experiments with Met, 1, 2, 3 or 4 copies of ubiquitinG76V fused to β-lactamase. The kinetics of turnover in vitro in (A) were determined by chase reactions at 37° C. and products analyzed by SDS-PAGE. The effect of the proteasome inhibitor MG132 at 50 μM in the TNT synthesis reaction is shown in (B).

To determine the half life of the constructs, 1 μl samples of the synthesis reactions were incubated at 37° C. in 9 μl of chase extract (crude rabbit reticulocyte lysate (Promega) supplemented with 100 μg/ml cycloheximide, 1 mM ATP, 20 mM phosphocreatine, 2.5 mM $MgCl_2$, 5 μg/ml creatine kinase, 200 μg/ml ubiquitin, and 50 μM methionine). The rabbit reticulocyte lysate system contains all of the components necessary for efficient recognition and degradation of proteins by the ubiquitin-proteasome pathway. Samples were removed at 0, 5, 10, 20, 30, 45 and 60 minutes of reaction and analyzed by polyacrylamide gel electrophoresis (SDS-PAGE). The gels were treated with Amplify (Amersham) and the labeled species detected by autoradiography. This analysis showed that wild-type β-lactamase was stable over the 1 hour chase period while the ubiquitinG76V-β-lactamase fusions were considerably less stable (FIG. 2A). In particular, the 1XUb-B1a fusions were modestly destabilized ($t_{1/2}$~20 min) and β-lactamase fusions containing 2, 3 or 4 copies of ubiquitinG76V (SEQ. ID. NO. 17) were strongly destabilized ($t_{1/2}$<5 min). In addition, the degradation of the 2XUb-B1a fusion was slightly slower than the degradation of β-lactamase fusions containing 3 or 4 copies of ubiquitinG76V (SEQ. ID. NO. 17) (FIG. 2A).

Figure 2B:
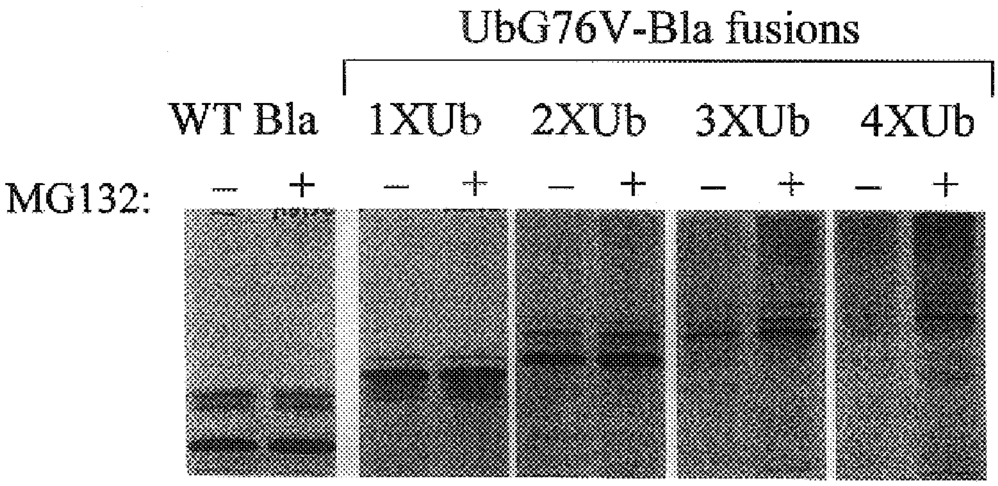

In order to test whether the degradation of multiUb-B1a fusions in vitro is dependent on the proteasome, TNT synthesis reactions were performed in the absence or presence of the proteasome inhibitor MG132 (Calbiochem) at 50 μM and analyzed by SDS-PAGE as described above. These experiments showed that inhibition of the proteasome resulted in a dramatic increase in the amount of fusion protein synthesized for β-lactamase fusions containing 2, 3 or 4 copies of ubiquitinG76V (SEQ. ID. NO. 17) while MG132 had very little or no significant effect on the synthesis of wild-type β-lactamase or 1XUb-B1a (FIG. 2B). Use of MG132 in these in vitro reactions also revealed the presence of labeled high molecular weight species that represent extended ubiquitin chains conjugated to the ubiquitinG76V-β-lactamase fusions (also see Example 16). Therefore, the uncleavable ubiquitinG76V domains (SEQ. ID. NO. 17) in the multiubiquitin destabilization domain may be acting as high affinity conjugation sites for further ubiquitination by E2/E3 ubiquitin ligases. The relative lack of these high molecular weight species in the absence of MG132 reflects the highly efficient recognition and degradation by the proteasome of proteins tagged with extended polyubiquitin chains.

Example 6

Figure 3:
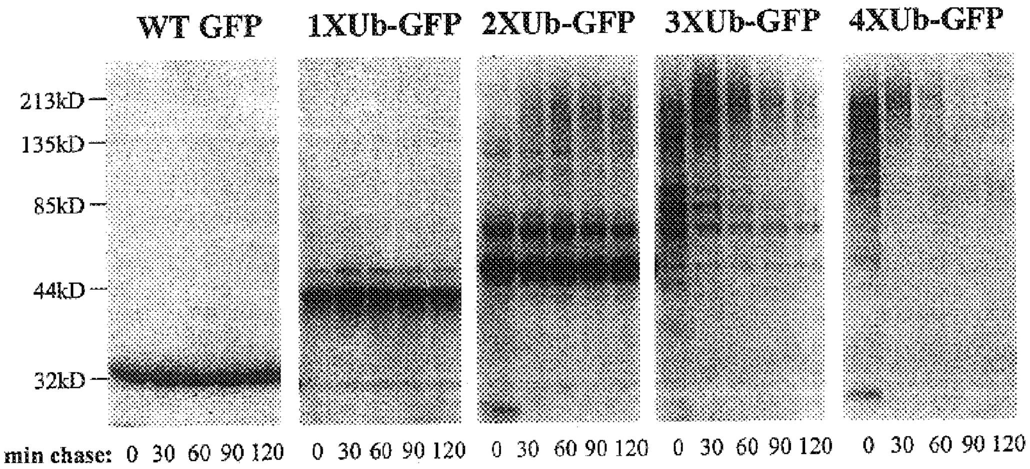
FIG. 3 Turnover in vitro of labeled fusion proteins of uncleavable ubiquitinG76V fused to GFP. TNT synthesis reactions were incubated in chase lysate at 37° C. and products analyzed by SDS-PAGE.

Characterization of Multimerized Destabilization Domain-Naturally Fluorescent Protein Fusions In Vitro Characterization of the turnover of multiubiquitin-GFP fusion proteins in vitro was similar to the multiubiquitin-β-lactamase analyses described in Example 5, except that time points were taken at 0, 30, 60, 90 and 120 min. These experiments showed that Emerald GFP (SEQ. ID. NO. 28) is extremely stable under these conditions, and that the multiubiquitin destabilization domain was able to impart a short half-life upon the multiUb-GFP fusion proteins (FIG. 3). A striking feature of this analysis was that significant destabilization of GFP required higher numbers of ubiquitinG76V (SEQ. ID. NO. 17) domains than was the case for β-lactamase; α-lactamase could be strongly destabilized in vitro by fusion with as few as two ubiquitinG76V domains (SEQ. ID. NO. 17) (FIG. 2A) whereas GFP required at least three ubiquitinG76V domains (SEQ. ID. NO. 17) to be strongly destabilized (FIG. 3). This relationship between the destabilization domain, and the protein to be destabilized, emphasizes the utility of the multiubiquitin destabilization system, in that the extent of destabilization can be manipulated to give the desired properties by altering the number of ubiquitinG76V (SEQ. ID. NO. 17) domains that are present in the destabilization domain.

Example 7

Figure 4:
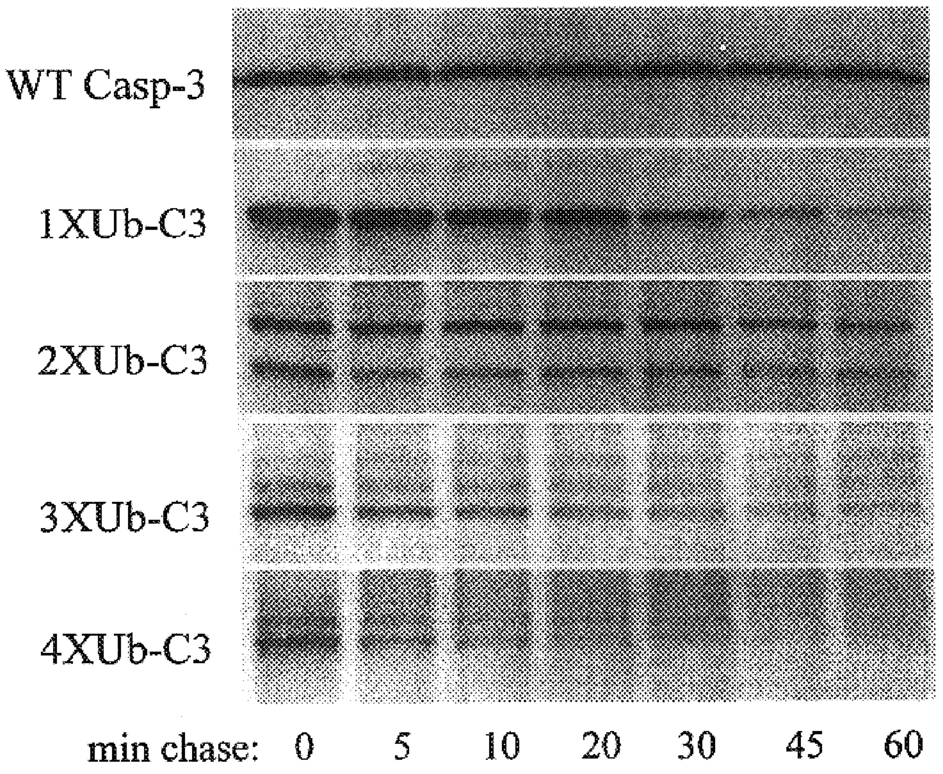
FIG. 4 Turnover reactions in vitro of labeled uncleavable ubiquitin caspase-3 fusions. TNT reactions were incubated in chase lysate at 37° C. and products analyzed by SDS-PAGE.

Characterization of Multimerized Destabilization Domain-Endogenous Mammalian Protein Fusions In Vitro Characterization of the turnover of multiubiquitin-caspase-3 fusion proteins in vitro was performed as described in Example 5. The TNT synthesis reactions were diluted into chase lysate in the presence of cycloheximide and chase time points were taken and analyzed by SDS-PAGE and autoradiography. FIG. 4 shows that wild-type caspase-3 is stable over a 60 minute chase in vitro, and that fusion to the multiubiquitin destabilization domain results in rapid degradation. In particular, the ubiquitinG76V-caspase-3 fusions are degraded in a very similar manner to the ubiquitinG76V-β-lactamase fusions although the Ub-caspase-3 fusions appear to be degraded slightly slower in vitro than the Ub-β-lactamase fusions. Altogether, these data demonstrate the generalized applicability of the multiubiquitin destabilization domain approach to provide for predictable destabilized of any given chosen target protein using this system.

Example 8

Characterization of the Half-Life of Multimerized Destabilization Domain-β-Lactamase Fusion Proteins Within Cells UbiquitinG76V-β-lactamase constructs in pcDNA3 (SEQ. ID. NOs. 23 to 26) were introduced into Jurkat T-lymphocytes by electroporation. Stable transfectants were selected in RPMI 1640 media containing 10% fetal bovine serum (Gibco) and 0.8 mg/ml G418 (Geneticin, Gibco). Analysis of β-lactamase activity in intact Jurkat cells stably transfected with the pcDNA3-1-4XUb-B1a (SEQ. ID. NOs. 23 to 26) constructs was accomplished by loading the cells with the fluorescent β-lactamase substrate CCF2/AM as described in Zlokarnik et al. (1998) (Science 279, 1848) followed by analysis by fluorescence activated cell sorter (Becton Dickinson FACS™ Vantage™) or CytoFluor microtiter plate fluorimeter (Perseptive Biosystems). For kinetic measurements, to determine the half-life of the fusion protein in vivo, direct measurements were made of β-lactamase activity in lysates prepared from cells expressing the various ubiquitinG76V-B1a fusions.

Figure 5:
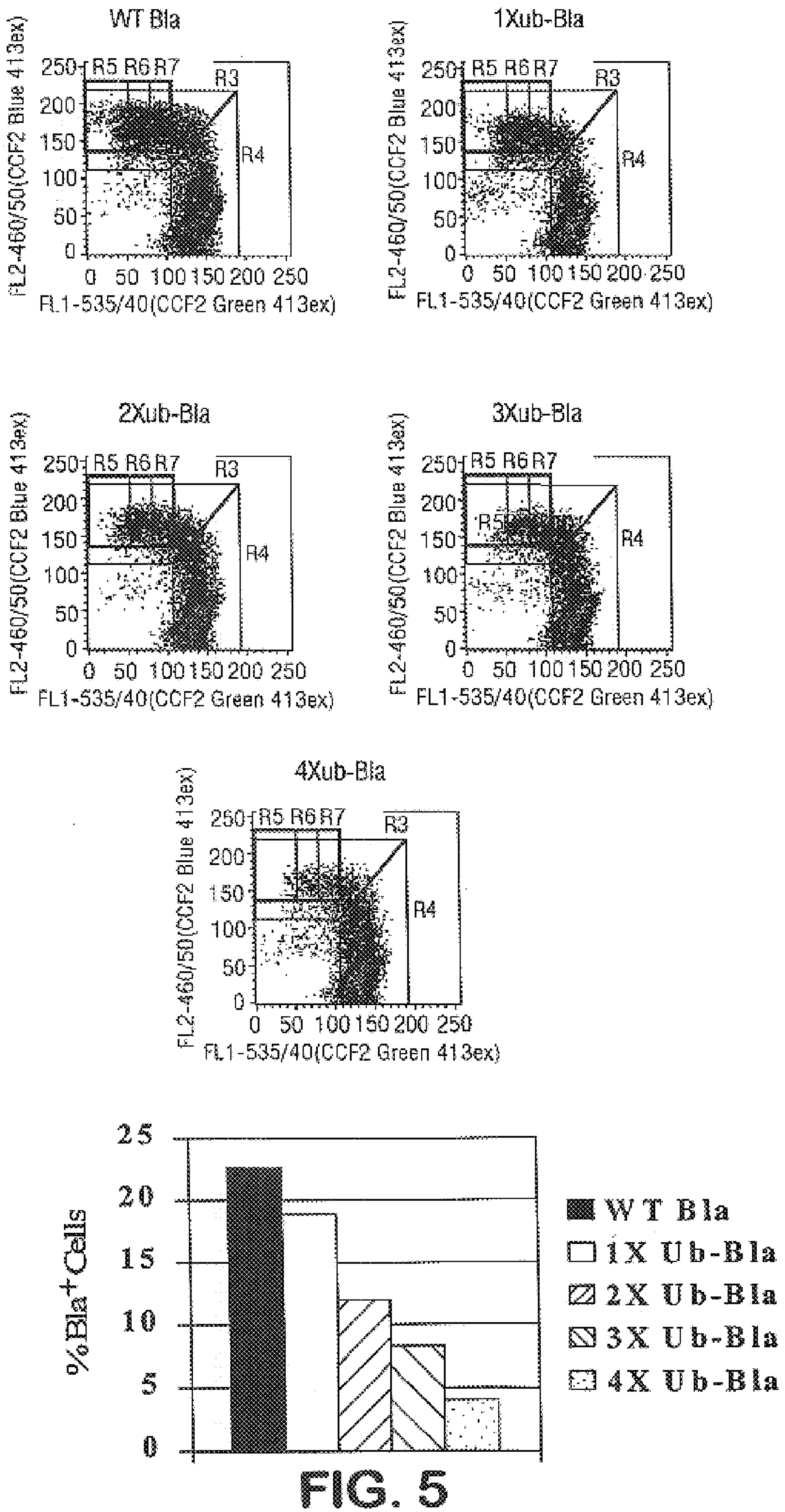
FIG. 5 FACS™ analysis of uncleavable ubiquitin β-lactamase fusions. Jurkat cells expressing ubiquitinG76V-B1a fusion proteins were analyzed for β-lactamase expression by flow cytometry. The R5+R6+R7 region was designated as $B1a^+$ and the percentage of cells in that region is shown in the bar graph.

Flow cytometry and cell sorting were conducted using a Becton Dickinson FACS™ Vantage™ with a Coherent Enterprise II™ argon laser producing 60 mW of 351-364 nm multi-line UV excitation. The flow cytometer was equipped with pulse processing and the Macrosort™ flow cell. Cells were loaded with 1 μM CCF2/AM for 1-2 hours at room temperature prior to sorting, and fluorescence emission was detected via 460/50 nm (blue) and 535/40 nm (green) emission filters, separated by a 490 nm long-pass dichroic mirror. The results from one such experiment are shown in FIG. 5, where the abundance of cells expressing relatively high levels of β-lactamase (regions R5+R6+R7) was determined. This analysis showed that the relative abundance of cells expressing high steady state levels of β-lactamase was inversely proportional to the number of copies of ubiquitinG76V (SEQ. ID. NO. 17) fused to β-lactamase, i.e., the lowest levels of β-lactamase expression were found in cells expressing β-lactamase fusions containing the most copies of ubiquitinG76V (SEQ. ID. NO. 17).

Similar cytometric analysis experiments were used to investigate the degradation properties of multiUb-B1a fusions in vivo. Jurkat cells expressing multiUb-B1a fusions were treated with 50 μM MG132 to investigate whether the low β-lactamase activity found in cells expressing 3-4XUb-B1a requires proteasome activity. The results, shown in Table 5, below show that the addition of inhibitor (+inh/−chx samples) results in a significant increase in the percentage of positive BLA expressing cells for the 2X, 3X and 4X ubiquitinG76V fusion protein constructs compared to the untreated controls (−inh/−chx samples.)

TABLE 5

| | − inh/− chx % Bla$^+$ cells | + inh/− chx % Bla$^+$ cells | − inh/+ chx % Bla$^+$ cells | + inh/+ chx % Bla$^+$ cells |
|---|---|---|---|---|
| WT Bla | 22.5 | 22.7 | 17.6 | 19.0 |
| 1XUb-Bla | 17.4 | 18.8 | 8.5 | 16.2 |
| 2XUb-Bla | 12.0 | 17.1 | 2.1 | 12.2 |
| 3XUb-Bla | 8.3 | 14.6 | 1.5 | 9.8 |
| 4XUb-Bla | 4.1 | 12.1 | 0.5 | 5.0 |

Furthermore, treating these cells with 100 μg/ml cycloheximide (to block protein synthesis) for one hour prior to CCF2 loading and cytometric analysis (compare columns [−inh/+chx] and [−inh/−chx]) resulted in a strong decrease in α-lactamase activity only in cells expressing 2-4XUb-B1a and this decrease could largely be blocked by preincubating the cells with 50 μM MG132 prior to cycloheximide addition (column +inh/+chx, in Table 5).

These data are strong evidence that the multiubiquitin domain in ubiquitinG76V-B1a fusions is acting as a destabilization motif that directs the rapid degradation of the fusions in a proteasome-dependent manner that is controlled by the number of ubiquitinG76V (SEQ, ID. NO. 17) domains within the multiubiquitin destabilization domain.

In order to determine accurate quantitative measurements of the kinetic characteristics of the degradation of UbG76V-β-lactamase fusions in vivo, β-lactamase activity was determined in cellular lysates. To do this, Jurkat cells expressing the various forms of multiUb-B1a fusion proteins were sorted by flow cytometry to obtain a pool of cells representative of the B1a+ population seen in FIG. 5 (Region R5+R6+R7). These cells were treated with 100 μg/ml cycloheximide to inhibit new protein synthesis, and aliquots of cells were taken at appropriate intervals, to measure the β-lactamase activity remaining. This approach enabled a determination of the rate of destruction of the cellular pool of β-lactamase fusion proteins within the cell. β-lactamase activity was determined in these cell samples by transferring them to ice to terminate further metabolism, and then pelleted by centrifugation. The cell pellets were converted to lysates and β-lactamase activity was measured in vitro using the free acid form of the β-lactamase substrate CCF2. Aliquots of the lysates were assayed using 10 μM CCF2 in PBS at room temperature. Hydrolysis of the fluorescent substrate was monitored in a Perseptive Biosystems CytoFluor plate reader using a 395/25 nm excitation filter and 460/40 nm emission filter.

Figure 6:
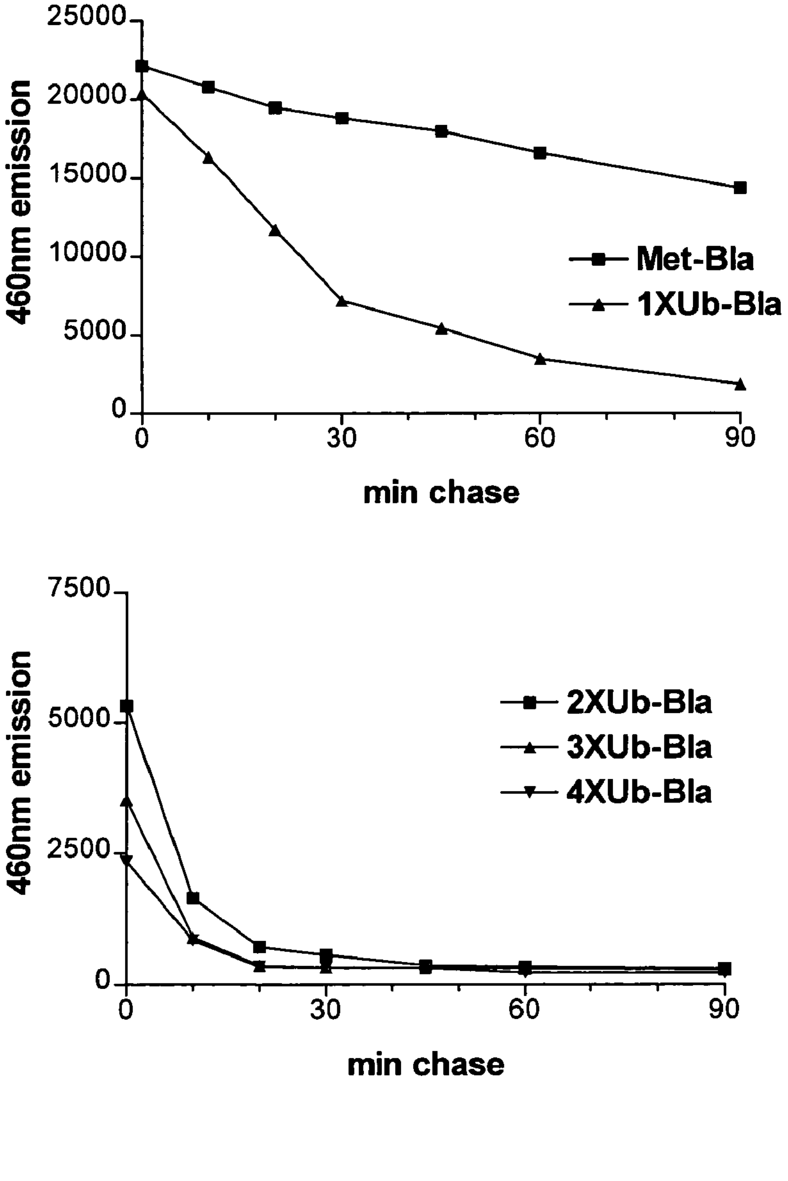
FIG. 6 Kinetics of degradation in vivo of ubiquitinG76V-β-lactamase fusion proteins. Jurkat cells expressing the various ubiquitinG76V-B1a fusions were treated with cycloheximide to initiate a chase and aliquots of cells were removed at the indicated times. The cells were lysed and the β-lactamase activity in the lysates was determined by an in vitro reaction using the fluorescent substrate CCF2. The β-lactamase activity was measured by cleavage of CCF2 and represented as emission at 460 nm.

In agreement with the cell analyses by flow cytometry, cells expressing wild-type β-lactamase had high levels of β-lactamase activity, that was relatively resistant to proteolytic degradation over a 90 minute incubation period with cycloheximide; wild-type β-lactamase activity decayed with a half-life >2 hours (FIG. 6). Cells expressing 1XUb-B1a fusions also contained relatively high levels of β-lactamase activity that decayed with a half-life of about 20-30 minutes. Cells expressing β-lactamase fused to 2 or more copies of ubiquitinG76V (SEQ. ID. NO. 17) had significantly less β-lactamase activity at steady state (compare 0 minute time points) and the half-lives of these pools of fusion proteins were strikingly short, with all three fusion proteins decaying with in vivo half-lives of less than 10 minutes.

The β-lactamase measurements from the Jurkat cell lysates allows a calculation of the intracellular concentration and copy number of β-lactamase fusion proteins in the respective cell lines. A standard curve created of the hydrolysis of CCF2 by purified β-lactamase enzyme was generated and used to calculate the steady state concentration of β-lactamase fusion protein for each cell line. This analysis showed that there was a ten-fold difference in intracellular concentration between wild-type β-lactamase and 4XUb-β-lactamase at steady state (Table 6). The calculated concentration of wild-type β-lactamase corresponds to 21,000 molecules per cell, in very good agreement with the values reported by Zlokarnik et al. (1998) (Science 279, 1848) for cells expressing high levels of wild-type β-lactamase.

TABLE 6

| Construct | Half-life | Intra-cellular Concen-tration |
|---|---|---|
| WT Bla | >120 min | 35 nM |
| 1XUb-Bla | 20-30 min | 30 nM |
| 2XUb-Bla | <10 min | 7 nM |
| 3XUb-Bla | <10 min | 5 nM |
| 4XUb-Bla | <10 min | 3.5 nM |

The kinetic data on fusion protein turnover, together with the steady state concentration measurements, demonstrate that the fusion of a multiubiquitin destabilization domain to a target protein allows for the manipulation of both the intracellular concentration, as well as, the turnover kinetics of the resulting fusion proteins. The present invention provides for a method of regulating the intracellular concentration of any target protein within a cell, independently of the rate of transcription of that protein. Unlike other systems of regulating the intracellular concentrations of target proteins, the present invention provides for the ability to "pre-set" the final concentration of the target protein within a ten-fold range of expression.

The data with multiubiquitinG76V-β-lactamase fusions demonstrate that fusions containing one to four copies of ubiquitinG76V fused to β-lactamase results in chimeric proteins with half-lives in vivo of from 5 to 30 minutes. There are likely to be applications that require proteins that have a half-life longer than that obtained with fusion to one copy of ubiquitinG76V. For such instances, it would be useful to have a form of uncleavable ubiquitin that is recognized by E2/E3 ubiquitin ligases with lower affinity and therefore result in less destabilization than with fusions to ubiquitinG76V. The efficient recognition and degradation of proteins by the proteasome requires the formation of extended polyubiquitin chains that are extended in isopeptide linkage between a critical lysine residue on ubiquitin to the C-terminus of the incoming ubiquitin. The internal lysine in ubiquitin most often used in such polyubiquitin chains is lysine-48. In order to create a longer half-life protein, it is recognized that it is possible to mutagenize the ubiquitin homolog fused to the protein of interest such that it is not recognized by E2/E3 ubiquitin ligases as efficiently as wild-type ubiquitin. It is likely that mutagenesis of lysine-48, (to Arg, His, Gln or Asn for example) and/or the residues surrounding it will yield a form of ubiquitin that is recognized and extended with lower affinity, than the non-mutant forms. The non extandable homologs would thus serve to create fusion proteins with longer half lives than is otherwise possible with wild-type ubiquitin. Typically such constructs would contain between one and five copies of the non-extendable, non-cleavable ubiquitin homologs to provide for a wide range of destabilization.

Alternatively, random mutagenesis of the ubiquitin or mutation of other lysines in ubiquitin may result in a form of ubiquitin with the desired properties.

Example 9

Characterization of the Stability of Multimerized Destabilization Domain-Naturally Fluorescent Protein Fusions Within Cells UbiquitinG76V-GFP constructs in pcDNA3 (SEQ. ID. NOs. 31 to 34) were introduced into CHO cells by Lipofectamine (Life Technologies) transfection. Stable transfectants were selected in RPMI 1640 media containing 10% fetal bovine serum (Gibco) and 0.8 mg/ml G418 (Geneticin, Gibco). Analysis of GFP fluorescence in CHO cells stably transfected with various ubiquitinG76V-GFP constructs was analyzed by flow cytometry on a Becton Dickinson FACS™ Vantage™ with a Coherent Enterprise II™ argon laser producing 60 mW of 488 nm UV excitation. The flow cytometer was equipped with pulse processing and the Macrosort™ flow cell. Fluorescence emission was detected via 530/30 nm emission filter. The FACS analyses of stable populations determined that the steady state percentage of bright green $GFP^+$ cells varied depending on the presence of the multiubiquitin destabilization domain. The relative percentages of $GFP^+$ cells are shown in the Table 7.

TABLE 7

| Stable CHO cell line | % $GFP^+$ cells |
|---|---|
| Wild-type GFP | 39.13 |
| 1XUb-GFP | 5.74 |
| 2XUb-GFP | 3.06 |
| 3XUb-GFP | 2.2 |
| 4XUb-GFP | 1.93 |

This analysis showed that the relative abundance of cells expressing high steady state levels of GFP fluorescence was inversely proportional to the number of copies of ubiquitinG76V (SEQ. ID. NO. 17) fused to the protein, i.e., the lowest levels of GFP-expressing cells were found in the fusions containing the most copies of ubiquitinG76V (SEQ. ID. NO. 17). The steady state concentration measurements demonstrate that fusions of a multiubiquitin destabilization domain to the highly stable GFP mutant Emerald (SEQ. ID. NO. 28) allows for the predictable and controllable manipulation of the intracellular concentrations of naturally fluorescent proteins.

Example 10

Construction of Destabilization Domain-Linker-Reporter Moiety Fusion Proteins Ubiquitin-β-lactamase fusion proteins containing a specific protease cleavage site were constructed by annealing the complementary oligonucleotides DEVD-1 (SEQ. ID. NO. 45) and DEVD-2 (SEQ. ID. NO. 46) that encode a caspase-3-type cleavage site and produce BamH I compatible ends. This oligonucleotide cassette was ligated into BamH I-digested pcDNA3-1-4XUb-B1a plasmid constructs (SEQ. ID. NOs. 23 to 26) described in Example 2. The resulting constructs encode an in-frame fusion protein consisting of from one, to four, copies of ubiquitinG76V (SEQ. ID. NO. 17) separated from β-lactamase by linker containing a caspase-3 cleavage site; the plasmids were designated as pcDNA3-1-4XUb-DEVD-B1a (SEQ. ID. NOs. 47-50). A control linker containing a DEVA site that should not serve as a cleavage site for caspase-3-like proteases was constructed in an identical manner using DEVA1 (SEQ. ID. NO. 51) and DEVA2 primers (SEQ. ID. NO. 52) and the resulting plasmids were designated as pcDNA3-1-4XUb-DEVA-B1a (SEQ. ID. Nos. 53-56).

Figure 7A:
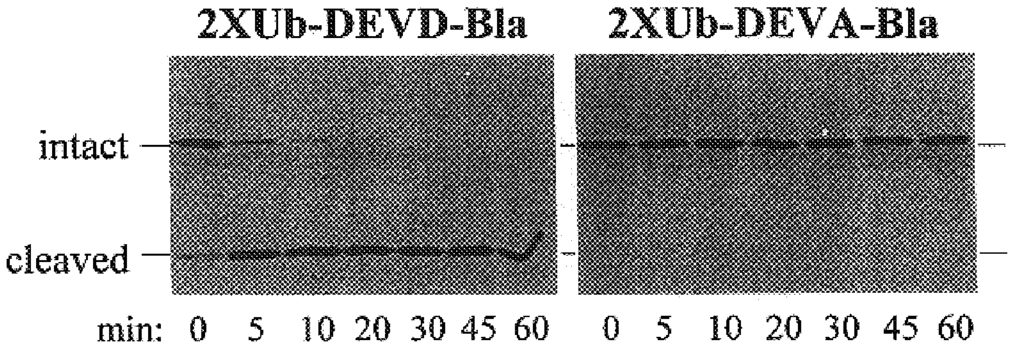
FIG. 7 Caspase cleavage of 2XUb-DEVD-B1a results in the stabilization of β-lactamase. TNT synthesis reactions were performed to generate labeled fusion proteins of the caspase substrate 2XUb-DEVD-B1a and control 2XUb-DEVA-B1a. In (A), the labeled proteins were incubated with purified caspase-3 to verify that 2XUb-DEVD-B1a can be cleaved by caspase-3 and 2XUb-DEVA-B1a cannot. In (B), the products of the caspase-3 cleavage reactions were incubated with chase extract and samples analyzed by SDS-PAGE.

1-4XUb-DEVD-B1a (SEQ. ID. NOs. 47-50) or control plasmids pcDNA3-1-4XUb-DEVA-B1a (SEQ. ID. NOs. 53-56) were used as templates. The $^{35}S$-labeled proteins were then used as substrates for purified caspase-3 in an in vitro cleavage reaction. The 12 μl reaction consisted of 4 μl of $^{35}S$-labeled ubiquitin-DEVD/A-B1a fusion proteins, 100 mM HEPES pH 7.5, 10% sucrose, 0.1% CHAPS, 10 mM DTT and 25 nM purified recombinant caspase-3. The reactions were incubated at 30° C. and samples taken at 0, 5, 10, 20, 30, 45, and 60 minutes and analyzed by SDS-PAGE and autoradiography. The results from 2XUb-DEVD-B1a and 2XUb-DEVA-B1a fusion proteins are shown in FIG. 7A. The 2XUb-DEVD-B1a fusion served as a very good substrate for caspase-3 with over 90% cleavage within 5 minutes. In contrast, the 2XUb-DEVA-B1a fusion was not cleaved by caspase-3 in vitro, even at extended incubation times. The 2XUb-DEVD-B1a cleavage product seen in FIG. 7A co-migrates on SDS-PAGE gels with β-lactamase fused to the short DEVD linker region (data not shown) and verifies the position of the cleavage site and identifies the labeled cleavage product as the β-lactamase portion of the cleaved fusion. The liberated destabilization domain is much smaller and has run off the gel in this experiment. These data demonstrate that the DEVD fusion serves as an efficient substrate for caspase-3 and the lack of cleavage with the DEVA fusion confirms that the cleavage is occurring ate the DEVD site.

Figure 7B:
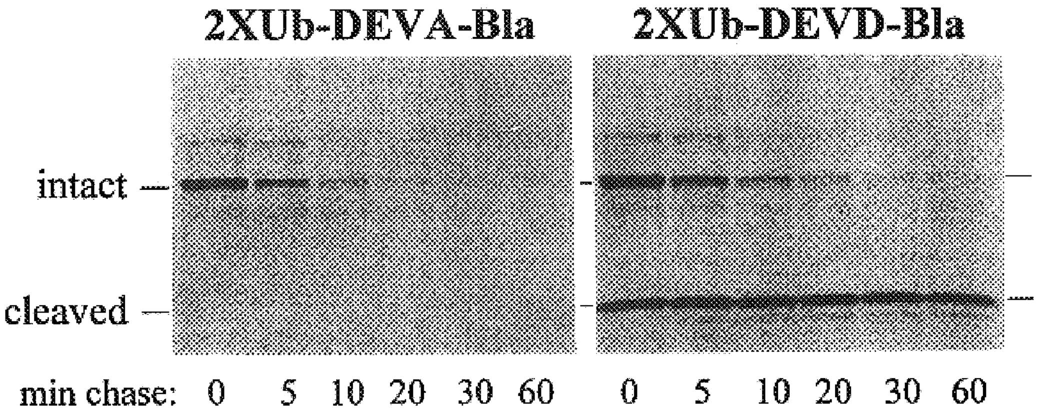

The protease assay outlined above requires that the protease cleavage result in a stabilization of the catalytic domain of the reporter. To test whether this is the case, we mixed approximately equal portions of cleaved and uncleaved $^{35}S$-labeled reporters from in vitro cleavage reactions identical to those in FIG. 7A and then diluted the fragments into crude chase lysate containing cycloheximide to perform a chase experiment. The reactions were incubated at 37° C. and samples were taken at 0, 5, 10, 20, 30 and 60 minutes and analyzed by SDS-PAGE and autoradiography. FIG. 7B shows that the uncleaved intact 2XUb-DEVD-B1a or 2XUb-DEVA-B1a reporters were degraded very rapidly in vitro with a half-life of less than 5 minutes. In contrast, the cleavage product from the 2XUb-DEVD-B1a reporter lacks the destabilization domain and as a result is very stable in vitro. These data confirm that the intact and cleaved versions of the β-lactamase reporters have dramatically different half-lives and provide evidence that this difference in stability may provide a format for assaying endoprotease activity in vivo.

```
End of Ubiquitin-G76V (SEQ. ID. NO. 17)      Start of β-lactamase
                    ↓                                       ↓
L V L R L R G V G S V G A V G S V G D E V D G S G A W L H P E T L V K V (SEQ ID NO. 74)
                                           ↑
Recognition site for post-translational activity
```

Example 11

Detection of Caspase Activity Using Destabilized Reporter Moieties In Vitro $^{35}S$-labeled ubiquitin-β-lactamase fusion proteins containing a cleavage site for the group II effector caspase-3 were produced by in vitro transcription/translation reactions as described in Example 2 except that plasmids pcDNA3-

Example 12

Detection of Effector Caspase Protease Activity Using Destabilized Reporter Moieties Within Cells Plasmids pcDNA3-1-4XUb-DEVD-B1a (SEQ. ID. NOs. 47-50) and pcDNA3-1-4XUb-DEVA-B1a (SEQ. ID. NOs. 53-56) were transfected into Jurkat cells and selected for stable transfectants as described in Example 8. The stable transfectants were sorted by flow cytometry using Becton Dickinson FACS™ Vantage™ SE and FACS™ Vantage™ flow cytometers. The FACS™ Vantage™ SE was equipped with Turbosort Option, pulse processing, ACDU, and Coherent Innova 302C krypton and Coherent Innova 70 Spectrum mixed-gas krypton-argon lasers. The FACS™ Vantage™ was equipped with pulse processing, ACDU, and Coherent Enterprise II and Coherent Innova 70 Spectrum mixed-gas krypton-argon (with violet option) lasers. For β-lactamase experiments, 60 mW of 413 nm laser emission was used for CCF2 excitation, with a 500 nm dichroic filter separating a 460/50 nm (CCF2 blue fluorescence) and a 535/40 nm bandpass filter (green fluorescence). Single cells with the desired level of β-lactamase expression were sorted into individual wells of 96-well plates using the Automatic Cell Deposition Unit (ACDU) on the FACS™ Vantage™ and expanded for analysis of homogeneous clonal populations. All results in this Example utilized clonal lines.

The clonal cell lines were initially screened for expression of β-lactamase and the ability to degrade the Ub-DEVD-B1a or Ub-DEVA-B1a fusion rapidly. This initial screen was accomplished by treating an aliquot of cells with 100 μg/ml cycloheximide followed by incubation at 37° C. for 1 hour (chase period). Treated and untreated cells were loaded with 1 μM CCF2-AM for 1 hour at room temperature and β-lactamase levels were quantified using a CytoFluor microtiter plate fluorimeter (Perseptive Biosystems) using 395/25 nm excitation and 460/40 (blue) nm and 530/30 (green) nm emission filters. Emission ratios were calculated from background-subtracted values (background=media+CCF2 alone) and expressed as a 460/530 nm ratio where a high ratio indicates high β-lactamase activity. This analysis showed that Ub-DEVD-B1a fusions with two or more copies of ubiquitinG76V (SEQ. ID. NO. 17) gave satisfactory chase characteristics, with fusions to two copies of UbiquitinG76V (SEQ. ID. NO. 17) giving the highest steady state levels (no chase) of fusion protein (data not shown). In contrast, 1XUb-DEVD-B1a fusions were not sufficiently destabilized to be usable with this assay format as cells expressing the fusion required extended cycloheximide treatments (data not shown). As the 2-4XUb-DEVD-B1a fusions all exhibited satisfactory rates of proteolytic turnover in cells, the 2X ubiquitinG76V destabilization domain was used with the DEVD-B1a fusions because it gave the best performance (expression levels vs. turnover kinetics) in this particular application. It is worth noting here that due to the variability in the intrinsic stability of different proteins fused to the ubiquitinG76V (SEQ. ID. NO. 17) destabilization domain; fusions of other cellular proteins with multimerized destabilization constructs would be expected to require a dissimilar number of copies of ubiquitinG76V (SEQ. ID. NO. 17) to impart sufficiently rapid turnover kinetics (data not shown). A key advantage of the present invention is the ability to meet this need by varying the number of destabilization domains present within the multimerized destabilization domain construct.

One clonal cell line from each of 2XUb-DEVD-B1a and 2XUb-DEVA-B1a cell populations was characterized in detail. To establish the background (no β-lactamase) control value, wild-type Jurkat cells containing no β-lactamase activity were loaded with CCF2-AM and the 460/530 fluorescence ratio measured. The value obtained, about 0.05, establishes the background ratio exhibited by cells in the absence of β-lactamase activity. When the 2XUb-DEVD-B1a and 2XUb-DEVA-B1a clones were treated with cycloheximide (chx) for 1 hour at 37° C. prior to CCF2-AM loading, they both exhibited 460/530 ratios very near the background ratio of 0.05, demonstrating that the cells retained the ability to degrade the 2XUb-B1a fusion very efficiently (Table 8).

TABLE 8

| | 2XUb-DEVD-Bla 460/530 emission ratio | 2XUb-DEVA-Bla 460/530 emission ratio |
|---|---|---|
| no chx | 1.80 | 1.60 |
| + chx | 0.07 | 0.07 |
| + αFas/− chx | 1.25 | 1.10 |
| + αFas/+ chx | 0.67 | 0.12 |
| + αFas/+ inh/+ chx | 0.08 | 0.09 |

The fact that there is a significant difference in stability between the uncleaved reporter and the cleavage product in vitro (FIG. 7B) forms the basis for an assay for protease activity in intact cells. As shown in Table 8, in the absence of caspase activity, both 2XUb-DEVD-B1a and 2X-Ub-DEVA-B1a fusions are rapidly degraded to very low levels in the presence of cycloheximide to inhibit new protein synthesis. Treatment of Jurkat cells with Fas ligand will result in the activation of Fas receptor-an apoptosis signaling receptor found on the surface of a number of cell types that belongs to the tumor necrosis factor (TNF)/nerve growth factor family. Fas activation ultimately leads to the activation of the group II caspases that efficiently cleave substrates containing DEVD recognition motifs. In order to activate this pathway and measure the activity of group II caspases using the DEVD-B1a reporter in intact cells, an anti-Fas antibody (CH-11 anti-Fas IgM; Kamiya Biomedical Co., Seattle, Wash.) was used to cross-link the receptor and stimulate the activation of group II caspases. Western blot analysis of the anti-Fas-treated cells confirmed the proteolytic activation of caspase-3 (data not shown), the major group II caspase activity in Jurkat cells. Treatment of Jurkat cells expressing 2XUb-DEVD-B1a or 2XUb-DEVA-B1a reporter with 50 ng/ml anti-Fas IgM for 6 hours at 37° C. resulted in a modest decrease in the steady-state levels of the reporter (Table 8), most likely due to the inhibition of protein synthesis that is known to accompany apoptosis. At this point, the activation of group II caspases will result in the cleavage and stabilization of some proportion of the DEVD-B1a (but not the control DEVA-B1a) reporters. Treatment of such cells with cycloheximide would then allow for the clearing of the uncleaved, short half-life reporters while leaving the stable cleaved reporters as the sole forms of β-lactamase activity in the cells. Table 8 shows that cycloheximide addition to anti-Fas treated cells (+αFas/+chx) resulted in the stabilization of a significant fraction of the DEVD-B1a reporters while the DEVA-B1a reporters cannot be cleaved and stabilized. To show that the stabilization of the DEVD-B1a reporters is due to caspase activation, we used the peptide inhibitor Z-VAD-fmk (Enzyme Systems Products, Livermore, Calif.) that is a potent broad inhibitor of caspases. Treatment of the cells with 10 μM Z-VAD-fmk coincident with anti-Fas addition blocked the stabilization of DEVD-B1a reporters. Treatment of the cells with cycloheximide resulted in the degradation of the non cleaved constructs to background levels of β-lactamase activity (+aFas/+Inh/+chx). Comparison of β-lactamase levels in antiFas-treated DEVD-B1a-expressing cells in the presence or absence of Z-VAD-fmk inhibitor determines the dynamic range of the assay; in this particular experiment the dynamic range is approximately 8-fold. These data demonstrate that the cleavage and stabilization of short half-life β-lactamase protease reporters provides a sensitive and specific assay for measuring the activation of caspases in intact cells.

Figure 8:
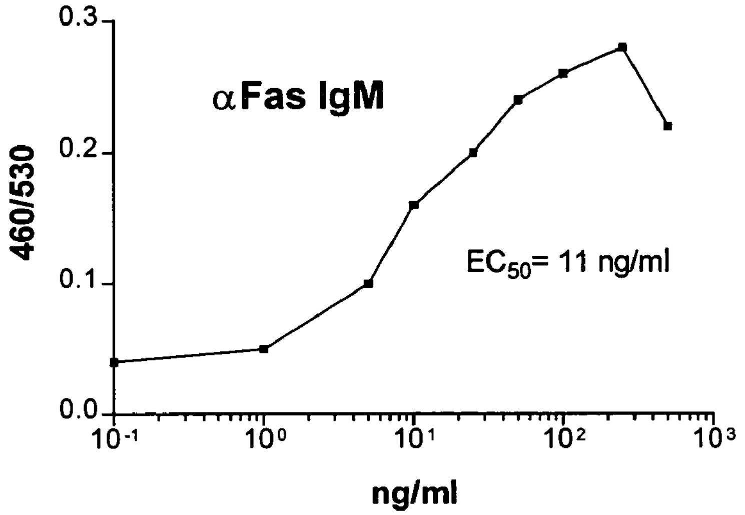
FIG. 8 Dose-response curves for an inducer and an inhibitor of caspase activation with Jurkat cells expressing 2XUb-DEVD-B1a. Varying concentrations of antiFas IgM were incubated with 2XUb-DEVD-B1a-expressing Jurkat cells for 6 hours at 37° C. and caspase activity was measured following a cycloheximide chase to clear uncleaved reporters. The cells were loaded with CCF2-AM and β-lactamase activity measured and expressed as a 460/530 nm ratio. Jurkat cells expressing 2XUb-DEVD-B1a were treated with varying concentrations of the caspase inhibitor ZVAD-fmk and then treated with 75 ng/ml antiFas IgM. The cells were incubated for 6 hours at 37° C., cycloheximide for 1 hour at 37° C. and β-lactamase activity measured using CCF2-AM as described above.
Figure 8:
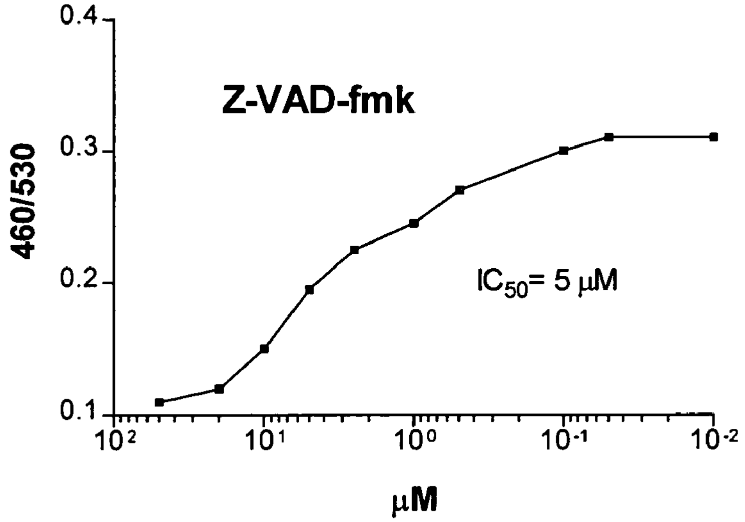

It is of note that this assay format would permit the identification of compounds that stimulate group II caspases and subsequent apoptosis (agonist/inducer format) as well as compounds that inhibit caspase activity stimulated by a known reagent such as anti-Fas IgM (antagonist/inhibitor format). As evidence for this assay being useful for both inducer and inhibitor applications, we generated dose-response curves for both an inducer of caspases and apoptosis (anti-Fas IgM) and an inhibitor of anti-Fas induced apoptosis (Z-VAD-fmk). FIG. 8 shows that the assay in Jurkat cells expressing 2XUb-DEVD-B1a generates sufficient dynamic range to detect low concentrations of the inducer anti-Fas IgM ($EC_{50}$=11 ng/ml). In addition, treatment of Jurkat cells expressing 2XUb-DEVD-B1a with 50 ng/ml anti-Fas IgM allows sensitive detection of inhibition by Z-VAD-fmk with $IC_{50}$=5 μM (FIG. 8).

Example 13

Creation of Reporters for Viral Self-Cleaving Proteases Using Multimerized Destabilization Domain-β-Lactamase-Rhinovirus 2A Protease Fusions The gene encoding the human rhinovirus 14 2A protease (SEQ. ID. NO. 57) was isolated by PCR amplification from genomic RNA by RT-PCR using oligonucleotides HRV145' (SEQ. ID. NO. 58) and HRV143', (SEQ. ID. NO. 59). The resulting PCR product had BamH I sites at both ends of the HRV14 2A protease sequence and could be inserted in frame into the pcDNA3-1-4XUb-B1a vectors (SEQ. ID. Nos. 23-26) from example 2. The PCR fragment from this reaction was digested with BamH I and ligated into pcDNA3-3XUb-B1a (SEQ. ID. NO. 25). The resulting construct, pcDNA3-3XUb-B1a HRV14 (SEQ. ID. NO. 60) was further characterized in vitro and within cells.

In addition to the HRV14 2A protease constructs, two additional constructs were made for the HRV16 2A protease. The gene for the human rhinovirus 16 sequence 2A protease (SEQ. ID. NO. 61) was isolated by polymerase chain reaction (PCR) amplification of a plasmid template. The PCR template was a plasmid construct containing the entire HRV16 genome (a gift from Dr. Wai Ming Lee at the University of Wisconsin). Oligonucleotides HRV165' (SEQ. ID. NO. 62) and HRV163', (SEQ. ID. NO. 63) were used in a PCR reaction with the HRV16 plasmid resulting in a PCR product that had BamH I sites at both ends of the HRV16 2A protease sequence. The PCR fragment from this reaction was digested with BamH I and ligated into pcDNA3-3XUb-B1a (SEQ. ID. NO. 25) and pcDNA3-Ub-Met B1a (SEQ. ID. NO. 27) via the BamH I site. The resulting constructs were pcDNA3-3XUb-B1a HRV16 (SEQ. ID. NO. 64) and pcDNA3-Ub-Met-B1a HRV16 (SEQ. ID. NO. 65). In addition, two mutant constructs were made for the HRV16 2A protease. These mutants corresponded to mutations at two residues of the putative catalytic triad for the 2A protease and should result in a catalytically inactive mutant, specifically, aspartate 35 was mutated to alanine (D35A) and cysteine 106 was mutated to alanine (C106A). These derivatives were generated by mutagenesis of the HRV16 2A protease using oligonucleotide HRV16 D35A (SEQ. ID. NO. 66) and oligonucleotide HRV16 C106A (SEQ. ID. NO. 67). The resulting plasmids were designated as pcDNA3-3XUb-B1a HRV16(C106A) (SEQ. ID. NO. 68), pcDNA3-3XUb-B1a HRV16(D35A) (SEQ. ID. NO. 69), pcDNA3-Ub-Met-B1a HRV16(C106A) (SEQ. ID. NO. 70) and pcDNA3-Ub-Met-B1a HRV16(D35A) (SEQ. ID. NO. 71).

Example 14

Figure 9A:
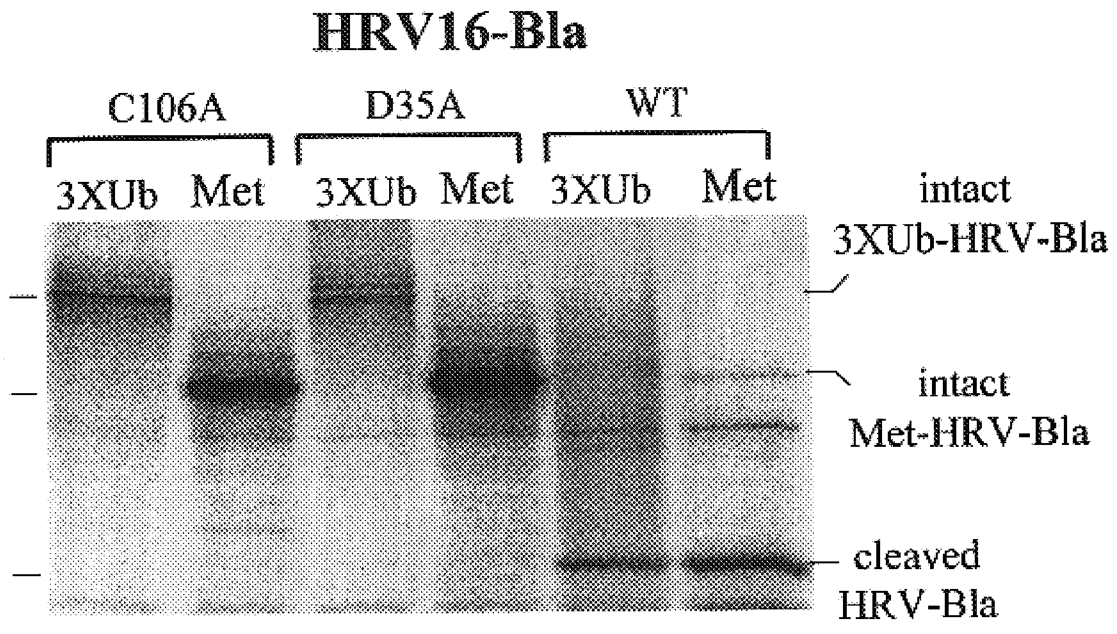
FIG. 9 In vitro cis-cleavage activity of UbG76V-HRV 2A-B1a fusions. Labeled UbiquitinG76V-HRV 2A protease β-lactamase fusions were produced in TNT reactions and then analyzed by SDS-PAGE. (A) shows that the cis-cleavage of HRV-B1a fusions is blocked by mutation of putative catalytic residues (C106 and D35). (B) The TNT reactions were incubated in chase extract to show the selective stabilization of the cleavage product.

Detection of Rhinovirus Protease Activity Using Destabilized Reporter Moieties In Vitro $^{35}$S-labeled ubiquitin-β-lactamase fusion proteins containing the HRV14 and HRV16 2A proteases, as well as the mutants above, were produced by in vitro transcription/translation reactions as described in Example 5. The plasmids pcDNA3-3XUb-B1a HRV16 (SEQ. ID. NO. 64), pcDNA3-3XUb-B1a HRV16(C106A) (SEQ. ID. NO. 68), pcDNA3-3XUb-B1a HRV16(D35A) (SEQ. ID. NO. 69), pcDNA3-Met Ub-B1a HRV16 (SEQ. ID. NO. 65), pcDNA3-3XUb-B1a HRV14 (SEQ. ID. NO. 60), and pcDNA3-MetUb-B1a HRV14 (SEQ. ID. NO. 72) were used as templates. The reactions were incubated at 30° C. for 45 min and analyzed by SDS-PAGE and autoradiography. FIG. 9A shows the results of TNT synthesis reactions for the wild-type HRV16 2A and the two mutant HRV16 2A constructs. Shown are the levels of expression for the stable (Met) and destabilized 3X ubiquitinG76V HRV16 2A-B1a fusions. As expected, the level of expression is higher in the stable methionine containing constructs than the destabilized 3XUb constructs (FIG. 9A). The wild-type HRV16 2A fusions also show significant accumulation of the lower molecular weight stable cleavage product indicating that the fusions exhibit robust autocatalytic cleavage activity in these in vitro reactions. In contrast, mutation of residues in the putative catalytic triad (aspartate 35 and cysteine 106) blocked formation of the stable cleavage product, indicating that these mutants are indeed catalytically inactive.

Figure 9B:
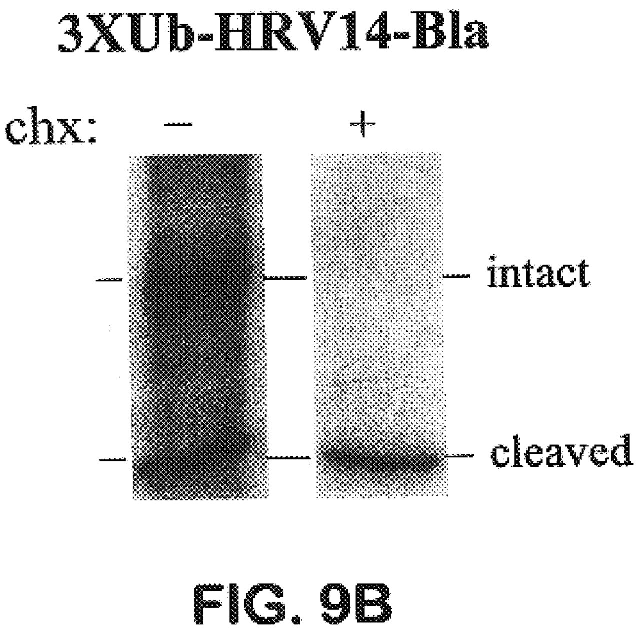

The protease assay outlined in Example 10 requires that protease cleavage results in a stabilization of the catalytic domain of the reporter. To test for this requirement the pcDNA3-3XUb-B1a HRV14 TNT reaction was diluted into chase lysate containing cycloheximide to perform a chase experiment. The reactions were incubated at 37° C. for 60 minutes and analyzed by SDS-PAGE and autoradiography. FIG. 9B shows that the uncleaved intact 3XUb-HRV14-B1a reporter was completely degraded during the 60 minute chase. In contrast, the cleavage product from the 3XUb-HRV14-B1a reporter lacks the destabilization domain, and as a result, is stable in vitro. These data confirm that the intact and cleaved versions of the HRV 2A-β-lactamase fusion reporters have dramatically different half-lives and provide evidence that this difference in stability can provide the basis for assaying self-cleaving protease activity in side intact cells.

Example 15

Detection of Rhinovirus Protease Activity Using Destabilized Reporter Moieties In Vivo The biochemical properties of self-cleaving cis proteases such as rhinovirus 2A pose several technical challenges that have hampered the development of a screening format to allow for the identification of inhibitors or activators in cell based assays. First, the activity of the protease is directed toward cleavage of itself. This rules out the use of separate reporters that are cleaved in trans and limit the catalytic output of the assay, i.e., a single protease molecule generates a single cleavage product and this fact eliminates the catalytic amplification used in traditional assays for trans-cleaving proteases. In order to address these limitations, the β-lactamase reporters are incorporated into the 2A protease itself, thereby measuring the cis cleavage reaction directly and gaining the advantage of a catalytic reporter that can cleave many CCF2 substrate molecules per reporter. Since the HRV 2A protease undergoes the self-cleavage reaction immediately upon synthesis, the screening assay must be performed on newly synthesized HRV 2A-β-lactamase reporters. A screen to identify inhibitors of the protease must incorporate a step where test compounds are added and their effect then measured. As cleaved stable β-lactamase reporters will accumulate in the cell as the HRV 2A-B1a reporters are being constitutively expressed, it is essential to eliminate the readout due to such cleavage products that are generated before the test compound is added. To do this, the β-lactamase inhibitor clavulanate was used. Clavulanate is a non-cytotoxic irreversible inhibitor of β-lactamase and overnight treatment of Jurkat cells reduces β-lactamase levels to background (See commonly owned U.S. patent application Ser. No. 09/067,612 filed Apr. 28, 1998). Therefore, clavulanate treatment of Jurkat cells expressing HRV 2A-B1a fusions eliminates the β-lactamase activity that is present in the cell resulting from both uncleaved and cleaved β-lactamase reporters. In essence, this has the effect of "zeroing out" the β-lactamase activity in the cells and bringing the cells back down to baseline activity. The clavulanate can then be washed out and test compound added. New synthesis of HRV 2A-B1a reporters will result in the accumulation of the fusion protein reporter in the cells and the self-cleavage reaction will now be subject to inhibition by the test compound. After an appropriate interval to allow for the cleavage of newly synthesized reporters has passed, the cells can be treated with cycloheximide to clear out the unstable uncleaved reporters and the resulting β-lactamase activity will be due exclusively to cleaved, stabilized reporters.

Plasmids pcDNA3-3XUb-B1a HRV16 (SEQ. ID. NO. 64) and pcDNA3-3XUb-B1a HRV14 (SEQ. ID. NO. 60) were transfected into Jurkat cells and selected for stable transfectants as described in Example 8. The stable transfectants were sorted by flow cytometry using Becton Dickinson FACS™ Vantage™ SE and FACS™ Vantage™ flow cytometers. The FACS™ Vantage™ SE was equipped with Turbosort Option, pulse processing, and Coherent Innova 302C krypton and Coherent Innova 70 Spectrum mixed-gas krypton-argon lasers. The FACS™ Vantage™ was equipped with pulse processing, and Coherent Enterprise II and Coherent Innova 70 Spectrum mixed-gas krypton-argon (with violet option) lasers. For β-lactamase experiments, 60 mW of 413 nm laser emission was used for CCF2 excitation, with a 500 nm dichroic filter separating a 460/50 nm (CCF2 blue fluorescence) and a 535/40 nm bandpass filter (CCF2 green fluorescence). Single cells with the desired level of β-lactamase expression were sorted into individual wells of 96-well plates using the Automatic Cell Deposition Unit (ACDU) on the FACS™ Vantage™ and expanded for analysis as homogeneous clonal populations. All results in Example 15 utilized clonal lines.

Selected clones (25-50 for each construct) were then expanded further for analysis. Clones were treated for 16 hours with 300 μM clavulanate, washed twice with phosphate buffered saline (PBS), incubated for 2 hours at 37° C., treated for 1 hour at 37° C. with 100 μg/ml cycloheximide, and then loaded with CCF2-AM for 2 hours at room temperature. The individual clones were then screened visually by fluorescence microscopy. At least 24 individual clones were tested in this manner for each construct and one clone chosen for each construct.

To assay HRV 2A protease activity, the selected Jurkat stable cell clones were treated for 16 hours with 300 μM clavulanate to inactivate pre-existing cleaved and uncleaved HRV 2A-B1a fusion protein. Cells were then washed twice with PBS, resuspended at 100,000 cells/well in 100 μl RPMI+10% FBS in 96-well plates. The cells were incubated at 37° C. for 4 hours in the presence or absence of an inhibitor of the 2A protease. Cells were treated with 100 μg/ml cycloheximide for 30 minutes at 37° C., loaded with CCF2-AM for 2 hours at room temperature and read on the CytoFluor plate reader as described in Example 8. Inhibitor compounds, radicicol and geldanamycin, were used for the validation of the HRV protease cell-based assay. These compounds are known inhibitors of the Hsp90 heat shock protein (see Roe et al., (1999) J. Med. Chem. 42 260-266), which is required for the folding and regulation of a number of cellular proteins and can inhibit HRV 2A protease activity in vitro (data not shown). Compounds were tested at 1 μM for their ability to inhibit the HRV 2A protease cell-based assay using clones expressing HRV16 and HRV14 2A protease reporters. Jurkat cells expressing 3XUb-B1a-HRV14 or HRV16 2A protease fusion proteins contained significant β-lactamase activity in the absence of the inhibitors (Table 9). Both radicicol and geldanamycin showed strong inhibition of cellular β-lactamase activity remaining after the cycloheximide chase. The inhibitors are not simply inhibiting β-lactamase enzyme activity because control experiments showed that radicicol and geldanamycin did not inhibit β-lactamase activity in Jurkat cells expressing wild-type β-lactamase (data not shown). These data demonstrate that the β-lactamase activity present after a cycloheximide chase is due to HRV 2A protease activity and that this β-lactamase activity can be blocked using inhibitors of HRV 2A protease. These results further demonstrate that Jurkat cells expressing 3XUb-B1a HRV 2A fusion proteins constitute a robust cell-based assay for HRV 2A cis-protease activity. The difference in β-lactamase activity between untreated and inhibitor-treated cells determines the dynamic range of this assay; in this particular experiment, the assay dynamic range is approximately 6-fold.

TABLE 9

| | 3XUb-HRV14-Bla 460/530 nm ratio | 3XUb-HRV16-Bla 460/530 nm ratio |
|---|---|---|
| no inhibitor | 1.022 | 0.895 |
| + radicicol | 0.152 | 0.229 |
| + geldanamycin | 0.153 | 0.239 |

Example 16

Detection of Proteasome Activity within Cells Using Destabilized Reporter Moieties and Use in the Identification of Proteasome Inhibitors A direct application of the destabilized reporter fusions is in the measurement of the activity of the proteolytic activity that responsible for the constitutive degradation of the reporter in cells. Ubiquitinated proteins are known to be degraded by the multi-subunit proteasome. In addition, the proteasome is responsible for the degradation of the large majority of cellular proteins see Lee and Goldberg, (1998) Trends Cell Biol., 8 397-403). The proteasome itself has been implicated in a number of pathological conditions resulting from either increased or decreased proteasome activity (see Ciechanover, (1998) EMBO J. 17 7151-7160).

As such, the proteasome represents an attractive target for intervention in pathological conditions using small molecule inhibitors or activators.

Figure 10:
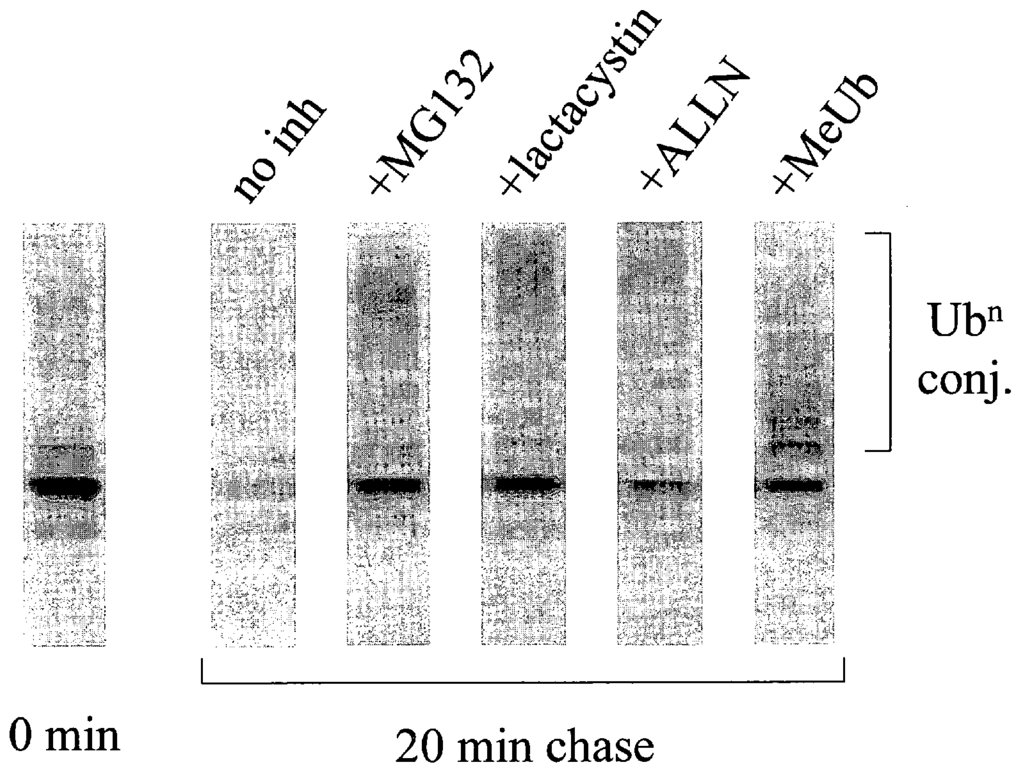
FIG. 10 Rapid degradation of 2XUb-B1a in vitro requires polyubiquitination and proteasome activity. TNT synthesis reactions were incubated in chase extract containing the indicated inhibitors for 20 minutes at 37° C. MG132 and ALLN were present at 50 μM, lactacystin at 10 mM and MeUb at 200 μg/ml.

Inhibitors of the proteasome were initially tested in vitro for inhibition of degradation of 2XUb-B1a. Transcription/translation reactions on the pcDNA3-2XUb-B1a (SEQ. ID. NO. 24) construct were preformed as described in Example 5. The $^{35}$S-labeled synthesis reactions were diluted into crude chase lysates in the presence of cycloheximide and inhibitor and incubated at 37° C. for 20 minutes. Samples were then analyzed by SDS-PAGE and autoradiography. FIG. 10 shows that >90% of the starting $^{35}$S-labeled fusion protein is degraded by the 20 minute time point in the absence of proteasome inhibitors. Addition of the inhibitor MG132 (Calbiochem) at 50 μM resulted in a significant increase in the intact, un-conjugated fusion protein as well as the appearance of high molecular weight labeled species that represent extensive further ubiquitination of the fusion protein. The high molecular weight ubiquitin conjugates accumulate prominently in the presence of MG132 because they are recognized so efficiently by the proteasome that they are barely visible without inhibiting their degradation. Additional proteasome inhibitors gave very similar results: 10 μM lactacystin β-lactone (Calbiochem) and 50 μM Ac-LLN (Sigma) stabilized the 2XUb-B1a fusion protein and caused the accumulation of high molecular weight ubiquitin conjugates.

Proteins destined to be degraded by the proteasome are initially modified by the covalent addition of ubiquitin to lysines within the targeted protein through an isopeptide linkage between the C-terminal residue of ubiquitin and the ϵ-amino groups of the substrate protein. The conjugated ubiquitin(s) acts as a high affinity conjugation site for the addition of additional ubiquitin polypeptides in isopeptide linkage between the C-terminus of the incoming ubiquitin to a lysine residue within the conjugated ubiquitin. When the ubiquitin chains reach a critical size four or more ubiquitin residues long (see Thrower et al., (2000) EMBO J. 19 94-102)), the ubiquitin-protein conjugate is recognized by the proteasome with high affinity, the substrate protein is degraded and the ubiquitin residues are recycled for further rounds of ubiquitination. To test whether poly-ubiquitination is required for the degradation of 2XUb-B1a, we used a form of ubiquitin where all amines had been reductively methylated, thereby producing a form of ubiquitin that can be conjugated but not extended. When methylated ubiquitin (MeUb) was added to the in vitro degradation system at 1 mg/ml, it significantly stabilized 2XUb-B1a and resulted in the appearance of ladders of labeled species that contain low (1-5 copies) numbers of conjugated ubiquitin polypeptides. (FIG. 10) It also inhibited the formation of the very high molecular weight ubiquitin-substrate conjugates observed with the proteasome inhibitors. Collectively, the in vitro inhibitor data demonstrate that the multiubiquitin destabilization domain targets degradation of the protein it is fused to in a proteasome-dependent manner that requires poly-ubiquitination of the substrate for high efficiency recognition/degradation.

Figure 11:
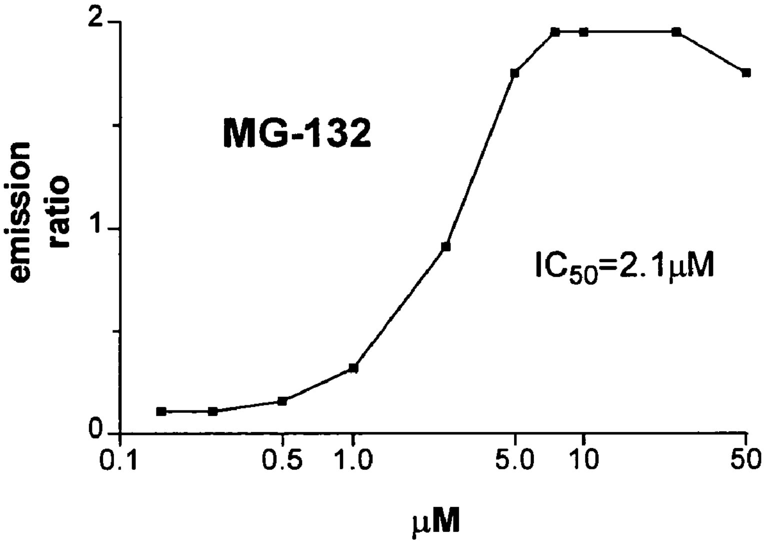
FIG. 11 Dose-response curves for proteasome inhibitors on Jurkat cells expressing 2XUb-B1a reporter. Cells were treated with varying concentrations of MG132 or ALLN for 30 minutes and then cycloheximide was added and the cells incubated at 37° C. for one hour. The cells were loaded with CCF2-AM to measure β-lactamase activity as described above.
Figure 11:
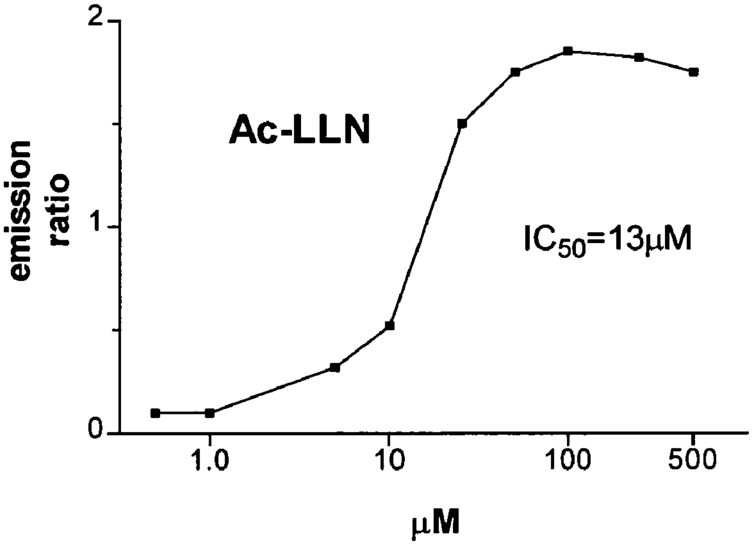

Jurkat cells expressing 2XUb-B1a fusion protein were used to test several inhibitors of proteasome function that were active in the in vitro system to determine if they were also active within living cells. Cells were treated with various concentrations of the proteasome inhibitors MG132 or Ac-LLN for 30 minutes at 37° C. and then cycloheximide was added to 100 μg/ml to initiate a chase period. After 1 hour at 37° C., the cells were cooled to room temperature and then loaded with 1 μM CCF2-AM and β-lactamase activity quantified using a CytoFluor plate reader. The background-subtracted emission values at 460 nm and 530 nm were expressed as a 460/530 ratio and dose-response curves were plotted. FIG. 11 shows that both MG132 and Ac-LLN exhibited a dose-dependent inhibition of the decay of β-lactamase activity indicating that they had inhibited the intracellular degradation of the ubiquitin-β-lactamase fusion protein. $IC_{50}$ values calculated from linear regression analysis were found to be 13 μM for Ac-LLN and 2.1 μM for MG132 and are within the characteristic range for inhibition of substrates degraded by the proteasome (see Lee and Goldberg, (1998) Trends Cell Biol., 8 397-403). These data demonstrate that the multiubiquitin destabilization domain fused to β-lactamase can serve as a robust cell-based 96-well format screening assay for inhibitors of the proteasome.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

We claim:

1. An in vitro method of detecting a protease activity in a cell, comprising:

a) providing a cell comprising a polynucleotide molecule encoding a polypeptide comprising:

i) at least one destabilization domain, wherein said destabilization domain is non-cleavable by α-NH-ubiquitin protein endoproteases;

ii) a reporter moiety; and iii) a linker moiety that operatively couples said destabilization domain to said reporter moiety, wherein said linker moiety comprises a protease cleavage site for said protease activity and cleavage of said linker moiety by said protease activity decreases the coupling of said destabilization domain to said reporter moiety thereby increasing the stability of said reporter moiety, and wherein said linker moiety is non-cleavable by said α-NH-ubiquitin protein endoproteases; and b) detecting said reporter moiety, or a product of said reporter moiety, thereby detecting the protease activity in the cell.

2. The method of claim 1, wherein said at least one destabilization domain is arranged as a linear multimer, and wherein said linear multimer comprises at least two copies of said destabilization domain and is non-cleavable by said α-NH-ubiquitin protein endoproteases.

3. The method of claim 1, wherein said linker moiety covalently couples said destabilization domain to said reporter moiety.

4. The method of claim 1, wherein said destabilization domain comprises a ubiquitin homolog comprising a mutation at glycine 76 of the amino acid sequence of wild-type ubiquitin.

5. The method of claim 1, wherein said reporter moiety is selected from the group consisting of a naturally fluorescent protein, β-lactamase, β-galactosidase, alkaline phosphatase, chloramphenicol acetyltransferase, β-glucuronidase, peroxidase, and luciferase.

6. The method of claim 5, wherein said reporter moiety comprises a β-lactamase.

7. The method of claim 5, wherein said reporter moiety comprises an *Aequorea* Green fluorescent protein.

8. The method of claim 5, wherein said reporter moiety comprises an *Anthozoan* Green fluorescent protein.

9. The method of claim 1, wherein said cell is a mammalian cell.

10. The method of claim 1, wherein said cell is a yeast cell.

11. The method of claim 1, wherein said cell is an insect cell.

12. The method of claim 1, wherein said cell is a plant cell.

13. The method of claim 1, wherein said method further comprises the step of adding a protein synthesis inhibitor to said cell.

14. The method of claim 1, wherein said method further comprises the step of adding an inhibitor of said reporter moiety to said cell.

15. The method of claim 1, wherein said method further comprises the step of adding a test chemical to said cell.

16. The method of claim 15, wherein said method further comprises the step of comparing the detection of said reporter moiety or a product of said reporter moiety before addition of said test chemical to the detection of said reporter moiety or a product of said reporter moiety after addition of said test chemical.

17. An in vitro method of increasing the concentration of one or more target proteins in a cell, comprising:

a) providing a cell comprising a polynucleotide molecule encoding a polypeptide comprising, i) a linear multimerized destabilization domain, wherein said linear multimerized destabilization domain is non-cleavable by α-NH-ubiquitin protein endoproteases, and comprises at least two copies of a destabilization domain;

ii) a target protein; and iii) a linker that operatively couples said linear multimerized destabilization domain to said target protein, wherein said linker comprises a protease cleavage site for a protease and cleavage of said linker by said protease decreases the coupling of said linear multimerized destabilization domain to said target protein, thereby increasing the stability of said target protein in said cell, and wherein said linker is non-cleavable by α-NH-ubiquitin protein endoproteases; and b) providing said protease to cause cleavage of said linker thereby increasing the stability and concentration of said target protein in said cell.

18. The method of claim 17, wherein said protease is naturally expressed in said cell.

19. The method of claim 17, wherein said protease is not naturally expressed in said cell.

20. The method of claim 17, further comprising the step of adding an inhibitor of said protease.

21. The method of claim 17, wherein said cell is a mammalian cell.

22. The method of claim 17, wherein said cell is a yeast cell.

23. The method of claim 17, wherein said cell is an insect cell.

24. The method of claim 17, wherein said destabilization domain comprises a ubiquitin homolog comprising a mutation of glycine 76 of the amino acid sequence of wild-type ubiquitin.

25. The method of claim 17, wherein said protease is provided by transfecting said cell with an expression vector comprising a nucleic acid sequence encoding said protease.

26. The method of claim 25, wherein said expression vector further comprises an inducible promoter.

27. The method of claim 25, wherein said expression vector is a retroviral expression vector.

28. The method of claim 25, wherein said protease is a viral protease.

29. An in vitro method of destabilizing a target protein in a cell, comprising:

a) introducing into the cell, one or more nucleic acid molecules that together encode a target protein and a linear multimerized destabilization domain, wherein the target protein is operatively coupled to a linear multimerized destabilization domain, wherein said linear multimerized destabilization domain is non-cleavable by α-NH-ubiquitin protein endoproteases, and comprises at least two copies of a destabilization domain, and wherein said destabilization domain comprises a ubiquitin homolog having a mutation at glycine 76 of the amino acid sequence of wild-type ubiquitin; and b) allowing the target protein to be recognized by one or more elements of a cellular protein degradation apparatus, thereby destabilizing the target protein.

30. A recombinant DNA molecule, comprising a nucleic acid sequence encoding:

a) a linear multimerized destabilization domain, wherein said linear multimerized destabilization domain is non-cleavable by α-NH-ubiquitin protein endoproteases, and comprises at least two copies of a destabilization domain, wherein at least one copy of the destabilization domain comprises a mutation of glycine 76 of the amino acid sequence of wild-type ubiquitin;

b) a target protein; and c) a linker moiety that operatively couples said multimerized destabilization domain to said target protein, wherein said linker is non-cleavable by α-NH-ubiquitin protein endoproteases.

31. An isolated host cell, comprising a nucleic acid sequence encoding;

a) a linear multimerized destabilization domain, wherein said linear multimerized destabilization domain is non-cleavable by α-NH-ubiquitin protein endoproteases, and comprises at least two copies of said destabilization domain, wherein at least one copy of the destabilization domain comprises a mutation of glycine 76 of the amino acid sequence of wild-type ubiquitin;

b) a target protein; and c) a linker moiety that operatively couples said linear multimerized destabilization domain to said target protein, wherein said linker is non-cleavable by α-NH-ubiquitin protein endoproteases, and wherein said linker moiety comprises a protease recognition site.

* * * * *